United States Patent
Smith et al.

(10) Patent No.: US 7,091,228 B2
(45) Date of Patent: Aug. 15, 2006

(54) PREPARATION AND USE OF ARYL ALKYL ACID DERIVATIVES FOR THE TREATMENT OF OBESITY

(75) Inventors: Roger Smith, Madison, CT (US); Ann-Marie Campbell, Monroe, CT (US); Philip Coish, New Haven, CT (US); Miao Dai, Briarwood, NY (US); Susan Jenkins, Milford, CT (US); Derek Lowe, Hamden, CT (US); Stephen O'Connor, Guilford, CT (US); Ning Su, Hamden, CT (US); Gan Wang, Wallingford, CT (US); Mingbao Zhang, Stamford, CT (US); Lei Zhu, Milford, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 77 days.

(21) Appl. No.: 10/839,833

(22) Filed: May 6, 2004

(65) Prior Publication Data
US 2004/0224997 A1 Nov. 11, 2004

Related U.S. Application Data

(60) Provisional application No. 60/469,619, filed on May 9, 2003.

(51) Int. Cl.
*A61K 31/428* (2006.01)
*A61K 31/426* (2006.01)
*C07D 277/82* (2006.01)
*C07D 277/42* (2006.01)

(52) U.S. Cl. .................. 514/367; 514/370; 548/161; 548/194; 548/198

(58) Field of Classification Search ............... 548/161, 548/194, 191; 514/367, 370
See application file for complete search history.

(56) References Cited

U.S. PATENT DOCUMENTS

| 3,997,589 A | 12/1976 | Seeger et al. |
| 4,021,479 A | 5/1977 | Seeger et al. |
| 5,254,577 A | 10/1993 | Carlson et al. |
| 5,789,434 A | 8/1998 | Kluender et al. |
| 5,886,022 A | 3/1999 | Kluender et al. |
| 6,100,077 A | 8/2000 | Sturley et al. |
| 6,110,939 A | 8/2000 | Janssen et al. |
| 6,344,548 B1 | 2/2002 | Farese, Jr. et al. |
| 6,607,893 B1 | 8/2003 | Ramharack et al. |

FOREIGN PATENT DOCUMENTS

| DE | 2112715 | 10/1972 |
| DE | 2112716 | 10/1972 |
| DE | 2112840 | 10/1972 |
| EP | 0352781 | 1/1990 |
| EP | 1031349 | 8/2000 |
| GB | 2273930 | 7/1994 |
| GB | 2276161 | 9/1994 |
| GB | 2276162 | 9/1994 |
| WO | 9615096 | 5/1996 |
| WO | 9967268 | 12/1999 |
| WO | 9967403 | 12/1999 |
| WO | 0001713 | 1/2000 |

OTHER PUBLICATIONS

Tabata, et al., "Xanthohumols, Diacylglycerol Acyltransferase Inhibitors, From Humulus Lupulus," *Phytochemistry*, 46 (4): 683-687 (1997).

Owen, et al., "Overt and Latent Activities of Diacylglycerol Acyltransferase in Rat Liver Microsomes: Possible Roles in Very-Low-Density Lipoprotein Triacylglycerol," *Biochemistry*, 323: 17-21 (1997).

Misra, et al., "Search for Potential Antiviral Drugs. Part I. Synthesis of Substituted Butyrophenone Thiosemicarbazones," *J. Indian Chem. Soc.*, 51 (7): 715-716 (1974).

Misra, et al., "Potential Anticonvulsant Drugs-I. Synthesis of Substituted-γ-Aminobutyrophenones," *J. Indian Chem. Soc.*, 51 (10): 898-899 (1974).

Tomoda, et al., "Amidepsines, Inhibitors of Diacylglycerol Acyltransferase Produced by *Humicola* sp. FO-2942, I Production, Isolation and Biological Properties," *J. of Antibiotics.*, 48 (9): 937-941 (1995).

Jamdar, et al., "Relationships Between Adipose Polyamine Concentrations and Triacylglycerol Synthetic Enzymes in Lean and Obese Zucker Rats," *Enzyme Protein*, 49: 222-230 (1996).

*Primary Examiner*—Golam M. M. Shameem
*Assistant Examiner*—Nyeemah Grazier
(74) *Attorney, Agent, or Firm*—Susan M. Pellegrino

(57) ABSTRACT

This invention relates to certain aryl alkyl acid compounds, compositions, and methods for treating or preventing obesity and related diseases.

20 Claims, No Drawings

PREPARATION AND USE OF ARYL ALKYL ACID DERIVATIVES FOR THE TREATMENT OF OBESITY

This application claims benefit of U.S. Provisional Application Ser. No. 60/469,619, filed May 9, 2003, the contents of which are incorporated herein by reference in their entirety.

FIELD OF THE INVENTION

This invention relates to certain aryl alkyl acid compounds, compositions, and methods for treating or preventing obesity and related diseases.

BACKGROUND OF THE INVENTION

Obesity, which is an excess of body fat relative to lean body mass, is a chronic disease that is highly prevalent in modern society. It is associated not only with a social stigma, but also with decreased life span and numerous medical problems, including adverse psychological development, coronary artery disease, hypertension, stroke, diabetes, hyperlipidemia, and some cancers. (see, e.g., Nishina, et al., Metab. 43:554–558, 1994; Grundy and Barnett, Dis. Mon. 36:641–731, 1990; Rissanen, et al., British Medical Journal, 301:835–837, 1990).

Obesity remains a problem, and treatment has been limited. There is, therefore, a need to develop pharmaceuticals and treatment regimes effective in the alleviation of obesity.

A hallmark characteristic of obesity is an increase in white adipose tissue (WAT) mass that is largely due to accumulation of triacylglycerol. This increase in WAT mass is a key contributor to obesity-associated complications. Diacylglycerol O-acyltransferases (DGATs, EC 2.3.1.2) are membrane-bound enzymes that catalyze the terminal step of triacylglycerol biosynthesis. Two enzymes that display DGAT activity have been characterized: DGAT-1 (diacylglycerol O-acyltransferase type 1) (see, e.g., U.S. Pat. No. 6,100,077; Cases, et al., Proc. Nat. Acad. Sci. 95:13018–13023, 1998) and DGAT-2 (diacylglycerol O-acyltransferase type 2) (Cases, et al., J. Biol. Chem. 276:38870–38876, 2001). DGAT-1 and DGAT-2 do not exhibit significant protein sequence identity. Importantly, DGAT-1 null mice do not become obese when challenged with a high fat diet in contrast to wild-type littermates (Smith, et al., Nature Genetics 25:87–90, 2000). DGAT-1 null mice display reduced postprandial plasma glucose levels and exhibit increased energy expenditure, but have normal levels of serum triglycerides (Smith, et al., 2000), possibly due to the preserved DGAT-2 activity. Since DGAT-1 is expressed in the intestine and adipose tissue (Cases, et al., 1998), there are at least two possible mechanisms to explain the resistance of DGAT-1 null mice to diet-induced obesity. First, abolishing DGAT-1 activity in the intestine may block the reformation and export of triacylglycerol from intestinal cells into the circulation via chylomicron particles. Second, knocking out DGAT-1 activity in the adipocyte may decrease deposition of triacylglycerol in WAT. The phenotype of the DGAT-1 null mouse, along with the results of our studies with DGAT-1 inhibitors in diet-induced obese (DIO) mice, indicate that a DGAT-1 inhibitor has utility for the treatment of obesity and obesity-associated complications.

DETAILED DESCRIPTION OF THE INVENTION

The invention relates to aryl alkyl acid derivatives, and pharmaceutical salts and esters thereof, that have utility in the inhibition of DGAT-1 (diacylglycerol O-acyltransferase type 1) and in the treatment of obesity and related diseases.

One embodiment of the invention is a compound of Formula (I)

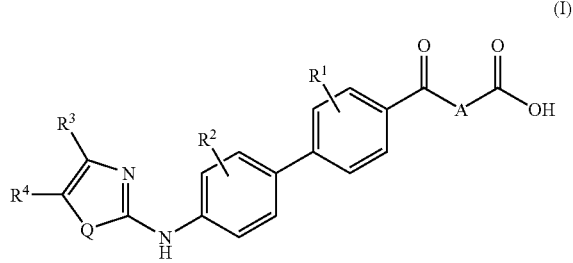

wherein
Q is O, S, or $NR^5$;
A is a linker selected from

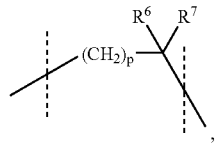

wherein p is 1 or 2
and

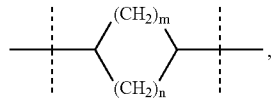

wherein m is 0 and n is 1, 2, 3, or 4,
or
m is 1 and n is 1, 2, or 3,
and
wherein said linker is optionally substituted by one or two $R^8$ groups;
$R^1$ and $R^2$ are independently selected from hydrogen, halo, $(C_1-C_6)$alkyl, and $(C_1-C_6)$alkoxy;
$R^3$ is selected from
  hydrogen,
  $(C_1-C_6)$alkyl optionally substituted by hydroxy,
  and
  phenyl optionally substituted with $(C_1-C_6)$alkyl, $(C_1-C_6)$alkoxy, or halo;
$R^4$ is selected from hydrogen, nitro, and $(C_1-C_6)$alkyl;
or
$R^3$ and $R^4$ may, when taken together with the carbon atoms to which they are attached, form a benzene ring optionally substituted with up to two substituents selected from
  halo, $(C_1-C_6)$alkyl, $(C_1-C_6)$alkoxy, nitro, cyano, $(C_1-C_6)$haloalkyl, $(C_1-C_6)$haloalkoxy, aminocarbonyl, $(C_1-C_6)$alkylaminocarbonyl, bis[$(C_1-C_6)$alkyl]aminocarbonyl, aminosulfonyl, $(C_1-C_6)$alkylaminosulfonyl, bis[$(C_1-C_6)$alkyl]aminosulfonyl, $(C_1-C_6)$alkylcarbonylamino, $(C_1-C_6)$alkylsulfonylamino, hydroxy-$(C_2-C_6)$alkylaminocarbonyl, 1-morpholinylcarbonyl, and 1-piperidinylcarbonyl, and
when two of said benzene ring substituents are $(C_1-C_6)$ alkyl and are attached to adjacent carbon atoms of the benzene ring, they may be joined together to form a 5–7-membered carbocyclic ring;

$R^5$ is hydrogen or $(C_1-C_6)$alkyl;

$R^6$ is hydrogen;

$R^7$ is hydrogen or $(C_1-C_6)$alkyl optionally substituted with $(C_1-C_6)$alkoxy, bis[$(C_1-C_3)$alkyl]amino or phenyl optionally substituted with halo, $(C_1-C_6)$alkyl, $(C_1-C_6)$alkoxy, or cyano;

or $R^6$ and $R^7$ are both $(C_1-C_6)$alkyl; or $R^6$ and $R^7$ may form, together with the carbon atom to which they are attached,
a 3- to 5-membered carbocyclic ring, or
a 6-membered ring represented by

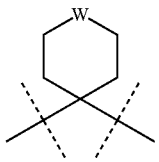

wherein W is $CH_2$, $C(CH_3)_2$, O, $NR^9$, S, or $SO_2$;

$R^8$ is $(C_1-C_6)$alkyl;

and $R^9$ is hydrogen or $(C_1-C_6)$alkyl;

or the pharmaceutically acceptable salts and esters thereof.

A second embodiment of this invention is a compound of Formula (Ia)

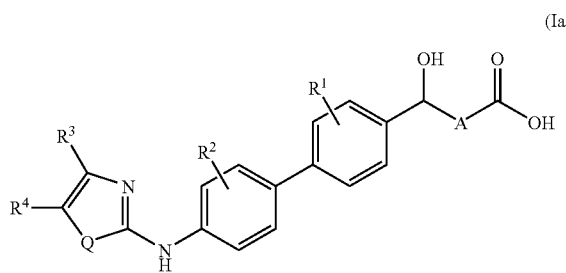

(Ia)

wherein

Q, A, and $R^1-R^4$ have the meanings as described above for Formula (I)

or the pharmaceutical salts and esters thereof.

A third embodiment of the invention is a compound of Formula (Ib)

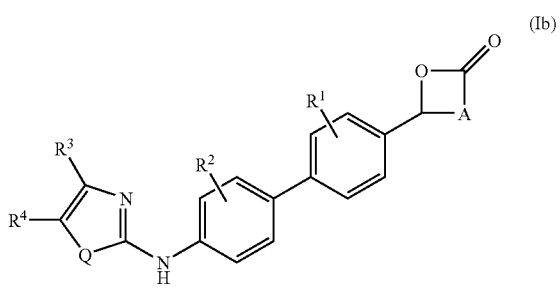

(Ib)

wherein

Q, A, and $R^1-R^4$ have the meanings as described above for Formula (I), or pharmaceutical salts and esters thereof.

Examples of the invention may be found in the Examples described below and in Tables 1 and 2. The compounds described in the Examples are intended to be representative of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

The terms identified above have the following meaning throughout:

The term "halo" means F, Br, Cl, and I.

The terms "$(C_1-C_6)$alkyl," and "$(C_2-C_6)$alkyl" mean a linear or branched saturated hydrocarbon groups having from about 1 to about 6 carbon atoms, or from 2 to about 6 carbon atoms, respectively. The hydrocarbon group may also include a cyclic alkyl radical as part of the alkyl group. Such groups include, but are not limited to, methyl, ethyl, n-propyl, isopropyl, butyl, isobutyl, pentyl, hexyl, cyclopropyl, cyclohexyl, cyclopropyl-methyl, and cyclopentyl-methyl groups.

The term "$(C_1-C_6)$alkoxy" means a linear or branched saturated hydrocarbon group having from about 1 to about 6 carbon atoms, said group being attached to an oxygen atom. The oxygen atom is the atom through which the alkoxy substituent is attached to the rest of the molecule. The hydrocarbon group may also include a cyclic alkyl radical as part of the alkyl group. Such groups include, but are not limited to, methoxy, ethoxy, n-propoxy, isopropoxy, n-butoxy, n-hexyloxy, 3,3-dimethylpropoxy, cyclopropoxy, cyclopropylmethoxy, cyclopentyloxy, and the like.

The term "$(C_1-C_6)$haloalkoxy" means a $(C_1-C_6)$alkoxy group substituted on carbon with a halogen atom. Such groups include trifluoromethoxy, difluoromethoxy, 2,2-difluoroethoxy, 2,2,2-trifluoroethoxy, 3-fluoropropoxy, 2-chloroethoxy, 3-chloropropoxy, 1-fluoro-2,2,-dichloroethoxy, and the like.

The term "$(C_1-C_6)$haloalkyl" means a $(C_1-C_6)$alkyl group substituted on carbon with a halogen atom. Such groups include trifluoromethyl, difluoromethyl, 2,2,2-trifluoroethyl, 3-fluoropropyl, difluoroethyl, 1-fluoro-2,2-dichloroethyl, 3-chloropropyl, 4-bromohexyl, and the like.

The terms "aminocarbonyl," "$(C_1-C_6)$alkylaminocarbonyl," and "bis[$(C_1-C_6)$alkyl]aminocarbonyl," mean a carbonyl [C(=O)] group substituted by nitrogen atom in which the nitrogen atom is unsubstituted, substituted by a single $(C_1-C_6)$alkyl group, or by two $(C_1-C_6)$alkyl groups, respectively. The carbonyl group is the point of attachment of the substituent to the rest of the molecule. Such groups include carboxamido [$NH_2C(=O)$—], N-methylcarboxamido [$CH_3NHC(=O)$], N-methyl-N-propylcarboxamido [$CH_3CH_2CH_2N(CH_3)C(=O)$—] and N,N-diethylcarboxamido [$(CH_3CH_2)_2NC(=O)$—], and the like.

The term "hydroxy-$(C_2-C_6)$alkylaminocarbonyl" means a carbonyl [C(=O)] group substituted by nitrogen atom in which the nitrogen atom is substituted by a single $(C_2-C_6)$ alkyl group, and said alkyl is further substituted by a hydroxy group. Such groups include 2-hydroxyethylamido-, 3-hydroxypropylamido, 4-hydroxyhexylamido, and the like.

The terms "aminosulfonyl," "$(C_1-C_6)$alkylaminosulfonyl," and "bis[$(C_1-C_6)$alkyl]aminosulfonyl" mean a $S(=O)_2$ group substituted by nitrogen atom in which the nitrogen atom is unsubstituted, substituted by a single $(C_1-C_6)$alkyl group, or by two $(C_1-C_6)$alkyl groups, respectively. The $S(=O)_2$ group is the point of attachment of the substituent to the rest of the molecule. Such groups include aminosulfonyl

[NH$_2$S(=O)$_2$—], N-methylaminosulfonyl-[CH$_3$NHS(=O)$_2$], N-methyl-N-propylaminosulfonyl [CH$_3$CH$_2$CH$_2$N(CH$_3$)S(=O)$_2$—] and N,N,-diethylaminosulfonyl [(CH$_3$CH$_2$)$_2$NS(=O)$_2$—], and the like.

The term "(C$_1$–C$_6$)alkylcarbonylamino" means an amino group in which the nitrogen atom is substituted by a carbonyl group, and said carbonyl group is further substituted by a (C$_1$–C$_6$)alkyl group. The nitrogen atom is the point of attachment of the substituent to the rest of the molecule. Such groups include acetylamino [CH$_3$C(=O)NH—], propanoylamino [CH$_3$CH$_2$C(=O)NH—],and i-butanoylamino [(CH$_3$)$_2$CHC(=O)NH—]groups, and the like.

The term "(C$_1$–C$_6$)alkylsulfonylamino" means an amino group in which the nitrogen atom is substituted by a sulfonyl [S(=O)$_2$] group, and said sulfonyl group is further substituted by a (C$_1$–C$_6$)alkyl group. The nitrogen atom is the point of attachment of the substituent to the rest of the molecule. Such groups include methylsulfonylamino [CH$_3$S(=O)$_2$NH—], propylsulfonylamino [CH$_3$CH$_2$CH$_2$S(=O)$_2$NH—], and i-propylsulfonylamino [(CH$_3$)$_2$CHS(=O)$_2$NH—] groups, and the like.

The terms "1-morpholinylcarbonyl" and "1-piperidinylcarbonyl" mean

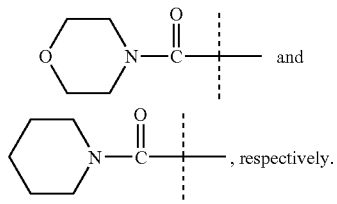

respectively.

The term "optionally substituted" means that the moiety so modified may have from none to up to at least the highest number of substituents indicated. Each substituent may replace any hydrogen atom on the moiety so modified as long as the replacement is chemically possible and chemically stable. When there are two or more substituents on any moiety, each substituent is chosen independently of any other substituent and can, accordingly, be the same or different.

When any moiety is described as being substituted, it can have one or more of the indicated substituents that can be located at any available position on the moiety. When there are two or more substituents on any moiety, each term shall be defined independently of any other in each occurrence.

Representative salts of the compounds of Formula (I), Formula (Ia), and Formula (Ib) include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine salts and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

The esters in the present invention are non-toxic, pharmaceutically acceptable ester derivatives of the compounds of Formula (I), Formula (Ia), and Formula (Ib). This includes, for example, ester derivatives of hydroxy-containing compounds of Formula (I), Formula (Ia), and Formula (Ib) prepared with acetic, benzoic, mandelic, stearic, lactic, salicylic, hydroxynaphthoic, glucoheptonic, and gluconic acid. This also includes, for example, ester derivatives of carboxylic acid-containing compounds of Formula (I) and Formula (Ia) prepared with pharmaceutically acceptable alcohols. Pharmaceutically acceptable alcohols include, but are not limited to methanol, ethanol, isopropanol, butanol, 2-methylpropanol, 2-methoxyethanol, 2-(dimethylamino) ethanol, 2-(diethylamino)ethanol, 2-(1-piperidinyl)ethanol, 2-(1-morpholinyl)ethanol, hydroxyacetic acid, N,N-dimethylglycolamide, hydroxyacetone, and the like. It will also be apparent to those skilled in the art that compounds of Formula (Ia) are hydroxy acids and therefore may form cyclic esters (i.e., lactones). These esters, including those represented by Formula (Ib), are encompassed within the scope of the invention. The compounds of Formula (I), Formula (Ia), and Formula (Ib) may be esterified by a variety of conventional procedures well known by those skilled in the art. One skilled in the art would readily know how to successfully carry out these as well as other methods of esterification.

Sensitive or reactive groups on the compounds of Formula (I), Formula (Ia), and Formula (Ib) may need to be protected during any of the above methods for forming esters, and protecting groups may be added and removed by conventional methods well known in the art.

The compounds of this invention may, either by nature of asymmetric centers or by restricted rotation, be present in the form of isomers. Any isomer may be present in which the asymmetric center is in the (R)—, (S)—, or (R,S) configuration.

It will also be appreciated that when two or more asymmetric centers are present in the compounds of the invention, that several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art.

Geometric isomers by nature of substituents about a double bond or a ring may be present in cis (=Z-) or trans (=E-) form, and both isomeric forms are encompassed within the scope of this invention.

The particular process to be utilized in the preparation of the compounds of this invention depends upon the specific compound desired. Such factors as the selection of the specific moieties and the specific substituents on the various moieties, all play a role in the path to be followed in the preparation of the specific compounds of this invention. These factors are readily recognized by one of ordinary skill in the art.

For synthesis of any particular compound, one skilled in the art will recognize that the use of protecting groups may be required for the synthesis of compounds containing certain substituents. A description of suitable protecting groups and appropriate methods of adding and removing such groups may be found, for example, in Protective Groups in Organic Synthesis, Second Edition, T. W. Greene, John Wiley and Sons, New York, 1991.

In the reaction schemes below, one skilled in the art will recognize that reagents and solvents actually used may be selected from several reagents and solvents well known in the art to be effective equivalents. When specific reagents or solvents are shown in a reaction scheme, therefore, they are meant to be illustrative examples of conditions desirable for the execution of that particular reaction scheme. Abbreviations not identified in accompanying text are listed later in this disclosure under "Abbreviations and Acronyms."

Another object of this invention is to provide methods of making the compounds of the invention. The compounds may be prepared from readily available materials by the methods outlined in the reaction scheme and Examples below, and by obvious modifications thereto.

General Preparation of Compounds of the Invention

Preparation of the compounds of the present invention having Formula (I), may be accomplished by either of the two general methods shown below in Reaction Scheme 1 and Reaction Scheme 2.

In Reaction Scheme 1, a coupling reaction of the compound of Formula (II) with nitrophenylboronic acid or boronic ester of Formula (III), in the presence of a palladium catalyst such as $PdCl_2(dppf)$, gives the intermediate of Formula (V). Reduction of the nitro group in the compound of Formula (V) can be accomplished by standard means such as iron/acetic acid to provide the corresponding amino compound of Formula (VI). An alternative route to the compounds of Formula (VI) is to carry out a palladium-catalyzed coupling reaction of the compound of Formula (II) with the optionally protected anilino boronic acid/boronic ester of Formula (IV), followed by deprotection, if necessary, to provide the compound of Formula (VI) directly. The nitro or amino boronic acid/boronic ester reagents (III and IV), respectively, are either commercially available or can be prepared from the corresponding readily available halonitrobenzenes by means well known in the art.

The compound of Formula (VI) is then allowed to react with the 2-halo-substituted heterocycle and related compounds of Formula (VI) to give the compounds of Formula (VIII) where R≠H or Formula (I) when R═H. The Formula (VIII) compounds can be hydrolyzed under standard ester hydrolysis conditions to give the compounds of Formula (I).

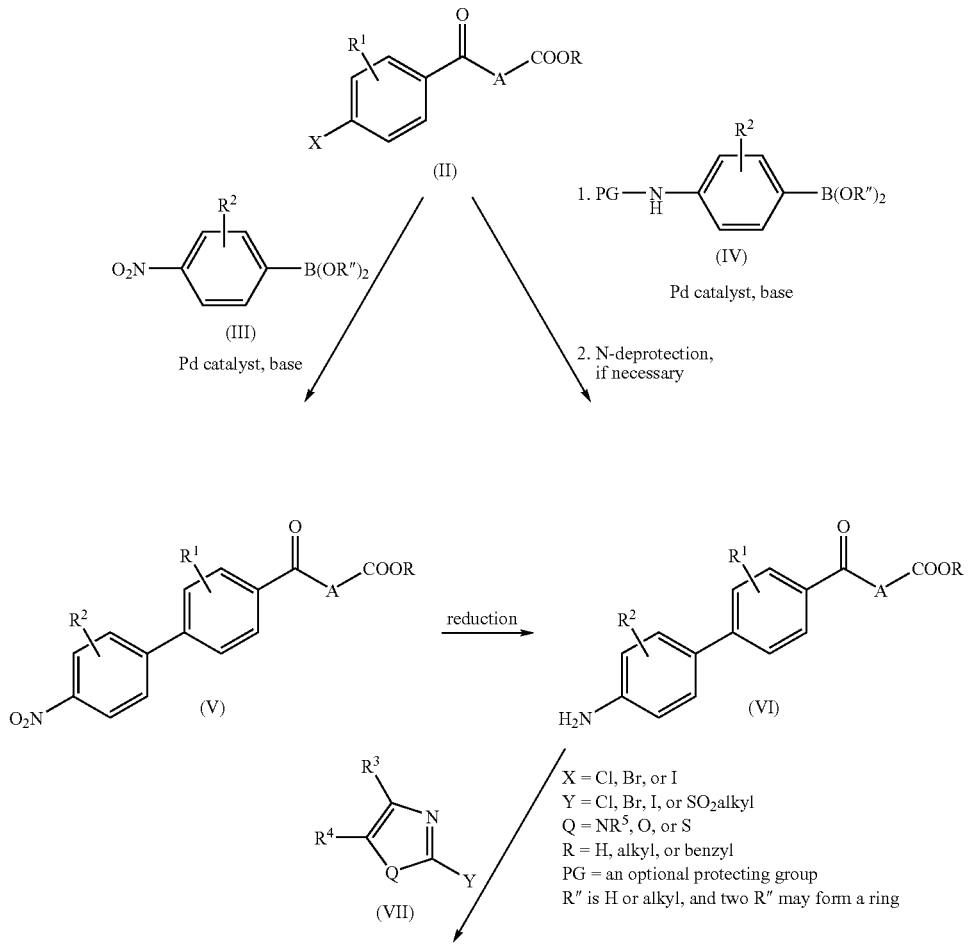

Reaction Scheme 1

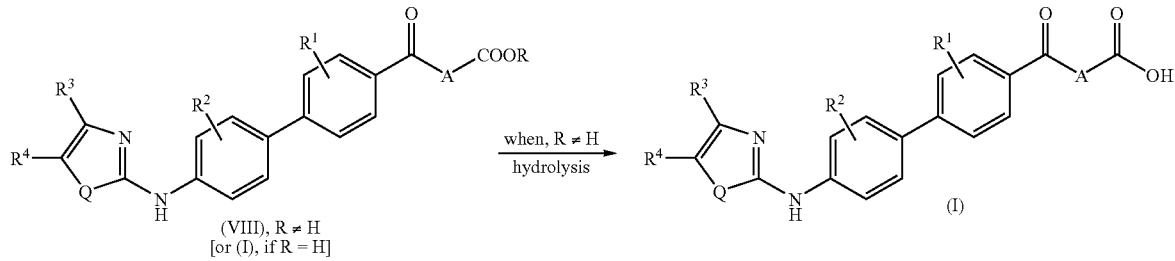

Alternatives for the preparation of compounds of Formula (VII), useful when boronic acids or boronic esters of Formulae (III) and (IV) are not readily accessible, are shown in Reaction Scheme 2 below. Preparation of the boronic ester of Formula (X) from the corresponding compound of Formula (II) is accomplished by reaction of (II) with a boronic ester reagent such as pinnacol borane to afford the intermediate of Formula (X). This boronic acid/ester reagent of Formula (X) can be coupled with the 2-anilino-heterocycle of Formula (IX) in the presence of a palladium catalyst and a base such as potassium carbonate, to give the intermediate of Formula (VIII). The Formula (VIII) compound can also be prepared by carrying out a coupling reaction of (X) with the optionally protected haloaniline of Formula (XI), providing an additional route to the intermediate of Formula (VI). Hydrolysis of (VIII), as described in Reaction Scheme 1, provides the compound of Formula (I).

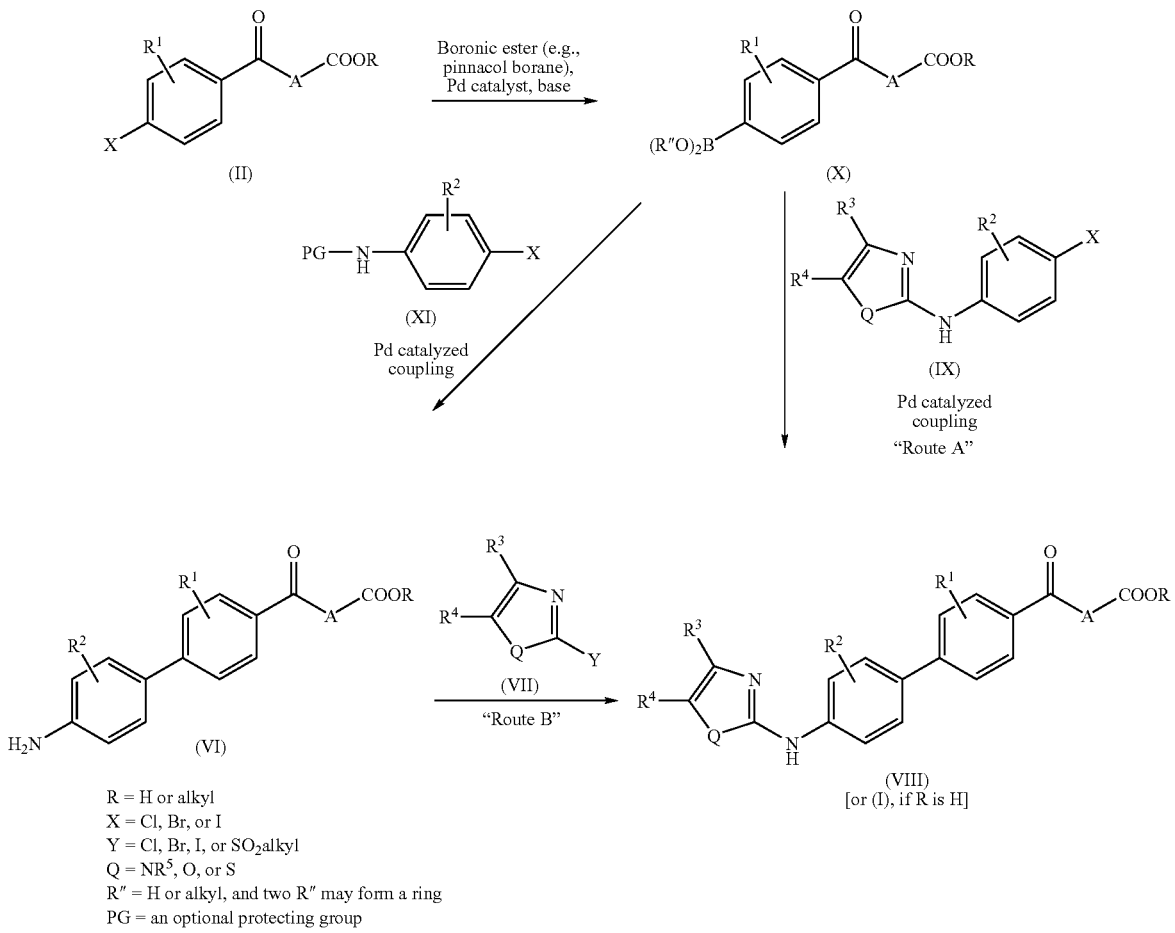

Compounds of Formula (II) may be prepared from a readily available anhydride of Formula (XI) or an acid chloride-ester of Formula (XII by a standard Friedel-Crafts acylation reaction as shown in Reaction Scheme 3.

Reaction Scheme 3

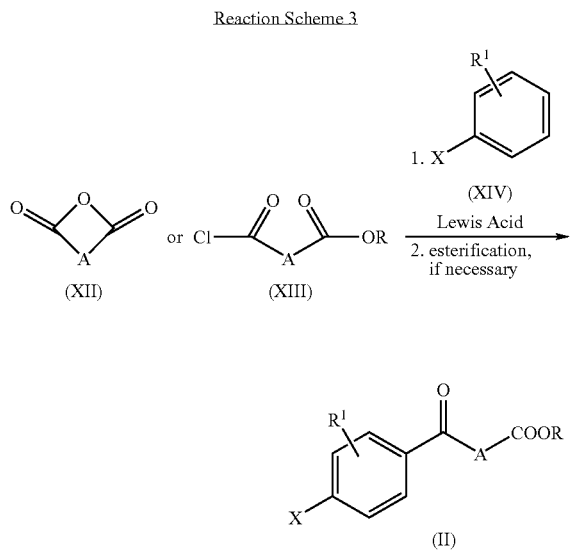

Reaction Scheme 4

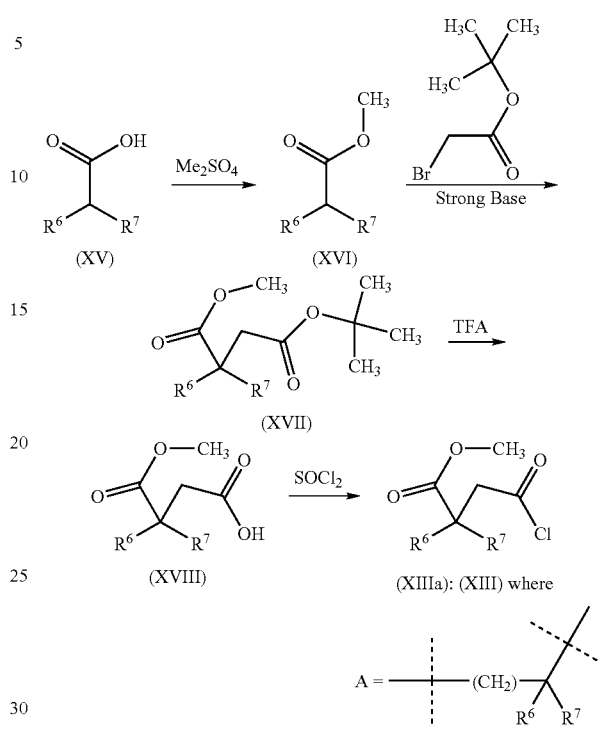

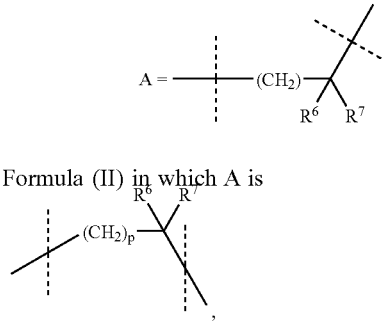

Intermediates of Formula (XIII) are either commercially available or can be prepared in straightforward manner from readily available precursors. A general method of preparation of Formula (XIIIa) [(XIII) where A=—(CH$_2$)C(R$^6$)(R$^7$)—] is shown in Reaction Scheme 4. Esterification of a substituted carboxylic acid of Formula (XV) gives a substituted ester of Formula (XVI); alkylation of the ester with t-butyl bromoacetate gives the diester of Formula (XVII). Selective removal of the t-butyl group under acidic conditions provides the monoacid monoester of Formula (XVIII) which can be converted by standard means (e.g., SOCl$_2$) to the ester-acid chloride of Formula (XIIIa).

Compounds of Formula (II) in which A is $R^6$ is H, and p is 1, can be prepared as shown in Reaction Scheme 5, by alkylating a substituted malonic ester of Formula (XIX) with the phenacyl bromide of Formula (XX), in the presence of a strong base such as sodium hydride, to give the intermediate of Formula (XXI). Hydrolysis and decarboxylation of (XXI) provides the compound of Formula (IIa) [(I) where A is —(CH$_2$)CH(R$^7$)—].

Reaction Scheme 5

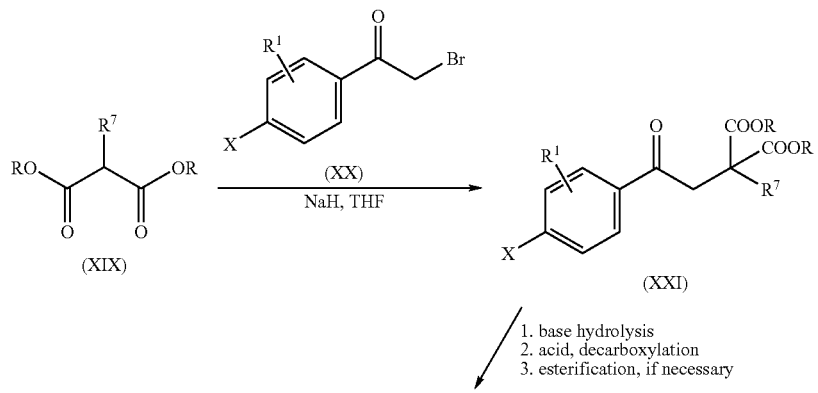

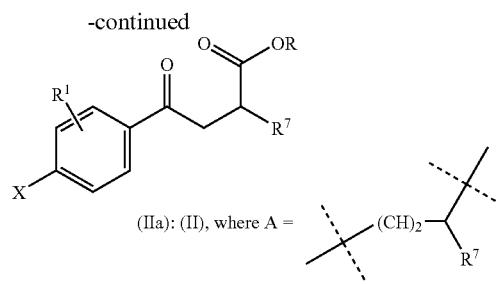

(IIa): (II), where A =

The preparation of Formula (II) compounds in which A is

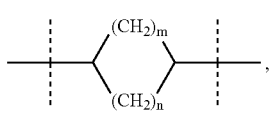

m is 0, and n is 1, 2, 3, or 4, and is optionally substituted by up to two $R^8$ groups is summarized in Reaction Scheme 6. This Reaction Scheme illustrates a general method of obtaining Formula (II) compounds where stereoisomers are possible, and specifically shows the preparation of (R,R) diastereomers of Formula (IId) and Formula (IIe).

In Reaction Scheme 6, the anhydride of Formula (XIIb) [Formula (XII) where A is

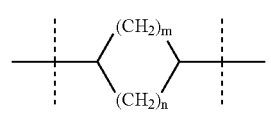

m is 0, n is 1, 2, 3, or 4, and is optionally substituted by up to two $R^8$ groups] is converted in two steps to the compound of Formula (XIb) [Formula (XII) where A is defined as above for Formula (XII)]. The method of Reaction Scheme 3 is followed to prepare the compound of Formula (IIb) from (XIIIb). Formula (IIb) may be converted to the compound of Formula (IIc) by basic hydrolysis. If desired, (IIc) may be resolved into its optical antipodes by standard means, for example, via selective crystallization of its diastereomeric salts with an optically active base such as (R)— or (S)-1-phenylethylamine, and liberating the optically purified compound by acidification of the salt. Thus, the compound of Formula (IId) can be prepared and converted to the corresponding ester of Formula (Ie).

It is to be understood that intermediates of Formulae (IIb) to (IIe) may be individually carried on to the corresponding Formula (I) compounds by the methods outlined in Reaction Schemes 1 and 2 above, thus allowing the preparation of different diastereomeric compounds of Formula (I).

Reaction Scheme 6

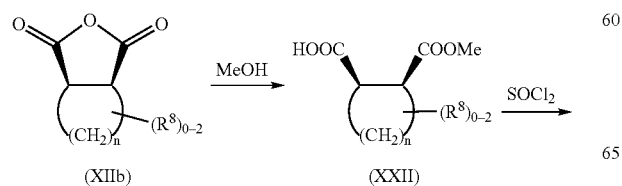

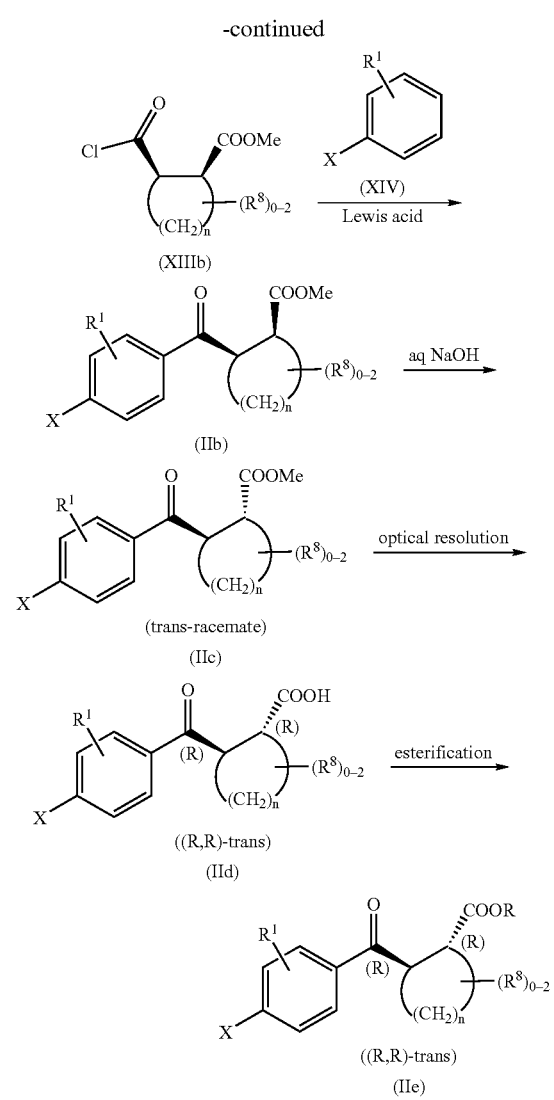

Formula (IIb)-(IIe) represent Formula (II) where A is

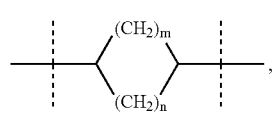

m is 0; n is 1, 2, 3, or 4; and A is optionally substituted by up to two $R^8$ groups Other compounds of Formula (II) can be prepared by methods known in the art and by the methods described herein, for example, by using compounds 1 (prepared as described in McDonald, et al., J. Org. Chem. 35:2666–2669, 1970), 2 (prepared as described in Hronowski, et al., Can. J. Chem. 66:61–70, 1988), 3 (prepared as described in Chung, et al., Bioorg. Med. Chem. Lett. 5:1097–1102, 1995; Seetz, et al., Rec. Trav. Chim. Pays-Bas 107:160–162, 1988), 4 (prepared as described in Jun, et al., Bull. Korean Chem. Soc. 9:206–209, 1988); 5 (see, e.g., methods described in U.S. Pat. No. 6,562,828); 6 and 7 (see, e.g., methods described in Carlon, et al., Org. Prep. Proc. Int. 9:94–96, 1977; U.S. Pat. No. 3,256,277; Bushweller, et al., J. Org. Chem. 54:2404–2409, 1989).

(see, e.g., methods described in WO 9717317); 10 (see, e.g., methods described in van der Mey, et al., J. Med. Chem. 44:2511–2522, 2001; Gaare, et al., Acta Chem. Scand. 51:1229–1233, 1997; Kuchar, et al., Coll. Czech. Chem. Commun. 51:2617–25, 1986); 11 (see, e.g., methods described in Kawamatsu, et al., Arzneim. Forsch. 30:454–459, 1980; Bajaj, et al., J. Indian Chem. Soc. 52:1076–1078, 1975); 12 and 13 (see, e.g., methods described in WO 9615096, and Sen, et al,. Indian J. Chem. 23B:821–824, 1984).

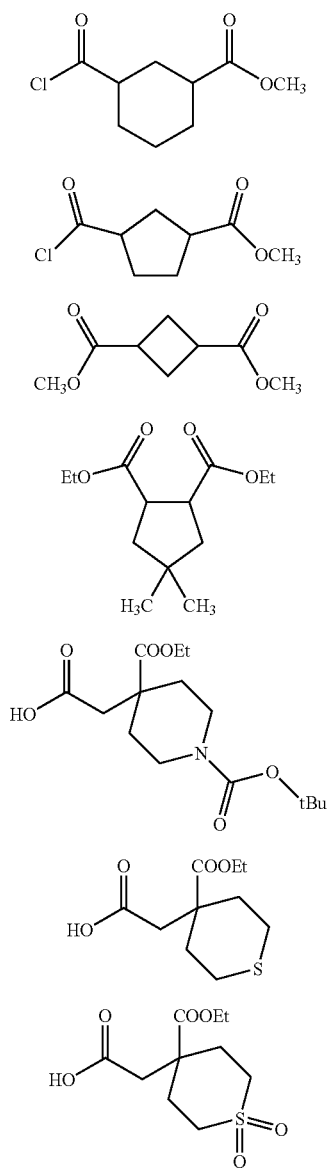

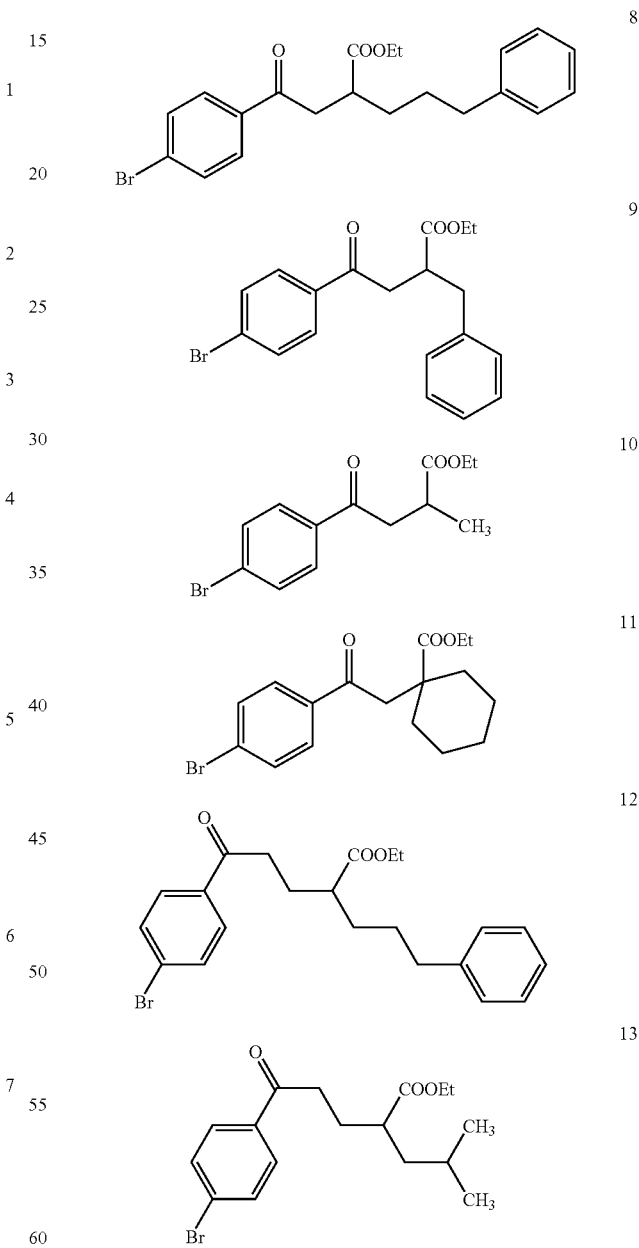

In addition, compounds of Formula (II) can be prepared by applying other methods known in the art. For example, to prepare the following specific compounds of Formula (II), designated 8–13, the following methods may be employed: 8 (see, e.g., WO 9615096 and U.S. Pat. No. 5,789,434); 9

Compounds of Formula (IX) can be prepared by reaction of an aniline of Formula (XXII) by allowing reaction with a compound of Formula (VII), generally by heating together in an inert solvent. This method is illustrated in Reaction Scheme 7.

Reaction Scheme 7

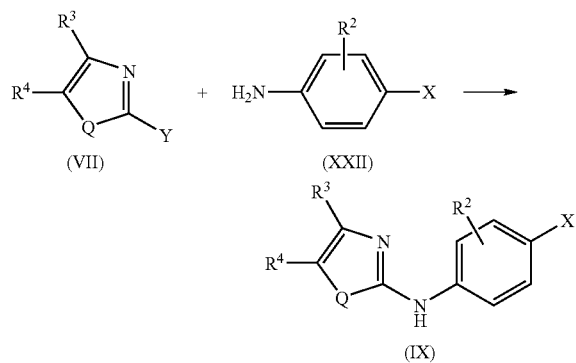

Y = Br, Cl, I, or SO₂alkyl
X = Cl, Br, or I

Other compounds of Formula (IX) can be prepared by other methods known in the art, for example, by the reaction of a 2-oxoethyl thiocyanate with an aniline of Formula (XXII) to form a 2-(arylamino)-thiazole as described in the art (Sharma, et al., Tetrahedron, 15:53–59, 1961; Schantl, et al., Synth. Commun. 28:1451–1462, 1998).

Compounds of Formula (VII) can be prepared by methods known in the art, such as the following: (a) 2-chloro-5-cyanobenzothiazole and 2-chloro-6-cyanobenzothiazole (WO 2002000633); (b) 5-acetamido-2-chlorobenzothiazole (Sharpe, et al., J. Med. Chem. 15:523–529, 1972); (c) 6-acetamido-2-chlorobenzothiazole (Katz, J. Am. Chem. Soc. 73:4007–4010, 1951); (d) 2-chloro-5-benzothiazolecarboxamide, 2-chloro-N-methyl-6-benzothiazolecarboxamide, 2-chloro-N-ethyl-5-benzothiazolecarboxamide, 2-chloro-N,N-dimethyl-5-benzothiazolecarboxamide, 2-chloro-N,N-dimethyl-6-benzothiazolecarboxamide, 2-chloro-N-(2-hydroxyethyl)-5-benzothiazolecarboxamide, 2-chloro-N-(2-hydroxyethyl)-6-benzothiazolecarboxamide, and 2-chloro-7-morpholinocarbonyl-benzothiazole (U.S. Pat. No. 3,654,296); (e) 6-butoxy-2-chloro-benzothiazole (Bordi, et al., Farmaco 49:153–166, 1994); (f) 2-chloro-6-isopropoxy-benzothiazole, 2-chloro-5-cyano-benzoxazole, and 5-cyano-2-methylthiobenzothiazole (Eur. Patent Appl. EP1308439A1); (g) 2-chloro-5-methylsulfonyl-benzoxazole (Lok, et al., J. Org. Chem. 61:3289–3297, 1996); (h) 2-chloro-5-(4-methyl-phenyl)-thiazole, 2-chloro-5-(4-isopropyl-phenyl)-thiazole, and 2-chloro-5-(2,4-dimethyl-phenyl)-thiazole (Merijanian, et al., J. Org. Chem. 51:543–545, 1986; (i) 2-chloro-5-(4-methoxy-phenyl)-thiazole (Fr. Demande FR 2152345); (j) 2-chloro-4,5-dimethylthiazole (Begtrup, et al., Acta Chem. Scand. 46:372–383, 1992); (k) 2-chloro-4-hydroxymethylthiazole (WO 2000078746); (l) 2-chloro-4-methylthiazole (Eur. Pat. Appl. EP1216997); (m) 2-chloro-5-cyanobenzoxazole, 2-chloro-benzimidazole-5-carbonitrile, 2-chloro-5-trifluoromethylbenzimidazole, 2-chloro-5-fluorobenzimidazole, 2,5-dichlorobenzimidazole, 2-chloro-5-nitrobenzimidazole, 2-chloro-1-methylbenzimidazole, 2-chloro-5-trifluoromethyl-1-methylbenzimidazole, and 2-chloro-5-fluoro-1-methylbenzimidazole (Eur. Pat. Appl. EP1308439A1); (n) 2-chloro-1-methyl-benzimidazole, 2-chloro-1-ethyl-benzimidazole, 2-chloro-1-isopropyl-benzimidazole, 2-chloro-1-benzyl-benzimidazole, and 2-chloro-6-fluoro-1-methyl-1-benzimidazole (WO 2001047898); (o) 2-chloro-1-cyclopropyl-benzimidaz (Orjales, et al., J. Med. Chem. 40:586–593, 1997); (p) 2-chloro-7-methoxy-1-isopropyl-benzimidazole and 2-chloro-5-fluoro-1-isopropyl-benzimidazole (Fr. Demande FR 2773800).

The compounds having Formula (Ia) can be prepared from compounds of Formula (I) or Formula (VI), by the use of selective reducing agents and methods for selective reduction known to those skilled in the art. For example, a compound of Formula (I) can be treated with sodium borohydride or similar reducing agent to afford the corresponding compound of Formula (Ia).

Formula (Ib) compounds are prepared from Formula (Ia) compounds by standard methods for lactonization of hydroxy acids (e.g. in the presence of an acid catalyst such as TsOH) in an anhydrous solvent such as toluene.

(Ia)

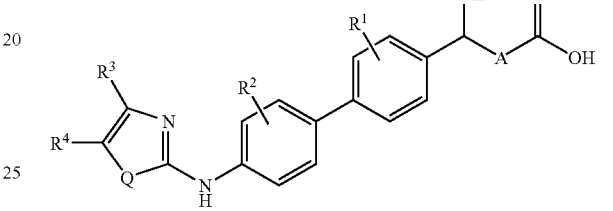

(Ib)

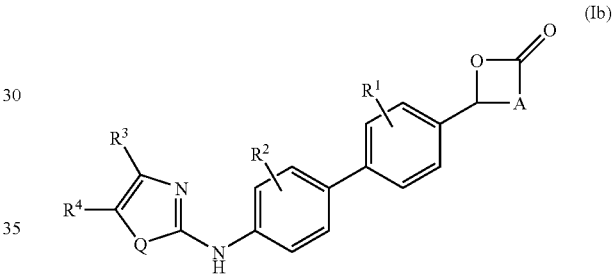

Examples of the invention may be found in the Examples described below and in Tables 1 and 2. The compounds described in the Examples are intended to be representative of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

PREPARATION OF COMPOUNDS OF THE INVENTION

General Information

Mass Spectra

Chemical ionization mass spectra (CI-MS) were obtained with a Hewlett Packard 5989A mass spectrometer equipped with a Hewlett Packard 5890 Gas Chromatograph with a J & W DB-5 column (0.25 uM coating; 30 m×0.25 mm). The ion source was maintained at 250° C. and spectra were scanned from 50–800 amu at 2 sec per scan.

Liquid chromatography—electrospray mass spectra (LC-MS) data were obtained by using one of the following two methods. In the Examples and Tables provided below, the LC-MS data are given with HPLC retention times (ret. time). Except as noted otherwise, Method 1 was used.

Method 1: Hewlett-Packard 1100 HPLC equipped with a quaternary pump, a variable wavelength detector set at 254 nm, a YMC pro C-18 column (2×23 mm, 120A), and a Finnigan LCQ ion trap mass spectrometer with electrospray ionization. Spectra were scanned from 120–1200 amu using a variable ion time according to the number of ions in the source. The eluants were A: 2% acetonitrile in water with 0.02% TFA, and B: 2% water in acetonitrile with 0.018% TFA. Gradient elution from 10% B to 95% B over 3.5 minutes at a flow rate of 1.0 mL/min was used with an initial hold of 0.5 minutes and a final hold of 0.5 minutes at 95% B. Total run time was 6.5 minutes.

Method 2: Gilson HPLC system equipped with two Gilson 306 pumps, a Gilson 215 Autosampler, a Gilson diode array detector, a YMC Pro C-18 column (2×23 mm, 120 A), and a Micromass LCZ single quadrupole mass spectrometer with z-spray electrospray ionization. Spectra were scanned from 120–800 amu over 1.5 seconds. ELSD (Evaporative Light Scattering Detector) data was also acquired as an analog channel. The eluants were A: 2% acetonitrile in water with 0.02% TFA, and B: 2% water in acetonitrile with 0.018% TFA. Gradient elution from 10% B to 90% B over 3.5 minutes at a flow rate of 1.5 mL/min was used with an initial hold of 0.5 minutes and a final hold of 0.5 minutes at 90% B. Total run time was 4.8 minutes. An extra switching valve was used for column switching and regeneration.

NMR Spectra

Routine one-dimensional NMR spectroscopy was performed on 300 MHz or 400 MHz Varian Mercury-plus spectrometers. The samples were dissolved in deuterated solvents obtained from Cambridge Isotope Labs, and transferred to 5 mm ID Wilmad NMR tubes. The spectra were acquired at 293° K. The chemical shifts were recorded on the ppm scale and were referenced to the appropriate solvent signals, such as 2.49 ppm for DMSO-$d_6$, 1.93 ppm for $CD_3CN$, 3.30 ppm for $CD_3OD$, 5.32 ppm for $CD_2Cl_2$, and 7.26 ppm for $CDCl_3$ for $^1H$ spectra; and 39.5 ppm for DMSO-$d_6$, 1.3 ppm for $CD_3CN$, 49.0 ppm for $CD_3OD$, 53.8 ppm for $CD_2Cl_2$ and 77.0 ppm for $CDCl_3$ for $^{13}C$ spectra.

Chiral Chromatography

Chiral chromatography was carried out by using Pirkle Covalent (R,R) Whelk-O 2 10/100 from Regis Technologies as the stationary phase. The mobile phase consisted of A=Hexane (containing 0.1% TFA) and B=isopropyl alcohol (containing 0.1% TFA). The usual gradient was 10% B to 60% B over 25 minutes. In some cases, a gradient of 10 to 90% B or 50 to 90% B was used. Quantification and fraction collection was based on UV detection at 330 nm (also at 280 nm). Samples were typically dissolved in DMF prior to injection; for analytical work, these sample solutions were diluted further with methanol. For analytical work, a 4.6× 250 mm column, flow rate=1 mL/min, and Shimadzu analytical HPLC were used. For preparative work, a 20×250 mm column, flow rate=25 mL/min, and Gilson HPLC were used, with a typical injected sample quantity of 50 mg.

Abbreviations and Acronyms

When the following abbreviations are used throughout the disclosure, they have the following meaning:

| | |
|---|---|
| aq | aqueous |
| BuOH | butanol |
| $CDCl_3$ | deuterated chloroform |
| Celite ® | diatomaceous earth filter agent, ® Celite Corp. |
| DCE | dichloroethane |
| DCM | dichloromethane |
| DMF | N,N-dimethylformamide |
| DMSO | dimethyl sulfoxide |
| DMSO-$d_6$ | deuterated dimethyl sulfoxide- |
| ee | enantiomeric excess |
| EI-MS | electron impact - mass spectrometry |
| ESI-MS | electrospray ionization - mass spectrometry |
| EtOH | ethanol |
| EtOAc | ethyl acetate |
| h | hour(s) |
| iPrOH | isopropanol |
| GC-MS | gas chromatography - mass spectrometry |
| HPLC | high pressure liquid chromatography |
| HRMS | high resolution mass spectrometry |
| LC-MS | liquid chromatography - mass spectrometry |
| MeI | methyl iodide |
| MeOH | methanol |
| min | minutes |
| MS | mass spectroscopy |
| NMR | nuclear magnetic resonance |
| $PdCl_2$(dppf) | 1,1'-bis(diphenylphosphino)ferrocene] dichloropalladium(II) |
| p.o. | orally administered |
| Rf | TLC retention factor |
| rt | room temperature |
| TFA | trifluoroacetic acid |
| THF | tetrahydrofuran |
| TLC | thin layer chromatography |

Preparation of Compounds of Formula (II), (V) and (VI)

Intermediate A

Methyl 4-(4'-amino-1,1'-biphenyl-4-yl)-2,2-dimethyl-4-oxobutanoate

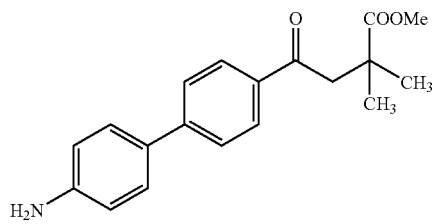

4-Iodoformanilide

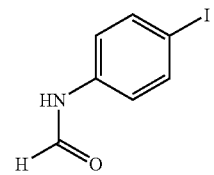

Step 1. To a solution of 4-iodoaniline (30.0 g, 137 mmol) in 100 mL THF and 100 mL toluene, a solution of acetic anhydride (16.0 g, 157 mmol) and formic acid (10.8 g, 235 mmol) was slowly added from an addition funnel under argon atmosphere. The reaction mixture temperature was maintained below 15° C. during the addition. After the addition was finished, the reaction mixture was stirred at rt overnight. The reaction mixture was diluted with water (300 mL) and ethyl acetate (200 mL). The organic layer was separated, washed with water (2×200 mL), and 200 mL saturated aqueous sodium bicarbonate solution. After drying over sodium sulfate, the mixture was concentrated under reduced pressure to afford 4-Iodoformanilide as an off-white solid (33.5 g, >98%). $^1$H NMR (DMSO-$d_6$) δ 10.27 (s, 1H), 8.26 (d, J=2 Hz, 1H), 7.64 (d, J=12 Hz, 2H), 7.40 (d, J=11.7 Hz, 2H) and 30% tautomer; ESI-MS m/z 248.0 (MH$^+$).

4-(4-Bromophenyl)-2.2-dimethyl-4-oxobutanoic acid

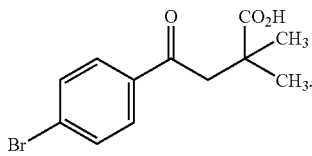

Step 2. To a chilled solution (ice/water bath) of bromobenzene (7.71 g, 49.1 mmol) and 3,3-dimethyldihydro-2,5-furandione (5.99 g, 46.7 mmol) in dichloroethane (150 mL) was added aluminum trichworide (13.28 g, 99.58 mmol). The ice bath was removed and the reaction mixture was stirred at rt overnight. The mixture was again chilled in an ice/water bath, and then quenched with 1 M aqueous hydrochloric acid. Water (70 mL) was added and the layers were separated. The aqueous layer was extracted with ethyl acetate (3×50 mL). The combined organic layers were dried over anhydrous magnesium sulfate and concentrated under reduced pressure. The residue was purified by flash chromatography (Biotage apparatus, 17:83 ethyl acetate/hexane) to give 4-(4-bromophenyl)-2,2-dimethyl-4-oxobutanoic acid as a white solid (8.34 g, 63%). LC-MS: ret. time 2.79 min; m/z 284.8 (MH$^+$); $^1$H NMR (300 MHz, CDCl$_3$) δ 1.36 (s, 6H), 3.27 (s, 2H), 7.60 (d, 2H), 7.81 (d, 2H).

Methyl 4-(4-bromophenyl)-2,2-dimethyl-4-oxobutanoate

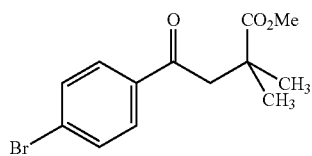

Step 3. To a solution of 4-(4-bromophenyl)-2,2-dimethyl-4-oxobutanoic acid (8.33 g, 29.2 mmol) and 2,2-dimethoxypropane (3.95 g, 37.9 mmol) in methanol (100 mL) was added 1 M HCl in dioxane (2.0 mL). The reaction mixture was stirred at 50° C. for 22 h. The mixture was concentrated under reduced pressure. Toluene (2×60 mL) was added and the mixture concentrated again (2×) to afford methyl 4-(4-bromophenyl)-2,2-dimethyl-4-oxobutanoate as an off-white, semi-solid (8.60 g, 99%). This material was used in the next step without further purification. LC-MS: ret. time 3.23 min; m/z 298.8 (MH$^+$); $^1$H NMR (300 MHz, CDCl$_3$) δ 1.34 (s, 6H), 3.28 (s, 2H), 3.67 (s,3H), 7.58 (d, 2H), 7.78 (d, 2H).

Methyl 4-[4'-(formylamino)-1.1'-biphenyl-4-yl]-2,2-dimethyl-4-oxobutanoate

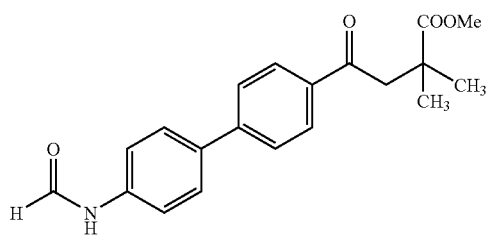

Step 4. To a 2-L three-necked round-bottomed flask were charged 4-iodoformanilide (30.0 g, 121 mmol, 1.0 eq), bis(pinacolato)diboron (30.8 g, 121 mmol, 1.0 eq), palladium acetate (0.82 g, 3.6 mmol, 3 mol %), potassium acetate (35.70 g, 364.3 mmol), and 500 mL N,N-dimethylformamide. The mixture was degassed by gently bubbling argon through the solution for 30 minutes at rt. The mixture was then heated at 80° C. under argon until the reaction was complete (2–3 hours). After the mixture was cooled to rt, methyl 4-(4-bromophenyl)-2,2-dimethyl-4-oxobutanoate (36.3 g, 121 mmol), cesium carbonate (59.4 g, 182 mmol), and palladium tetrakistriphenylphosphine (4.2 g, 3.6 mmol, 3 mol%) were added. The reaction mixture was then heated at 80° C. overnight under argon. The mixture was cooled to rt, and slowly diluted with water (1.5 L), which caused solid material to precipitate. The solids were removed by filtration, and washed with 500 mL water. Then the solids were dissolved in 500 mL methylene chloride, and black particles were removed by passing the solution through a pad of Celite®. The filtrate was washed with 150 mL water (2×). After the solution was dried over sodium sulfate, the solution was concentrated under reduced pressure to afford a dark, brown residue. The residue was stirred in ethyl acetate (200 mL) and hexane (200 mL) for 1 h. After filtration and drying, methyl 4-[4'-(formylamino)-1,1'-biphenyl-4-yl]-2,2-dimethyl-4-oxobutanoate was obtained as a yellow solid (28.0 g, 68%). $^1$H NMR (CDCl$_3$) δ 8.42 (d, J=2 Hz, 1H), 7.98 (d, J=8 Hz, 2H), 7.62 (m, 6H), 3.70 (s, 3H), 3.33 (s, 2H), 1.35 (s, 6H) and 40% tautomer; ESI-MS m/z 340.1 (MH$^+$).

Methyl 4-(4'-amino-1,1'-biphenyl-4-yl)-2,2-dimethyl-4-oxobutanoate

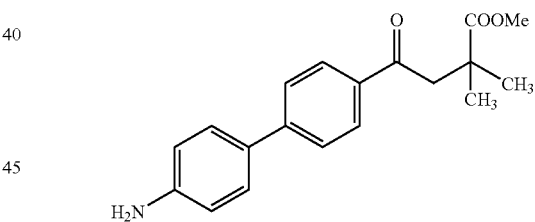

Step 5. To a suspension of methyl 4-[4'-(formylamino)-1,1'-biphenyl-4-yl]-2,2-dimethyl-4-oxobutanoate (2.40 g, 7.07 mmol) in 20 mL methanol, was added 7 mL concentrated hydrochloric acid at below rt. The reaction mixture was stirred at rt overnight. The mixture was concentrated under reduced pressure and saturated aqueous sodium bicarbonate solution was slowly added until pH>8.0. The aqueous layer was then extracted with methylene chloride (2×25 mL), and the combined organic layer was dried over sodium sulfate. The mixture was concentrated under reduced pressure to afford methyl 4-(4'-amino-1,1'-biphenyl-4-yl)-2,2-dimethyl-4-oxobutanoate as a light red solid (2.1 g, 95%). $^1$H NMR (CDCl$_3$) δ 7.96 (d, J=9 Hz, 2H), 7.60 (d, J=9 Hz, 2H), 7.46 (d, J=9 Hz, 2H), 6.76 (d, J=9 Hz, 2H), 3.85 (br s, 2H), 3.69 (s, 3H), 3.32 (s, 2H), 1.35 (s, 6H); ESI-MS m/z 312.4 (MH$^+$); HRMS m/z calcd for MH$^+$312.1594, found 312.1597.

Intermediate B

Ethyl 4-(4'-amino-1,1'-biphenyl-4-yl)-4-oxo-2-(2-phenyl-ethyl)butanoate

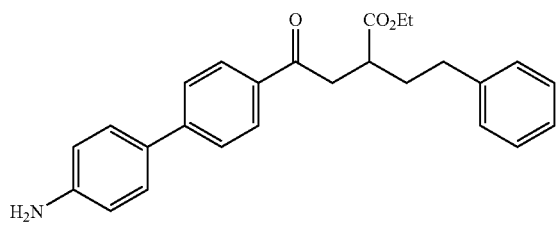

Diethyl 2-[2-(4-bromophenyl)-2-oxoethyl]-2-(2-phenyl-ethyl)-malonate

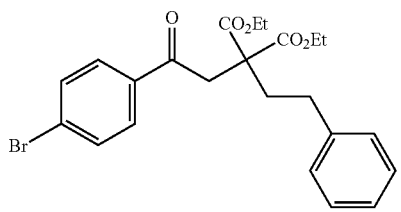

Step 1. To a 500 mL 3-neck round-bottom flask equipped with an argon inlet and an addition funnel, was added sodium hydride (95%, 1.40 g, 58.3 mmol) followed by tetrahydrofuran (30 mL). The resulting suspension was then cooled to 0° C. and diethyl 2-(2-phenylethyl)malonate (14.0 g, 53.0 mmol) in tetrahydrofuran (20 mL) was added dropwise over 20 minutes. The cooling bath was removed and the reaction mixture was allowed to warm to rt over 45 minutes. A solution of 2-bromo-1-(4-bromophenyl)ethanone (14.72 g, 58.26 mmol) in tetrahydrofuran (40 mL) was rapidly added and the resulting orange-red mixture was stirred at rt for 16 h. The mixture was carefully poured into 300 mL of 1N hydrochloric acid, and the resulting mixture was stirred for 10 minutes and extracted twice with ethyl acetate. The combined extracts were dried over anhydrous sodium sulfate and concentrated under reduced pressure. The resulting residue was purified by flash chromatography (Biotage flash 75, 10:90 ethyl acetate/hexane) to afford diethyl 2-[2-(4-bromophenyl)-2-oxoethyl]-2-(2-phenylethyl)malonate (14.8 g, 61%). LC-MS ret. time 3.89 min, m/z 461.2 (MH$^+$); $^1$H NMR (300 MHz, CDCl$_3$) δ 1.26 (t, 6H), 2.41–2.45 (m, 2H), 2.56–2.59 (m, 2H), 3.67 (s, 2H), 4.23 (q, 4H), 7.14–7.22 (m, 3H), 7.22 (d, 2H), 7.61 (d, 2H), 7.79 (d, 2H).

Ethyl 4-(4-bromophenyl)-4-oxo-2-(2-phenylethyl)butanoate

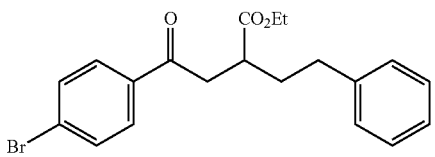

Step 2. To a solution of diethyl 2-[2-(4-bromophenyl)-2-oxoethyl]-2-(2-phenylethyl)malonate (7.89 g, 17.1 mmol) in acetone (18.5 mL) and ethanol (17.0 mL) was added 1 N aqueous sodium hydroxide solution (17.1 mL), and the resulting solution was heated at 50° C. for 3 h. Solvent was then removed under reduced pressure via rotary evaporation and the resulting residue was further concentrated under high vacuum for 1 h. The residue was redissolved in dimethoxyethane (18.5 mL) and the solution was heated at 80° C. for 2.5 h. The mixture was cooled to rt, diluted with ethyl acetate, and washed with water. The organic layer was dried over anhydrous sodium sulfate and concentrated under high vacuum. The resulting residue was purified by flash chromatography (Biotage flash 75, 10:90 ethyl acetate/hexane) to afford ethyl 4-(4-bromophenyl)-4-oxo-2-(2-phenylethyl)butanoate (4.32 g, 65%). LC-MS ret. time 3.79 min, m/z 389.2 (MH$^+$); $^1$H NMR (300 MHz, CDCl$_3$) δ 1.20 (t, 3H), 1.78–1.94 (m, 2H), 2.62 (t, 2H), 2.86–3.01 (m, 2H), 3.26–3.36 (m, 1H), 4.10 (q, 2H), 7.05–7.11 (m, 3H), 7.18–7.23 (m, 2H), 7.51 (d, 2H), 7.72 (d, 2H).

Ethyl 4-(4'-nitro-1,1'-biphenyl-4-yl)-4-oxo-2-(2-phenyl-ethyl)butanoate

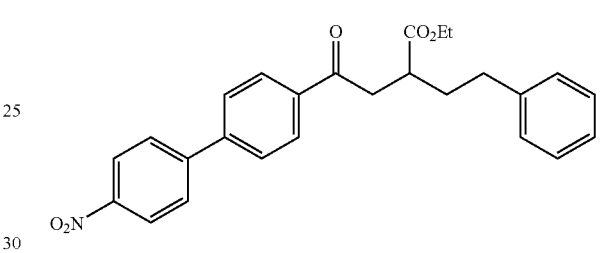

Step 3. Ethyl 4-(4-bromophenyl)-4-oxo-2-(2-phenyl-ethyl)butanoate (4.32 g, 11.1 mmol) and 4-nitrophenylboronic acid (2.22, 13.3 mmol) was added to a dry flask under argon. Toluene (100 mL), dioxane (25 mL), saturated aqueous sodium carbonate (30 mL), and [1,1'-bis(diphenyl-phosphino)-ferrocene]dichloro palladium(II) (1:1 complex with dichloromethane, 453 mg, 0.55 mmol) were added and the mixture was thoroughly degassed. The resulting mixture was then heated at 85° C. for 16 h before it was cooled to rt. Water was added and the mixture was extracted twice with ethyl acetate. The combined extracts were dried over anhydrous sodium sulfate and concentrated under reduced pressure. The residue was purified by flash chromatography (Biotage flash 75, 5:1 ethyl acetate/hexane) to afford ethyl 4-(4'-nitro-1,1'-biphenyl-4-yl)-4-oxo-2-(2-phenylethyl)butanoate (3.6 g, 75%). HPLC ret. time 3.99 min, $^1$H NMR (300 MHz, CDCl$_3$) δ 1.29 (t, 3H), 1.85–2.08 (m, 2H), 2.71 (t, 2H), 3.05–3.20 (m, 2H), 3.45–3.52 (m, 1H), 4.20 (q, 2H), 7.18–7.31 (m, 5H), 7.72 (d, 2H), 7.78 (d, 2H), 8.05 (d, 2H), 8.33 (d, 2H).

Ethyl 4-(4'-amino-1,1'-biphenyl-4-yl)-4-oxo-2-(2-phenyl-ethyl)butanoate

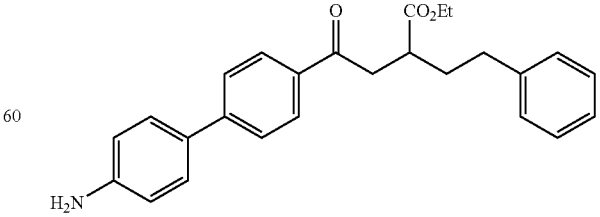

Step 4. To a solution of ethyl 4-(4'-nitro-1,1'-biphenyl-4-yl)-4-oxo-2-(2-phenylethyl)butanoate (5.35 g, 12.4 mmol)

in 85% ethanol (160 mL) was added iron powder (6.94 g) followed by a 2 N aqueous solution of hydrochloric acid (6.2 mL). The resulting mixture was refluxed for 2.5 h, filtered through a pad of Celite®, and extracted with ethyl acetate. The combined organic extracts were dried over anhydrous sodium sulfate and concentrated under reduced pressure to afford ethyl 4-(4'-amino-1,1'-biphenyl-4-yl)-4-oxo-2-(2-phenylethyl)butanoate (4.74 g, 95%). LC-MS ret. time 3.22 min, m/z 402.0 (MH$^+$); $^1$H NMR (300 MHz, CDCl$_3$) δ 1.18 (t, 3H), 1.83–2.10 (m, 2H), 2.65 (t, 2H), 3.03–3.12 (m, 2H), 3.41–3.48 (m, 1H), 4.12 (q, 2H), 6.70 (d, 2H), 7.19 (d, 4H), 7.25 (m, 1H), 7.38 (d, 2H), 7.53 (d, 2H), 7.89 (d, 2H).

This intermediate compound ethyl 4-(4'-amino-1,1'-biphenyl-4-yl)-4-oxo-2-(2-phenylethyl)-butanoate, a racemic mixture, was separated into its two (R) and (S) enantiomeric isomers by preparative chiral HPLC using a Pirkle Covalent (R,R) Whelk-O 2 10/100 column (25 cm×21.1 mm), and a solvent elution gradient of 50% isopropanol in hexane to 85% isopropanol in hexane, containing 0.1% trifluoroacetic acid, at a flow rate of 30 mL/min. Monitoring by ultraviolet detection (254 nm) enabled the identification and isolation of enantio-enriched samples of the two isomers, which could be used to prepare individual (R) and (S) enantiomers of compounds of the invention.

Intermediate C

Ethyl 2-[2-(4'-amino-1,1'-biphenyl-4yl)-2-oxoethyl]pentanoate

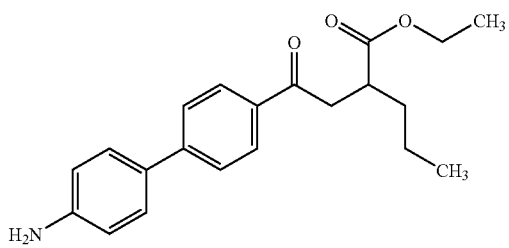

Diethyl 2-[2-(4-bromophenyl)-2-oxoethyl]-2-propylmalonate

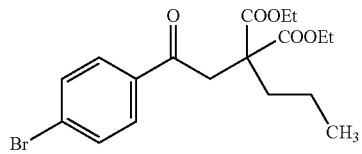

Step 1. To a 100 mL 3-neck flask was added sodium hydride (95%, 0.55 g, 22 mmol) followed by tetrahydrofuran (13 mL). The suspension was cooled to 0° C., and a solution of diethyl propylmalonate (4.00 g, 19.8 mmol) in tetrahydrofuran (10 mL) was added dropwise over 10 minutes. The cooling bath was removed and the reaction mixture was allowed to warm to rt over 45 minutes. A solution of 2,4'-bromoacetophenone (5.50 g, 19.8 mmol) in tetrahydrofuran (30 mL) was added via addition funnel over 10 minutes, and the resulting orange-red reaction mixture stirred at rt for 16 h. The reaction mixture was slowly poured into 1.0 N aqueous hydrochloric acid solution (100 mL) cooled to 0° C. stirred for 15 minutes, followed by addition of ethyl acetate (100 mL) and water (100 mL), and the layers separated. The aqueous layer was extracted with additional ethyl acetate (75 mL), the combined organic layers were washed with saturated aqueous sodium chloride solution (75 mL), dried over anhydrous sodium sulfate, filtered in vacuo through 2.5 cm Celite®/2.5 cm silica, and the filtrate was concentrated under reduced pressure, to afford diethyl 2-[2-(4-bromophenyl)-2-oxoethyl]-2-propylmalonate (7.62 g, 86%). LC-MS ret. time 3.74 min, m/z 399.0 (MH$^+$); $^1$HNMR (300 MHz, CDCl$_3$) δ 0.82–0.98 (m, 3H), 1.10–1.45 (m, 8 H), 2.01–2.12 (m, 2H), 3.60 (s, 2H), 4.10–4.30 (m, 4H), 7.60 (d, 2H), 7.85 (d, 2H).

Ethyl 2-[2-(4-bromophenyl)-2-oxoethyl]pentanoate

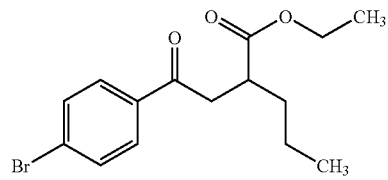

Step 2. To a 200 mL flask was added crude 2-[2-(4-bromophenyl)-2-oxoethyl]-2-propylmalonate (7.62 g, 19.2 mmol), acetone (21 mL), and ethanol (19 mL), followed by addition of 1 N aqueous sodium hydroxide solution (19.1 mL). The reaction mixture was heated to 55° C. for 3 h. The clear, orange-red reaction mixture was then concentrated under reduced pressure and the residue was redissolved in dimethoxyethane (30 mL). The mixture was heated to 80° C. for 3 h. The reaction mixture was cooled to rt, diluted with ethyl acetate (100 mL) and water (100 mL), and stirred for 15 minutes until almost all color was extracted into the organic layer. The layers were separated and the aqueous layer extracted with additional ethyl acetate (75 mL). The combined organic layers were washed with saturated aqueous sodium chloride solution (75 mL), dried over anhydrous sodium sulfate, and concentrated under reduced pressure to afford an orange oil. The crude product was purified by flash chromatography (10:1 hexane:ethyl acetate) to afford ethyl 2-[2-(4-bromophenyl)-2-oxoethyl]pentanoate (1.33 g, 20%). LC-MS ret. time 3.60 min, m/z 326.05 (MH$^+$); $^1$H NMR (300 MHz, CDCl$_3$) δ 0.87 (t, 3H), 1.25 (t, 3H), 1.29–1.43 (m, 2H), 1.57–1.73 (m, 2H), 2.90–3.08 (m, 2H), 3.34–3.47 (m, 2H), 4.15 (q, 2H), 7.59 (d, 4H), 7.82 (d, 2H).

Ethyl 2-[2-(4'-nitro-1,1'-biphenyl-4-yl)-2-oxoethyl]pentanoate

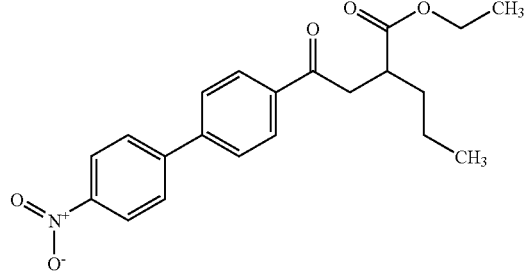

Step 3. To a 150 mL 3-neck flask fitted with a reflux condenser was added ethyl 2-[2-(4-bromophenyl)-2-oxoethyl]pentanoate (1.33 g, 4.10 mmol) and 4-nitro phenyl boronic acid (0.81 g, 4.9 mmol), dissolved in toluene (37 mL) and dioxane (10 mL), followed by addition of saturated aqueous sodium carbonate (11 mL). A thin-gauge needle was inserted into the bi-phasic mixture and the mixture was degassed with argon over 30 minutes, at which point 1,2-bis[(diphenylphosphino) ferrocene] dichloropalladium(II) (0.17 g, 0.20 mmol) was added, followed by 15 minutes of degassing. The mixture was heated to 85° C. for 16 h. The very darkly colored reaction mixture was allowed to cool, and diluted with ethyl acetate (100 mL) and saturated aqueous sodium chloride solution (100 mL). The layers were separated, the aqueous layer extracted twice with ethyl acetate (50 mL), and the combined organic layers were washed with saturated aqueous sodium chloride solution (75 mL), dried over anhydrous magnesium sulfate, and filtered in vacuo through 2 cm Celite®/2 cm silica. The filtrate was concentrated under reduced pressure, leaving a dark red-brown oil, that was purified by flash chromatography (10:1 hexane:ethyl acetate, then 7:1 hexane:ethyl acetate, then 4:1 hexane:ethyl acetate) to afford ethyl 2-[2-(4'-nitro-1,1'-biphenyl-4-yl)-2-oxoethyl]pentanoate (0.71 g, 48%). LC-MS ret. time 3.88 min, m/z 369.8 (MH$^+$); $^1$H NMR (300 MHz, CDCl$_3$) δ 0.95 (t, 3H), 1.30 (t, 3H), 1.35–1.50 (m, 2H), 1.60–1.83 (m, 2H), 3.0–3.18 (m, 2H), 3.5 (dd, 1H), 4.20 (q, 2H), 7.65–7.88 (overlapping d, 4H), 8.10 (d, 2H), 8.35 (d, 2H).

Ethyl 2-[2-(4'-amino-1,1'-biphenyl-4-yl)-2-oxoethyl]pentanoate

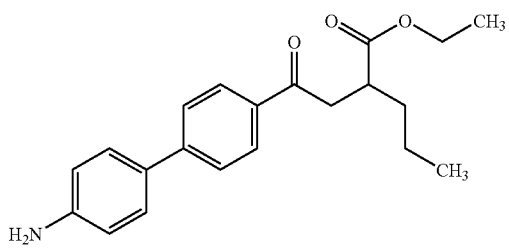

Step 4. To a 100 mL flask fitted with a reflux condenser was added ethyl 2-[2-(4'-nitro-1,1'-biphenyl-4-yl)-2-oxoethyl]pentanoate (0.71 g, 1.9 mmol) dissolved in 85% aqueous ethanol (24 mL), followed by addition of 2 N aqueous hydrochloric acid solution (0.95 mL) and finely powdered iron (0) (1.10 g, 19.1 mmol), and the reaction mixture heated to 85° C. over 2 h. Upon cooling, the darkly colored reaction mixture was filtered in vacuo through 2 cm Celite®/2 cm silica, resulting in all iron particulates/baseline material being removed. The yellow filtrate was concentrated under reduced pressure, resulting in a solid that was triturated in 20 mL diethyl ether/20 mL hexane, affording methyl 2-[2-(4'-amino-1,1'-biphenyl-4-yl)-2-oxoethyl]pentanoate as a tan solid (0.56 g, 88%). LC-MS ret. time 2.82 min, m/z 340.4 (MH$^+$); $^1$H NMR (300 MHz, CDCl$_3$) δ 0.87 (t, 3H), 1.13 (t,3H), 1.25–1.40 (m, 2H), 1.44–1.64 (m, 2H), 2.78–2.90 (m, 1H), 3.06–3.40 (m, 2H), 3.95–4.10 (m, 2H), 5.30–5.64 (br s, 1H), 6.65 (d, 2H), 7.46 (d, 2H), 7.67 (d, 2H), 7.93 (d, 2H).

Intermediate D

Ethyl 4-(4'-amino-1,1'-biphenyl-4-yl)-2-(2-methoxyethyl)-4-oxobutanoate

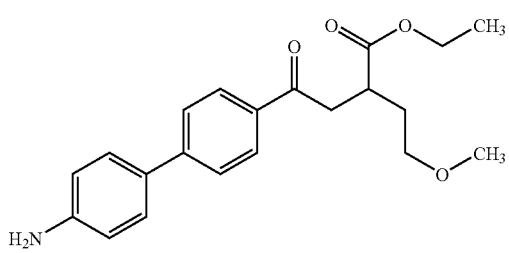

Diethyl 2-[2-(4-bromophenyl)-2-oxoethyl]-2-(2-methoxyethyl)malonate

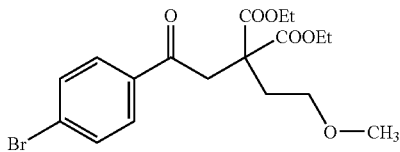

Step 1. In a 100 mL flask was added sodium hydride (95%, 0.25 g, 10.1 mmol) followed by tetrahydrofuran (5 mL). The suspension was cooled to 0° C., and a solution of diethyl (2-methoxyethyl)-malonate (2.0 g, 9.16 mmol) in tetrahydrofuran (10 mL) was added dropwise over 10 minutes. The cooling bath was removed, and the reaction mixture was allowed to warm to rt over 45 minutes. A solution of 2,4'-bromoacetophenone (2.55 g, 19.6 mmol) in tetrahydrofuran (15 mL) was added via addition funnel over 10 minutes, and the resulting orange-red reaction mixture was stirred at rt for 16 h. The reaction mixture was slowly poured into 1 N aqueous hydrochloric acid solution (50 mL) with cooling at 0° C., and stirred for 15 minutes. Ethyl acetate (75 mL) and water (75 mL) were added, and the layers were separated. The aqueous layer was extracted with additional ethyl acetate (50 mL), and the combined organic layers were washed with saturated aqueous sodium chloride solution (75 mL), dried over anhydrous sodium sulfate, filtered, and the filtrate was concentrated in vacuo to yield 3.7 g of a yellow oil. This oil was purified by flash chromatography (10:1 hexane/ethyl acetate, then 4:1 hexane/ethyl acetate) to afford diethyl 2-[2-(4-bromophenyl)-2-oxoethyl]-2-(2-methoxyethyl)malonate (1.59 g, 42%). LC-MS ret. time 3.40 min, m/z 415 (MH$^+$); $^1$H NMR (300 MHz, CDCl$_3$) δ 1.20 (t, 6H), 2.38 (t, 2H), 3.09 (s, 3H), 3.40 (t, 2H), 3.74 (s, 2H), 4.19 (q, 4H), 7.60 (d, 2H), 7.83 (d, 2H).

Ethyl 4-(4-bromophenyl)-2-(2-methoxyethyl)-4-oxobutanoate

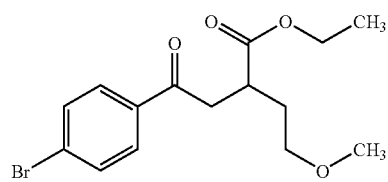

Step 2. To a 150 mL flask was added diethyl 2-[2-(4-bromophenyl)-2-oxoethyl]-2-(2-methoxyethyl)malonate (1.59 g, 3.59 mmol) dissolved in acetone (16 mL) and ethanol (16 mL), followed by addition of 1N aqueous sodium hydroxide solution (3.6 mL). The reaction mixture was then heated at 55° C. for 3 h. The reaction mixture was concentrated in vacuo to remove solvents, the residue redissolved in dimethoxyethane (32 mL), and the reaction mixture heated at 80° C. for 3 h. The reaction mixture was cooled to rt, diluted with ethyl acetate (50 mL) and water (50 mL), and stirred for 15 minutes until almost all color was extracted into the organic layer. The layers were separated, the aqueous layer was extracted with additional ethyl acetate (50 mL), and the combined organic layers were washed with saturated aqueous sodium chloride solution (50 mL), dried over anhydrous sodium sulfate, and concentrated in vacuo, to afford ethyl 4-(4-bromophenyl)-2-(2-methoxyethyl)-4-oxobutanoate (1.06 g, 86%). No further purification of this material was required. LC-MS ret. time 3.18 min, m/z 342.8

(MH+); 1H NMR (300 MHz, CDCl3) δ 1.35 (t, 3H), 1.77–1.92 (m, 1H), 1.94–2.10 (m, 1H), 3.05–3.2 (m, 2H), 3.35–3.50 (m, 3H), 4.09–4.25 (m, 2H), 7.60 (d, 2H), 7.83 (d, 2H).

Ethyl 2-(2-methoxyethyl-4-(4'-nitro-1,1'-biphenyl-4-yl)-4-oxobutanoate

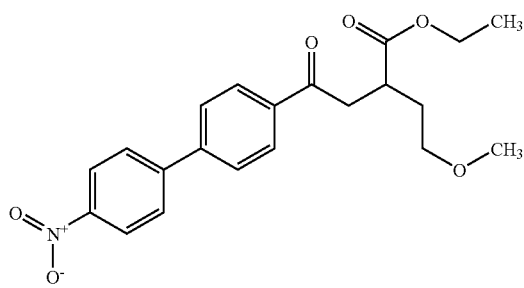

Step 3. To a 150 mL 3-neck flask fitted with a reflux condenser was added ethyl 4-(4-bromophenyl)-2-(2-methoxyethyl)-4-oxobutanoate (1.06 g, 3.09 mmol) and 4-nitrophenyl boronic acid (0.62 g, 3.70 mmol) dissolved in toluene (30 mL) and dioxane (8.50 mL), followed by addition of saturated aqueous sodium carbonate solution (8.50 mL). A thin-gauge needle was inserted into the bi-phasic mixture and degassed with argon over 30 minutes, at which point 1,2-bis[(diphenylphosphino) ferrocene] dichloropalladium (II) (0.13 g, 0.15 mmol) was added, followed by an additional 15 minutes of degassing. The reaction mixture was heated at 85° C. for 16 h, and then the resulting dark-colored reaction mixture was allowed to cool, and was diluted with ethyl acetate (75 mL) and saturated aqueous sodium chloride solution (75 mL). The layers were separated, the aqueous layer was extracted twice with ethyl acetate (50 mL), and the combined organic layers were washed with saturated aqueous sodium chloride solution (75 mL), dried over anhydrous magnesium sulfate, and filtered in vacuo through 2 cm Celite®/2 cm silica. The filtrate was concentrated in vacuo, leaving a dark red-brown oil, that was purified by flash chromatography (4:1 hexane/ethyl acetate, then 3:1 hexane/ethyl acetate, then 2:1 hexane/ethyl acetate) to afford ethyl 2-(2-methoxyethyl)-4-(4'-nitro-1,1'-biphenyl-4-yl)-4-oxobutanoate (1.04 g, 88%). LC-MS ret. time 3.38 min, m/z 385.9 (MH+); 1H NMR (300 MHz, CDCl3) δ 1.27 (t, 3H), 1.80–1.95 (m, 1H), 1.95–2.10 (m, 1H), 3.10–3.25 (m, 2H), 3.40–3.58 (m, 3H), 4.17 (q, 2H), 7.67–7.82 (2d, 4H), 8.10 (d, 2H), 8.33 (d, 2H).

Ethyl 4-(4'-amino-1,1'-biphenyl-4-yl)-2-(2-methoxyethyl)-4-oxobutanoate

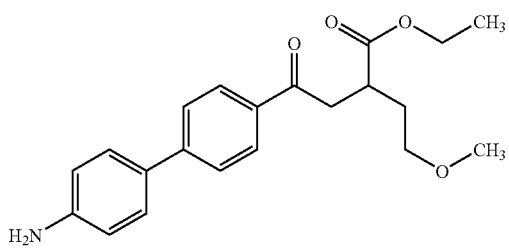

Step 4. To a 100 mL flask fitted with a reflux condenser was added ethyl 2-(2-methoxyethyl)-4-(4'-nitro-1,1'-biphenyl-4-yl)-4-oxobutanoate (1.04 g, 2.71 mmol) dissolved in 85% aqueous ethanol (24 mL), followed by addition of 2 N aqueous hydrochloric acid solution (1.35 mL) and finely powdered iron (0) (1.51 g, 27.1 mmol), and the reaction mixture was heated at 85° C. for 2 h. Upon cooling, the darkly-colored reaction mixture was filtered in vacuo through 2 cm Celite®/2 cm silica, resulting in all iron particulates and polar material being removed. The yellow filtrate was concentrated in vacuo, resulting in a solid that was purified by flash chromatography (3:1 hexane/ethyl acetate) affording ethyl 4-(4'-amino-1,1'-biphenyl-4-yl)-2-(2-methoxyethyl)-4-oxobutanoate as a tan solid (0.89 g, 93%). LC-MS ret. time 2.33 min, m/z 356.2 (MH+); 1H NMR (300 MHz, CDCl3) δ 1.18–1.33 (m, 3H), 1.79–2.10 (overlapping m, 2H), 3.10–3.21 (m, 2H), 3.30 (s, 3H), 3.48 (t, 3H), 4.16 (t, 3H), 7.15 (d, 2H), 7.55 (d, 2H), 7.62 (d, 2H), 8.03 (d, 2H).

Intermediate E

Methyl 1-[2-(4'-amino-1,1'-biphenyl-4-yl)-2-oxoethyl]cyclopentanecarboxylate

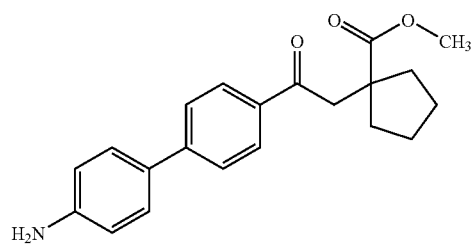

Methyl 1-[2-(4-bromophenyl)-2-oxoethyl]cyclopentanecarboxylate

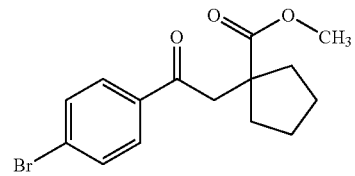

Step 1. To a 150 mL flask was added dichloromethane (70 mL), methyl 1-(2-chloro-2-oxoethyl)cyclopentanecarboxylate] (3.50 g, 16.8 mmol) [prepared as described by Bajaj, et al., J. Indian Chem. Soc. 52:1076–78, 1975] and bromobenzene (2.77 g, 17.6 mmol), and the reaction mixture cooled to 0° C. before aluminum trichloride (4.77 g, 35.7 mmol) was slowly added. The mixture was stirred for 1 h at 0° C. then for 12 h at rt. The reaction mixture was slowly poured into 50 mL chilled (0° C.) 1 N aqueous hydrochloric acid solution. Water (50 mL) was added, followed by ethyl acetate (100 mL), and the mixture stirred for 30 minutes. The layers were separated and the aqueous layer extracted with additional ethyl acetate (100 mL). The combined organic layer was washed with saturated aqueous sodium chloride (100 mL), dried over anhydrous sodium sulfate, and concentrated under reduced pressure to yield a brown oil which was purified by flash chromatography (10:1/hexane:ethyl acetate) to afford methyl 1-[2-(4-bromophenyl)-2-oxoethyl] cyclopentane carboxylate as a yellow, crystalline solid (1.62 g, 30%). LC-MS ret. time 3.45 min, m/z 324.8 (MH+); 1HNMR (300 MHz, CDCl3) δ 1.50–1.83 (overlapping signals, 6H), 2.22–2.33 (m, 2H), 3.37 (s, 2H), 3.66 (s, 3H), 7.59 (d, 2H), 7.80 (d, 2H).

Methyl 1-[2-(4'-nitro-1,1'-biphenyl-4-yl)-2-oxoethyl]cyclopentanecarboxylate

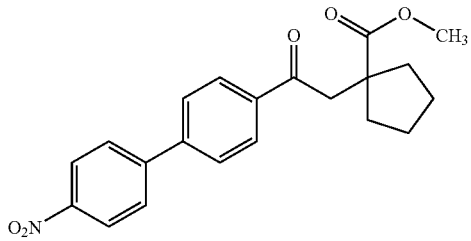

Step 2. To a 150 mL 3-neck flask fitted with a reflux condenser was added methyl 1-[2-(4-bromophenyl)-2-oxoethyl]cyclopentanecarboxylate (1.58 g, 4.64 mmol), 4-nitro phenyl boronic acid (0.93 g, 5.6 mmol), toluene (45 mL), and dioxane (13 mL), followed by the addition of a saturated aqueous sodium carbonate solution (13 mL). The mixture was degassed using argon and 1,2-bis[(diphenylphosphino)ferrocene] dichloropalladium(II) (0.19 g, 0.23 mmol) was added, followed by an additional 15 minutes of degassing, and the deep red reaction mixture was heated to 85° C. for 16 h. The very darkly colored reaction mixture was allowed to cool, and then was diluted with ethyl acetate (100 mL) and saturated aqueous sodium chloride solution (100 mL). The layers were separated and the aqueous layer was extracted twice with ethyl acetate (50 mL). The combined organic layer was washed with saturated aqueous sodium chloride solution (100 mL), dried over anhydrous magnesium sulfate, and filtered under reduced pressure through 2 cm Celite®/2 cm silica. The filtrate was concentrated under reduced pressure, leaving a dark red-brown oil, that was purified by flash chromatography (4:1/hexane:ethyl acetate, then 3:1/hexane:ethyl acetate, then 2:1/hexane:ethyl acetate) to afford methyl 1-[2-(4'-nitro-1,1'-biphenyl-4-yl)-2-oxoethyl]cyclopentanecarboxylate (1.65 g, 93%). LC-MS ret. time 3.56 min, m/z 368.0 (MH$^+$); $^1$HNMR(300 MHz, CDCl$_3$) δ 1.56–1.85 (overlapping signals, 6H), 2.23–2.37 (m, 2H), 3.45 (s, 2H), 3.67 (s, 3H), 7.70 (d, 2H), 7.77 (d, 2H), 8.06 (d, 2H), 8.34 (d, 2H).

Methyl 1-[2-(4'-amino-1,1'-biphenyl-4-yl)-2-oxoethyl] cyclopentanecarboxylate

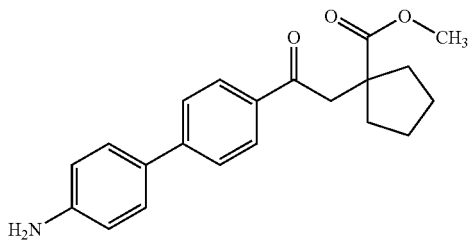

Step 3. To a 100 mL flask fitted with a reflux condenser was added methyl 1-[2-(4'-nitro-1,1'-biphenyl-4-yl)-2-oxoethyl]cyclopentanecarboxylate (1.68 g, 4.40 mmol) dissolved in 85% aqueous ethanol (55 mL), followed by addition of 2 N aqueous hydrochloric acid solution (2.20 mL) and finely powdered iron (0) (2.46 g, 44.1 mmol). The reaction mixture was heated to 85° C. over 2 h. Upon cooling, the darkly-colored reaction mixture was filtered under reduced pressure through 2 cm Celite®/2 cm silica, in order to remove iron particulates and polar impurities. The yellow filtrate was concentrated under reduced pressure, resulting in a solid that was triturated with 20 mL diethyl ether/20 mL hexane to afford methyl 1-[2-(4'-amino-1,1'-biphenyl-4-yl)-2-oxoethyl] cyclopentanecarboxylate as a light tan solid (1.20 g, 76%). LC-MS ret. time 2.71 min, m/z 338.1 (MH$^+$); $^1$HNMR (300 MHz, CDCl$_3$) δ 1.55–1.84 (overlapping signals, 6H), 2.25–2.35 (m, 2 H), 3.44 (s, 2H), 3.67 (s, 3H), 7.40–8.10 (overlapping signals, 8H).

Intermediate F

Methyl 4-[2-(4'-amino-1,1'-biphenyl-4-yl)-2-oxoethyl]tetrahydro-2H-pyran-4-carboxylate

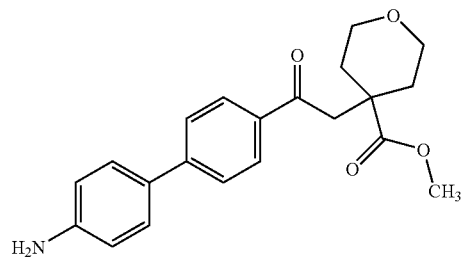

Methyl tetrahydro-2H-pyran-4-carboxylate

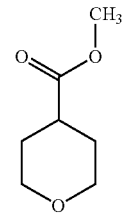

Step 1. Tetrahydro-2H-pyran-4-carboxylic acid (1.00 g, 7.68 mmol) was slowly added to a stirred suspension of anhydrous potassium carbonate (1.17 g, 8.45 mmol) in acetone (40 mL), followed by dimethyl sulfate (0.8 mL, 8.45 mmol). The mixture was stirred and heated for 3 h. The inorganic salts were then removed by filtration and washed with acetone, and the filtrate was dried and concentrated to give methyl tetrahydro-2H-pyran-4-carboxylate (1.1 g, 99%), which was used in the next step without further purification. GC-MS m/z 145 (MH$^+$); $^1$H NMR (300 MHz, CDCl$_3$) δ 11.70–1.80 (m, 4H), 2.47–2.52 (m, 1H), 3.34–3.43 (m, 2H), 3.65 (s, 3H), 3.88–3.95 (m, 2H).

Methyl 4-(2-tert-butoxy-2-oxoethyl)tetrahydro-2H-pyran-4-carboxylate

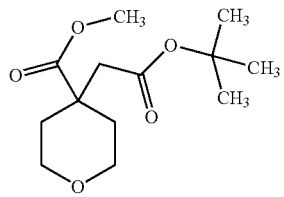

Step 2. Diisopropylamine (1.28 mL, 9.16 mmol) was diluted with tetrahydrofuran (2 mL) and cooled to −78° C. n-Butyllithium (2.5 M, 3.66 mL, 9.16 mmol) was added dropwise, and the solution was allowed to stir for 1 h. Methyl tetrahydro-2H-pyran-4-carboxylate (1.1 g, 7.63 mmol) was added as a solution in tetrahydrofuran (1.5 mL) at −78° C. The mixture was allowed to warm to −35° C. and stirred for 1 h. tert-Butyl bromoacetate (1.58 mL, 10.7 mmol) was added neat at −35° C. The mixture was allowed to warm to 0° C. and stirred for 2 h. The mixture was stirred at rt overnight. Water was added at 0° C. and the mixture extracted with ethyl acetate. The organic phase was washed with brine, and dried over sodium sulfate. The crude product was purified by flash chromatography (Biotage Flash 40M, 6:1 hexane/ethyl acetate) to afford methyl 4-(2-tert-butoxy-2-oxoethyl)tetrahydro-2H-pyran-4-carboxylate (1.12 g, 56%). LC-MS ret. time 2.47 min, m/z 258.7 (MH+); $^1$H NMR (300 MHz, CDCl$_3$) δ 1.38 (s, 9H), 1.52–1.61 (m, 2H), 2.00–2.07 (m, 2H), 2.50 (s, 2H), 3.52–3.60 (m, 2H), 3.70 (s, 3H), 3.71–3.77 (m, 2H).

[4-(Methoxycarbonyl)tetrahydro-2H-pyran-4-yl]acetic acid

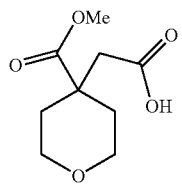

Step 3. To a solution of methyl 4-(2-tert-butoxy-2-oxoethyl)tetrahydro-2H-pyran-4-carboxylate (1.1 g, 4.26 mmol) in dichloromethane (5.0 mL) was added trifluoroacetic acid (5.0 mL) and the resulting solution was stirred at rt for 5 h. The mixture was concentrated under reduced pressure to afford [4-(methoxycarbonyl)tetrahydro-2H-pyran-4-yl]acetic acid (900 mg, 94%), which was used in the next step without further purification. LC-MS ret. time 0.93 min, m/z 202.9 (MH+); $^1$H NMR (300 MHz, DMSO-d$_6$) δ 1.60–1.70 (m, 2H), 2.10–2.15 (m, 2H), 2.68 (s, 2H), 3.62–3.71 (m, 2H), 3.72 (s, 3), 3.79–3.86 (m, 2H).

Methyl 4-(2-chloro-2-oxoethyl-1tetrahydro-2H-pyran-4-carboxylate

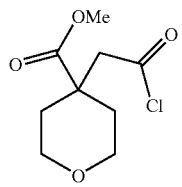

Step 4. Thionyl chloride (20 mL) was added to [4-methoxycarbonyl)tetrahydro-2H-pyran-4-yl]acetic acid (970 mg, 4.80 mmol) and the solution was stirred at rt for 3 h. The solvent was then removed and mixture was azeotroped with dichloroethane three times to afford methyl 4-(2-chloro-2-oxoethyl)tetrahydro-2H-pyran-4-carboxylate (1.05 g, 99%), which was used without purification in the next step.

Methyl 4-[2-(4-bromophenyl)-2-oxoethyl]tetrahydro-2H-pyran-4-carboxylate

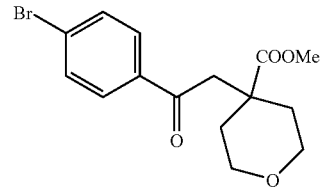

Step 5. To a solution of methyl 4-(2-chloro-2-oxoethyl)tetrahydro-2H-pyran-4-carboxylate (1.06 g, 4.8 mmol) and bromobenzene (1.13 g, 7.21 mmol) in dichloromethane (20 mL) at 0° C. was added aluminum chloride (1.92 g, 14.4 mmol). The ice-water bath was removed and the reaction mixture was stirred at rt for 16 h. The mixture was then cooled at 0° C. and quenched by the addition of 1 N HCl solution and water. The mixture was extracted with dichloromethane, and the combined organic phases were dried over sodium sulfate. The crude material was then purified by flash chromatography (Biotage Flash 40 M, 2:1 hexane/ethyl acetate, to afford methyl 4-[2-(4-bromo-phenyl)-2-oxoethyl]tetrahydro-2H-pyran-4-carboxylate (900 mg, 55%). LC-MS ret. time 2.76 min; m/z 342.9 (MH+); $^1$H NMR (300 MHz, CDCl$_3$) δ 1.58–1.69 (m, 2H), 2.12–2.18 (m, 2H), 3.28 (s, 2H), 3.64 (s, 3H), 3.69–3.77 (m, 4H), 7.59 (d, 2H), 7.77 (d, 2H).

Methyl 4-[2-(4'-nitro-1,1'-biphenyl-4-yl)-2-oxoethyl]tetrahydro-2H-pyran-4-carboxylate

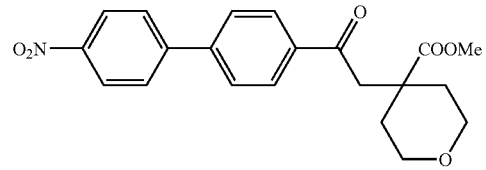

Step 6. Methyl 4-[2-(4-bromophenyl)-2-oxoethyl]tetrahydro-2H-pyran-4-carboxylate (820 mg, 2.40 mmol) and 4-nitrophenyl boronic acid (481 mg, 2.88 mmol) were combined in a dry flask under argon. Toluene (20 mL) and dioxane (5 mL) were added, and the resulting solution was degassed for 30 minutes by a flow of argon. The degassing was continued during the addition of saturated aqueous sodium carbonate (6 mL) and [1,1'-bis(diphenylphosphino)-ferrocene]dichloro palladium(II), 1:1 complex with dichloromethane (98 mg, 0.12 mmol). The resulting mixture was then heated at 85° C. for 16 h before it was cooled to rt. Water was added, and the aqueous layer was extracted twice with ethyl acetate. The combined organic phases were then dried over anhydrous sodium sulfate and concentrated under reduced pressure. The resulting residue was purified by flash chromatography (Biotage Flash 40) using 1:1 ethyl acetate/hexane to afford methyl 4-[2-(4'-nitro-1,1'-biphenyl-4-yl)-2-oxoethyl]tetrahydro-2H-pyran-4-carboxylate (730 mg, 79%). LC-MS ret. time 3.03; m/z 383.9 (MH+); $^1$H NMR (300 MHz, CDCl$_3$) δ 1.65–1.73 (m, 2H), 2.17–2.21 (m, 2H), 3.37 (s, 2H), 3.68 (s, 3H), 3.71–3.78 (m, 4H), 7.70 (d, 2H), 7.77 (d, 2H), 8.02 (d, 2H), 8.31 (d, 2H).

Methyl 4-[2-(4'-amino-1,1'-biphenyl-4-4-yl-2-oxoethyl]tetrahydro-2H-pyran-4-carboxylate

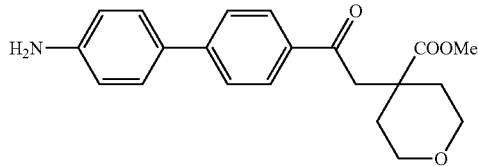

Step 7. To a solution of methyl 4-[2-(4'-nitro-1,1'-biphenyl-4-yl)-2-oxoethyl]tetrahydro-2H-pyran-4-carboxylate (1.24 g, 3.25 mmol) in 85% ethanol (50 mL) was added iron powder (1.81 g), followed by 2 N aqueous HCl (1.62 mL), and the resulting mixture was refluxed for 2.5 h. The mixture was then filtered through a pad of Celite® and the filtrate was extracted with dichloromethane. The combined organic phases were then dried over anhydrous sodium sulfate and concentrated in vacuo to afford methyl 4-[2-(4'-amino-1,1'-biphenyl-4-yl)-2-oxoethyl]tetrahydro-2H-pyran-4-carboxylate (1.05 g, 91%). LC-MS ret. time 2.20; m/z 354.0 (MH$^+$); $^1$H NMR (300 MHz, CDCl$_3$) δ 1.57–1.66 (m, 2H), 2.09 (m, 2H), 3.28 (s, 2H), 3.61 (s, 3H), 3.64–3.71 (m, 4H), 6.76 (d, 2H), 7.42 (d, 2H), 7.54 (d, 2H), 7.88 (d, 2H).

Intermediate G

Methyl cis-2-[(4'-amino-1,1'-biphenyl-4-yl)carbonyl]cyclohexanecarboxylate

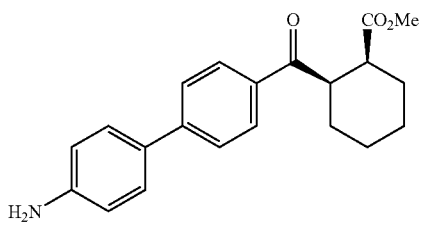

Methyl cis-2-(4-bromobenzoyl)cyclohexanecarboxylate

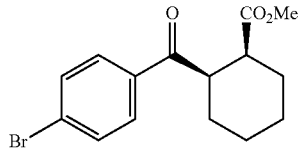

Step 1. To a solution of cis-2-(4-bromobenzoyl)-1-cyclohexanecarboxylic acid (4.0 g, 12.85 mmol) in MeOH (50 mL) was added 2,2-dimethoxypropane (2.01 g, 19.28 mmol) and HCl (4.0 M in dioxane, 1.20 mL). The resulting solution was stirred at 40° C. for 3 days, and then evaporated to dryness. The resulting residue was purified by flash chromatography (Biotage Flash 40M) using 3 to 6% ethyl acetate in hexanes to afford methyl cis-2-(4-bromobenzoyl)cyclohexane-carboxylate (1.76 g, 42%). LC-MS ret. time 3.40; m/z 326 (MH$^+$); $^1$H NMR (400 MHz, CD$_2$Cl$_2$) δ 1.35–1.51 (m, 3H), 1.72–1.86 (m, 2H), 1.91–2.05 (m, 2H), 2.11–2.20 (m, 1H), 2.74 (m, 1H), 3.58 (s, 3H), 3.82 (q, 1H), 7.62 (m, 2H), 7.73 (m, 2H).

Methyl cis-2-[(4'-amino-1,1'-biphenyl-4-yl)carbonyl]cyclohexanecarboxylate

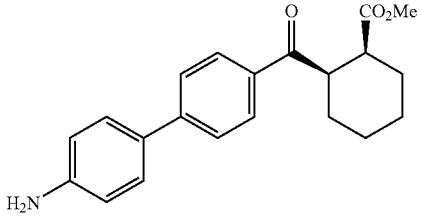

Step 2. Methyl cis-2-(4-bromobenzoyl)cyclohexanecarboxylate (1.76 g, 5.41 mmol) and 4-amino phenyl boronic acid (1.13 g, 6.49 mmol) were added to a clean dry flask under argon. Toluene (50 mL), EtOH (20 mL), and 3 M aqueous Na$_2$CO$_3$ (14 mL, 43 mmol) were added, and resulting solution was degassed for 30 minutes by using a flow of argon. Then [1,1'-bis(diphenylphosphino)-ferrocene] dichloro palladium(II), 1:1 complex with dichloromethane (442 mg, 0.54 mmol) was added and the resulting mixture was heated at 85° C. for 16 h. The mixture was cooled to rt, and then diluted with EtOAc and passed through a Celite® pad. The solvent was removed by rotary evaporation. Water and EtOAc were added, and the aqueous layer was extracted with EtOAc. The combined organic phases were washed with water, brine, dried over anhydrous sodium sulfate, filtered and concentrated in vacuo. The residue was purified by flash chromatography (Biotage Flash 40M) using 33 to 40% ethyl acetate in hexane to afford methyl cis-2-[(4'-amino-1,1'-biphenyl-4-yl)carbonyl]cyclohexanecarboxylate.(1.54 g, 84%). LC-MS ret. time 3.99; m/z 338 (MH$^+$); $^1$H NMR (400 MHz, CD$_2$Cl$_2$) δ 1.37–1.53 (m, 3H), 1.74–1.88 (m, 2H), 1.90–1.99 (m, 1H), 2.04–2.22 (m, 2H), 2.75 (m, 1H), 3.59 (s, 3H), 3.90 (q, 1H), 6.79 (m, 2H), 7.48 (m, 2H), 7.63 (m, 2H), 7.89 (m, 2H).

Intermediate H trans-(Trimethylsilyl)ethyl 2-(4-bromobenzoyl)cyclohexanecarboxylate

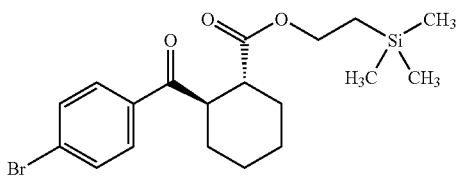

To a solution of trans-2-(4-bromobenzoyl)cyclohexanecarboxylic acid (5.0 g, 16.07 mmol) in DCM (80 mL) was added 2-(trimethylsilyl)ethanol (2.1 g, 17.68 mmol), N,N'-dimethylamino-pyridine (98 mg, 0.80 mmol), and EDCI (4.0 g, 20.89 mmol). The resulting reaction mixture was stirred at rt for 2 days. Water was added, and the mixture was diluted with DCM. The aqueous layer was separated and extracted with DCM. The combined organic phases were washed with water and brine, dried over anhydrous sodium sulfate, filtered, and concentrated under reduced pressure. Silica gel chromatography (Biotage cartridge), eluting with 10% EtOAc in hexane gave trans-(trimethylsilyl)ethyl 2-(4-bromobenzoyl)cyclohexanecarboxylate (2.44 g, 37%). $^1$H NMR (400 MHz, CD$_2$Cl$_2$) δ −0.01 (s, 9H), 0.85 (m, 2H), 1.45 (m, 3H), 1.73 (m, 2H), 1.90 (m, 2H), 2.18 (m, 1H), 2.71 (m, 1H), 3.80 (m, 1H), 4.05 (m, 2H), 7.58 (d, 2H), 7.70 (d, 2H).

Intermediate I

Methyl trans-2-(4bromobenzoyl)cyclopropanecarboxylate

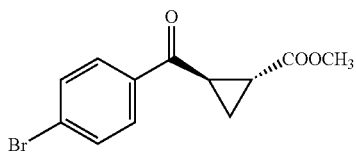

cis-2-(4-Bromobenzoyl)cyclopropanecarboxylic acid

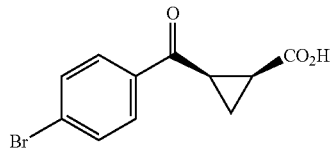

Step 1. To a cold (0° C.) stirred solution of bromobenzene (9.09 g, 57.89 mmol) and AlCl$_3$ (18.36 g, 137.84 mmol) in dry DCM (150 mL) was added 3-oxabicyclo[3.1.0]hexane-2,4-dione (5.40 g, 48.24 mmol). The reaction mixture was stirred at rt for 3 days. The dark-red solution was then poured into ice-cold water (120 mL), and conc. HCl (10 mL) was added. The solution was stirred for few minutes, and the layers were separated. The aqueous layer was extracted with DCM and the combined organic phases were washed with water, brine, dried over Na$_2$SO$_4$ and concentrated to give cis-2-(4-bromobenzoyl)cyclopropanecarboxylic acid (9.69 g, 65%). LC-MS ret. time 2.50; m/z 270 (MH$^+$); $^1$H NMR (400 MHz, CD$_2$Cl$_2$) δ 1.54 (m, 1H), 1.85 (m, 1H), 2.37 (m, 1H), 2.88 (m, 1H), 7.65 (m, 2H), 7.90 (m, 2H).

Methyl cis-2-(4-bromobenzoyl)cyclopropanecarboxylate

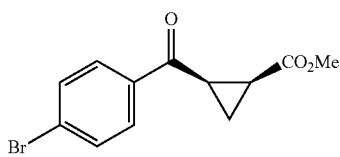

Step 2. To a solution of cis-2-(4-bromobenzoyl)cyclopropanecarboxylic acid (10.6 g, 36.63 mmol) in MeOH (250 mL) was added 2,2-dimethoxypropane (9.54 g, 91.59 mmol) and HCl (4.0 M in dioxane, 3.50 mL). The resulting solution was stirred at 40° C. for 3 days, and then evaporated to dryness. The resulting residue was purified by flash chromatography (Biotage Flash 40M) using 15 to 25% ethyl acetate in hexanes to afford methyl cis-2-(4-bromobenzoyl)-cyclopropanecarboxylate (10.34 g, 99%). $^1$H NMR (400 MHz, CD$_2$Cl$_2$) δ 1.39 (m, 1H), 1.82 (m, 1H), 2.34 (m, 1H), 2.77 (m, 1H), 3.54 (s, 3H), 7.65 (m, 2H), 7.89 (m, 2H).

trans-2-(4-Bromobenzoyl)cyclopropanecarboxylic acid.

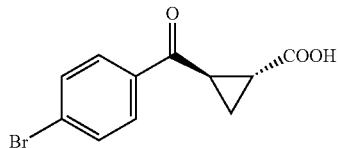

Step 3. Methyl cis-2-(4-bromobenzoyl)cyclopropanecarboxylate (10.34 g, 36.52 mmol) was dissolved in MeOH (100 mL), and then 15 mL 50% aqueous NaOH solution was added. The reaction mixture was stirred at 40° C. for 3 days. Solvent was removed by rotary evaporation and the residue was dissolved in water. Concentrated HCl was added to adjust the acidity to pH 1. The precipitate that formed was collected by filtration and dried in a vacuum oven overnight to give trans-2-(4-bromobenzoyl)cyclopropanecarboxylic acid (9.43 g, 95%). LC-MS ret. time 2.51, m/z 270 (MH$^+$); $^1$H NMR (400 MHz, CD$_2$Cl$_2$) δ 1.68 (m, 2H), 2.38 (m, 1H), 3.22 (m, 1H), 7.67 (m, 2H), 7.90 (m, 2H).

Methyl trans-2-(4-bromobenzoyl)cyclopropanecarboxylate.

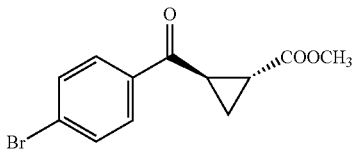

Step 4. To a solution of trans-2-(4-bromobenzoyl)cyclopropanecarboxylic acid (9.43 g, 32.59 mmol) in MeOH (200 mL) was added 2,2-dimethoxypropane (10.18 g, 97.77 mmol) and HCl (4.0 M in dioxane, 4.0 mL). The resulting solution was stirred at 40° C. overnight, and then evaporated to dryness. The resulting residue was purified by flash chromatography (Biotage Flash 40M) using 15 to 25% ethyl acetate in hexanes to afford methyl trans-2-(4-bromobenzoyl)cyclopropanecarboxylate (7.7 g, 83%). $^1$H NMR (400 MHz, CD$_2$Cl$_2$) δ 1.68 (m, 2H), 2.37 (m, 1H), 3.21 (m, 1H), 3.65 (s, 3H), 7.68 (m, 2H), 7.90 (m, 2H).

Intermediate J

Methyl trans-2-[(4'-amino-1,1'-biphenyl-4-yl) carbonyl]cyclopropanecarboxylate

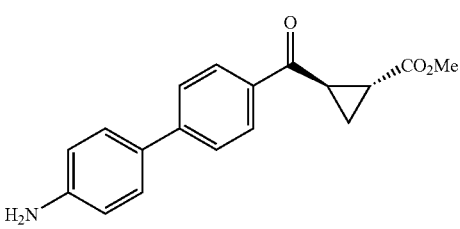

Methyl trans-2-(4-bromobenzoyl)cyclopropanecarboxylate (1.33 g, 4.70 mmol) and 4-amino-phenyl boronic acid (0.98 g, 5.64 mmol) were combined in a dry flask under argon. Toluene (25 mL), EtOH (10 mL), and 3 M aqueous Na$_2$CO$_3$ (7 mL, 20 mmol) were added, and the resulting solution was degassed for 30 minutes by using a flow of argon. Then [1,1'-bis(diphenylphosphino)-ferrocene] dichloro palladium(II), 1:1 complex with dichloromethane (383 mg, 0.47 mmol) was added, and the resulting mixture was heated at 85° C. for 16 h. The mixture was cooled to rt, then diluted with EtOAc and passed through a Celite® pad. The solvent was removed by rotary evaporation. Water and EtOAc were added, and the aqueous layer was extracted with EtOAc. The combined organic phases were washed with water, brine, dried over anhydrous sodium sulfate, filtered and concentrated in vacuo. The residue was purified by flash chromatography (Biotage Flash 40M) using 33 to 40% ethyl acetate in hexane to afford methyl trans-2-[(4'-amino-1,1'-biphenyl-4-yl)carbonyl]-cyclopropanecarboxylate (0.92 g, 66%). $^1$H NMR (400 MHz, CD$_2$Cl$_2$) δ 1.60 (m, 2H), 2.35 (m, 1H), 3.22 (m, 1H), 3.73 (s, 3H), 6.80 (m, 2H), 7.51 (m, 2H), 7.68 (m, 2H), 8.05 (m, 2H).

Intermediate K

Methyl trans-2-[(4'-amino-1,1'-biphenyl-4-yl)carbonyl]cyclobutanecarboxylate

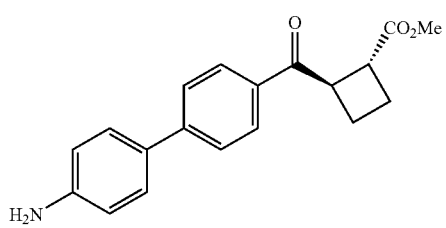

trans-2-(4-Bromobenzoyl)cyclobutanecarboxylic acid

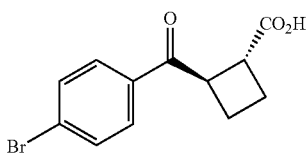

Step 1. To a cold (0° C.) stirred solution of bromobenzene (10.98 g, 69.94 mmol) and AlCl$_3$ (19.41 g, 145.71 mmol) in dry DCM (150 mL) was added cyclobutane dicarboxylic anhydride (7.35 g, 58.28 mmol). The reaction mixture was stirred at rt for 3 days. The dark-red solution was then poured into ice-cold water (120 mL), and conc. HCl (10 mL) was added. The solution was stirred for a few minutes, the aqueous layer was extracted with DCM, and then the combined organic phases were extracted with 1 N aqueous NaOH. The aqueous layer was stirred at rt overnight. The solution was acidified by addition of conc. HCl to pH 1.5, extracted with EtOAc, and the combined organic phases were washed with water, brine, dried over Na$_2$SO$_4$ and concentrated to give trans-2-(4-bromobenzoyl)cyclobutanecarboxylic acid (8.20 g, 49). $^1$H NMR (400 MHz, CD$_2$Cl$_2$) δ 2.20–2.44 (m, 4H), 3.67 (m, 1H), 4.21 (m, 1H), 7.64 (m, 2H), 7.80 (m, 2H).

Methyl trans-2-(4-bromobenzoyl)cyclobutanecarboxylate

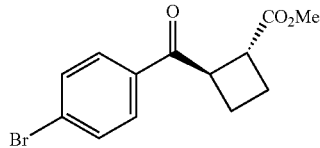

Step 2. To a solution of trans-2-(4-bromobenzoyl)cyclobutanecarboxylic acid (8.2 g, 28.94 mmol) in MeOH (250 mL) was added 2,2-dimethoxypropane (3.65 g, 35.02 mmol) and HCl (4.0 M in dioxane) (2.0 mL). The resulting solution was stirred at rt for 3 days, and then evaporated to dryness. The resulting residue was purified with flash chromatography (Biotage Flash 40M) using 4 to 11% ethyl acetate in hexanes to afford methyl trans-2-(4-bromobenzoyl)cyclobutanecarboxylate (6.21 g, 78%). $^1$H NMR (400 MHz, CD$_2$Cl$_2$) δ 2.14–2.39 (m, 4H), 3.62 (m, 1H), 3.68 (s, 3H), 4.24 (m, 1H), 7.63 (m, 2H), 7.80 (m, 2H).

Methyl trans-2-[(4'-amino-1,1'-biphenyl-4-yl)carbonyl]cyclobutanecarboxylate

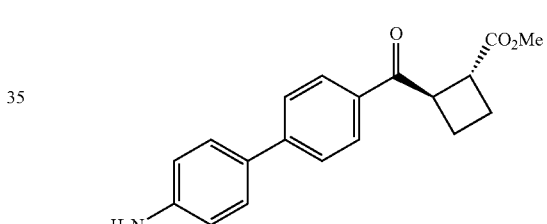

Step 3. Methyl trans-2-[(4'-amino-1,1'-biphenyl-4-yl)carbonyl]cyclobutanecarboxylate (1.25 g, 4.21 mmol) and 4-aminophenyl boronic acid (0.88 g, 5.05 mmol) were combined in a dry flask under argon. Toluene (25 mL), EtOH (10 mL), and 3 M aqueous Na$_2$CO$_3$ (5.0 mL, 15 mmol) were added, and the resulting solution was degassed for 30 minutes by using a flow of argon. Then [1,1'-bis(diphenylphosphino)-ferrocene]dichloro palladium(II), 1:1 complex with dichloromethane (343 mg, 0.42 mmol), was added and the resulting mixture was heated at 85° C. for 16 h. The mixture was cooled to rt, diluted with EtOAc, and passed through a Celite® pad. The solvent was removed by rotary evaporation. Water and EtOAc were added, and the aqueous layer was extracted with EtOAc. The combined organic phases were washed with water, brine, dried over anhydrous sodium sulfate, filtered and concentrated in vacuo. The residue was purified by flash chromatography (Biotage Flash 40M) using 29 to 37% ethyl acetate in hexane to afford methyl trans-2-[(4'-amino-1,1'-biphenyl-4-yl)-carbonyl]cyclobutanecarboxylate (0.91 g, 70%). LC-MS ret. time 2.24; m/z 310.4 (MH$^+$); $^1$H NMR (400 MHz, CD$_2$Cl$_2$) δ 2.13–2.36

(m, 4H), 3.60 (m, 1H), 3.64 (s, 1H), 4.24 (m, 1H), 6.73 (m, 2H), 7.43 (m, 2H), 7.59 (m, 2H), 7.88 (m, 2H).

Intermediate L

Methyl trans-2-[(4'-amino-1,1'-biphenyl-4-yl) carbonyl]cyclopentanecarboxylate

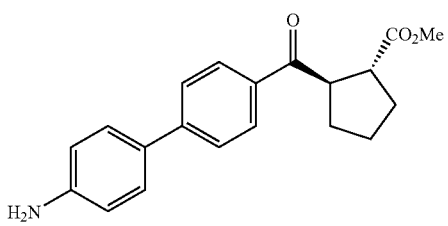

Methyl trans-2-(4-bromobenzoyl)cyclopentanecarboxylate

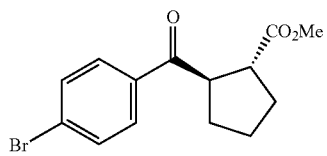

Step 1. To a solution of trans-2-(4-bromobenzoyl)cyclopentanecarboxylic acid (2.0 g, 6.26 mmol) in MeOH (70 mL) was added 2,2-dimethoxypropane (1.63 g, 15.65 mmol) and HCl (4.0 M in dioxane) (1.0 mL). The resulting solution was stirred at 40° C. overnight and then evaporated to dryness. The resulting residue was purified by flash chromatography (Biotage Flash 40M) using 7 to 11% ethyl acetate in hexanes to afford methyl trans-2-(4-bromobenzoyl)cyclopentanecarboxylate (1.62 g, 83%). $^1$H NMR (400 MHz, CD$_2$Cl$_2$) δ 1.70–1.95 (m, 4H), 2.08–2.21 (m, 2H), 3.40 (m, 1H), 3.64 (s, 3H), 4.04 (m, 1H), 7.64 (m, 2H), 7.86 (m, 2H).

Methyl trans-2-[(4'-amino-1,1'-biphenyl-4-yl)carbonyl] cyclopentanecarboxylate

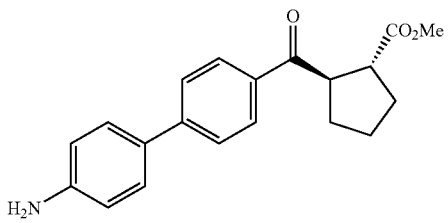

Step 2. Methyl trans-2-(4-bromobenzoyl)cyclopentanecarboxylate (1.60 g, 5.14 mmol) and 4-aminophenyl boronic acid (1.07 g, 6.17 mmol) were combined in a dry flask under argon. Toluene (25 mL), EtOH (10 mL), and 3 M aqueous Na$_2$CO$_3$ (8.50 mL, 25 mmol) were added and resulting solution was degassed for 30 minutes by using a flow of argon. Then [1,1'-bis(diphenylphosphino)-ferrocene] dichloro palladium(II), 1:1 complex with dichloromethane (419.9 mg, 0.51 mmol), was added and the resulting mixture was heated at 85° C. for 16 h. The mixture was cooled to rt, diluted with EtOAc, and passed through a Celite® pad. The solvent was removed by rotary evaporation. Water and EtOAc were added and the aqueous layer was extracted with EtOAc. The combined organic phases were washed with water, brine, dried over anhydrous sodium sulfate, filtered and concentrated in vacuo. The residue was purified by flash chromatography (Biotage Flash 40M) using 29 to 33% ethyl acetate in hexane to afford methyl trans-2-[(4'-amino-1,1'-biphenyl-4-yl)carbonyl]-cyclopentanecarboxylate (1.12 g, 67%). $^1$H NMR (400 MHz, CD$_2$Cl$_2$) δ 1.71–1.97 (m, 4H), 2.17 (m, 2H), 3.44 (m, 1H), 3.65 (s, 3H), 4.12 (m, 1H), 6.84 (m, 2H), 7.51 (m, 2H), 7.66 (m, 2H), 8.00 (m, 2H).

Intermediate M (R,R)-2-(4-Bromo-benzoyl)-cyclopentanecarboxylic acid methyl ester

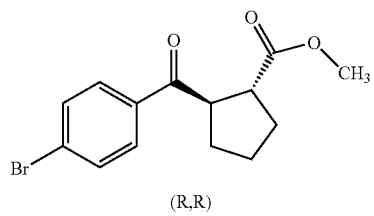

(±)-Cyclopentane-1,2-dicarboxylic acid monomethyl ester

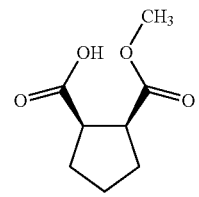

Step 1. The anhydride tetrahydro-cyclopenta[c]furan-1,3-dione (50.0 g, 356.8 mmol, prepared as described by Wilkening, et al., Syn Comm. 14(3):227, 1984) was dissolved in methanol (250 mL), and the mixture was then heated at 50–55° C. under N$_2$ for 5 h. NMR analysis showed no starting material remaining. Methanol was removed by rotary evaporation, and the residue was dried in vacuo to afford the desired product as a colorless oil (60.0 g, 98%). $^1$H NMR (CDCl$_3$) δ 3.65 (s, 3H), 3.08 (m, 2H), 2.04 (m, 4H), 1.90 (m, 1H), 1.65 (m, 1H).

(±)-cis-2-(4-Bromo-benzoyl)-cyclopentanecarboxylic acid methyl ester

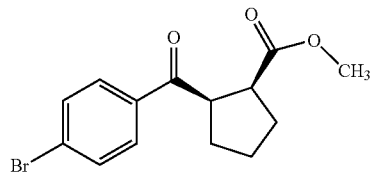

Step 2. A solution of the monomethyl ester (92.0 g, 534.3 mmol), SOCl$_2$ (116.3 mL, 1.60 mol), and DMF (1 mL) in 850 mL CH$_2$Cl$_2$ was stirred at rt overnight under N$_2$. NMR analysis showed little starting material remaining. The solvent was removed by rotary evaporation at <40° C., and the residue was dried in vacuo for 1 h. This dried residue was dissolved in bromobenzene (337.6 mL, 3.2 mol), and AlCl₃ (142.5 g, 1.07 mol) was then added portionwise at <5° C. The reaction mixture turned dark brown, and was stirred at <5° C. for 4 h under N₂. NMR analysis then showed little starting material remaining. The reaction mixture was then slowly poured into 2 L ice-water, and then 1 L EtOAc was added. After the mixture was stirred for 10 minutes, the aqueous (top) layer was separated, and extracted with 500 mL EtOAc. The combined organic layers were washed with water (2×1 L) and saturated NaHCO₃ solution (200 mL), and dried over Na₂SO₄. Removal of solvent and drying in vacuo provided 175.0 g (>95%) of the desired product. ¹H NMR (CDCl₃) δ 7.80 (d, 2H), 7.60 (d, 2H), 4.07 (m, 1H), 3.53 (s, 3H), 3.07 (m, 1H), 2.20 (m, 1H), 2.00 (m, 4H), 1.70 (m, 1H).

(±)-trans-2-(4-Bromo-benzoyl)-cyclopentanecarboxylic acid

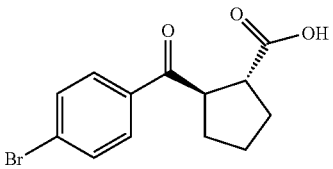

Step 3. A solution of NaOH (128.2 g, 3.2 mol) in 700 mL water was added to a solution of cis-2-(4-bromo-benzoyl)-cyclopentanecarboxylic acid methyl ester (166.3 g, 534.3 mmol) in MeOH (700 mL). The reaction mixture was stirred at rt overnight. NMR analysis showed that little starting material remained. After ca. 1 L solvent was removed by rotary evaporation, the mixture was diluted with 1 L water. Conc. HCl was slowly added with stirring at <15° C., to adjust the acidity to pH <6. A precipitate formed, and stirring was continued for 1 h. The solid precipitate was filtered, and rinsed with water. The dried filter cake was dissolved in 1 L EtOAc, and dried over Na₂SO₄. Removal of solvent and drying in vacuo afforded the desired product (131 g, 83%). ¹H NMR (CDCl₃) δ 7.83 (d, 2H), 7.60 (d, 2H), 4.05 (m, 1H), 3.50 (m, 1H), 2.20 (m, 2H), 2.00 (m, 1H), 1.78 (m, 3H).

(R,R)-trans-2-(4-Bromo-benzoyl)-cyclopentanecarboxylic acid

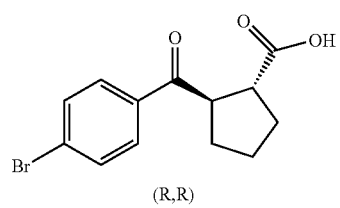

Step 4. A mixture of (±)-trans-2-(4-bromo-benzoyl)-cyclopentanecarboxylic acid (114.3 g, 384.7 mmol) and (R)-(+)-alpha-methyl-benzylamine (23.3 g, 192.3 mmol) in CH₃CN (1125 mL) was heated at 90–95° C. under N₂ to provide a solution. The hot solution was allowed to cool slowly with slow stirring overnight. The crystallized solid was filtered, and rinsed with CH₃CN (50 mL). Drying in vacuo to a constant weight afforded 64.5 g of white solid (56% ee, by chiral HPLC). This solid was then dissolved in a mixture of solvents (258 mL EtOH and 516 mL water) with heating at 90–95° C. under N₂. The hot solution was allowed to cool slowly with slow stirring overnight. The solid formed was filtered, and rinsed with 60 mL of 1:2 EtOH/water. After drying in vacuo to a constant weight, this white solid was stirred with 1 N HCl (500 mL) and EtOAc (500 mL) for 10 minutes. The organic layer was separated, washed with water (2×200 mL), and dried over Na₂SO₄. Removal of solvent and drying in vacuo provided an off-white solid (30.5 g, 26.7%, >99% ee based on chiral HPLC). Chiral HPLC method: ChiralPAK AD analytical column, 5:95 iPrOH/hexanes (both containing 0.1% TFA), 1.0 mL/min flow rate, retention times were 21.08 min and 23.40 min for the (S,S) and (R,R) isomers, respectively. ¹H NMR (CDCl₃) spectra were identical to that for the racemic (±)-trans-2-(4-bromo-benzoyl)-cyclopentanecarboxylic acid.

(R,R)-trans-2-(4-Bromo-benzoyl)-cyclopentanecarboxylic acid methyl ester

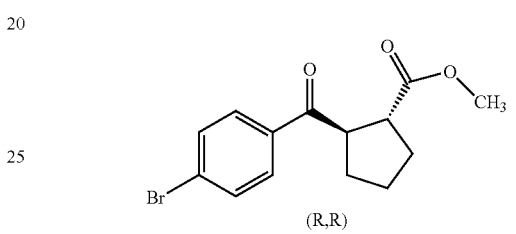

Step 5. A suspension of (R,R)-trans-2-(4-bromo-benzoyl)-cyclopentanecarboxylic acid (30.5 g, 102.6 mmol), MeI (9.6 mL, 154.0 mmol), and NaHCO₃ (25.9 g, 307.9 mmol) in 360 mL DMF was stirred at rt under argon overnight. NMR analysis showed little starting material remaining. Water (1 L) was added to the reaction mixture, and then concentrated HCl was slowly added with stirring at <15° C. to adjust the acidity to pH <7, and a precipitate was formed. After the mixture was stirred for 1 h, the solid was filtered and rinsed with water (200 mL). The solid was dried in vacuo to a constant weight, to afford the desired product as a light yellow solid (29.5 g, 92.5%, 94.5% ee based on chiral HPLC). HPLC method: ChiralPAK AD analytical column, 5:95 iPrOH/hexanes (both containing 0.1% TFA), 1.0 mL/min flow rate, retention times were 10.64 min and 12.98 min for the (S,S) and (R,R) isomers, respectively. ¹H NMR (CDCl₃) δ 7.82 (d, 2H), 7.60 (d, 2H), 4.05 (m, 1H), 3.65 (s, 3H), 3.42 (m, 1H), 2.18 (m, 2H), 1.90 (m, 1H), 1.80 (m, 3H).

Intermediate N (R,R)-2-(4-Bromo-benzoyl)-cyclopentanecarboxylic acid tert-butyl ester

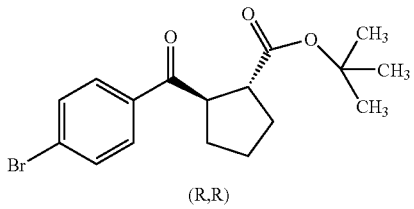

(R,R)-trans-2-(4-Bromo-benzoyl)-cyclopentanecarboxylic acid (2.0 g, 6.73 mmol) was dissolved in CH₂Cl₂ (40 mL) at rt, followed by addition of a few drops of conc. sulfuric acid. Isobutylene (ca. 2.0 g) was then introduced by gentle bubbling while the reaction mixture was cooled in an ice-water bath. The reaction was then stirred at rt for 60 h and quenched by adding 40 mL saturated aqueous $Na_2CO_3$ solution. The organic layer was separated, washed with water, and dried over anhydrous sodium sulfate. Removal of solvent under reduced pressure afforded the desired tert-butyl ester as a clear oil which solidified upon standing (1.9 g, 80% yield). $^1$H NMR (DMSO-$d_6$) δ 7.90 (d, 2H), 7.88 (d, 2H), 4.00 (q, 1H), 3.10 (q, 1H), 2.10 (m, 1H), 1.90 (m, 1H), 1.50–1.80 (m, 4H), 1.30 (s, 9H).

Intermediate O

Methyl (1R,2R)-2-[(4'-amino-3'-fluoro-1,1'-biphenyl-4-yl)carbonyl]cyclopentanecarboxylate

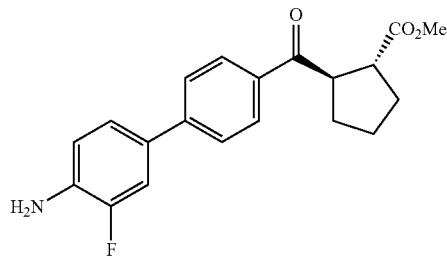

2-Fluoro-4-iodophenylformamide

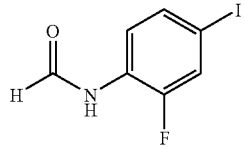

Step 1. To a cooled solution (0° C.) of 4-iodo-2 fluoroaniline (3.05 g, 12.9 mmol) in tetrahydrofuran (15 mL) and toluene (15 mL), was slowly added a mixture of acetic anhydride (1.39 mL, 14.7 mmol) and formic acid (0.83 mL, 22.0 mmol). The reaction mixture was stirred at rt overnight, then diluted with ethyl acetate (100 mL) and 1N aqueous HCl (100 mL). The layers were separated, and the organic layer was washed with water and saturated sodium carbonate solution, and dried over sodium sulfate. The solvent was removed under reduced pressure to afford 2-fluoro-4-iodophenylformamide as an off-white solid (3.32 g, 97%). GC-MS ret. time 2.27 min, m/z 265 (M$^+$); $^1$H NMR (300 MHz, CDCl$_3$) δ: 7.37–7.51 (m, 3H), 8.13 (t, 1H), 8.46 (s, 1H).

Methyl (1R 2R)-2-{[-3'-fluoro-4'-(formylamino)-1,1'-biphenyl-4-yl]carbonyl}cyclopentane-carboxylate

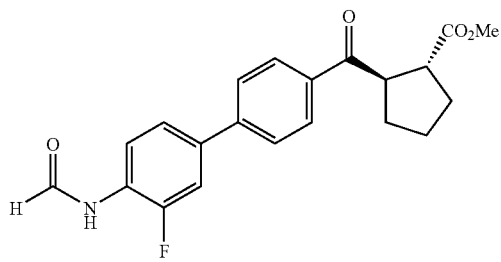

Step 2. To a suspension of 2-fluoro-4-iodophenylformamide (5.11 g, 19.28 mmol) bis(pinacolato)diboron (4.89 g, 19.28 mmol), potassium acetate (5.67 g, 57.84 mmol), and palladium acetate (129 mg, 0.58 mmol) in N,N-dimethylformamide (125 mL) was bubbled through argon for 30 minutes. The reaction mixture was then heated at 80° C. for 3 h. After the mixture was cooled to rt, methyl (R,R)-2-(4-bromobenzoyl)cyclopentanecarboxylate (2.2 g, 7.35 mmol, 97% ee), tetrakis(triphenylphosphine)palladium(0) (668 mg, 0.58 mmol), and cesium carbonate (9.43 g, 28.92 mmol) were added, and the reaction mixture was then heated at 80° C. for 16 h. The mixture was then cooled to rt, quenched with water, extracted with ethyl acetate, and dried over anhydrous sodium sulfate. Solvent was then removed under reduced pressure and the crude product was purified by flash chromatography (Biotage 75) using 1:1 ethylacetate/hexane to afford methyl 2-{[3'-fluoro-4'-(formylamino)-1,1'-biphenyl-4-yl]carbonyl}cyclopentanecarboxylate (4.6 g, 65%). LC-MS ret. time 3.15 min, m/z 342.0 (MH$^+$); $^1$H NMR (300 MHz, DMSO-$d_6$) δ 1.52–1.94 (m, 1H), 1.92–2.07 (m, 1H), 2.10–2.21 (m, 1H), 3.48 (m, 1H), 3.55 (s, 3H), 4.12 (q, 1H), 7.59 (dd, 1H), 7.62 (dd, 1H), 7.87 (d, 2H), 8.09 (d, 2H), 8.25 (t, 1H), 8.34 (s, 1H), 10.62 (s, 1H).

Methyl (1R,2R)-2-[(4'-amino-3'-fluoro-1,1'-biphenyl-4-yl)carbonyl]cyclopentane-carboxylate

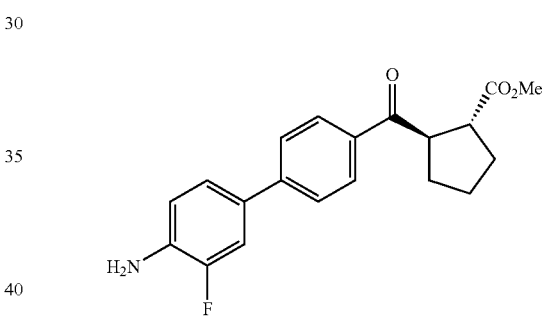

Step 3. To a solution of methyl 2-{[3'-fluoro-4'-(formylamino)-1,1'-biphenyl-4-yl]-carbonyl}cyclopentanecarboxylate (4.24 g, 11.48 mmol) in methanol (34 mL) was added conc. HCl (11.4 mL), and the resulting solution was stirred at rt for 2 h. Solvent was then removed, the residual mixture was dissolved in water, and the acidity of the mixture was adjusted to pH ~7 by slow addition of saturated aqueous sodium bicarbonate solution. The mixture was then extracted with dichloromethane and washed with saturated sodium chloride solution, dried over sodium sulfate, and the solvent was removed in vacuo. The crude mixture was then triturated with ethyl acetate/hexane to afford methyl 2-[(4'-amino-3'-fluoro-1,1'-biphenyl-4-yl)carbonyl]cyclopentane-carboxylate (3.5 g, 89%, 80% ee). LC-MS ret. time 3.00 min, m/z 370.0 (MH$^+$); $^1$H NMR (300 MHz, DMSO-$d_6$) δ 1.52–1.84 (m, 4H), 1.97–2.02 (m, 1H), 2.14–2.18 (m, 1H), 3.24–3.33 (m, 1H), 3.56 (s, 3H), 4.08 (q, 1H), 5.47 (br s, 2H), 6.84 (t, 1H), 7.34 (dd, 1H), 7.48 (dd, 1H), 7.78 (d, 2H), 7.99 (d, 2H).

Intermediate P

Methyl 4-(4'-amino-3'-fluoro-1,1'-biphenyl-4-yl)-2,2-dimethyl-4-oxobutanoate

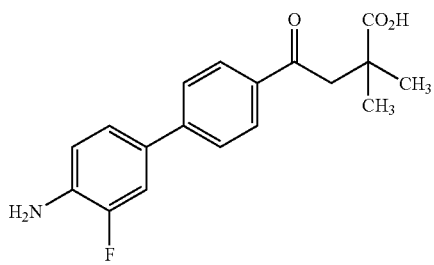

Methyl 4-[3'-fluoro-4'-(formylamino)-1,1'-biphenyl-4-yl]-2,2-dimethyl-4-oxobutanoate

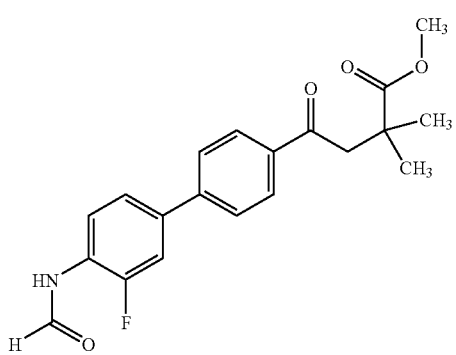

Step 1. A suspension of 2-fluoro-4-iodophenylformamide (1.94 g, 7.35 mmol, prepared as described above), bis(pinacolato)diboron (1.86 g, 7.35 mmol), potassium acetate (2.16 g, 22.1 mmol), and palladium acetate (49.4 mg, 0.22 mmol) in N,N-dimethylformamide (50 mL) was degassed by bubbling a flow of argon through the mixture for 30 minutes. The mixture was then heated at 80° C. for 3 h. After the mixture was cooled to rt, methyl 4-(4-bromophenyl)-2,2-dimethyl-4-oxobutanoate (2.2 g, 7.4 mmol), tetrakis(triphenylphosphine)palladium(0) (254.8 mg, 0.22 mmol), and cesium carbonate (3.59 g, 11.0 mmol) were added, and the reaction mixture was heated at 80° C. for 16 h. The mixture was then cooled to rt and water was added. The mixture was extracted with ethyl acetate and the combined extracts were dried over sodium sulfate. The mixture was concentrated under reduced pressure and the crude was purified by flash chromatography (Biotage Flash 40M, 1:1 ethyl acetate/hexane) to afford methyl 4-[3'-fluoro-4'-(formylamino)-1,1'-biphenyl-4-yl]-2,2-dimethyl-4-oxobutanoate (1.2 g, 46%). LC-MS ret. time 2.80 min, m/z 358.1 (MH$^+$); $^1$H NMR (300 MHz, DMSO-d$_6$) δ 1.19 (s, 6H), 3.36 (s, 2H), 3.51 (s, 3H), 7.56 (d, 1H), 7.69 (dd, 1H), 7.82 (d, 2H), 7.99 (d, 3H), 8.21 (t), 10.25 (s, 1H).

Methyl 4-(4'-amino-3'-fluoro-1,1'-biphenyl-4-yl)-2,2-dimethyl-4-oxobutanoate

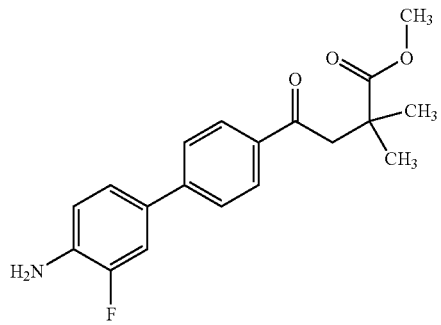

Step 2. To a solution of methyl 4-[3'-fluoro-4'-(formylamino)-1,1'-biphenyl-4-yl]-2,2-dimethyl-4-oxobutanoate (1.21 g, 3.39 mmol) in methanol (10 mL) was added conc. HCl (3.5 mL), and the resulting solution was stirred at rt for 16 h. The mixture was then concentrated, diluted with water, and the acidity was adjusted to pH ~7 by slow addition of saturated aqueous sodium bicarbonate solution. The mixture was then extracted with dichloromethane, and the combined organic layers were washed with saturated sodium chloride solution, dried over sodium sulfate, and concentrated under reduced pressure. The residue was then triturated with ethyl acetate/hexane to afford methyl 4-(4'-amino-3'-fluoro-1,1'-biphenyl-4-yl)-2,2-dimethyl-4-oxobutanoate (998 mg, 89%). LC-MS ret. time 3.11 min, m/z 329.9 (MH$^+$); $^1$H NMR (300 MHz, CDCl$_3$) δ 1.31 (s, 6H), 3.28 (s, 2H), 3.66 (s, 3H), 6.84 (t, 1H), 7.21–7.35 (m, 2H), 7.55 (d, 2H), 7.93 (d, 2H).

Intermediate Q

Methyl 4-(4'-amino-3'-methyl-1,1'-biphenyl-4-yl)-2,2-dimethyl-4-oxobutanoate

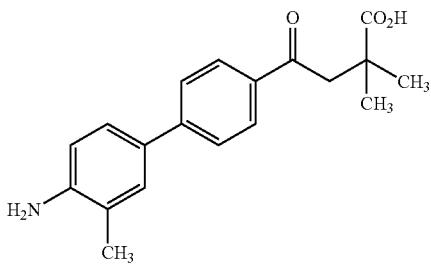

4-Iodo-2-methylphenylformamide

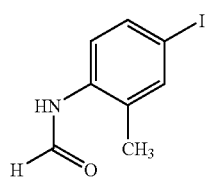

Step 1. This intermediate was prepared by using a procedure similar to that described above for 2-fluoro-4-iodophenylformamide. LC-MS ret. time 2.43 min, m/z 262.0 (MH$^+$); $^1$H NMR (300 MHz, DMSO-d$_6$) δ 2.14 (s, 3H), 7.49 (dd, 1H), 7.52–7.59 (m, 2H), 8.24 (s, 1H), 9.56 (s, 1H).

Methyl 4-[4'-(formylamino)-3'-methyl-1,1'-biphenyl-4-yl]-2,2-dimethyl-4-oxobutanoate

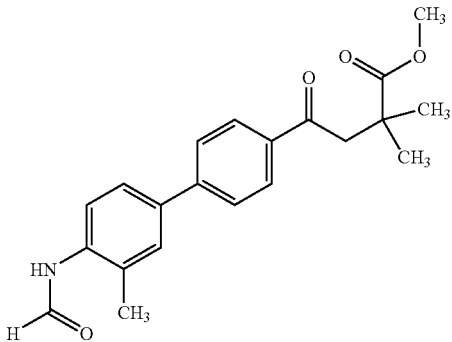

Step 2. This intermediate was prepared by using a procedure similar to that described above for methyl 4-[3'-fluoro-4'-(formylamino)-1,1'-biphenyl-4-yl]-2,2-dimethyl-4-oxobutanoate. LC-MS ret. time 2.78 min, m/z 354.1 (MH$^+$); $^1$H NMR (300 MHz, DMSO-d$_6$) δ 1.02 & 1.13 (s, 6H 2.22 & 2.28 (s, 3H), 3.36 (s, 2H), 3.51 (s, 3H), 7.29 (d) & 7.40 (s) (2H), 7.78 (d, 2H), 7.90 & 7.96 (d, 3H), 8.46 (d) (1H), 9.82 (d) (1H).

Methyl 4-(4'-amino-3'-methyl-1,1'-biphenyl-4-yl)-2,2-dimethyl-4-oxobutanoate

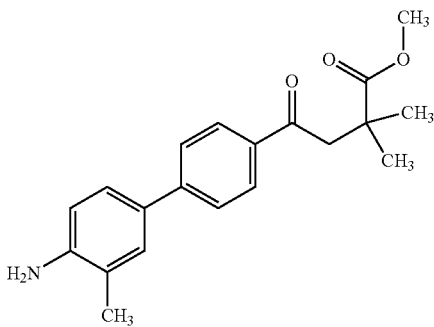

Step 3. This intermediate was prepared by using a procedure similar to that described above for methyl 4-(4'-amino-3'-fluoro-1,1'-biphenyl-4-yl)-2,2-dimethyl-4-oxobutanoate. LC-MS ret. time 2.64 min, m/z 326.1 (MH$^+$); $^1$H NMR (300 MHz, CDCl$_3$) δ 1.31 (s, 6H), 2.25 (s, 3H), 3.29 (s, 2H), 3.66 (s, 3H), 6.80 (s, 1H), 7.35 (s, 2H), 7.60 (d, 2H), 7.93 (d, 2H).

Intermediate R

Methyl 4-(4'-amino-3'-methoxy-1,1'-biphenyl-4-yl)-2,2-dimethyl-4-oxobutanoate

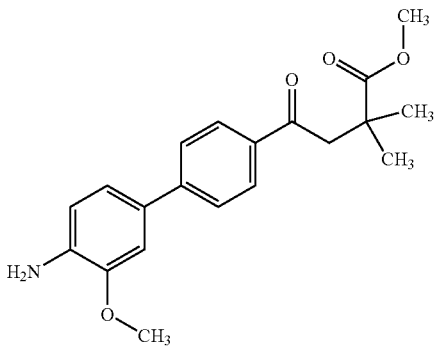

Methyl 4-(3'-methoxy-4'-nitro-1,1'-biphenyl-4-yl)-2,2-dimethyl-4-oxobutanoate

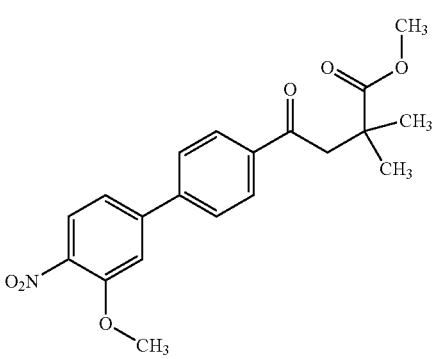

Step 1. A suspension of methyl 4-(4-bromophenyl)-2,2-dimethyl-4-oxobutanoate (200 mg, 0.67 mmol), bis(pinacolato)diboron (170 mg, 0.67 mmol), potassium acetate (197 mg, 2.01 mmol), and palladium acetate (5 mg, 0.02 mmol) in N,N-dimethylformamide (4.0 mL) was degassed by bubbling a flow of argon for 30 minutes. The reaction mixture was then heated at 80° C. for 3 h. After the mixture was cooled to rt, 5-chloro-2-nitroanisole (125 mg, 0.67 mmol), tetrakis(triphenyl-phosphine)palladium(0) (23 mg, 0.02 mmol), and cesium carbonate (327 mg, 1.0 mmol) were added and the reaction mixture was heated at 80° C. for 16 h. The mixture was then cooled to rt, and water was added. The aqueous layer was extracted with ethyl acetate and the combined organic phases were dried over anhydrous sodium sulfate. Solvent was removed under reduced pressure and the residue was purified by flash chromatography (Biotage Flash 40M, 1:3 ethyl acetate/hexane) to afford methyl 4-(3'-methoxy4'-nitro-1,1'-biphenyl-4-yl)-2,2-dimethyl-4-oxobutanoate (120 mg, 48%). LC-MS ret. time 3.38 min, m/z 371.8 (MH$^+$); $^1$H NMR (300 MHz, CDCl$_3$) δ 1.19 (s, 6H), 3.36 (s, 2H), 3.51 (s, 3H), 4.02 (s, 3H), 7.21–7.24 (m, 2H), 7.64–7.69 (m, 2H), 7.93 (d, 1H), 8.00–8.04 (m, 2H).

Methyl 4-(4'-amino-3'-methoxy-1,1'-biphenyl-4-yl)-2,2-dimethyl-4-oxobutanoate

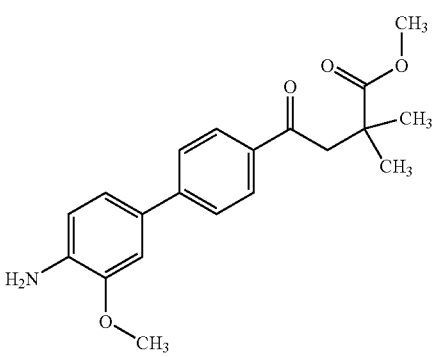

Step 2. To a solution of methyl 4-(3'-methoxy-4'-nitro-1,1'-biphenyl-4-yl)-2,2-dimethyl-4-oxobutanoate (670 mg, 1.80 mmol) in 85% aqueous ethanol (27 mL) was added iron powder (1.01 g, 18.04 mmol) and 2 N aqueous HCl (0.9 mL, 1.8 mmol), and the resulting suspension was heated at reflux for 2.5 h. The mixture was then cooled to rt, and filtered through a pad of Celite®. Water was added, the mixture was extracted with ethyl acetate, and the combined organic phases were dried over anhydrous sodium sulfate. Solvent was removed under reduced pressure and the residue was triturated with ethyl acetate/hexane to afford methyl 4-(4'-amino-3'-methoxy-1,1'-biphenyl-4-yl)-2,2-dimethyl-4-oxobutanoate (410 mg, 67%). LC-MS ret. time 2.58 min, m/z 342.1 (MH⁺); ¹H NMR (300 MHz, CDCl₃) δ 1.31 (s, 6H), 3.28 (s, 2H), 3.66 (s, 3H), 3.90 (s, 3H), 6.75 (d, 1H), 7.02–7.09 (m, 2H), 7.59 (d, 2H), 7.94 (d, 2H).

Intermediate S

Ethyl 4-(4'-amino-3-methyl-1,1'-biphenyl-4-yl)-4-oxo-2-(2-phenylethyl)butanoate

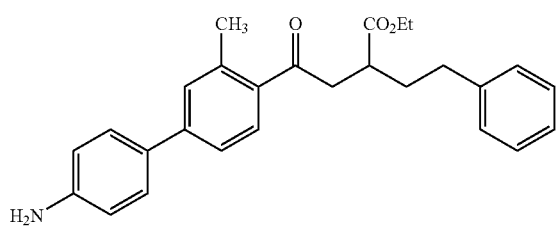

4-Acetyl-3-methylphenyl trifluoromethanesulfonate

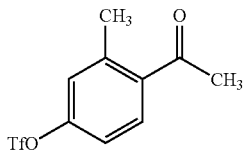

Step 1. To a cooled solution (0–5° C.) of 1-(4-hydroxy-2-methylphenyl)ethanone (22.1 g, 0.147 mol) and pyridine (40.0 mL, 0.500 mol) in dichloromethane (100 mL) was slowly added trifluoromethanesulfonic anhydride (35.0 mL, 0.207 mol). After the addition was completed, the ice bath was removed, and the reaction mixture was stirred at rt for 1.5 h. Water (50 mL) was added and the layers were separated. The organic layer was washed with water (2×20 mL) and 0.5 N aqueous HCl, dried over magnesium sulfate, and concentrated under reduced pressure. The crude product was purified by flash chromatography (Biotage Flash 75, 10/90 ethyl acetate/hexane) to give 4-acetyl-3-methylphenyl trifluoromethanesulfonate as a light yellow oil (40.83 g, 90% yield). GC-MS m/z 282 (M⁺), ret. time 8.20 min ¹H NMR (CDCl₃) δ 2.56 (s, 3H), 2.58 (s, 3H), 7.05–7.14 (m, 2H), 7.78 (d, 1H).

1-(3-Methyl-4'-nitro-1,1'-biphenyl-4-yl)ethanone

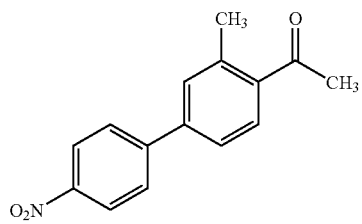

Step 2. A mixture of 4-acetyl-3-methylphenyl trifluoromethanesulfonate (6.90 g, 24.0 mmol), 4-nitrophenylboronic acid (3.80 g, 24 mmol), 2 N aqueous sodium carbonate (88.0 mL), dioxane (88.0 mL), and toluene (296 mL) was purged with argon for 30 minutes before [1,1'-bis(diphenylphosphino)-ferrocene]dichloro palladium(II) (1:1 complex with dichloromethane, 1.90 g, 2.30 mmol) was added. The reaction mixture was heated at 85° C. and stirred overnight. The layers were separated and the organic layer was washed with water (2×50 mL), dried over magnesium sulfate, and concentrated under reduced pressure to give a dark brown oil. This material was purified by flash chromatography (7 to 20% ethyl acetate/hexane) to give 1-(3-methyl-4'-nitro-1,1'-biphenyl-4-yl)ethanone as a light yellow solid (6.12 g, 99% yield). GC-MS m/z 255 (M⁺), ret. time 9.89 min; ¹H NMR (CDCl₃) δ: 2.61 (s, 3H), 2.62 (s, 3H), 7.49–55 (m, 2H), 7.78 (d, 2H), 7.81 (d, 1H), 8.32 (d, 2H).

2-Bromo-1-(3-methyl-4'-nitro-1,1'-biphenyl-4-yl)ethanone

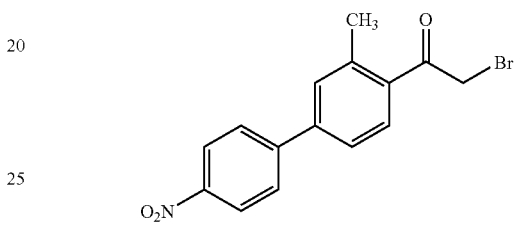

Step 3. A mixture of 1-(3-methyl-4'-nitro-1,1'-biphenyl-4-yl)ethanone (5.66 g, 22 mmol), pyridinium tribromide (10.63 g, 33.0 mmol), and glacial acetic acid (60 mL) was stirred at 110° C. for 3 h. The reaction mixture was cooled to 0–5° C., and the precipitated product was collected by filtration and washed with small amounts of water, ethanol, and diethyl ether. The crude material was purified by flash chromatography (5:95 ethyl acetate/hexane) to give 2-bromo-1-(3-methyl-4'-nitro-1,1'-biphenyl-4-yl)ethanone as a light yellow solid (4.33 g, 59% yield). HPLC ret. time 3.63 min; ¹H NMR (CDCl₃) δ: 2.63 (s, 3H), 2.25 (s, 2H), 7.52–7.58 (m, 2H), 7.72–7.83 (m, 3H), 8.32 (d, 2H).

Diethyl 2-[2-(3-methyl-4'-nitro-1,1'-biphenyl-4-yl)-2-oxoethyl]-2-(2-phenylethyl)malonate

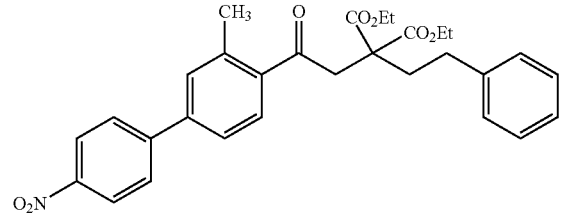

Step 4. To a cold suspension (0–5° C.) of 95% sodium hydride (3.53 g, 13.0 mmol) in dry tetrahydrofuran (30 mL) was slowly added diethyl 2-phenylethylmalonate (3.53 g, 13 mmol). The ice bath was removed and the reaction mixture was stirred at rt for 45 minutes. A solution of 2-bromo-1-(3-methyl-4'-nitro-1,1'-biphenyl-4-yl)ethanone (4.06 g, 12.0 mmol) in dry tetrahydrofuran (50 mL) was slowly added, and the resulting mixture was stirred at rt for about 70 h. Ethyl acetate (80 mL) and water (20 mL) were added, and the layers were separated. The organic layer was washed with water (2×30 mL), dried over magnesium sulfate, and concentrated under reduced pressure to give a dark, brown oil. This material was purified by flash chromatography (10:90 ethyl acetate/hexane) to give diethyl 2-[2-(3-methyl-4'-nitro-1,1'-biphenyl-4-yl)-2-oxoethyl]-2-(2-phenylethyl) malonate as a light yellow oil (5.30 g, 82% yield). LC-MS ret. time 4.01 min, m/z 517.9 (MH$^+$); $^1$H NMR (CDCl$_3$) δ 1.23–1.35 (m, 6H), 2.41–2.50 (m, 2H), 2.56 (s, 3H), 2.59–2.66 (m, 3.71 (s, 2H), 4.21–4.32 (m, 4H), 7.13–7.19 (m, 3H), 7.22–7.30 (m, 2H), 7.49–7.55 (m, 2H), 7.73–7.82 (m, 3H), 8.31 (d, 2H).

Ethyl 4-(3-methyl-4'-nitro-1,1'-biphenyl-4-yl)-4-oxo-2-(2-phenylethyl)butanoate.

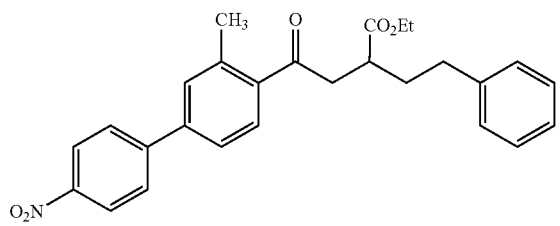

Step 5. A mixture of diethyl 2-[2-(3-methyl-4'-nitro-1,1'-biphenyl-4-yl)-2-oxoethyl]-2-(2-phenylethyl)malonate (4.87 g, 9.41 mmol), 1 N aqueous sodium hydroxide (10.4 mL, 10.40 mmol), ethanol (10 mL), and acetone (10 mL) was stirred at 50° C. overnight. The mixture was concentrated and the residue was dissolved in dimethoxyethane (20 mL), and stirred at 80° C. overnight. The mixture was concentrated, and the residue was dissolved in ethyl acetate (30 mL). The solution was washed with water (2×5 mL), dried over magnesium sulfate, and concentrated under reduced pressure. The material obtained was purified by flash chromatography (10:90 ethyl acetate/hexane) to give ethyl 4-(3-methyl-4'-nitro-1,1'-biphenyl-4-yl)-4-oxo-2-(2-phenylethyl)butanoate as a light yellow oil (3.53 g, 99% yield). LC-MS ret. time 4.18 min, m/z 446.0 (MH$^+$); $^1$H NMR (CDCl$_3$) δ: 1.33 (t, 3H), 1.83–2.17 (m, 2H), 2.58 (s, 3H), 2.67–2.78 (m, 2H), 3.00 (dd, 1H), 3.14 (m, 1H), 3.49 (dd, 1H), 4.09 (q, 2H), 7.14–7.36 (m, 5H), 7.47–7.55 (m, 2H), 7.72–7.83 (m, 3H), 8.33 (d, 2H).

Ethyl 4-(4'-amino-3-methyl-1,1'-biphenyl-4-yl)-4-oxo-2-(2-phenylethyl)butanoate

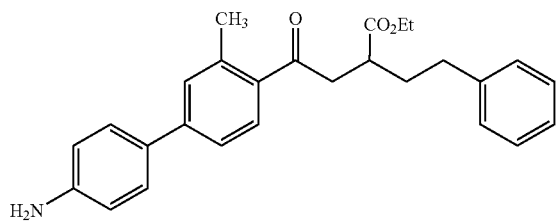

Step 6. A mixture of ethyl 4-(3-methyl-4'-nitro-1,1'-biphenyl-4-yl)-4-oxo-2-(2-phenylethyl)butanoate (3.40 g, 7.60 mmol), iron powder (4.20 g, 76.00 mmol), 2 N aqueous hydrochloric acid (3.80 mL, 7.60 mmol), and 85/15 ethanol/water (100 mL) was stirred at reflux for 2.5 h. The reaction mixture was filtered through a pad of Celite®, and concentrated to give ethyl 4-(4'-amino-3-methyl-1,1'-biphenyl-4-yl)-4-oxo-2-(2-phenylethyl)butanoate as a light, brown solid (2.94 g, 93% yield). LC-MS ret. time 3.23 min, m/z 416.1 (MH$^+$); $^1$H NMR (CDCl$_3$) δ 1.32 (t, 3H), 1.82–2.17 (m, 2H), 2.58 (s, 3H), 2.68–2.77 (m, 2H), 2.98–3.09 (m, 2H), 3.49 (dd, 1H), 3.74 (br s, 2H), 4.10 (q, 2H), 6.79 (d, 2H), 7.12–7.37 (m, 5H), 7.38–7.54 (m, 4H), 7.78 (d, 1H).

Intermediate T 3-(4'-Amino-biphenyl-4-carbonyl)-cyclohexanecarboxylic acid methyl ester

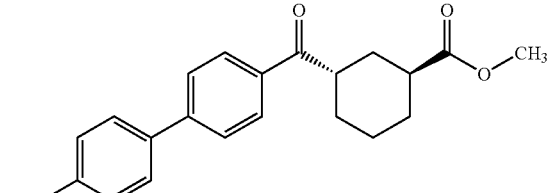

3-(4-Bromo-benzoyl)-cyclohexanecarboxylic acid methyl ester

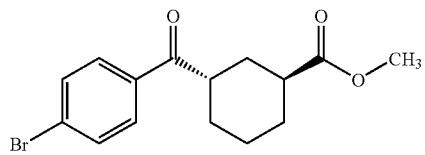

Step 1. To a solution of trans-3-(4-bromobenzoyl)cyclohexane-1-carboxylic acid (500 mg, 1.61 mmol, obtained from Rieke Metals Inc., Lincoln, Nebr., USA) and 2,2-dimethoxypropane (669 mg, 6.43 mmol) in methanol (20 mL), 5 drops of 4 M HCl in dioxane was added, and this reaction mixture was heated at 50° C. overnight. The solvent was removed by rotary evaporation to give the product 3-(4-bromo-benzoyl)-cyclohexanecarboxylic acid methyl ester as a brown oil (500 mg, yield 95.7%). $^1$H NMR (300 MHz, DMSO) δ 7.80 (d, 2 H), 7.60 (d, 2 H), 3.70 (s, 3 H), 3.25 (m, 1 H), 2.50 (m, 1 H), 2.20–1.90 (m, 4 H), 1.70–1.50 (m, 4 H); LC-MS ret. time 3.30 min, m/z 324.9 (MH$^+$).

3-(4'-Amino-biphenyl-4-carbonyl)-cyclohexanecarboxylic acid methyl ester

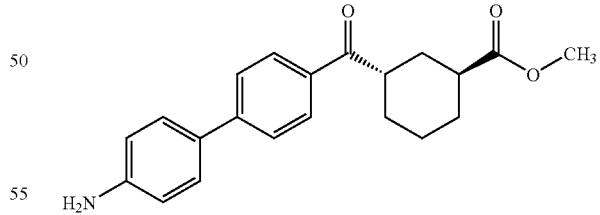

Step 2. To a solution of 3-(4-bromo-benzoyl)-cyclohexanecarboxylic acid methyl ester (500 mg, 1.54 mmol) and 4-aminophenyl boronic acid (252 mg, 1.85 mmol) in toluene (40 mL) and dioxane (10 mL), 2 N aqueous Na$_2$CO$_3$ (10 mL) was added, and the mixture was degassed by bubbling with a flow of argon for 45 minutes. (1,1-Bis(diphenylphosphino)ferrocene)-dichloropalladium (63 mg, 0.08 mmol) was added to the mixture, which was then heated at 80° C. overnight. The reaction mixture was cooled to rt, and then filtered through a pad of Celite®, rinsing with ethyl acetate.

The organic layer was separated, washed with water and brine, and dried (Na₂SO₄). The solvent was removed by rotary evaporation, and the solid residue was purified by using a Biotage QuadUV flash chromatography system (eluant: 3:1 hexane/EtOAc). The product 3-(4'-amino-biphenyl-4-carbonyl)-cyclohexanecarboxylic acid methyl ester was obtained as a brown solid (200 mg, yield 38.5%). $^1$H NMR (300 MHz, DMSO) δ 7.90 (d, 2 H), 7.60 (d, 2 H), 7.45 (d, 2 H), 6.80 (d, 2 H), 3.70 (s, 3 H), 3.25 (m, 1 H), 2.50 (m, 1 H), 2.20–1.90 (m, 4 H), 1.70–1.50 (m, 4 H); LC-MS ret. time 3.80 min (method 2), m/z 338.17 (MH⁺).

Preparation of Compounds of Formula (VII)

Intermediate U

2-Chloro-6-(trifluoromethyl)-1,3-benzothiazole

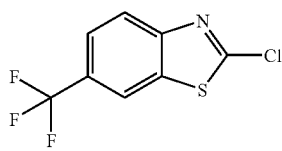

In a three-necked flask fitted with a condenser, a suspension of copper II chloride (370 mg, 2.75 mmol) in acetonitrile (5 mL) was treated with tert-butyl nitrite (0.41 mL, 3.44 mmol) and stirred at rt for 10 minutes. A solution of 2-amino-6-trifluoromethylbenzthiazole (500 mg, 2.29 mmol) in acetonitrile (1 mL) was then added dropwise. The mixture was heated at 65° C. for 30 minutes, then cooled and diluted with an excess of 1 N aqueous hydrochloric acid solution. The mixture was extracted with ethyl acetate. The organic phase was separated, dried (MgSO₄), and concentrated under reduced pressure. An orange semi-solid (501 mg, 92%) was obtained and used without further purification. $^1$H NMR (300 MHz, CDCl₃) δ 8.10–8.05 (m, 2 H), 7.74 (d, 1 H); LC-MS m/z 238.2 (MH⁺), ret. time 3.76 min TLC R$_f$=0.50 (9:1 hexanes/ethyl acetate).

Intermediate V

2-Chloro-4-methyl-1,3-benzothiazole

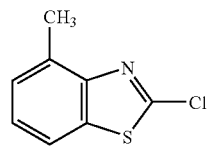

To a solution containing copper chloride (II) (1.96 g, 14.61 mmol) and tri(ethylene glycol) dimethyl ether (6 mL) in acetonitrile (100 mL) was added isoamyl nitrite (2.14 g, 18.27 mmol), and the reaction mixture was stirred at rt for 30 minutes. To this suspension was added dropwise a solution of 2-amino-4-methylbenzothiazole (2.0 g, 12.18 mmol) in tri(ethylene glycol) dimethyl ether (10 mL). The reaction mixture was stirred at rt for 10 minutes, and then heated at 50° C. for 2.5 h. The reaction mixture was cooled to rt, and then poured cautiously into cold aqueous 6 M HCl (400 mL). The solution was extracted with EtOAc. The organic layer was washed with HCl (1.0 M), water, brine, filtered and concentrated in vacuo. The residue was purified by flash chromatography (Biotage Flash 40M) using 5% ethyl acetate in hexane to afford 2-chloro-4-methyl-1,3-benzothiazole (1.6 g, 71%). $^1$H NMR (400 MHz, CD₂Cl₂) δ 2.70 (s, 3H), 7.32 (m, 2H), 7.64 (m, 1H).

Intermediate W

2-Chloro-4,6-difluoro-1,3-benzothiazole

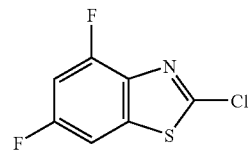

To a solution containing copper chloride (II) (0.87 g, 6.45 mmol) and tri(ethylene glycol) dimethyl ether (3 mL) in acetonitrile (50 mL) was added isoamyl nitrite (0.94 g, 8.06 mmol), and the reaction mixture was stirred at rt for 30 minutes. To this suspension was added dropwise a solution of 4,6-difluoro-1,3-benzothiazol-2-amine (1.0 g, 5.37 mmol) in tri(ethylene glycol) dimethyl ether (5 mL). The reaction mixture was stirred at rt for 10 minutes, and then heated at 50° C. for 2.5 h. The reaction mixture was cooled to rt, and then poured cautiously into cold aqueous 6 M HCl (200 mL). The solution was extracted with EtOAc. The organic layer was washed with HCl (1.0 M), water and brine, filtered and concentrated down to afford 2-chloro-4,6-difluoro-1,3-benzothiazole (1.1 g, 99%). $^1$H NMR (400 MHz, DMSO-d₆) 7.05 (m, 1H), 7.36 (m, 1H).

Intermediate X

2-Chloro-6-trifluoromethoxy-1,3-benzothiazole

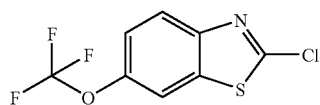

To a solution containing dry copper (II) chloride (3.44 g, 25.62 mmol) and tri(ethylene glycol) dimethyl ether (10 g) in acetonitrile (150 mL) was added isoamyl nitrite (4.5 mL, 32.02 mmol). The reaction mixture was stirred at rt under argon for 30 minutes. To this suspension was added dropwise, a solution containing 6-trifluoromethoxy-1,3-benzothiazol-2-ylamine (5 g, 21.35 mmol) and tri(ethylene glycol) dimethyl ether (10 g). The reaction mixture was stirred at rt for 10 minutes, and then heated at 50° C. for 3 h. The mixture was cooled to rt, poured cautiously into aqueous 6 N HCl, and extracted with ethyl acetate. The organic layer was washed with 1N aqueous HCl and brine, and concentrated under reduced pressure to give the desired compound in near-quantitative yield, which was used without further purification in the next step.

Intermediate Y

2-Chloro-5,7-difluoro-1,3-benzothiazole

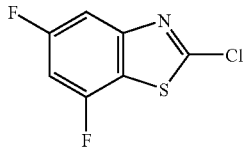

N-(3,5-Difluorophenyl) thiourea

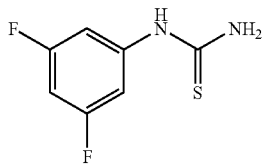

Step 1. Benzoyl chloride (5.44 g, 38.73 mmol) was added to a stirred solution of ammonium thiocyanate (3.83 g, 50.35 mmol) in acetone (80 mL) at 30° C. The mixture was stirred at reflux for 30 minutes, then cooled to 50° C., and a solution of 3,5-difluoroaniline (5.00 g, 38.73 mmol) in acetone (10 mL) was added in one portion. The mixture was stirred at reflux for 30 minutes. A solution of NaOH (5.42 g, 135.54 mmol) in water (65 mL) was added, and the mixture was stirred at reflux for 20 minutes and then cooled to 20° C. Concentrated HCl was added to adjust the acidity to pH=5, and then the mixture was adjusted to slightly alkaline by the addition of conc. ammonium hydroxide. After 30 minutes, the mixture was cooled to 10° C. and extracted with EtOAc, and the combined organic layer was washed with brine, filtered, and concentrated to afford N-(3,5-difluorophenyl) thiourea (3.52 g, 48%). ret. time 1.73; m/z 189.0 (MH$^+$); $^1$H NMR (400 MHz, MeOH-d$_4$) δ 6.72 (m, 1H), 7.16 (m, 2H).

5,7-Difluoro-1,3-benzothiazol-2-amine

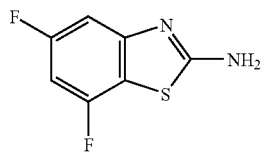

Step 2. To a suspension of N-(3,5-difluorophenyl) thiourea (3.40 g, 18.07 mmol) in DCE (95 mL) was added a solution of bromine in DCE (5 mL) below 30° C. The mixture was heated at reflux for 2.5 h, then cooled to 10° C., and the precipitate formed was collected by filtration and washed with DCE. The solid was stirred with water (200 mL), basified by treatment with conc. ammonium hydroxide, filtered, and dried in a vacuum oven to afford 5,7-difluoro-1,3-benzothiazol-2-amine (3.05 g, 90%). ret. time 2.18; m/z 187.1 (NH$^+$); $^1$H NMR (400 MHz, DMSO-d$_6$) δ 6.92 (m, 1H), 7.00 (m, 2H), 7.92 (s, 2H).

2-Chloro-5,7-difluoro-1,3-benzothiazole

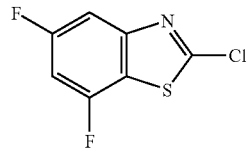

Step 3. To a solution containing copper chloride (H) (0.89 g, 6.64 mmol) and tri(ethylene glycol) dimethyl ether (6 mL) in acetonitrile (60 mL) was added isoamyl nitrite (0.97 g, 8.30 mmol) and the reaction mixture was stirred at rt for 30 minutes. To this suspension was added dropwise a solution of 5,7-difluoro-1,3-benzothiazol-2-amine (1.03 g, 5.53 mmol) in tri(ethylene glycol) dimethyl ether (20 mL) and acetonitrile (30 mL). The reaction mixture was stirred at rt for 10 minutes and heated at 50° C. for 2.5 h. The reaction mixture was cooled to rt, and then poured cautiously into cold aqueous 6 M HCl (400 mL). The solution was extracted with EtOAc. The organic layer was washed with HCl (1.0 M), water and brine, filtered, and concentrated. The residue was purified by flash chromatography (Biotage Flash 40M) using 5% ethyl acetate in hexane to afford 2-chloro-5,7-difluoro-1,3-benzothiazole (0.55 g, 48%). $^1$H NMR (400 MHz, CD$_2$Cl$_2$) 7.02 (m, 1H), 7.52 (m, 1H).

In a similar manner to the procedures described above, additional 2-chloro-1,3-benzothiazoles were prepared from the corresponding 2-amino-1,3-benzothiazoles, such as:

(a) 2-chloro-6-ethoxy-1,3-benzothiazole (LC-MS m/z 214.2 (MH$^+$), ret. time 3.09 min);
(b) 2-chloro-6-fluoro-1,3-benzothiazole (HPLC ret. time 2.85 min);
(c) 2-chloro-6-methyl-1,3-benzothiazole (LC-MS m/z 184.2 (MH$^+$), ret. time 3.09 min);
(d) 2-chloro-5,7-dimethyl-1,3-benzothiazole (LC-MS m/z 198.1 (MH$^+$), ret. time 3.36 min);
(e) 2-chloro-5,6-dimethyl-1,3-benzothiazole (LC-MS m/z 198.2 (MH$^+$), ret. time 3.34 min);
(f) 2-chloro-6-methylsulfonyl-1,3-benzothiazole (HPLC ret. time 2.18 min); and
(g) 2-chloro-5,7-difluoro-1,3-benzothiazole (TLC Rf 0.65, 40% EtOAc in hexane).

In certain cases the requisite 2-amino-1,3-benzothiazole was prepared from the corresponding thiourea as described above for the preparation of N-(3,5-difluorophenyl) thiourea and 5,7-difluoro-1,3-benzothiazol-2-amine.

Intermediate Z

2-Chloro-5-fluoro-1,3-benzothiazole

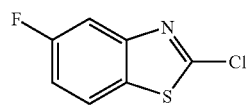

Sulfuryl chloride (50 μL, 0.65 mmol) was added neat to 5-fluoro-1,3-benzothiazole-2-thiol (100 mg, 0.54 mmol). The mixture was stirred at ambient temperature for 1 h, then heated at 60° C. for 30 minutes. The resulting solution was cooled to rt, and poured onto ice. The title compound was collected by filtration, washed with water, and dried under vacuum. The solid obtained was used without further purification; LC-MS m/z 188.1 (MH⁺), ret. time 3.27 min.

Intermediate AA

2-Chloro-5-(trifluoromethyl)benzothiazole

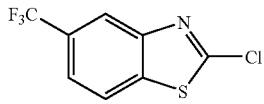

2-Mercapto-5-(trifluoromethyl)benzothiazole

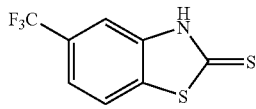

Step 1. To a mixture of sodium hydride (0.98 g, 40.91 mmol) and diethylene glycol monoethyl ether (25 mL) was added 2-chloro-5-(trifluoromethyl)aniline (5.00 g, 25.57 mmol) under a nitrogen atmosphere. The resulting mixture was stirred at rt for 30 minutes, and then carbon disulfide (3.89 g, 51.13 mmol) was added. The reaction mixture was then heated at 140° C. for 6 hours. After cooling the solution to rt, the product was precipitated by addition of conc. HCl, collected by filtration, and recrystallized from isopropyl ether to afford 2-mercapto-5-(trifluoromethyl)benzothiazole (2.65 g, 44%). ¹H NMR (400 MHz, DMSO-d₆) δ 7.49 (s, 1H), 7.61 (d, 1H), 7.94 (d, 1H).

2-Chloro-5-(trifluoromethyl)benzothiazole

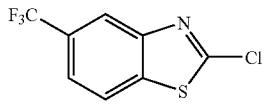

Step 2. Sulfuryl chloride (9.09 g, 67.33 mmol) was added with stirring to 2-mercapto-5-(trifluoromethyl)benzothiazole (2.64 g, 11.22 mmol) over a period of 5 minutes. The reaction mixture was then allowed to stand for approximately 1 h. Ice water was added to the reaction mixture with stirring to decompose the excess of sulfuryl chloride, and the product was then extracted with ethyl acetate. The organic layer was washed with water (3×) and brine, dried over anhydrous Na₂SO₄ and concentrated. The resulting solid was dissolved in EtOAc and filtered though a short silica-gel column, eluting with EtOAc, to give 2-chloro-5-(trifluoromethyl)benzothiazole (2.50 g, 94%). LC-MS m/z 238.0 (MH⁺), ret. time 2.55 min; ¹H NMR (400 MHz, DMSO-d₆) δ 7.81 (d, 1H), 8.38 (m, 2H).

Intermediate BB

2-Chloro-6-(trifluoromethyl)benzothiazole

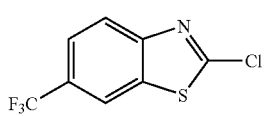

2-Mercapto-6-(trifluoromethyl)benzothiazole

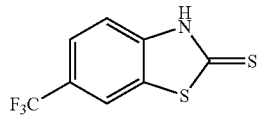

Step 1. A mixture of 2-chloro-4-trifluoromethylaniline (15.0 g, 76.7 mmol) and potassium O-ethyl dithiocarbonate (29.5 g, 184.1 mmol) in 75 mL anhydrous DMF was heated at 130° C. overnight under a nitrogen atmosphere. The reaction mixture was cooled to rt, and then 1 N HCl solution (200 mL) was added with stirring to induce precipitation. After the mixture was stirred for 30 minutes, the solid precipitate was collected by filtration and rinsed with water. The filter cake was dissolved in 100 mL EtOAc, and the solution was dried over Na₂SO₄. EtOAc was removed by rotary evaporation, and the residue was dried in vacuo to afford the desired product as a white solid (18.0 g, 99%). ¹H NMR (DMSO-d₆) δ 14.00 (bs, 1 H), 8.20 (s, 1 H), 7.70 (d, 1 H), 7.40 (d, 1 H); GC-EIMS m/z 235 (M⁺).

2-Chloro-6-(trifluoromethyl)benzothiazole

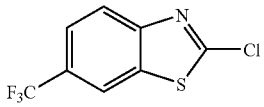

Step 2. Sulfuryl chloride (40 mL) was added with stirring to 2-mercapto-6-(trifluoromethyl)-benzothiazole (18.0 g, 76.7 mmol) at <20° C. under a nitrogen atmosphere, and the suspension was then stirred at rt for 2 h. The reaction mixture was poured into ice water with stirring. Precipitation was formed, and stirring was continued for 2 h. The solid precipitate was filtered, and rinsed with water. The wet filter cake was dissolved in 100 mL EtOAc, and the solution was washed with 100 mL water and 50 mL saturated aqueous NaHCO₃ solution, then dried over Na₂SO₄. EtOAc was removed by rotary evaporation, and the residue was dried in vacuo to afford the desired product as a light yellow solid (16.5 g, 91%). GC-EIMS m/z 237 (M⁺); ¹H NMR (CDCl₃) δ 8.10 (s, 1 H), 8.00 (d, 1 H), 7.70 (d, 1 H).

In a similar manner to the procedures described above, additional 2-chloro-1,3-benzothiazoles were prepared from the corresponding 2-mercapto-1,3-benzothiazoles, such as 2-chloro-5-fluoro-1,3-benzothiazole (LC-MS m/z 188.1 (MH⁺), ret. time 3.27 min). Additional 2-chloro-1,3-benzothiazoles were commercially available, such as 2-chlorobenzothiazole, 2,6-dichlorobenzothiazole, 2,4-dichlorobenzothiazole, 2-chloro-6-methoxy-1,3-benzothiazole, 2-chloro-5-methoxy-1,3-benzothiazole, and 2-chloro-6-nitro-1,3-benzothiazole. Certain 2-bromo-thiazoles were commercially available, such as 2-bromo-thiazole and 2-bromo-5-nitro-thiazole.

Intermediate CC

5-Chloro-2-methanesulfonylbenzothiazole

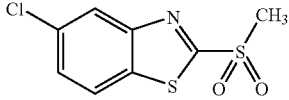

5-Chloro-2-methylsulfanyl-benzothiazole

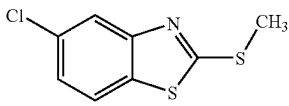

Step 1. To 5-chlorobenzothiazole-2-thiol (1.00 g, 4.96 mmol) in anhydrous tetrahydrofuran (20 mL) was added powdered potassium carbonate (1.37 g, 9.92 mmol) as a solid. Iodomethane (0.62 mL, 1.41 g, 9.92 mmol) was then added neat to the mixture, with rapid stirring. After stirring for 18 h, solids were removed by filtration. The filtrate was concentrated under vacuum to provide the title compound as a waxy yellow solid (1.0 g, 93%). $^1$H NMR (300 MHz, CDCl$_3$) δ 7.77 (s, 1 H), 7.57 (d, 1 H), 7.21–7.17 (m, 1 H), 2.72 (s, 3 H); LC-MS m/z 216.2 (MH$^+$), retention time 3.20 minutes. TLC R$_f$ 0.72 (2:1 hexanes/ethyl acetate).

5-Chloro-2-methanesulfonylbenzothiazole

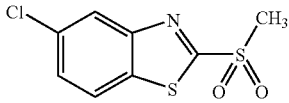

Step 2. To a 0° C. solution of 5-chloro-2-methylsulfanyl-benzothiazole (1.00 g, 4.64 mmol) in dichloromethane (25 mL) was added 3-chloroperoxybenzoic acid (50%, 3.20 g, 9.27 mmol). The solution was stirred at rt for 24 h, and saturated aqueous Na$_2$S$_2$O$_5$ solution was added to destroy any unreacted peracid. The layers were separated, and the organic layer was washed with saturated aqueous sodium bicarbonate solution and brine, then dried (MgSO$_4$) and concentrated under reduced pressure to a yellow solid. The crude solid was triturated with hexanes, collected by filtration, and air-dried to provide the title compound as a pale yellow solid (0.96 g, 83%). $^1$H NMR (300 MHz, CDCl$_3$) δ 8.17 (s, 1 H), 8.04 (d, 1 H), 7.41 (dd, 1 H), 3.40 (s, 3 H); LC-MS m/z 248.0 (MH$^+$), retention time 3.05 minutes. TLC R$_f$ 0.36 (2:1 hexanes/ethyl acetate).

Intermediate DD

6-Methyl-2-(methylsulfonyl)-1,3-benzoxazole

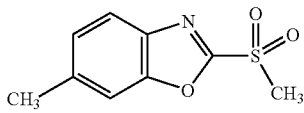

6-Methyl-1,3-benzoxazole-2(3H)-thione

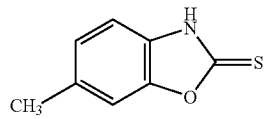

Step 1. A mixture of 6-amino-m-cresol (593.7 mg, 4.82 mmol) and potassium O-ethyl xanthate (850 mg, 5.30 mmol) in pyridine (10 mL) was stirred and heated to reflux for 2 h. It was cooled to rt, poured into a mixture of ice-water (40 mL), and concentrated HCl (4 mL). The solid was collected, washed with water, and dried in the hood overnight and then in a vacuum oven at 45° C. for 3 h. The product 6-methyl-1,3-benzoxazole-2(3H)-thione was obtained as beige powder (735 mg, yield 92.3%). $^1$H NMR (300 MHz, DMSO-d$_6$) δ 7.10 (s, 1 H), 7.03 (d, 2 H), 2.42 (s, 3H); LC-MS ret. time 2.37 min (method 2), m/z 166.0 (MH$^+$).

6-Methyl-2-(methylsulfanyl)-1,3-benzoxazole

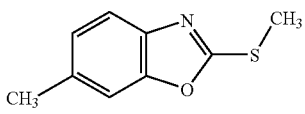

Step 2. 6-Methyl-1,3-benzoxazole-2(3H)-thione (375 mg, 2.27 mmol) was dissolved in THF (2.0 mL), and iodomethane (1610.8 mg, 11.35 mmol) and potassium carbonate (627.36 mg, 4.54 mmol) were added. This reaction mixture was stirred vigorously at rt overnight. The reaction mixture was filtered and the solid was rinsed with additional THF. The filtrate was concentrated in vacuo to a yellow solid. The solid was partitioned between ethyl acetate and water. The organic layer was separated and washed with brine, dried with MgSO$_4$, and concentrated. The solid was dried for 1 h in a 50° C. oven. The product 6-methyl-2-(methylsulfanyl)-1,3-benzoxazole was obtained as yellow solid (145 mg, 35.6%). $^1$H NMR (300 MHz, DMSO-d$_6$) δ 7.50 (d, 1 H), 7.20 (s, 1 H), 7.10 (d, 1 H), 2.78 (s, 3 H), 2.42 (s, 3 H); LC-MS ret. time 2.90 min (method 2), m/z 180.1 (MH$^+$).

6-Methyl-2-(methylsulfonyl)-1,3-benzoxazole

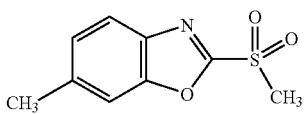

Step 3. meta-Chloroperoxybenzoic acid (1.37 g, 6.14 mmol) was added to a solution of 6-methyl-2-(methylsulfanyl)-1,3-benzoxazole (500 mg, 2.79 mmol) in dichloromethane (20 mL) at 0° C. The reaction was warmed to rt and stirred at rt for a total of 48 h. The reaction was transferred to a separatory funnel, washed with saturated aqueous NaHCO$_3$ (3×5 mL) and brine (10 mL), dried with MgSO$_4$, and concentrated without heating. The product 6-methyl-2-(methylsulfonyl)-1,3-benzoxazole (200 mg, 33.9%) was obtained as pale yellow solid. GC-MS ret. time 10.53 min, m/z 211 (MH$^+$).

In a similar manner to the preceding example, the following 2-(methylsulfonyl)-1,3-benzoxazoles were prepared:
(a) 6-chloro-2-(methylsulfonyl)-1,3-benzoxazole;
(b) 6-methoxy-2-(methylsulfonyl)-1,3-benzoxazole;
(c) 5-methyl-2-(methylsulfonyl)-1,3-benzoxazole;
(d) 4-methyl-2-(methylsulfonyl)-1,3-benzoxazole;
(e) 2-(methylsulfonyl)-5,6,7,8-tetrahydronaphtho[2,3-d][1,3]oxazole;
(f) 5-fluoro-2-(methylsulfonyl)-1,3-benzoxazole;
(g) 6-fluoro-2-(methylsulfonyl)-1,3-benzoxazole;
(h) 5-isopropyl-2-(methylsulfonyl)-1,3-benzoxazole;
(i) 5-n-propyl-2-(methylsulfonyl)-1,3-benzoxazole; and
(j) 5,6-dimethyl-2-(methylsulfonyl)-1,3-benzoxazole.

Intermediate EE

2-Chloro-5,6-difluoro-1H-benzimidazole

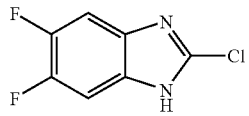

5,6-Difluoro-1H-benzimidazol-2-amine

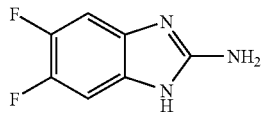

Step 1. The procedure used was similar to that reported in J. Med. Chem. 40:811–818, 1997. A solution of 1,2-diamino-4,5-difluorobenzene (500 mg, 3.47 mmol) in water (5 mL) was cooled to 0° C. and then treated with a solution of cyanogen bromide (0.83 mL, 4.16 mmol, 5 M in acetonitrile) and solid sodium bicarbonate (583 mg, 6.94 mmol). The solution was stirred at rt overnight and was then concentrated in vacuo. The dark residue was suspended in ethanol and heated at reflux for 15 minutes. The hot suspension was filtered, rinsing with hot ethanol, and the filtrate was concentrated in vacuo to afford 5,6-difluoro-1H-benzimidazol-2-amine (580 mg, 59%), which was used in the next step without further purification. LC-MS m/z 170.2 (MH$^+$), ret. time 0.85 min; $^1$H NMR (300 MHz, DMSO-d$_6$) δ 6.30 (br s, 2H), 7.06 (dd, 2H), 10.79 (br s, 1H).

2-Chloro-5,6-difluoro-1H-benzimidazole

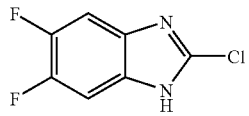

Step 2. The procedure used was similar to that reported in J. Med. Chem. 40:811–818, 1997. To a mixture of copper(II) chloride (795 mg, 5.91 mmol) in acetone (20 mL) was added tert-butyl nitrite (0.53 mL, 4.43 mmol). The reaction mixture was stirred at rt for 20 minutes, 5,6-difluoro-1H-benzimidazol-2-amine (500 mg, 2.96 mmol) was then added, and the mixture was heated at reflux for 2 h (with additional portions of tert-butyl nitrite added every 0.5 h). The reaction mixture was then cooled to rt, treated with 2 N HCl, and extracted with ethyl acetate. The organic phase was dried over sodium sulfate and concentrated in vacuo to afford 2-chloro-5,6-difluoro-1H-benzimidazole (580 mg, 73%), which was used without further purification in the next step. LC-MS m/z 189.2 (MH$^+$), ret. time 1.96 min; $^1$H NMR (300 MHz, DMSO-d$_6$) δ 7.62 (t, 2H), 13.5 (br s, 1H).

Certain 2-chlorobenaimidazoles were commercially available such as 2-chlorobenzimidazole and 2-chloro-5-methoxybenzimidazole.

Preparation of Compounds of Formula (IX)

Intermediate FF

N-(4-Bromophenyl)-6-(trifluoromethyl)-1H-benzimidazol-2-amine

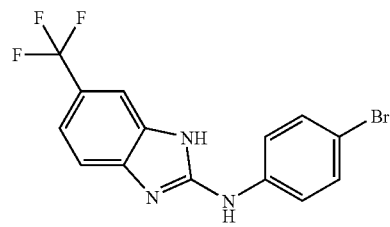

1,2-Diamino-5-trifluoromethylbenzene (0.25 g, 1.42 mmol) was diluted in toluene (5 mL) and treated with 4-bromophenylisothiocyanate (0.30 g, 1.42 mmol). The dark solution was stirred at 100° C. for 15 minutes, then treated with 1,3-dicyclohexylcarbodiimide (0.44 g, 2.13 mmol). The reaction was maintained at 100° C. for 5 h. The reaction was concentrated and partitioned between ethyl acetate and water. The organic layer was separated, dried (MgSO$_4$), and concentrated under reduced pressure. The dark brown oil was purified by flash chromatography on silica gel, eluting with a gradient from 9:1 hexanes/ethyl acetate to 100% ethyl acetate. The title compound was obtained as a light pink solid (0.50 g, 30%). $^1$H NMR (300 MHz, DMSO-d$_6$) δ 11.3 (broad d, 1 H), 9.87 (d, 1 H), 7.50 (d, 2 H), 7.61 (d, 1 H), 7.55–7.42 (m, 3 H), 7.35–7.30 (m, 1 H); LC/MS m/z 356.2 (MH$^+$), retention time 2.33 minutes.

Intermediate GG

N-(4-Bromo-2-fluorophenyl)-N-[5-(trifluoromethyl)-1H-benzimidazol-2-yl]amine

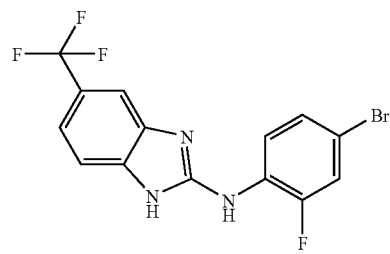

1,2-Diamino-5-trifluoromethylbenzene (0.50 g, 2.84 mmol) was diluted in dichloromethane (5 mL) and treated with 4-bromo-2-fluoro-phenylisothiocyanate (0.66 g, 2.84 mmol). The dark solution was stirred at 45° C. for 15 minutes, then 1,3-dicyclohexylcarbodiimide (0.44 g, 2.13 mmol) was added all at once. The reaction was heated in a 45° C. oil bath overnight, then cooled and concentrated at reduced pressure. The dark residue was diluted with ethyl acetate, and the organic layer was washed with water. The organic layer was dried (MgSO₄) and concentrated in vacuo. The resulting dark brown oil was purified by flash chromatography on silica gel eluted on a gradient from 9:1 hexanes/ethyl acetate to 100% ethyl acetate. The title compound was collected as a light pink solid (0.60 g, 57%). $^1$H NMR (300 MHz, DMSO-d₆) δ 11.3 (broad d, 1H), 9.87 (d, 1H), 7.50 (d, 2H), 7.61 (d, 1H), 7.55–7.41 (m, 3H), 7.35–7.30 (m, 1H); LC/MS m/z 356.2 (MH⁺), retention time 2.33 minutes.

Intermediate HH

N-(4-Iodophenyl)6-methyl-1,3-benzothiazol-2-amine

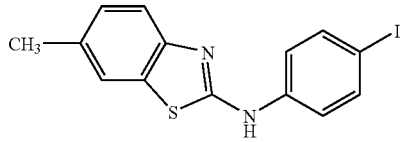

N-(4-Iodophenyl)-N'-(4-methylphenyl) thiourea

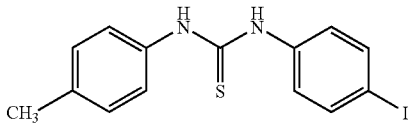

Step 1. A solution of p-tolyl thiocyanate (0.65 g, 4.35 mmol) and p-iodo-aniline (1.00 g, 4.57 mmol) in EtOH was heated at reflux for 3 h. Then the reaction mixture was diluted with EtOH and the precipitate was collected by filtration, washed with EtOH and ether, and dried in a vacuum oven to give N-(4-iodophenyl)-N'-(4-methylphenyl) thiourea (1.32 g, 90% purity, 74% yield). $^1$H NMR (400 MHz, DMSO-d₆) δ 1.78 (s, 3H), 7.12 (d, 2H), 7.29 (m, 4H), 7.63 (m, 2H), 9.72 (s, 1H), 9.76 (s, 1H).

N-(4-Iodophenyl)-6-methyl-1,3-benzothiazol-2-amine

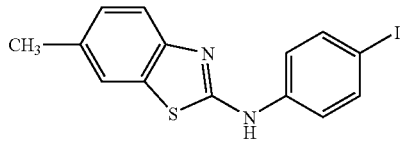

Step 2. A suspension of N-(4-iodophenyl)-N'-(4-methylphenyl) thiourea (0.62 g, 4.68 mmol) in chloroform (23 mL) was treated with a solution of bromine (2.65 g, 16.59 mmol) in chloroform (1 mL). The reaction mixture was stirred at rt for 5 minutes and then heated at 50° C. for 5 minutes. Then the reaction mixture was allowed to cool, and was treated with sulphurous acid until the orange color disappeared. The reaction mixture was neutralized by treatment with conc. ammonium hydroxide. More chloroform was then added to dissolve the precipitate. The layers was separated, and the organic layer was washed with water and brine, dried over sodium sulfate, filtered and, concentrated to give N-(4-iodophenyl)-6-methyl-1,3-benzothiazol-2-amine (0.6 g, 97%). $^1$H NMR (400 MHz, DMSO-d₆) δ 2.36 (s, 3H), 7.12 (m, 1H), 7.48 (d, 1H), 7.60 (m, 3H), 7.65 (m, 2H), 10.50 (s, 1H).

Intermediate II

N-(4-Bromo-2-fluorophenyl)-4-methyl-1,3-benzothiazol-2-amine

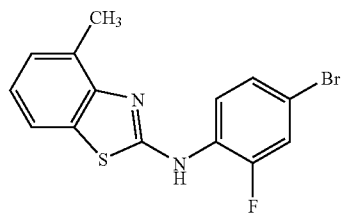

To a solution of 2-chloro-4-methyl-1,3-benzothiazole (0.25 g, 1.36 mmol) in n-BuOH (8 mL) was added 4-bromo-2-fluoroaniline (0.52 g, 2.72 mmol) and HCl (4.0 M in dioxane, 0.5 mL). The reaction was heated at 90° C. overnight. Solvent was removed by rotary evaporation and 1 N aqueous HCl was added. The aqueous layer was separated and extracted with EtOAc. The combined organic phases were washed with 1 N aqueous HCl and brine, dried over Na₂SO₄, filtered, and concentrated in vacuo. The residue was brought up in MeOH and the precipitate was collected by filtration, washed with MeOH, and dried in a vacuum oven to give N-(4-bromo-2-fluorophenyl)-4-methyl-1,3-benzothiazol-2-amine (0.41 g, 89%). $^1$H NMR (400 MHz, DMSO-d₆) δ 2.62 (s, 3H), 7.07 (t, 1H), 7.15 (d, 1H), 7.36 (m, 2H), 7.51 (d, 1H), 8.72 (t, 1H).

Intermediate JJ

N-(4-Bromo-2-fluorophenyl)-N-(6-trifluoromethoxy-1,3-benzothiazo-1-2-yl)amine

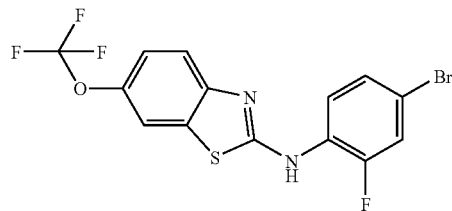

In a 250-mL round-bottom flask, 2-chloro-6-trifluoromethoxy-1,3-benzothiazole (5.36 g, 21.14 mmol) and 4-bromo-2-fluoroaniline (4.82 g, 25.36 mmol) were combined in 100 mL n-butanol containing 1% 4.0 M HCl in dioxane, and heated at 90° C. overnight. The mixture was cooled to rt and the solvent was removed under reduced pressure. Ethyl acetate (50 mL) was added, and the mixture was ultrasonicated by suspending the flask in an ultrasonication bath for 30 minutes. The mixture was filtered, and the filtrate was concentrated under reduced pressure. Acetonitrile (50 mL) was added to the mixture, which was then ultrasonicated for 30 minutes and then filtered to provide the product as a white solid (5 g, 58%). LC-MS m/z 409.1 (MH⁺), ret. time 4.02 min.

Intermediate KK

N-(4-Bromo-2-fluorophenyl)-N-(6-fluoro-1,3-benzothiazol-2-yl)amine

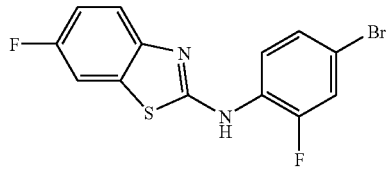

In a similar manner to that described above for the preparation of N-(4-bromo-2-fluorophenyl)-4-methyl-1,3-benzothiazol-2-amine and N-(4-bromo-2-fluorophenyl)-N-(6-trifluoromethoxy-1,3-benzothiazol-2-yl)amine, using 2-chloro-6-fluoro-1,3-benzothiazole and 2-fluoro-4-bromoaniline, was prepared the desired product as a white solid (78% yield). $^1$H NMR (400 MHz, DMSO-d$_6$) δ 10.50 (s, 1H), 8.60 (t, 1H), 7.80 (d, 1H), 7.60 (m, 2H), 7.40 (d, 1H), 7.20 (m, 1H).

In a similar manner to the procedures described above, the following N-(4-bromophenyl)-N-(1,3-benzothiazol-2-yl) amines were prepared from the appropriate 4-bromoanilines and 2-chloro-1,3-benzothiazoles:
(a) N-(4-bromophenyl)-N-(5-trifluoromethyl-1,3-benzothiazol-2-yl)amine (LC-MS m/z 373.0 (MH$^+$), ret. time 3.92 min);
(b) N-(4-bromo-2-fluorophenyl)-N-(5-trifluoromethyl-1,3-benzothiazol-2-yl)amine (LC-MS m/z 391.0 (MH$^+$), ret. time 4.04 min (method 2));
(c) N-(4-bromo-2-fluorophenyl)-N-(6-trifluoromethyl-1,3-benzothiazol-2-yl)amine (LC-MS m/z 391.0 (MH$^+$), ret. time 3.95 min);
(d) N-(4-bromo-2-fluorophenyl)-N-(5,7-dimethyl-1,3-benzothiazol-2-yl)amine (LC-MS m/z 353.1 (MH$^+$), ret. time 4.09 min);
(e) N-(4-bromo-2-fluorophenyl)-N-(5,7-difluoro-1,3-benzothiazol-2-yl)amine (LC-MS m/z 359.1 (MH$^+$), ret. time 3.86 min);
(f) N-(4-bromo-2-fluorophenyl)-N-(6-methoxy-1,3-benzothiazol-2-yl)amine (LC-MS m/z 353.2 (MH$^+$), ret. time 3.55 min);
(g) N-(4-bromo-2-fluorophenyl)-N-(1,3-benzothiazol-2-yl) amine (LC-MS m/z 323.1 (MH$^+$), ret. time 3.55 min);
(h) N-(4-bromophenyl)-N-(6-isopropyl-1,3-benzothiazol-2-yl)amine (LC-MS m/z 347.2 (MH$^+$), ret. time 4.44 min); and
(i) N-(4-bromo-2-fluorophenyl)-N-(6-isopropyl-1,3-benzothiazol-2-yl)amine (LC-MS m/z 365.2 (MH$^+$), ret. time 4.57 min).

Intermediate LL

N-(4-Iodo-2-fluorophenyl)-6-chloro-1,3-benzothiazol-2-amine

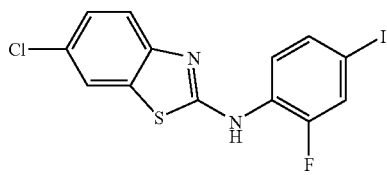

A mixture of 2,6-dichlorobenzothiazole (1.0 g, 4.9 mmol) and 2-fluoro-4-iodoaniline (2.32 g, 9.8 mmol) in 20 mL BuOH was stirred at 90° C., and then HCl (4 M in dioxane, 1.0 mL) was added. The reaction mixture was stirred with heating at 90° C. overnight, under argon. NMR analysis then showed little 2,6-dichlorobenzothiazole remaining. After BuOH was removed by rotary evaporation, EtOAc (100 mL) and 1 N aqueous HCl (100 mL) were added. The organic layer was separated and washed with 1 N aqueous HCl (100 mL), saturated Na$_2$O$_2$S$_3$ solution (50 mL), water (100 mL), and then dried over Na$_2$SO$_4$. Removal of solvent under reduced pressure afforded a residue, which was triturated with EtOAc (10 mL) and hexanes (40 mL). The solid was filtered and dried in vacuo to a constant weight, to afford the desired product as a light purple solid (0.75 g, 38%). $^1$H NMR (DMSO-d$_6$) δ 10.45 (s, 1H), 8.35 (t, 1H), 7.95 (s, 1H), 7.70 (d, 1H), 7.58 (d, 2H), 7.30 (d, 1H).

Intermediate MM

N-(4-Bromophenyl)-N-(5-methyl-1,3-benzoxazol-2-yl)amine

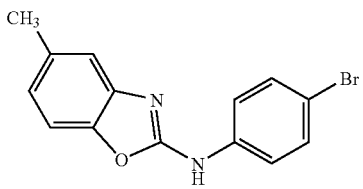

In a 250-mL round-bottom flask, 1-bromo-4-isothiocyanatobenzene (4.28 g, 20 mmol) and 2-amino-4-methylphenol (2.46 g, 20 mmol) were stirred in 120 mL ethanol at rt overnight. The formation of N-(4-bromophenyl)-N'-(2-hydroxy-5-methylphenyl)thiourea was confirmed by LC-MS. To the mixture, 1.5 eq. 1-(3-dimethylaminopropyl)-3-ethylcarbodiimide hydrochloride (EDCI) was added, and the reaction was stirred at rt for another 2 h. The reaction mixture was then heated at reflux for 6 h. The mixture was cooled to rt and the solvent was removed under reduced pressure. The solid was dissolved in EtOAc and washed with 2 N aqueous HCl and H$_2$O. The organic layer was dried (MgSO$_4$) and the solvent was removed under reduced pressure. The solid obtained was ultrasonicated in 30 mL ether and filtered to give the desired compound (3.64 g, 60%). $^1$H NMR (400 MHz, DMSO-d$_6$) δ 10.70 (s, 1 H), 7.70 (m, 2 H), 7.55 (m, 2 H), 7.35 (d, 1 H), 7.25 (s, 1 H), 6.95 (d, 1 H), 2.40 (s, 3 H). LC-MS m/z 303.3 (MH$^+$), ret. time 3.46 min.

Intermediate NN

N-(4-Bromophenyl)-5-(trifluoromethyl)-1,3-benzoxazol-2-amine

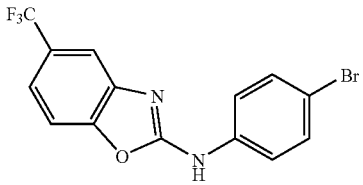

2-Amino-4-(trifluoromethyl)phenol

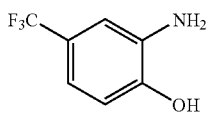

Step 1. To a suspension of palladium hydroxide (3.05 g, 21.7 mmol) in methanol was added a methanol solution of 2-nitro-4-(trifluoromethyl)phenol (1.00 g, 4.8 mmol) followed by solid ammonium formate (3.04 g, 48.3 mmol). The mixture was heated at 85° C. and monitored by TLC. The completed reaction was allowed to cool to rt and was filtered through a pad of Celite®, washing with ethyl acetate. The filtrate was concentrated under reduced pressure to provide the title compound (0.58 g, 67%). LC-MS m/z 178.1 (MH$^+$), retention time 0.55 minutes.

N-(4-Bromophenyl)-5-(trifluoromethyl)-1,3-benzoxazol-2-amine

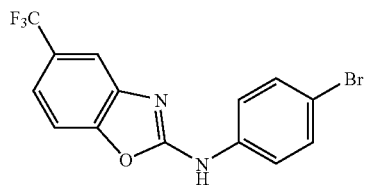

Step 2. 2-Amino-4-(trifluoromethyl)phenol (250 mg, 1.41 mmol) and 1-bromo-4-isothio-cyanatobenzene (302 mg, 1.41 mmol) were stirred in ethyl alcohol at ambient temperature for 18 h. The flask was charged with 1-[3-(dimethylamino)propyl]-3-ethylcarbodiimide hydrochloride (EDCI) (405 mg, 2.12 mmol), and the mixture was stirred for 2 h before being heated at reflux overnight. The reaction was allowed to cool to rt and was concentrated under reduced pressure. The residue was dissolved in ethyl acetate and washed with 2 N aqueous hydrochloric acid solution and water, dried (Na$_2$SO$_4$), and concentrated in vacuo. The residue was purified by flash chromatography on silica gel, eluting with 85:15 hexanes/ethyl acetate to provide the title compound (315 mg, 62%). LC-MS m/z 357.1 (MH$^+$), retention time 4.20 minutes.

Intermediate OO

N-(4-Bromo-2-fluorophenyl)-5(trifluoromethyl-1,3-benzoxazol-2-amine

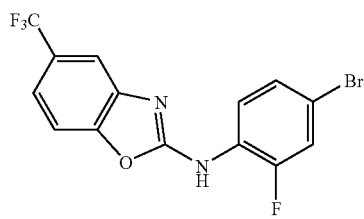

2-Amino-4-(trifluoromethyl)phenol (580 mg, 3.25 mmol) and 4-bromo-2-fluoro-1-isothio-cyanatobenzene (750 mg, 3.25 mmol) were stirred in ethyl alcohol at ambient temperature for 18 h. The flask was charged with 1-[3-(dimethylamino)propyl]-3-ethylcarbodiimide hydrochloride (EDCI) (405 mg, 2.12 mmol), and the mixture was stirred for 2 h before being heated at reflux overnight. The reaction was allowed to cool to rt and was concentrated under reduced pressure. The residue was dissolved in ethyl acetate and washed with 2 N aqueous hydrochloric acid solution and water, dried (Na$_2$SO$_4$), and concentrated in vacuo. The crude material was suspended in ether, sonicated, and the resulting solid was collected by filtration to provide the title compound (214 mg, 18%). LC-MS m/z 375.1 (MH$^+$), retention time 3.70 minutes.

In a similar manner to the procedures described above, the following N-(4-bromophenyl)-N-(1,3-benzoxazol-2-yl) amines were prepared from the appropriate 4-bromo-1-isothiocyanatobenzene and 2-aminophenol:

(a) N-(4-bromo-2-fluorophenyl)-N-(5-methyl-1,3-benzoxazol-2-yl)amine (LC-MS m/z 321.2 (MH$^+$), ret. time 3.69 min);

(b) N-(4-bromophenyl)-N-(6-methyl-1,3-benzoxazol-2-yl) amine (LC-MS m/z 303.2 (MH$^+$), ret. time 3.49 min).

Preparation of Compounds of Formula (I)

EXAMPLE 1

4-[4'-(1,3-Benzothiazol-2-ylamino)-1,1'-biphenyl-4-yl]-2,2-dimethyl-4-oxobutanoic acid

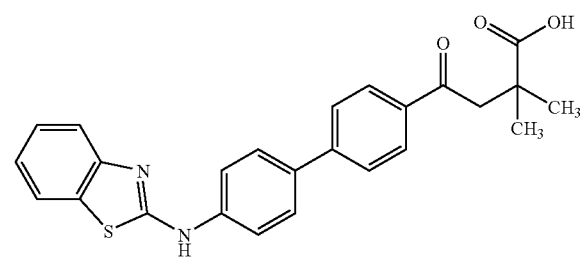

In a 8-mL screw-cap vial, a mixture of methyl 4-(4'-amino-1,1'-biphenyl-4-yl)-2,2-dimethyl-4-oxobutanoate (60 mg, 0.19 mmol) and 2chloro-1,3-benzothiazole (40 mg, 0.23 mmol) in 3 mL n-butanol were heated at 90° C. overnight. The formation of methyl 4-[4'-(1,3-benzothiazol-2-ylamino)-1,1'-biphenyl-4-yl]-2,2-dimethyl-4-oxobutanoate was monitored by LC-MS. The solvent was removed under reduced pressure. The residue was dissolved in 2 mL tetrahydrofuran/dioxane (1:1), and 3 equivalents of 1 N aqueous sodium hydroxide was added to the solution. The mixture was shaken at rt overnight and then at 50° C. for 2 h. The progress of the hydrolysis reaction was monitored by LC-MS. A solution of 1N aqueous HCl (3.1 equivalents) was then added to the mixture, and the solvent was removed under reduced pressure. The residue was redissolved in 2 mL methanol and a minimum amount of DMF, and the product was isolated and purified by preparative reverse-phase HPLC (water/acetonitrile gradient, containing 0.1% TFA) to give 40 mg of 4-[4'-(1,3-benzothiazol-2-ylamino)-1,1'-biphenyl-4-yl]-2,2-dimethyl-4-oxobutanoic acid (Yield: 45%). $^1$H NMR (400 MHz, DMSO-d$_6$) δ 11.90 (bs, 1 H), 10.65 (s, 1 H), 8.00 (d, 2 H), 7.90 (d, 2 H), 7.80 (m, 5 H), 7.60 (d, 1 H), 7.35 (t, 1 H), 7.20 (t, 1 H), 3.30 (s, 2 H), 1.10 (s, 6 H); LC-MS m/z 431.2 (MH$^+$), ret. time 3.40 min.

EXAMPLE 2

4-[4'-(1H-Benzimidazol-2-ylamino)-1,1'-biphenyl-4-yl]-2,2-dimethyl-4-oxobutanoic acid

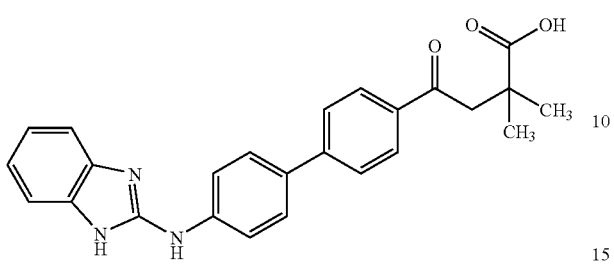

This compound was prepared from methyl 4-(4'-amino-1,1'-biphenyl-4-yl)-2,2-dimethyl-4-oxobutanoate (64 mg, 0.21 mmol) and 2-chloro-1H-benzimidazole (37.6 mg, 0.25 mmol) in a similar manner to the method described for 4-[4'-(1,3-benzothiazol-2-ylamino)-1,1'-biphenyl-4-yl]-2,2-dimethyl-4-oxobutanoic acid, providing 40.7 mg (48%) of the desired product. $^1$H NMR (400 MHz, DMSO-$d_6$) δ 12.00 (br s, 1 H), 11.05 (br s, 1 H), 8.05 (d, 2 H), 7.85 (m, 4 H), 7.65 (d, 2 H), 7.40 (m, 2 H), 7.10 (m, 2 H), 3.35 (s, 2 H), 1.25 (s, 6 H). LC-MS m/z 414.3 (MH$^+$), ret. time 2.27 min.

EXAMPLE 3

2,2-Dimethyl-4-oxo-4-[4'-(1,3-thiazol-2-ylamino)-1,1'-biphenyl-4-yl]butanoic acid

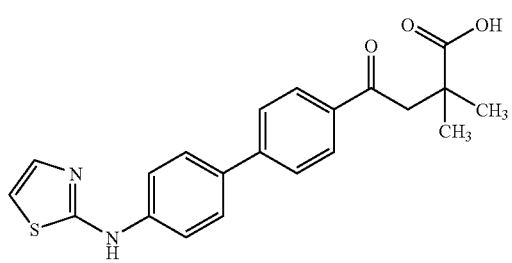

This compound was prepared from methyl 4-(4'-amino-1,1'-biphenyl-4-yl)-2,2-dimethyl-4-oxobutanoate (64 mg, 0.21 mmol) and 2-bromothiazole (41 mg, 0.25 mmol) in a similar manner to the method described for 4-[4'-(1,3-benzothiazol-2-ylamino)-1,1'-biphenyl-4-yl]-2,2-dimethyl-4-oxobutanoic acid, providing 18.6 mg (24%) of the desired product. LC-MS m/z 381.4 (MH$^+$), ret. time 2.53 min.

EXAMPLE 4

4-{4'-[(6-Chloro-1,3-benzothiazol-2-yl)amino]-1,1'-biphenyl-4-yl}-4-oxo-2-(2-phenylethyl)butanoic acid

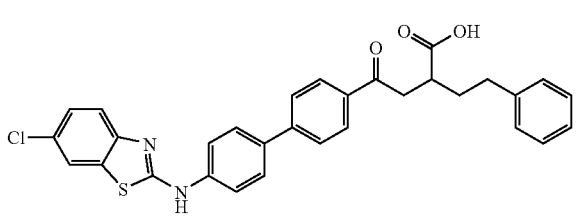

This compound was prepared from methyl 4-(4'-amino-1,1'-biphenyl-4-yl)-4-oxo-2-(2-phenylethyl)butanoate (78 mg, 0.20 mmol), 2,6-dichloro-1,3-benzothiazole (61.6 mg, 0.30 mmol) in a similar manner to the method described for 4-[4'-(1,3-benzothiazol-2-ylamino)-1,1'-biphenyl-4-yl]-2,2-dimethyl-4-oxobutanoic acid, providing 26.7 mg (25%) of the desired product. $^1$H NMR (400 MHz, DMSO-$d_6$) δ 10.80 (br s, 1 H), 7.75–8.05 (m, 9 H), 7.60 (d, 1 H), 7.10–7.40 (m, 6 H), 3.50 (q, 1 H), 3.10 (m, 1 H), 2.85 (m, 1 H), 2.65 (m, 2 H), 1.80 (m, 2 H). LC-MS m/z 541.3 (MH$^+$), ret. time 4.07 min.

EXAMPLE 5

2-(2-{4'-[(6-Chloro-1,3-benzothiazol-2-yl)amino]-1,1'-biphenyl-4-yl}-2-oxoethyl)pentanoic acid

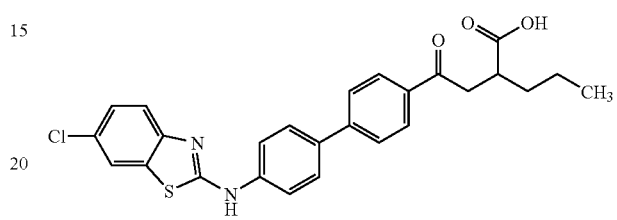

This compound was prepared from methyl 2-[2-(4'-amino-1,1'-biphenyl-4-yl)-2-oxoethyl]-pentanoate (68 mg, 0.20 mmol) and 2,6-dichloro-1,3-benzothiazole (61.3 mg, 0.30 mmol) in a similar manner to the method described for 4-[4'-(1,3-benzothiazol-2-ylamino)-1,1'-biphenyl-4-yl]-2,2-dimethyl-4-oxobutanoic acid, providing 17.2 mg (18%) of the desired product. $^1$H NMR (400 MHz, DMSO-$d_6$) δ 12.10 (br s, 1 H), 10.75 (br s, 1 H), 7.75–8.05 (m, 9 H), 7.60 (d, 1 H), 7.35 (m, 1 H), 3.40 (q, 1 H), 3.10 (m, 1 H), 1.55 (m, 2 H), 1.35 (m, 2 H), 0.85 (t, 3 H). LC-MS m/z 479.3 (MH$^+$), ret. time 3.88 min.

EXAMPLE 6

4-[4'-(1,3-Benzothiazol-2-ylamino)-1,1'-biphenyl-4-yl]-2-(2-methoxyethyl-4-oxobutanoic acid

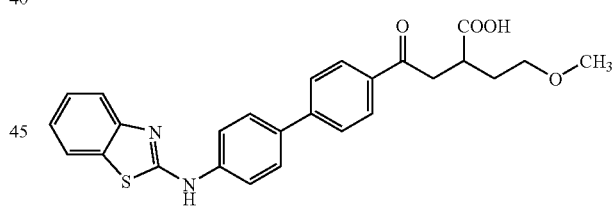

To a solution of ethyl 4-(4'-amino-1,1'-biphenyl-4-yl)-2-(2-methoxyethyl)-4-oxobutanoate (75 mg, 0.21 mmol) in butanol (4 mL), 2-chloro-benzothiazole (43 mg, 0.25 mmol) was added and the reaction mixture was heated at 90° C. overnight. The solvent was removed by rotary evaporation, the residue was redissolved in DMF (1 mL), a solution of 1 N aqueous NaOH (0.63 mL, 0.63 mmol) was added, and the mixture was stirred at rt overnight. A solution of 1 N aqueous HCl (0.3 mL, 0.3 mmol) and methanol (5 mL) were added to the reaction mixture, and the crude product was purified by preparative reverse-phase HPLC (water/acetonitrile gradient, containing 0.1% TFA) to afford 4-[4'-(1,3-benzothiazol-2-ylamino)-1,1'-biphenyl-4-yl]-2-(2-methoxyethyl)-4-oxobutanoic acid as a white solid (30 mg, 31%). $^1$H NMR (300 MHz, DMSO-$d_6$) δ 8.05 (d, 2 H), 7.95 (d, 2 H), 7.70 (m, 5 H), 7.60 (d, 1 H), 7.30 (t, 1 H), 7.15 (t, 2 H), 3.35 (m, 2 H), 3.25 (s, 3 H), 3.20 (m, 2 H), 2.90 (m, 1 H), 1.95–1.75 (m, 2 H); LC-MS ret. time 3.29 min (method 2), m/z 461.15 (MH$^+$).

EXAMPLE 7

4-{4'-[(6Chloro-1,3-benzothiazol-2-yl)amino]-1,1'-biphenyl-4-yl}-2-[2-(dimethylamino)ethyl]-4-oxobutanoic acid

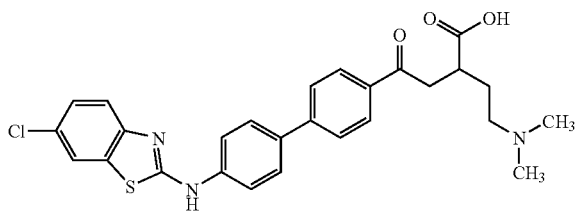

This compound was prepared from methyl 4-(4'-amino-1,1'-biphenyl-4-yl)-2-[2-(dimethyl-amino)ethyl]-4-oxobutanoate (60 mg, 0.17 mmol) and 2,6-dichloro-1,3-benzothiazole (51.8 mg, 0.25 mmol)) in a similar manner to the method described for 4-[4'-(1,3-benzothiazol-2-ylamino)-1,1'-biphenyl-4-yl]-2,2-dimethyl-4-oxobutanoic acid, providing 14.1 mg (13%) of the desired product as the trifluoroacetate salt. $^1$H NMR (400 MHz, CD$_3$OD) δ 8.10 (d, 2 H), 7.70–8.10 (m, 8 H), 7.30 (m, 1H), 3.60 (m, 1 H), 3.30–3.40 (m, 3 H), 3.10 (m, 1 H), 2.95 (s, 6 H), 2.20 (m, 1 H), 2.00 (m, 1 H). LC-MS m/z 508.1 (MH$^+$), ret. time 2.66 min.

EXAMPLE 8

(1R,2R)-2-({3'-Fluoro-4'-[(6-methoxy-1,3-benzothiazol-2-yl)amino]-1,1'-biphenyl-4-yl}carbonyl)cyclopentanecarboxylic acid

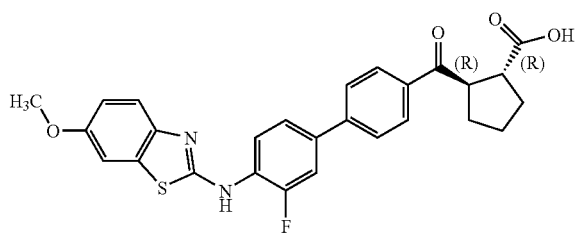

Butyl (1R,2R)-2-({3'-fluoro-4'-[(6-methoxy-1,3-benzothiazol-2-yl)amino]-1,1'-biphenyl-4-yl}carbonyl)cyclopentanecarboxylate

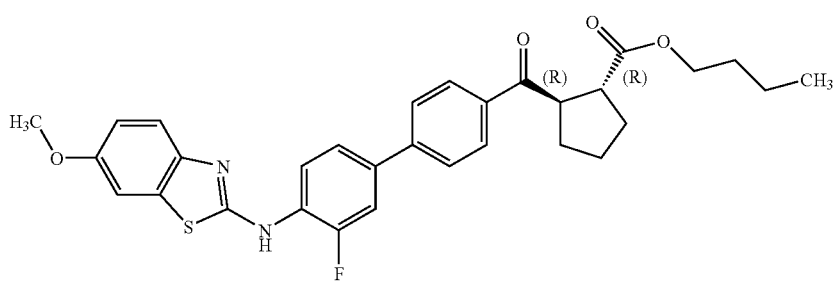

Step 1. Methyl (1R,2R)-2-[(4'-amino-3'-fluoro-1,1'-biphenyl-4-yl)carbonyl]cyclo-pentanecarboxylate (462 mg, 1.35 mmol) was dissolved in n-butanol (15 mL), and 6-methoxy-2-(methylsulfonyl)-1,3-benzothiazole (162 mg, 0.8 mmol) and 4 M aqueous HCl (1.5 mL) were added. The mixture was heated at 90° C. for 5 h. An additional portion of 6-methoxy-2-(methylsulfonyl)-1,3-benzothiazole (162 mg, 0.8 mmol) was added, and the mixture was stirred overnight at 90° C. Solvent was then removed by rotary evaporation, and the residue was purified by flash chromatography (Biotage Flash 40 M, 3:1 hexane/EtOAc) to afford butyl (1R,2R)-2-({3'-fluoro-4'-[(6-methoxy-1,3-benzothiazol-2-yl)amino]-1,1'-biphenyl-4-yl}carbonyl)cyclopentanecarboxylate (480 mg, 65%). LC-MS ret. time 4.36 min, m/z 547.3 (MH$^+$); $^1$H NMR (300 MHz, CDCl$_3$) δ 0.85 (t, 3H), 1.25–1.35 (m, 2H), 1.40–1.58 (m, 2H), 1.74–1.84 (m, 3H), 1.91–1.96 (m, 1H), 2.11-2.20 (m, 2H), 3.40–3.46 (m, 1H), 3.84 (s, 3H), 4.03 (t, 2H), 6.81–6.87 (m, 1H), 6.98 (dd, 1H), 7.18 (d, 1H), 7.40–7.52 (m, 2H), 7.64 (d, 2H), 8.14 (d, 2H), 8.42 (t, 1H).

(1R,2R)-2-({3'-Fluoro-4'-[(6-methoxy-1,3-benzothiazol-2-yl)amino]-1,1'-biphenyl-4-yl}-carbonyl)cyclopentanecarboxylic acid

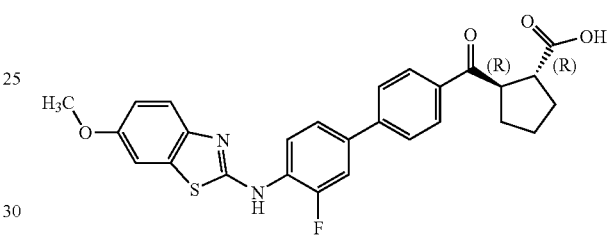

Step 2. To a solution of butyl (1R,2R)-2-({3'-fluoro-4'-[(6-methoxy-1,3-benzothiazol-2-yl)-amino]-1,1'-biphenyl-4-yl}carbonyl)cyclopentanecarboxylate in methanol (8 mL) was added 1 N aqueous sodium hydroxide (6.15 mL), and the mixture was stirred at 50° C. overnight. The solvent was then removed by rotary evaporation. Water (5 mL) was added to the residue, and the mixture was extracted with ethyl acetate. The aqueous layer was then treated with 1 N aqueous HCl to adjust the acidity to pH 2, and then extracted with ethyl acetate. The organic phase was evaporated under reduced pressure, and the residue was purified by flash chromatography (Biotage Flash 40S, 6:1 EtOAc/hexane) to afford (1R,2R)-2-({3'-fluoro-4'-[(6-methoxy-1,3-benzothiazol-2-yl)amino]-1,1'-biphenyl-4-yl}carbonyl)cyclopentanecarboxylic acid (129 mg, 30%, 89% ee). LC-MS ret. time 3.56 min, m/z 491.3 (MH$^+$); $^1$H NMR (300 MHz, DMSO-d$_6$) δ 1.58–1.84 (m, 4H), 1.96–2.01 (m, 1H), 2.14–2.17 (m, 1H), 3.22 (q, 1H), 3.77 (s, 3H), 4.02–4.10 (q, 1H), 6.94 (dd, 1H), 7.46 (d, 1H), 7.53 (d, 1H), 7.65–7.76 (m, 2H), 7.86 (d, 2H), 8.04 (d, 2H), 8.72 (t, 1H), 10.33 (br s, 1H).

EXAMPLE 9

2,2-Dimethyl-4-{4'-[(5-nitro-1,3-thiazol-2-yl)amino]-1,1'-biphenyl-4-yl}-4-oxobutanoic acid

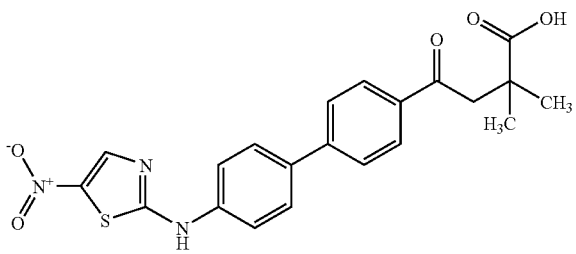

In a 8-mL screw-cap vial, a mixture of 4-(4'-amino-1,1'-biphenyl-4-yl)-2,2-dimethyl-4-oxobutanoic acid (60 mg, 0.20 mmol) and 2-bromo-5-nitro-1,3-thiazole (63.3 mg, 0.30 mmol) in 4 mL n-butanol was heated at 90° C. overnight. The solvent was removed under reduced pressure. The mixture was dissolved in 5 mL 1:4 MeOH/DMF and purified by reverse-phase HPLC to provide 8.9 mg (10%) of the desired product. $^1$H NMR (400 MHz, DMSO-$d_6$) δ 11.55 (br s, 1 H), 8.50 (s, 1 H), 7.70–8.05 (m, 8 H), 3.15 (d, 1 H), 1.25 (s, 6 H); LC-MS m/z 426.2 (MH$^+$), ret. time 3.12 min.

EXAMPLE 10

4-(4'-{[4-(4-Chlorophenyl)-1,3-thiazol-2-yl]amino}-1,1'-biphenyl-4-yl)-2,2-dimethyl-4-oxobutanoic acid

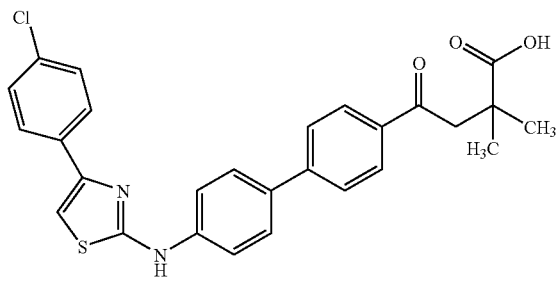

In a 8-mL screw-cap vial, a mixture of 4-(4'-amino-1,1'-biphenyl-4-yl)-2,2-dimethyl-4-oxobutanoic acid (60 mg, 0.20 mmol) and 2-(4-chlorophenyl)-2-oxoethyl thiocyanate (64 mg, 0.30 mmol) in 4 mL n-butanol was heated at 90° C. overnight. The solvent was removed under reduced pressure. The mixture was dissolved in 5 mL 1:4 MeOH/DMF and purified by reverse-phase HPLC to provide 6.8 mg (7%) of the desired product. $^1$H NMR (400 MHz, DMSO-$d_6$) δ 11.90 (br s, 1 H), 10.50 (s, 1 H), 7.75–8.00 (m, 10 H), 7.50 (m, 3 H), 3.30 (m, 2 H), 1.05 (s, 6 H); LC-MS m/z 491.2 (MH$^+$), ret. time 3.83 min.

EXAMPLE 11

4-[4'-(1,3-Benzoxazol-2-ylamino)-1,1'-biphenyl-4-yl]-4-oxo-2-(2-phenylethyl)butanoic acid

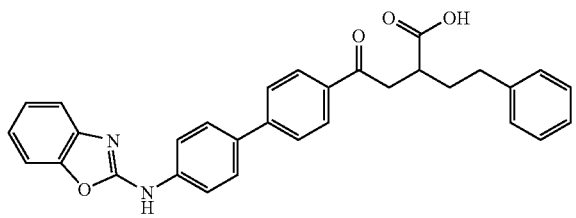

A solution of ethyl 4-(4'-amino-1,1'-biphenyl-4-yl)-4-oxo-2-(2-phenylethyl)butanoate (100 mg, 0.25 mmol) and 2-chlorobenzoxazole (38.3 mg, 0.25 mmol) in toluene (1.0 mL) was heated at reflux for 16 h. Solvent was removed under reduced pressure, and the residue was dissolved in dichloromethane. The solution was washed with water, solvent was again removed under reduced pressure, and the residue was dissolved in methanol (1 mL) and tetrahydrofuran (1 mL). A 1 N aqueous solution of sodium hydroxide (0.77 mL, 0.77 mmol) was added, and the mixture was stirred at rt for 16 h and then concentrated under reduced pressure. The residue was purified by preparative reverse-phase HPLC (water/acetonitrile gradient, containing 0.1% TFA) to afford 4-[4'-(1,3-benzoxazol-2-ylamino)-1,1'-biphenyl-4-yl]4-oxo-2-(2-phenylethyl)butanoic acid (40 mg, 33% yield). LC-MS ret. time 4.14 min, m/z 519.5 (MH$^+$); $^1$H NMR (300 MHz, DMSO-$d_6$) δ 1.82–1.90 (m, 2H), 2.68 (m, 2H), 2.80–2.85 (m, 1H), 3.16 (dd, 1H), 3.41 (m, 1H), 7.10–7.30 (m, 8H), 7.48 (t, 2H), 7.78–7.86 (m, 4H), 7.89 (d, 2H), 8.02 (d, 2H), 10.83 (br s, 1H).

EXAMPLE 12

2,2-Dimethyl-4-{4'-[(6-methyl-1,3-benzoxazol-2yl)amino]-1,1'-biphenyl-4-yl}-4-oxobutanoic acid

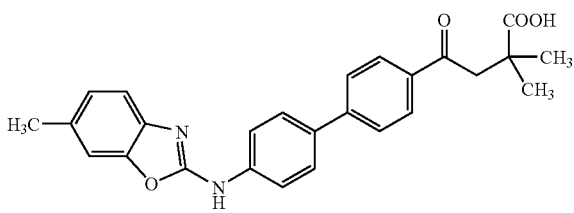

To a solution of methyl 4-(4'-amino-1,1'-biphenyl-4-yl)-2,2-dimethyl-4-oxobutanoate (74 mg, 0.24 mmol) in dichloroethane (3 mL), 6-methyl-2-(methylsulfonyl)-1,3-benzoxazole (50 mg, 0.24 mmol) was added, and the mixture was heated at 85° C. overnight. The solvent was removed by rotary evaporation, and the residue was redissolved in DMF (5 mL). A solution of 1 N aqueous NaOH (0.72 mL, 0.72 mmol) was added, and the mixture was heated at 65° C. overnight. A solution of 1 N aqueous HCl (0.24 mL, 0.24 mmol) and methanol (5 mL) were added to the reaction mixture and the crude product was purified by preparative reverse-phase HPLC (water/acetonitrile gradient, containing 0.1% TFA) to afford 2,2-dimethyl 4-{4'-[(6-methyl-1,3-benzoxazol-2-yl)amino]-1,1'-biphenyl-4-yl}4-oxobutanoic acid as a white solid (32.6 mg, 32.1%). $^1$H NMR (300 MHz, DMSO-$d_6$) δ 8.00–7.50 (m, 8 H), 7.30 (d, 2 H), 7.05 (d, 1 H), 3.30 (s, 2 H), 2.50 (s, 3 H), 1.10 (s, 6 H); LC-MS ret. time 3.53 min (method 2), m/z 429.17 (MH$^+$).

EXAMPLE 13

2,2-Dimethyl-4-{4'-[(4-methyl-1,3-benzoxazol-2-yl)amino]-1,1'-biphenyl-4-yl}-4-oxobutanoic acid

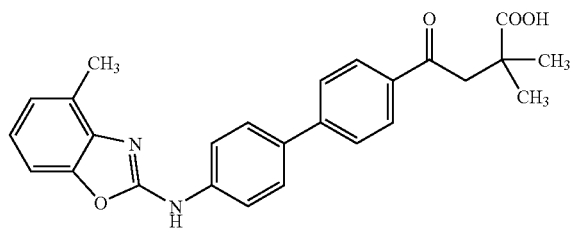

To a solution of methyl 4-(4'-amino-1,1'-biphenyl-4-yl)-2,2-dimethyl-4-oxobutanoate (74 mg, 0.24 mmol) in dichloroethane (3 mL), 4-methyl-2-(methylsulfonyl)-1,3-benzoxazole (50 mg, 0.24 mmol) was added, and the mixture was heated at 85° C. overnight. The solvent was removed by rotary evaporation and the residue was redissolved in DMF (5 mL). A solution of 1 N aqueous NaOH (0.72 mL, 0.72 mmol) was added, and the mixture was heated at 65° C. overnight. A solution of 1 N aqueous HCl (0.24 mL, 0.24 mmol) and methanol (5 mL) was added to the reaction mixture and the crude product was purified by preparative reverse-phase HPLC (water/acetonitrile gradient, containing 0.1% TFA) to afford 2,2-dimethyl-4-{4'-[(4-methyl-1,3-benzoxazol-2-yl)amino]-1,1'-biphenyl-4-yl}4-oxobutanoic acid as a white solid (32.6 mg, 32.1%). $^1$H NMR (300 MHz, DMSO-$d_6$) δ 8.00–7.80 (m, 8 H), 7.30 (d, 1 H), 7.05 (d, 2 H), 3.30 (s, 2 H), 2.50 (s, 3 H), 1.10 (s, 6 H); LC-MS ret. time 3.77 min (method 2), m/z 429.2 (MH$^+$).

EXAMPLE 14 trans-2-({4'-[(5-Fluoro-1,3-benzoxazol-2-yl)amino]-1,1'-biphenyl-4-yl}carbonyl)cyclopentanecarboxylic acid

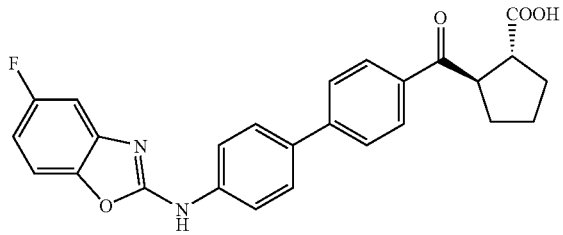

To a solution of methyl trans-2-[(4'-amino-1,1'-biphenyl-4-yl)carbonyl]cyclopentane carboxylate (100 mg, 0.31 mmol) in dichloroethane (3 mL), 5-fluoro-2-(methylsulfonyl)-1,3-benzoxazole (80 mg, 0.37 mmol) was added and the mixture was heated at 85° C. overnight. The solvent was removed by rotary evaporation, and the residue was redissolved in DMF (5 mL). A solution of 1 N aqueous NaOH (0.93 mL, 0.93 mmol) was added and the mixture was heated at 65° C. overnight. A solution of 1 N aqueous HCl (0.31 mL, 0.31 mmol) and methanol (5 mL) were added to the reaction mixture, and the crude product was purified by preparative reverse-phase HPLC (water/acetonitrile gradient, containing 0.1% TFA) to afford 2-({4'-[(5-fluoro-1,3-benzoxazol-2-yl)amino]-1,1'-biphenyl-4-yl}carbonyl)cyclopentanecarboxylic acid as a white solid (43.7 mg, 31.4%). $^1$H NMR (300 MHz, DMSO-$d_6$) δ 8.05 (d, 2 H), 7.90–7.80 (m, 6 H), 7.50 (m, 1 H), 7.30 (m, 1 H), 6.95 (m, 1 H), 4.05 (m, 1 H), 3.20 (m, 1 H), 2.20 (m, 1 H), 1.95 (m, 1 H), 1.80–1.60 (m, 4 H); LC-MS ret. time 3.66 min (method 2), m/z 445.1 (MH$^+$).

EXAMPLE 15

(1R,2R)-2-({3'-Fluoro-4'-[(6-methyl-1,3-benzoxazol-2-yl)amino]-1,1'-biphenyl-4-yl}carbonyl)cyclopentanecarboxylic acid

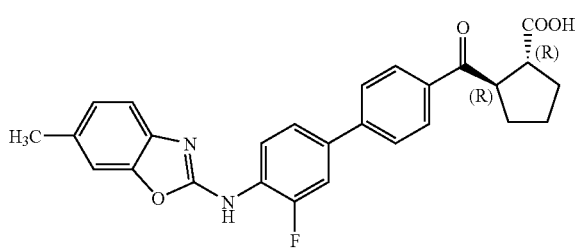

To a solution of methyl (1R,2R)-2-[(4'-amino-3'-fluoro-1,1'-biphenyl-4-yl)carbonyl]-cyclopentanecarboxylate (800 mg, 2.34 mmol, 78% ee) in dichloroethane (15 mL), 6-methyl-2-(methylsulfonyl)-1,3-benzoxazole (891 mg, 4.22 mmol) was added, and the mixture was heated at 85° C. overnight. The solvent was removed by rotary evaporation, and the residue was purified by using a Biotage QuadUV flash chromatography system (eluant: 80:20 hexane/EtOAc) to give methyl (1R,2R)-2-({3'-fluoro-4'-[(6-methyl-1,3-benzoxazol-2-yl)amino]-1,1'-biphenyl-4-yl}carbonyl)-cyclopentanecarboxylate (472 mg). This ester intermediate was redissolved in 1:1 dioxane/THF 20 mL), a solution of 1 N aqueous NaOH (7.02 mL, 7.02 mol) was added, and the mixture was heated at 50° C. overnight. The solvent was removed by rotary evaporation, and water (20 mL) and EtOAc (40 mL) were added to the residue. The aqueous layer was separated, acidified to pH 5 by the addition of 1 N aqueous HCl, and then extracted with EtOAc (2×60 mL). The combined organic phases were washed with saturated NaCl and dried (Na$_2$SO$_4$). The solvent was removed by rotary evaporation and the residue was redissolved in DMF (10 mL) and methanol (20 mL). The crude product was purified by preparative reverse-phase HPLC (water/acetonitrile gradient, containing 0.1% TFA) to afford (1R,2R)-2-({3'-fluoro-4'-[(6-methyl-1,3-benzoxazol-2-yl)amino]-1,1'-biphenyl-4-yl}carbonyl)cyclopentanecarboxylic acid as an off-white solid (161 mg, 15% yield, 80% ee). $^1$H NMR (300 MHz, DMSO-$d_6$) δ 8.40 (m, 1 H), 8.00–7.60 (m, 6 H), 7.30 (d, 2 H), 7.00 (d, 2 H), 4.05 (m, 1 H), 3.20 (m, 1 H), 2.40 (s, 3 H), 2.20 (m, 1 H), 1.95 (m, 1 H), 1.80–1.60 (m, 4 H); LC-MS ret. time 3.57 min, m/z 459.3 (MH$^+$).

EXAMPLE 16 trans-2-({4'-[(5-Fluoro-1,3-benzothiazol-2-yl)amino]-1,1'-biphenyl-4-yl}carbonyl)cyclopentanecarboxylic acid

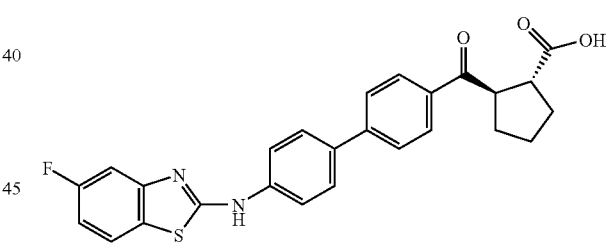

Methyl trans-2-({4'-[(5-fluoro-1,3-benzothiazol-2-yl)amino]-1,1'-biphenyl-4yl-}carbonyl)-cyclopentanecarboxylate

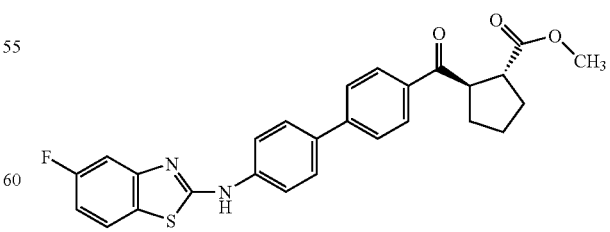

Step 1. 2-Chloro-5-fluoro-1,3-benzothiazole (29 mg, 0.16 mmol) and methyl trans-2-[(4'-amino-1,1'-biphenyl-4-yl)carbonyl]cyclopentanecarboxylate (50 mg, 0.16 mmol) were combined in 1-butanol. The solution was treated with 4 M HCl in dioxane (4 μL, 0.016 mmol) and heated at 90° C. for 18 h. The reaction mixture was concentrated under reduced pressure. The residue was suspended in methanol, and the resulting solid was collected by filtration and dried in vacuo. The title compound was obtained as a pale yellow solid (55 mg, 77%); LC-MS m/z 475.3 (MH+), retention time 3.97 minutes.

trans-2-({4'-[(5-Fluoro-1,3-benzothiazol-2-yl)amino]-1,1'-biphenyl-4-yl}carbonyl)-cyclopentanecarboxylic acid

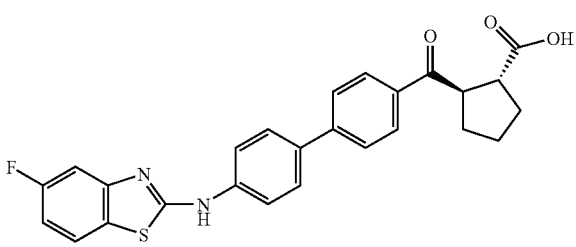

Step 2. A solution of 1 N aqueous sodium hydroxide solution (1 mL) was added to trans-methyl 2-({4'-[(5-fluoro-1,3-benzothiazol-2-yl)amino]-1,1'-biphenyl-4-yl}carbonyl) cyclopentane-carboxylate (55 mg, 0.12 mmol) in THF (2 mL). Methanol was added until the mixture became homogeneous, and the resulting solution was heated at 60° C. for 1 h. The reaction was concentrated under reduced pressure to remove excess solvents, and the residue was partitioned between water and chloroform/isopropanol (4:1). The aqueous layer was adjusted to pH 2 by addition of aqueous phosphoric acid solution, with stirring. The organic layer was then separated, dried ($Na_2SO_4$), and concentrated under reduced pressure. The residue was suspended in acetone, and the resulting solid was collected by filtration and dried in vacuo to provide the title compound (45 mg, 84%). $^1$H NMR (300 MHz, acetone-$d_6$) δ 10.40–10.10 (br s, 1 H), 8.15 (d, 2 H), 8.01 (d, 2 H), 7.87–7.82 (m, 5 H), 7.41 (dd, 1 H), 7.05–6.95 (m, 1 H), 4.26–4.17 (m, 1 H), 3.43–3.34 (m, 1 H), 2.31–2.23 (m, 1 H), 1.98–1.70 (m, 5 H); LC-MS m/z 461.3 (MH+), retention time 3.56 minutes.

EXAMPLE 17

(1R,2R)-2-[(4'-{[6-(Trifluoromethyl)-1,3-benzothiazol-2-yl]amino}-1,1'-biphenyl-4-yl)carbonyl]cyclopentanecarboxylic acid

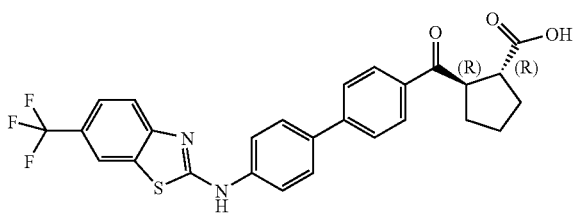

A mixture of methyl (1R,2R)-2-[(4'-amino-1,1'-biphenyl-4-yl)carbonyl]cyclopentane-carboxylate (150 mg, 0.464 mmol) and 2-chloro-6-(trifluoromethyl)-1,3-benzothiazole (132 mg, 0.557 mmol) was diluted with n-butanol (3 mL) and treated with a catalytic amount of 4 M HCl in dioxane. The suspension was heated at 90° C. overnight. The reaction mixture was concentrated under reduced pressure and purified by flash chromatography on silica gel, eluting with a gradient from 9:1 to 3:2 hexanes/ethyl acetate. The product obtained was suspended in diethyl ether, and the resulting solid was collected by filtration and washed with additional diethyl ether and hexanes. LC-MS for the n-butyl ester: LC-MS m/z 567.3 (MH+), 4.67 min; $^1$H NMR (300 MHz, CDCl$_3$) δ 8.14–8.10 (m, 3 H), 7.80–7.71 (m, 6 H), 7.62 (d, 2 H), 4.17–4.13 (m, 1 H), 4.09–4.04 (m,2 H), 3.51–3.41 (m, 1 H), 2.21–2.13 (m, 2 H), 1.97–1.90 (m, 1 H), 1.81–1.78 (m, 3 H), 1.58–1.51 (m, 2 H), 1.35–1.28 (m, 2 H),1.23–1.18 (t, 3 H), 0.88 (t, 2 H). The off-white solid was diluted with methanol (2 mL) and tetrahydrofuran (2 mL) and treated with 2 M aqueous sodium hydroxide solution (2 mL). The solution was stirred overnight at rt. The mixture was acidified by the addition of an excess of 2 M aqueous hydrochloric acid solution. The acidic solution was extracted with ethyl acetate. The organic phases were combined, dried (MgSO$_4$), and concentrated under reduced pressure. The residue was suspended in methanol and the resulting solids were removed by filtration. The filtrate, which contained the product, was concentrated under reduced pressure to provide the title compound as a pale orange solid (30 mg, 13% overall yield). $^1$H NMR (tetrahydrofuran-$d_8$) δ 10.85 (s, 1 H), 8.11–8.07 (m, 3 H), 7.96–7.91 (m, 2 H), 7.79–7.71 (m, 5 H), 7.63–7.59 (dd, 1 H), 4.18 (q, 1 H), 3.37 (q, 1 H), 2.2–1.77 (m, 6 H); LC-MS m/z 511.3 (MH+), retention time 4.27 minutes.

EXAMPLE 18

(1R,2R)-2-({4'-[(6-Chloro-1,3-benzothiazol-2-yl)amino]-3'-fluoro-1,1'-biphenyl-4-yl}carbonyl)cyclopentanecarboxylic acid

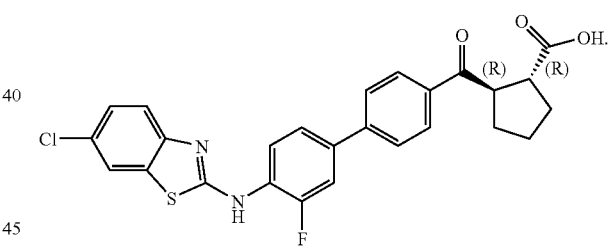

A suspension of N-(4-iodo-2-fluorophenyl)-6-chloro-1,3-benzothiazol-2-amine (200 mg, 0.49 mmol), bis(pinacolato) diboron (130 mg, 0.52 mmol), KOAc (150 mg, 1.48 mmol), and PdCl$_2$(dppf) (30 mg, 0.04 mmol) in DMF (5.0 mL) was degassed by bubbling a flow of nitrogen for 30 minutes. The reaction mixture was heated under nitrogen at 85° C. for 3 h. After the mixture was cooled to rt, (1R,2R)-2-(4-bromobenzoyl)cyclopentanecarboxylic acid (140 mg, 0.49 mmol, >99% ee), Cs$_2$CO$_3$ (400 mg, 1.23 mmol) and PdCl$_2$ (dppf) (30 mg, 0.04 mmol) were added, and the reaction mixture was heated at 85° C. under nitrogen for 3 h. TLC analysis showed little starting materials remaining. The reaction mixture was cooled to rt, and diluted with water (50 mL). After the mixture was filtered through a pad of Celite®, 1 N HCl was added to the filtrate to adjust the acidity to pH<3. The solid that formed was collected by filtration, then dissolved in EtOAc (50 mL), and the resulting solution was dried over Na$_2$SO$_4$. Removal of solvent and drying in vacuo provided the desired product (120 mg, 60%, >99% ee). LC-MS m/z 495.3 (MH+), retention time 4.01 min.

EXAMPLE 19 trans-2-({4'-[(6-Chloro-1,3-benzothiazol-2-yl)amino]-1,1'-biphenyl-4-yl}carbonyl)cyclobutanecarboxylic acid

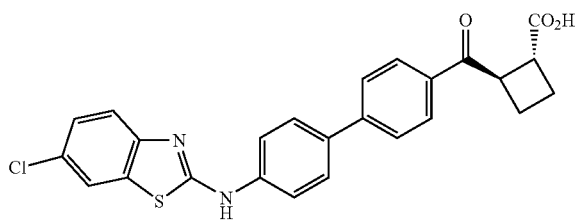

To a solution of methyl trans-2-[(4'-amino-1,1'-biphenyl-4-yl) carbonyl]cyclobutane-carboxylate (100 mg, 0.32 mmol) in n-butanol (15 mL) was added 2,6-dichloro-1,3-benzothiazole (396 mg, 1.94 mmol), and the resulting reaction mixture was heated at 90° C. overnight. The mixture was evaporated to dryness and the residue was brought up in MeOH. Then 1 N aqueous NaOH (1.0 mL, 1.0 mmol) was added to the suspension, and the reaction mixture was stirred at 50° C. overnight. The reaction mixture was concentrated, and the residue was suspended in water. Concentrated HCl was added to adjust the acidity to pH 1, and the precipitate that formed was collected by filtration, washed with water and MeOH, and dried in a vacuum oven to give trans-2-({4'-[(6-chloro-1,3-benzothiazol-2-yl) amino]-1,1'-biphenyl-4-yl}carbonyl)cyclobutanecarboxylic acid (16 mg, 10%). LC-MS ret. time 3.69; m/z 463.1 (MH$^+$); $^1$H NMR (400 MHz, DMSO-d$_6$) δ 2.01–2.23 (m, 3 H), 2.32 (m, 1H), 3.43 (m, 1H), 4.32 (m, 1H), 7.35 (m, 1H), 7.31 (m, 1H), 7.62 (d, 1H), 7.81 (m, 4H), 7.90 (d, 2H), 7.98 (m, 3H), 10.77 (s, 1H), 12.29 (s, 1H).

EXAMPLE 20 trans-2-({4'-[(6-Methyl-1,3-benzothiazol-2-yl)amino]-1,1'-biphenyl-4-yl}carbonyl)cyclopentanecarboxylic acid

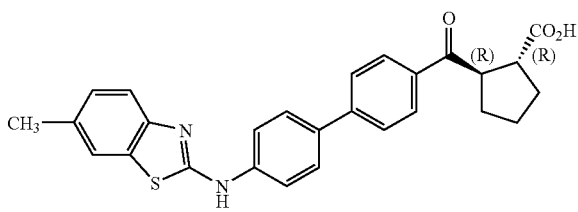

N-(4-iodophenyl)-6-methyl-1,3-benzothiazol-2-amine (0.28 g, 0.78 mmol) and methyl trans-2-[4-(4,4,5,5-tetramethyl-1,3,2-dioxaborolan-2-yl)benzoyl]cyclopentanecarboxylate (0.25 g, 0.71 mmol) were combined in a dry flask under argon. Toluene (15 mL), EtOH (6 mL), and saturated aqueous NaHCO$_3$ (2 mL) were then added, and the resulting solution was degassed by bubbling a flow of argon for 30 minutes. Then [1,1'-bis(diphenylphosphino)-ferrocene]dichloro-palladium (II), complex with dichloromethane (1:1) (57 mg, 0.07 mmol) was added, and the resulting mixture was heated at 85° C. for 16 h. The reaction mixture was then diluted with EtOAc and filtered through a Celite® pad. The solvent was removed by rotary evaporation and the residue was brought up in MeOH. Then 1 N aqueous NaOH (2.0 mL, 2.0 mmol) was added to the suspension, and the reaction mixture was stirred at 50° C. overnight. The reaction mixture was concentrated under reduced pressure and the residue was suspended in water. Concentrated HCl was added to adjust the acidity to pH 1, and the suspension was extracted with EtOAc. The combined organic phases were washed with brine, dried over sodium sulfate, passed through a pad of silica gel, and concentrated in vacuo. The residue was brought up in EtOAc and the precipitate was collected by filtration, washed with EtOAc, MeOH, and DCM, and dried in a vacuum oven to afford trans-2-({4'-[(6-methyl-1,3-benzothiazol-2-yl)amino]-1,1'-biphenyl-4-yl}carbonyl)-cyclopentanecarboxylic acid (0.24 g, 19%). LC-MC ret. time 3.57; m/z 457.3 (MH$^+$); $^1$H NMR (400 MHz, DMSO-d$_6$) δ 1.57–1.86 (m, 4H), 2.00 (m, 1H), 2.17 (m, 1H), 2.37 (s, 3H), 3.22 (q, 1H), 4.08 (q, 1H), 7.14 (m, 1H), 7.51 (d, 1H), 7.61 (s, 1H), 7.80 (m, 3H), 7.89 (d, 2H), 8.05 (d, 2H), 10.58 (s, 1H), 12.19 (s, 1H).

EXAMPLE 21

(1R,2R)-2-({3'-fluoro-4'-[(4-methyl-1,3-benzothiazol-2-yl)amino]-1,1'-biphenyl-4-yl}carbonyl)cyclopentanecarboxylic acid

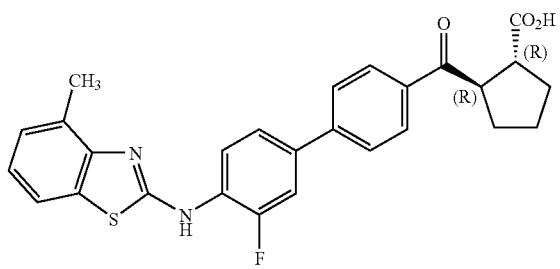

Methyl (R,R)-trans-2-({3'-fluoro-4'-[(4-methyl-1,3-benzothiazol-2-yl)amino]-1,1'-biphenyl-4-yl}carbonyl)cyclopentanecarboxylate

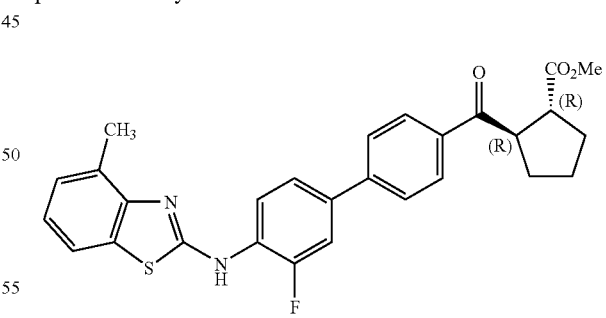

Step 1 N-(4-bromo-2-fluorophenyl)-4-methyl-1,3-benzothiazol-2-amine (0.10 g, 0.30 mmol) and methyl (R,R)-trans-2-[4-(4,4,5,5-tetramethyl-1,3,2-dioxaborolan-2-yl) benzoyl]cyclopentanecarboxylate (0.19 g, 0.54 mmol, 94% ee) were combined in a dry flask under argon. Toluene (25 mL), EtOH (8 mL), and saturated aqueous NaHCO$_3$ (5 mL) were added, and the resulting suspension was degassed by bubbling with a flow of argon for 30 minutes. Then [1,1'-bis(diphenylphosphino)-ferrocene]dichloropalladium(II), complex with dichloromethane (1:1) (40 mg, 0.05 mmol)

was added, and the resulting mixture was heated at 85° C. for 16 h. The reaction mixture was then diluted with EtOAc and the layers were separated. The organic layer was washed with aqueous HCl (1.0 M), water and brine, filtered, and concentrated in vacuo. The residue was purified by flash chromatography (Biotage Flash 25S) using 10 to 15% ethyl acetate in hexane to afford methyl (R,R)-trans-2-({3'-fluoro-4'-[(4-methyl-1,3-benzothiazol-2-yl)amino]-1,1'-biphenyl-4-yl}carbonyl)cyclopentanecarboxylate (0.09 g, 37%). $^1$H NMR (400 MHz, CD$_2$Cl$_2$) δ 1.75–1.86 (m, 3H), 1.93 (m, 1H), 2.12–2.26 (m, 2H), 2.69 (s, 3H), 3.45 (q, 1H), 3.66 (s, 3H), 4.12 (q, 1H), 7.14 (t, 1H), 7.22 (d, 1H), 7.50 (m, 2H), 7.56 (t, 2H), 7.73 (d, 2H), 8.07 (d, 2H), 8.72 (t, 1H).

(R,R)-trans-2-({3'-fluoro-4'-[(4-methyl-1,3-benzothiazol-2-yl)amino]-1,1'-biphenyl-4-yl}-carbonyl)cyclopentanecarboxylic acid

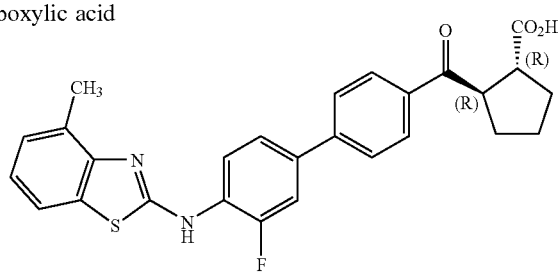

Step 2 Methyl (R,R)-trans-2-({3'-fluoro-4'-[(4-methyl-1,3-benzothiazol-2-yl)amino]-1,1'-biphenyl-4-yl}carbonyl)cyclopentanecarboxylate (90 mg, 0.18 mmol) was brought up in MeOH. Then 1 N aqueous NaOH (1.0 mL, 1.0 mmol) was added to the suspension, and the reaction mixture was stirred at 50° C. overnight. The reaction mixture was concentrated, and the residue was suspended in water. Conc. HCl was added to adjust the acidity to pH 1, and the mixture was extracted with EtOAc. The combined organic phases were washed with brine, dried over sodium sulfate, filtered and concentrated to give (R,R)-trans-2-({3'-fluoro-4'-[(4-methyl-1,3-benzothiazol-2-yl)amino]-1,1'-biphenyl-4-yl}carbonyl)cyclopentanecarboxylic acid (32 mg, 36%). LC-MS ret. time 3.97; m/z 475.3 (MH$^+$); $^1$H NMR (400 MHz, DMSO-d$_6$) δ 1.56–1.83 (m, 4H), 2.00 (m, 1H), 2.16(m, 1H), 2.57 (s, 3H), 3.22 (q, 1H), 4.09 (q, 1H), 7.07 (t, 1H), 7.16 (d, 1H), 7.63 (m, 1H), 7.70 (m, 1H), 7.75 (m, 1H), 7.88 (d, 1H), 8.05 (d, 2H), 8.84 (t, 1H), 10.47 (s, 1H).

EXAMPLE 22 trans-2-({4'-[(4,6-Difluoro-1,3-benzothiazol-2-yl)amino]-1,1'-biphenyl-4-yl}carbonyl)cyclopentanecarboxylic acid

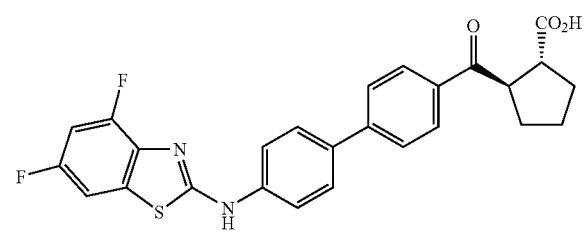

To a solution of racemic methyl trans-2-[(4'-amino-1,1'-biphenyl-4-yl)carbonyl]cyclobutane-carboxylate (250 mg, 0.77 mmol) in n-butanol (15 mL) was added 2-chloro-4,6-difluoro-1,3-benzothiazole (318 mg, 1.55 mmol), and the resulting solution was heated at 90° C. overnight. The mixture was then evaporated to dryness under reduced pressure, and the residue was brought up in MeOH. Then 1 N aqueous NaOH (8.0 mL, 8.0 mmol) was added to the suspension, and the reaction mixture was stirred at 50° C. overnight. The reaction mixture was concentrated under reduced pressure, and the residue was suspended in water. Conc. HCl was added to adjust the acidity to pH 1, and the mixture was extracted with EtOAc. The combined organic phases were washed with brine, dried over sodium sulfate, filtered, and concentrated. The residue was brought up in MeOH, and the precipitate was collected by filtration, washed with MeOH, EtOAc, and DCM, and dried in a vacuum oven to afford racemic trans-2-({4'-[(4,6-difluoro-1,3-benzothiazol-2-yl)amino]-1,1'-biphenyl-4-yl}-carbonyl)cyclopentanecarboxylic acid (160 mg, 43%). LC-MS ret. time 4.12; m/z 479.3 (MH$^+$); $^1$H NMR (400 MHz, DMSO-d$_6$) δ 1.55–1.86 (m, 4H), 2.00 (m, 1H), 2.18 (m, 1H), 3.22 (q, 1H), 4.01 (q, 1H), 7.28 (m, 1H), 7.65 (m, 1H), 7.82 (m, 4H), 7.88 (d, 2H), 8.05 (d, 2H), 10.83(s, 1H), 12.23 (s, 1H).

EXAMPLE 23

(1R,2R)-2-({4'-[(4,6-Difluoro-1,3-benzothiazol-2-yl)amino]-1,1'-biphenyl-4-yl}carbonyl)cyclopentanecarboxylic acid

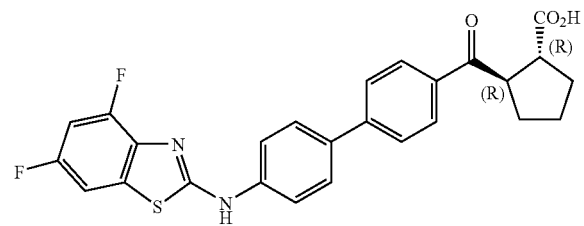

Racemic trans-2-({4'-[(4,6-difluoro-1,3-benzothiazol-2-yl)amino]-1,1'-biphenyl-4-yl}-carbonyl)cyclopentanecarboxylic acid (140 mg, 0.29 mmol) was separated by chiral HPLC to afford (1R,2R)-2-({4'-[(4,6-difluoro-1,3-benzothiazol-2-yl)amino]-1,1'-biphenyl-4-yl}carbonyl)-cyclopentanecarboxylic acid as the first-eluting enantiomer (13.2 mg, 9%, 99% ee). LC-MS ret. time 3.64; m/z 479.2 (MH$^+$); $^1$H NMR (400 MHz, DMSO-d$_6$) δ 1.58–1.86 (m, 4H), 2.00 (m, 1H), 2.17 (m, 1H), 3.21 (q, 1H), 4.10 (q, 1H), 7.29 (m, 1H), 7.66 (m, 1H), 7.82 (m, 4H), 7.88 (d, 2H), 8.06 (d, 2H), 10.83 (s, 1H), 12.23 (s, 1H).

EXAMPLE 24

(1S,2S)-2-({4'-[(4,6-Difluoro-1,3-benzothiazol-2-yl)amino]-1,1'-biphenyl-4-yl}carbonyl)cyclopentanecarboxylic acid

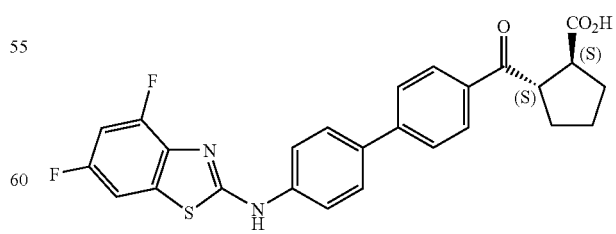

Racemic trans-2-({4'-[(4,6-difluoro-1,3-benzothiazol-2-yl)amino]-1,1'-biphenyl-4-yl}-carbonyl)cyclopentanecarboxylic acid (140 mg, 0.29 mmol) was separated by chiral HPLC to afford (1S,2S)-2-({4'-[(4,6-difluoro-1,3-benzothiazol-2-yl)amino]-1,1'-biphenyl-4-yl}carbonyl)-cyclopentanecarboxylic acid as the second-eluting enantiomer (23.8 mg, 17%, 74% ee). LC-MS ret. time 3.65; m/z 479.2 (MH⁺); ¹H NMR (400 MHz, DMSO-d₆) δ 1.56–1.87 (m, 4H), 2.01 (m, 1H), 2.18 (m, 1H), 3.22 (q, 1H), 4.09 (q, 1H), 7.28 (m, 1H), 7.66 (m, 1H), 7.82 (m, 4H), 7.89 (d, 2H), 8.06 (d, 2H), 10.83 (s, 1H), 12.22 (s, 1H).

EXAMPLE 25

(1R,2R)-2-({3'-fluoro-4'-[(6-trifluoromethoxy-1,3-benzothiazol-2-yl)amino]-1,1'-biphenyl-4-yl}carbonyl)cyclopentanecarboxylic acid

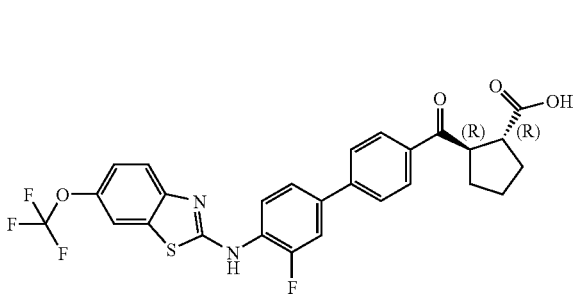

Methyl (1R,2R)-2-[(3'-fluoro-4'-{[6-(trifluoromethoxy)-1,3-benzothiazol-2-yl]amino}-1,1'-biphenyl-4-yl)carbonyl]cyclopentanecarboxylate

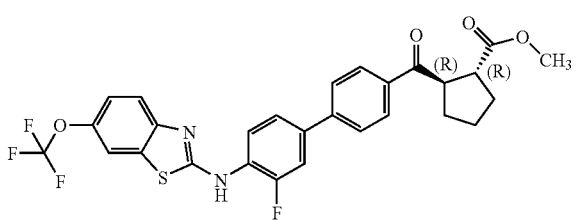

Step 1. In a 100 mL 3-neck round bottom flask, a mixture of methyl (1R,2R)-2-(4-bromobenzoyl)cyclopentanecarboxylate (3.11 g, 10 mmol, 94.5% ee), 4,4,4',4',5,5,5',5'-octamethyl-2,2'-bi-1,3,2-dioxaborolane (2.54 g, 10 mmol), and potassium acetate (2.94 g, 30 mmol) in 50 mL N,N-dimethylformamide was degassed by bubbling a flow of nitrogen gas for 30 minutes. Palladium (II) acetate (0.07 g, 0.30 mmol) was added to the reaction mixture, and the mixture was heated at 85° C. for 3 h. The transformation of methyl (1R,2R)-2-(4-bromobenzoyl)cyclopentanecarboxylate to methyl (1R,2R)-2-[4-(4,4,5,5-tetramethyl-1,3,2-dioxaborolan-2-yl)benzoyl]cyclopentanecarboxylate was confirmed by TLC analysis. The mixture was cooled to rt and poured into a separation funnel. Ethyl acetate (100 mL) and H₂O (100 mL) were added. The organic layer was washed with water (2×50 mL) and treated with Na₂SO₄ and activated charcoal. The mixture was filtered through a pad of silica gel, and the filtrate was concentrated under reduced pressure to provide methyl (1R,2R)-2-[4-(4,4,5,5-tetramethyl-1,3,2-dioxaborolan-2-yl)benzoyl]cyclopentanecarboxylate as an oil. This oil was transferred to a 250-mL 3-neck round-bottom flask. To the flask, N-(4-bromo-2-fluorophenyl)-N-(6-trifluoromethoxy-1,3-benzothiazol-2-yl)amine (3.66 g, 9 mmol), 150 mL toluene, 60 mL ethanol, and 20 mL saturated aqueous NaHCO₃ were added. The mixture was degassed by bubbling nitrogen gas for 30 minutes. 1,1'-Bis(diphenylphosphino)ferrocene)dichloropalladium(II) dichloromethane complex (0.82 g, 1.0 mmol) was added to the reaction mixture. The mixture was heated at 85° C. overnight. The workup procedure was then carried out in a similar to that described above. The filtrate was concentrated under reduced pressure and the solid residue was ultrasonicated in 100 mL acetonitrile for 30 minutes and filtered to give the desired compound as a white solid (2.59 g, 52%). LC-MS m/z 559.3 (MH), ret. time 4.75 min.

(1R,2R)-2-({3'-Fluoro-4'-[(6-trifluoromethoxy-1,3-benzothiazol-2-yl)amino]-1,1'-biphenyl-4-yl}carbonyl)-cyclopentanecarboxylic acid

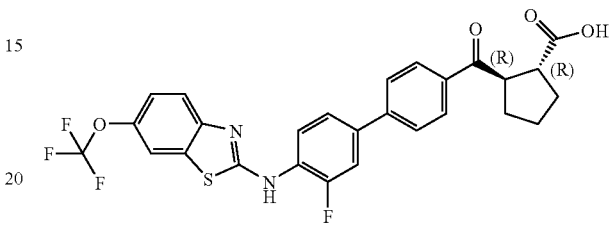

Step 2. In 250-mL round-bottom flask, methyl (1R,2R)-2-[(3'-fluoro-4'-{[6-(trifluoromethoxy)-1,3-benzothiazol-2-yl]amino}-1,1'-biphenyl-4-yl)carbonyl]cyclopentanecarboxylate (2.53 g, 4.53 mmol) was dissolved in 100 mL of 1:1 THF/dioxane containing 5.0 molar equivalents of 1 N aqueous NaOH. The mixture was stirred at rt overnight. The mixture was concentrated under reduced pressure to a volume of about 20 mL. Ethyl acetate (100 mL), water (30 mL), and 5.1 molar equivalents of 1 N aqueous HCl were added to the mixture. The mixture was transferred to a separation funnel. The organic layer was washed with water (1×50 mL), dried (Na₂SO₄), and concentrated under reduced pressure. The solid was ultrasonicated in 30 mL acetonitrile and filtered to give the desired compound as a white solid (1.96 g, 80%, 94.5% ee). ¹H NMR (400 MHz, DMSO-d₆) δ 12.20 (br s, 1 H), 10.60 (bs, 1 H), 8.70 (t, 1 H), 7.60–8.20 (m, 8 H), 7.30 (d, 2 H), 4.70 (q, 1 H), 3.20 (q, 1 H), 2.20 (m, 1 H), 2.00 (m, 1 H), 1.50–1.90 (m, 4 H); LC-MS m/z 545.3 (MH⁺), ret. time 3.93 min.

EXAMPLE 26

(1R,2R)-2-({3'-Fluoro-4'-[(6-fluoro-1,3-benzothiazol-2-yl)amino]-1,1'-biphenyl-4-yl}carbonyl)cyclopentanecarboxylic acid

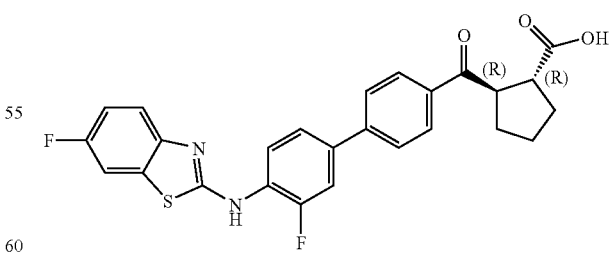

tert-Butyl (1R,2R)-2-({3'-fluoro-4'-[(6-fluoro-1,3-benzothiazol-2-yl)amino]-1,1'-biphenyl-4-yl}carbonyl)cyclopentanecarboxylate was prepared from tert-butyl (1R,2R)-2-(bromobenzoyl)-cyclopentanecarboxylate and N-(4-bromo-2-fluorophenyl)-N-(6-fluoro-1,3-benzothiazol-2-yl)amine in a similar manner to that described above for methyl (1R,2R)-2-[(3'-fluoro-4'-{[6-(trifluoromethoxy)-1,3-benzothiazol-2-yl]amino}-1,1'-biphenyl-4-yl)carbonyl]cyclopentanecarboxylate. A solution of the tert-butyl ester (1.5 g, 2.81 mmol) in 2.0 mL TFA and 10 mL CH$_2$Cl$_2$ was stirred at rt overnight. After the solvent was removed by rotary evaporation, 50 mL EtOAc and 50 mL water were added. The organic layer was separated, washed with 50 mL water, and then dried over Na$_2$SO$_4$. After the solvent was removed by rotary evaporation, 5 mL EtOAc was added to the residue, followed by 5 mL hexanes. The precipitate that formed was collected by filtration to afford the desired product as a light yellow solid (1.0 g, 77%, 95.2% ee). $^1$H NMR (400 MHz, DMSO-d$_6$) δ 12.20 (br s, 1 H), 10.50 (bs, 1 H), 8.70 (t, 1 H), 7.60–8.10 (m, 8 H), 7.20 (t, 1 H), 4.10 (m, 1 H), 3.20 (m, 1 H), 2.20 (m, 1 H), 2.00 (m, 1 H), 1.50–1.90 (m, 4 H); LC-MS m/z 479.3 (MH$^+$), ret. time 3.64 min.

EXAMPLE 27

(1R,2R)-2-({4'-[(5-methyl-1,3-benzoxazol-2-yl)amino]-1,1'-biphenyl-4-yl}carbonyl)cyclopentanecarboxylic acid

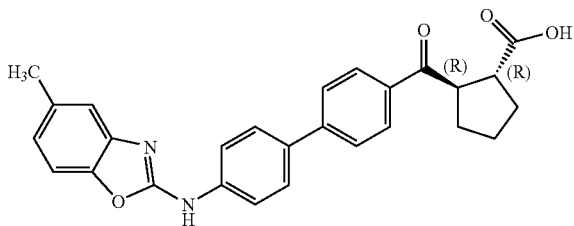

This compound was prepared from N-(4-bromophenyl)-N-(5-methyl-1,3-benzoxazol-2-yl)amine (0.50 g, 1.65 mmol), methyl (1R,2R)-2-(4-bromobenzoyl) cyclopentanecarboxylate (0.57 g, 1.83 mmol, 94.5% ee) in a similar manner to the method described for (1R,2R)-2-({3'-fluoro-4'-[(6-trifluoromethoxy-1,3-benzothiazol-2-yl)amino]-1,1'-biphenyl-4-yl}carbonyl)cyclopentanecarboxylic acid. Yield: 17%. $^1$H NMR (400 MHz, DMSO-d$_6$) δ 10.80 (s, 1 H), 8.05 (d, 2 H), 7.75–7.90 (m, 6 H), 7.35 (d, 1 H), 7.25 (s, 1 H), 6.95 (d, 1 H), 4.05 (q, 1 H), 3.20 (s, 1 H), 2.40 (s, 3 H), 2.15 (m, 1 H), 2.00 (m, 1 H), 1.55–1.80 (m, 4 H). LC-MS m/z 441.3 (MH$^+$), ret. time 3.48 min.

EXAMPLE 28 trans-2-({4'-[(5,7-Difluoro-1,3-benzothiazol-2-yl)amino]-1,1'-biphenyl-4-yl}carbonyl)cyclopentanecarboxylic acid

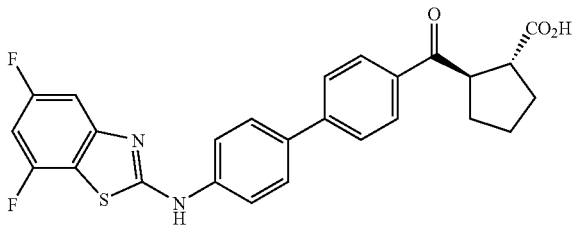

To a solution of methyl trans-2-[(4'-amino-1,1'-biphenyl-4-yl)carbonyl]cyclobutanecarboxylate (80 mg, 0.25 mmol) in n-butanol (8 mL) was added 2-chloro-5,7-difluoro-1,3-benzothiazole (102 mg, 0.49 mmol) and HCl (4.0 M in dioxane, 0.2 mL). The resulting reaction mixture was heated at 90° C. overnight. The mixture was evaporated to dryness, and the residue was brought up in MeOH. Then 1 N aqueous NaOH (2.0 mL, 2.0 mmol) was added, and the reaction mixture was stirred at 50° C. overnight. The reaction mixture was concentrated and the residue was suspended in water. Conc. HCl was added to adjust the acidity to pH 1, and the suspension was extracted with EtOAc. The combined organic phases were washed with brine, dried over sodium sulfate, filtered, and concentrated. The residue was brought up in MeOH, and the precipitate was collected by filtration and dried under vacuum oven to afford trans-2-({4'-[(5,7-difluoro-1,3-benzothiazol-2-yl)amino]-1,1'-biphenyl-4-yl}carbonyl)cyclopentanecarboxylic acid (65 mg, 58%). LC-MS ret. time 3.75; m/z 479.2 (MH$^+$). $^1$H NMR (400 MHz, DMSO-d$_6$) δ 1.55–1.84 (m, 4H), 2.01 (m, 1H), 2.18 (m, 1H), 3.22 (q, 1H), 4.09 (q, 1H), 7.15 (m, 1H), 7.40 (m, 1H), 7.83 (m, 4H), 7.87 (d, 2H), 8.05 (d, 2H), 11.00 (s, 1H), 12.12 (s, 1H).

EXAMPLE 29

(1R,2R)-2-{[4'-(1H-benzimidazol-2-ylamino)-3'-fluoro-1,1'-biphenyl-4-yl]carbonyl}cyclopentanecarboxylic acid

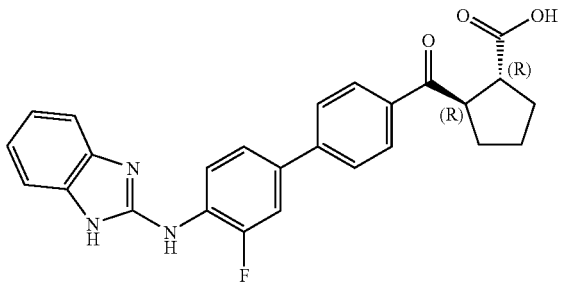

Methyl (1R 2R)-2-{[4'-(1H-benzimidazol-2-ylamino)-3'-fluoro-1,1'-biphenyl-4-yl]carbonyl}-cyclopentanecarboxylate.

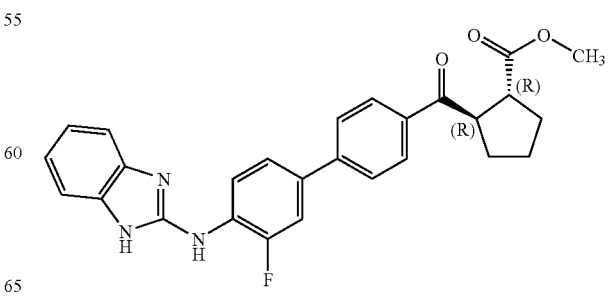

Step 1. Methyl (1R,2R)-2-[(4'-amino-3'-fluoro-1,1'-biphenyl-4-yl)carbonyl]cyclopentane-carboxylate (100 mg, 0.29 mmol, 80% ee) and 2-chlorobenzimiazole (49 mg, 0.32 mmol) were combined in 1,4-dioxane (2 mL) and treated with one molar equivalent of 4 M HCl in dioxane (73 µL). The mixture was heated at 90° C. for 18 h, then cooled to rt and concentrated under reduced pressure to an orange oil. The residue was purified by flash chromatography on silica gel, eluting with 2:1 hexanes/ethyl acetate followed by methanol to provide the title compound as a dark oil (0.12 g, 90%). $^1$H NMR (300 MHz, MeOD-d$_4$) δ 8.09 (d, 2 H), 7.81 (d, 2 H), 7.75–7.67 (m, 3 H), 7.46–7.40 (m, 2 H), 7.32–7.28 (m, 2 H), 4.17–4.09 (m, 1 H), 3.26–3.23 (m, 1 H), 2.24–2.16 (m, 1 H), 2.10–2.02 (m, 1 H), 1.91–1.68 (m, 4 H); LC-MS m/z 458.4 (MH$^+$), retention time 2.48 minutes; TLC R$_f$ 0.28 (2:1 hexanes/ethyl acetate).

(1R,2R)-2-{[4'-(1H-benzimidazol-2-ylamino)-3'-fluoro-1,1'-biphenyl-yl]carbonyl}-cyclopentanecarboxylic acid.

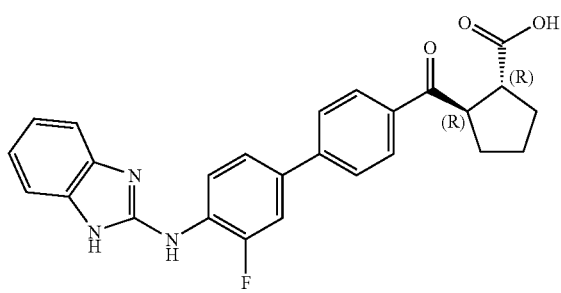

Step 2. Methyl (1R,2R)-2-{[4'-(1H-benzimidazol-2-ylamino)-3'-fluoro-1,1'-biphenyl-4-yl]-carbonyl}cyclopentanecarboxylate (100 mg, 0.22 mmol) was dissolved in methanol and treated with an excess of 1 N aqueous sodium hydroxide solution (2.19 mL, 2.19 mmol). The solution was stirred at rt for 1 h, and then was concentrated under reduced pressure. The residue was partitioned between water and ethyl acetate, and the aqueous layer was adjusted to pH 2 by the addition of 1 N aqueous HCl. The organic layer was separated, washed with brine, dried (MgSO$_4$), and concentrated under reduced pressure to provide an orange oil. The oil was suspended in THF and stirred until a precipitate formed. The precipitate was collected by filtration and washed with additional THF to provide the title compound as a yellow solid (30 mg, 31%, 80% ee). $^1$H NMR (300 MHz, DMSO-d$_6$) δ 13.12 (br s, 1 H), 11.30 (br s, 1 H), 8.12 (d, 2 H), 7.96-7.76 (m, 5 H), 7.46–7.42 (m, 2 H), 7.30–7.26 (m, 2 H), 4.15–4.07 (m, 1 H), 3.27–3.19 (m, 1 H), 2.21–2.12 (m, 1 H), 2.05–1.96 (m, 1 H), 1.86–1.55 (m, 4 H); LC-MS m/z 444.4 (MH$^+$), retention time 2.79 minutes.

EXAMPLE 30 trans-2-({4'-[(6-Chloro-1,3-benzothiazol-2-yl)amino]biphenyl-4-yl}carbonyl) cyclohexanecarboxylic acid

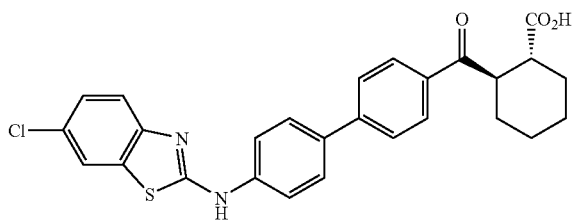

To a solution of cis-methyl 2-[(4'-amino-1,1'-biphenyl-4-yl)carbonyl]cyclohexanecarboxylate (200 mg, 0.59 mmol) in n-butanol (8 mL) was added 2,6-dichloro-1,3-benzothiazole (241 mg, 1.19 mmol), and the resulting reaction mixture was heated at 90° C. overnight. The mixture was evaporated to dryness and the residue was combined with MeOH. Then 1 N NaOH (6.0 mL, 6.0 mmol) was added to the suspension, and the reaction mixture was stirred at 50° C. overnight. The reaction mixture was concentrated under reduced pressure, and the residue was suspended in water. Concentrated aqueous HCl was added to adjust the acidity to pH 1, and the precipitate was collected by filtration, washed with water and MeOH, and dried in a vacuum oven to give trans-2-({4'-[(6-chloro-1,3-benzothiazol-2-yl)amino]-1,1'-biphenyl-4-yl}carbonyl)cyclohexanecarboxylic acid (45 mg, 15%). LC-MS m/z 491.1 (MH$^+$), ret. time 3.90 min; $^1$H NMR (400 MHz, DMSO-d$_6$) δ 1.13 (m, 1H), 1.28~1.51 (m, 3H), 1.78 (m, 1H), 1.93 (m, 1H), 2.09 (m, 1H), 2.68 (m, 1H), 3.63 (m, 1H), 7.35 (m, 1H), 7.60 (m, 1H), 7.80 (m, 4H), 7.90 (d, 1H), 7.96 (m, 1H), 8.05 (d, 2H), 10.75 (s, 1H).

EXAMPLE 31 trans-2-({4'-[(5-Methyl-1,3-benzoxazol-2-yl)amino]biphenyl-4-yl}carbonyl) cyclohexanecarboxylic acid

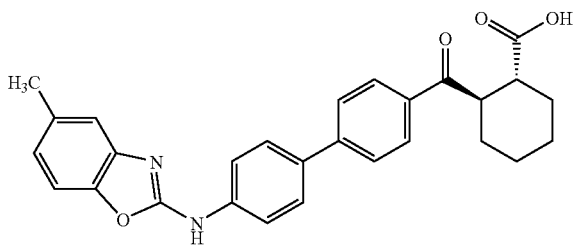

trans-2-(Trimethylsilyl)ethyl-2-({4'-[(5-methyl-1,3-benzoxazol-2-yl)amino]biphenyl-4-yl-}-carbonyl)cyclohexanecarboxylate

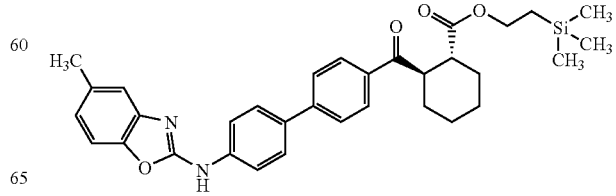

Step 1. N-(4-Bromophenyl)-5-methyl-1,3-benzoxazol-2-amine (76.70 mg, 0.25 mmol) and trans-2-(trimethylsilyl)ethyl-2-(4-bromobenzoyl)cyclohexanecarboxylate (105.45 mg, 0.23 mmol) were combined in a clean dry flask under argon. Toluene (25 mL), EtOH (8 mL), and saturated aqueous NaHCO$_3$ (5 mL) were added, and the resulting solution was degassed by bubbling with argon for 30 minutes. Then, [1,1'-bis(diphenylphosphino)-ferrocene]dichloro palladium (II), 1:1 complex with dichloromethane (18.78 mg, 0.02 mmol) was added, and the resulting mixture was heated at 90° C. for 16 h. The reaction mixture was then diluted with EtOAc and passed through a Celite® pad, and the solvent was removed by rotary evaporation. Silica gel chromatography (Biotage cartridge), eluting with 25% EtOAc in hexane gave trans-2-(trimethylsilyl)ethyl-2-({4'-[(5-methyl-1,3-benzoxazol-2-yl)amino]biphenyl-4-yl}carbonyl)cyclohexanecarboxylate (64 mg, 50%). $^1$H NMR (400 MHz, CD$_2$Cl$_2$) δ −0.013 (s, 9H), 0.88 (m, 2H), 1.41 (m, 3H), 1.71~2.15 (m, 5H), 2.44 (s, 3H), 2.73 (m, 1H), 3.88 (m, 1H), 4.08 (m, 2H), 7.08 (d, 1H), 7.21 (s, 1H), 7.33 (d, 1H), 7.67 (m, 2H), 7.69 (m, 2H), 7.73 (m, 2H), 7.89 (m, 1H), 7.91 (m, 1H).

trans-2-({4'-[(5-Methyl-1,3-benzoxazol-2-yl)amino]biphenyl-4-yl}carbonyl)cyclohexane-carboxylic acid.

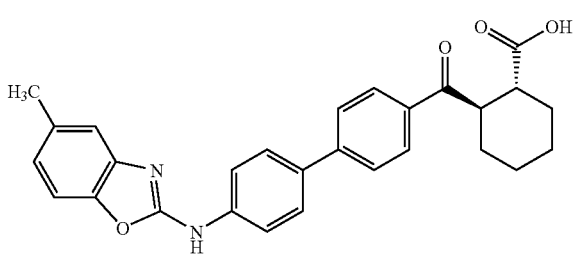

Step 2. To a solution of trans-2-(trimethylsilyl)ethyl-2-({4'-[(5-methyl-1,3-benzoxazol-2-yl)-amino]biphenyl-4-yl}carbonyl)cyclohexanecarboxylate (64 mg, 0.12mmol) in THF (2 mL) was added tetrabutylammonium fluoride (1.0 M in THF, 0.70 mL), and then the reaction mixture was stirred at rt for 16 h. Saturated aqueous NH$_4$Cl was added, and the reaction mixture was diluted with EtOAc and water. The organic layer was separated and the aqueous layer was extracted with EtOAc. The combined organic phases were washed with water and brine, dried over Na$_2$SO$_4$, filtered, and evaporated under reduced pressure. The residue was treated with MeOH, and the precipitate was collected by filtration and dried in a vacuum oven to give trans-2-({4'-[(5-methyl-1,3-benzoxazol-2-yl)amino]biphenyl-4-yl}carbonyl)cyclohexanecarboxylic acid (44.3 mg, 84%). LC-MS m/z 455.3 (MH$^+$), ret. time 3.57 min. $^1$H NMR (400 MHz, DMSO-d$_6$) δ 1.21 (m, 1H), 1.37 (m, 2H), 1.63 (m, 1H), 1.85 (m, 3H), 2.05 (m, 1H), 2.38 (s, 3H), 2.69 (m, 1H), 3.95 (m, 1H), 7.03 (d, 1H), 7.33 (d, 2H), 7.76 (m, 4H), 7.85 (d, 2H), 7.93 (d, 2H), 10.73 (s, 1H).

EXAMPLE 32 cis-3-[4'-(6-Chloro-benzothiazol-2-ylamino)-biphenyl-4-carbonyl]-cyclohexanecarboxylic acid

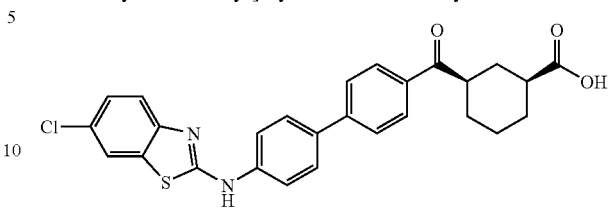

cis-3-[4'-(6-Chloro-benzothiazol-2-ylamino)-biphenyl-4-carbonyl]-cyclohexanecarboxylic acid

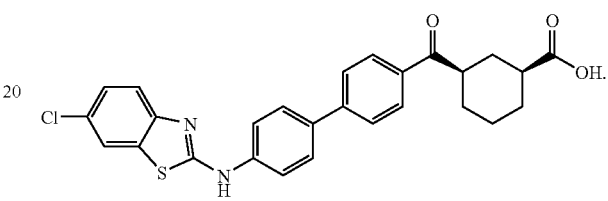

To a solution of 3-(4'-amino-biphenyl-4-carbonyl)-cyclohexanecarboxylic acid methyl ester (100 mg, 0.3 mmol) in butanol (5 mL), 2,6-dichloro-benzothiazole (60 mg, 0.3 mmol) and 5 drops of 4 M HCl in dioxane were added, and the reaction mixture was heated at 90° C. for 5 h. An additional sample of 2,6-dichlorobenzothiazole (60 mg, 0.3 mmol) and 5 drops of 4 M HCl in dioxane were then added, and the reaction mixture was heated overnight at 90° C. The solvent was removed by rotary evaporation, the residue was dissolved in DMF (2 mL), 1 N aqueous NaOH (0.3 mL, 0.3 mmol) was added, and the mixture was heated at 75° C. overnight. A solution of 1 N aqueous HCl (0.3 mL, 0.3 mmol) and methanol (5 mL) were added to the reaction mixture, and the crude product was purified by preparative reverse-phase HPLC (water/acetonitrile gradient, containing 0.1% TFA) to afford cis-3-[4'-(6-chloro-benzothiazol-2-ylamino)-biphenyl-4-carbonyl]-cyclohexanecarboxylic acid as a white solid (12.6 mg, yield 23.4%). $^1$H NMR (300 MHz, DMSO) δ 8.05 (d, 2 H), 7.75–8.00 (m, 7 H), 7.50 (d, 1 H), 7.35 (d, 1 H), 3.25 (m, 1 H), 2.50 (m, 1 H), 2.20–1.90 (m, 4 H), 1.70–1.50 (m, 4 H); LC-MS ret. time 3.99 min (method 2), m/z 491.11 (MH$^+$).

EXAMPLE 33 trans-2-({4'-[(5,6-difluoro-1H-benzimidazol-2-yl)amino]biphenyl-4-yl}carbonyl)cyclopentanecarboxylic acid

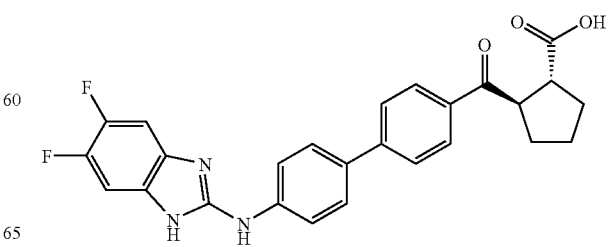

Methyl 2-[(4'-aminobiphenyl-4-yl)carbonyl]cyclopentanecarboxylate (264 mg, 0.02 mmol) was dissolved in n-butanol (8 mL), 2-chloro-5,6-difluoro-1H-benzimidazole (185 mg, 0.98 mmol) and 4 N HCl (0.2 mL) were then added, and the resulting mixture was heated at 90° C. for 5 h. The mixture was then cooled to rt, and solvent was removed under reduced pressure. The residue was dissolved in methanol (5 mL) and tetrahydrofuran (5 mL), and then treated with 1 N aqueous sodium hydroxide (2.45 mL, 2.45 mmol). The mixture was stirred at rt for 16 h and then concentrated under reduced pressure. The residue was purified by preparative reverse-phase HPLC (water/acetonitrile gradient, containing 0.1% TFA) to afford trans-2-({4'-[(5,6-difluoro-1H-benzimidazol-2-yl)amino]biphenyl-4-yl}carbonyl)cyclopentanecarboxylic acid (9.1 mg, 3%). LC-MS m/z 462.3 (MH⁺), ret. time 3.23 min; $^1$H NMR (300 MHz, DMSO-$d_6$) δ 1.69–1.81 (m, 4H), 1.98–2.18 (m, 2H), 3.14–3.22 (m, 1H), 4.04–4.09 (m, 1H), 7.38 (t, 2H), 7.77–7.84 (m, 6H), 8.05 (d, 2H).

Preparation of Compounds of Formula (Ia)

EXAMPLE 34

(1R,2R)-2-[{3-fluoro-4'-[(6-fluoro-1,3-benzothiazol-2-yl)amino]biphenyl-4-yl}(hydroxy)methyl]cyclopentanecarboxylic acid

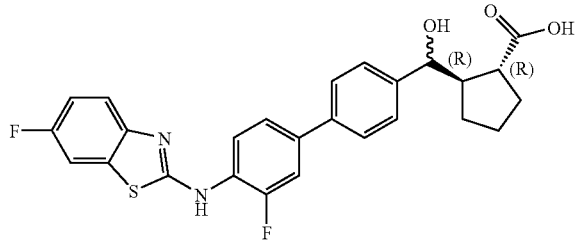

To a solution of (1R,2R)-2-({3'-fluoro-4'-[(6-fluoro-1,3-benzothiazol-2-yl)amino]biphenyl-4-yl}carbonyl)cyclopentanecarboxylic acid (300 mg, 0.63 mmol) in THF (6 mL), a solution of sodium borohydride (23.82 mg, 0.63 mmol) in water (3 mL) was added. The reaction mixture was stirred at rt for 3 hours. The solvent was removed, the residue was then dissolved in methanol (2 mL), and the desired product was isolated by preparative reverse-phase HPLC (water/acetonitrile gradient, containing 0.1% TFA). Two diastereomers of (1R,2R)-2-[{3'-fluoro-4'-[(6-fluoro-1,3-benzothiazol-2-yl)amino]biphenyl-4-yl}(hydroxy)methyl]cyclopentanecarboxylic acid were obtained: a more polar isomer (15 mg, yield 5%). LC-MS m/z 481.3 (MH⁺), ret. time 3.33 min; $^1$H NMR (300 MHz, DMSO-$d_6$) δ 8.60 (t, 1 H), 7.60 (d, 1 H), 7.50 (m, 5 H), 7.35 (d, 2 H), 7.15 (t, 1 H), 4.60 (d, 1 H), 2.65 (m, 1 H), 2.45 (m, 1 H), 1.85 (m, 1 H), 1.70–1.40 (m, 5 H); and a less polar isomer (10 mg, yield 3%); LC-MS m/z 481.3 (MH⁺), ret. time 3.46 min; $^1$H NMR (300 MHz, DMSO-$d_6$) δ 8.60 (t, 1 H), 7.60 (d, 1 H), 7.50 (m, 5 H), 7.35 (d, 2 H), 7.15 (t, 1 H), 4.60 (d, 1 H), 2.65 (m, 1 H), 2.45 (m, 1 H), 1.85 (m, 1 H), 1.65 (m, 1 H), 1.50 (m, 3 H), 1.25 (m, 1 H).

Preparation of Compounds of Formula (Ib)

It will be recognized by those skilled in the art that compounds of Formula (Ia) can be converted to and isolated as the corresponding cyclic ester (lactone) having Formula (Ib), for example by spontaneous dehydration of the compound of Formula (Ia), or by dehydration of the compound of Formula (Ib) induced by methods known in the art. For example, such methods for the formation of compounds of Formula (Ib) from compounds of Formula (Ia) include heating under dry conditions such as in a vacuum oven; treatment with a catalytic amount of acid such as acetic acid, 4-toluenesulfonic acid, or trifluoroacetic acid in a suitable solvent such as acetonitrile, methylene chloride, or toluene; and treatment with a dehydrating reagent such as dicyclohexylcarbodiimide in the presence of 4-dimethylaminopyridine in a suitable solvent such as acetonitrile, methylene chloride, or toluene.

Using appropriate starting materials and the experimental procedures described above, compounds of Formula (I) were prepared as listed in Table 1. Additional compounds of Formula (Ia) can be prepared by using appropriate starting materials and experimental procedures similar to that described above for (1R,2R)-2-[{3'-fluoro-4'-[(6-fluoro-1,3-benzothiazol-2-yl)amino]biphenyl-4-yl}(hydroxy)methyl] cyclopentanecarboxylic acid. Compounds of Formula (Ib) can be prepared by using appropriate compounds of Formula (Ia) as starting materials and applying methods such as described above. Additional compounds of Formula (I), Formula (Ia), and Formula (Ib) such as the compounds listed in Table 2, can be prepared by the methods described herein. It will be understood by those skilled in the art that some minor modifications to the described procedures may have been made, but such modifications do not significantly affect the results of the preparation. LC-MS characterization of compounds, as listed in the table, was carried out by using the instrumentation and methods set forth above.

By using the above described methods and by substituting the appropriate starting material(s), other compounds of the invention were made and characterized. These compounds, together with Examples 1–34, are summarized in Table 1 below. In Table 1, "Synthetic route A" refers to the conversion of compounds of Formula (X) to Formula (VIII) [or (I), when R=H], by reaction with intermediates of Formula (IX), as indicated in Scheme 2. "Synthetic route B" refers to conversion of compounds of Formula (VI) to Formula (VIII) [or (I), when R=H], by reaction with intermediates of Formula (VII), as indicated in Schemes 1 and 2.

TABLE 1

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 1 | 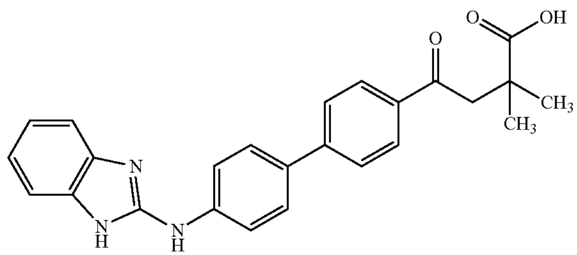 | 4-[4'-(1H-benzimidazol-2-ylamino)-1,1'-biphenyl-4-yl]-2,2-dimethyl-4-oxobutanoic acid | 414.3 | 2.27 | 1 | B | not chiral | | 2 |
| 2 | 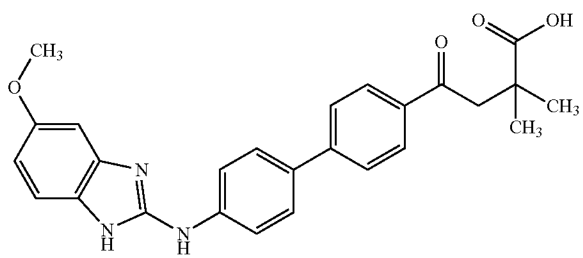 | 4-{4'-[(5-methoxy-1H-benzimidazol-2-yl)amino]-1,1'-biphenyl-4-yl}-2,2-dimethyl-4-oxobutanoic acid | 444.4 | 2.37 | 1 | B | not chiral | | |
| 3 | 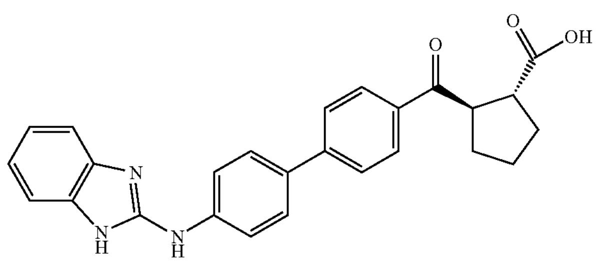 | 2-[[4'-(1H-benzimidazol-2-ylamino)-1,1'-biphenyl-4-yl]carbonyl]cyclopentanecarboxylic acid | 426.4 | 2.82 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 4 | 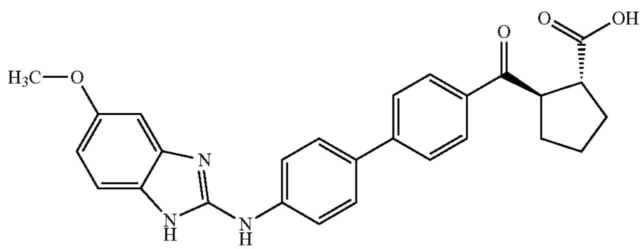 | 2-({4'-[(5-methoxy-1H-benzimidazol-2-yl)amino]-1,1'-biphenyl-4-yl}carbonyl)cyclopentane-carboxylic acid | 456.3 | 2.31 | 1 | B | trans racemic mixture | | |
| 5 | 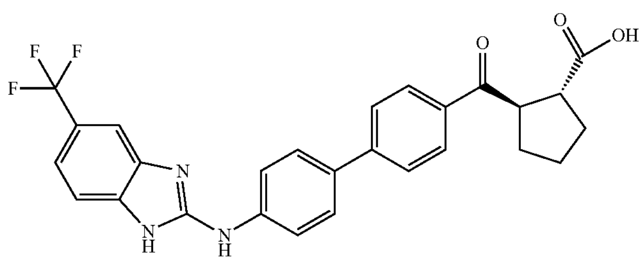 | 2-[(4'-{[5-(trifluoromethyl)-1H-benzimidazol-2-yl]amino}-1,1'-biphenyl-4-yl)carbonyl]cyclopentane-carboxylic acid | 494.3 | 2.56 | 1 | A | trans racemic mixture | | 33 |
| 6 | 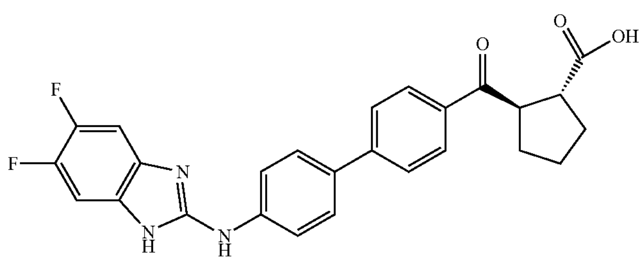 | 2-({4'-[(5,6-difluoro-1H-benzimidazol-2-yl)amino]-1,1'-biphenyl-4-yl}carbonyl)cyclopentane-carboxylic acid | 462.3 | 3.23 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 7 | 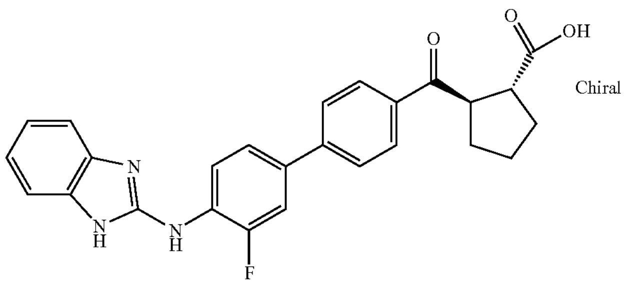 | (1R, 2R)-2-[{4'-(1H-benzimidazol-2-ylamino)-3'-fluoro-1,1'-biphenyl-4-yl]carbonyl}cyclopentanecarboxylic acid | 444.4 | 2.80 | 1 | B | R, R-trans (from chiral intermediate) | 80 | 29 |
| 8 | 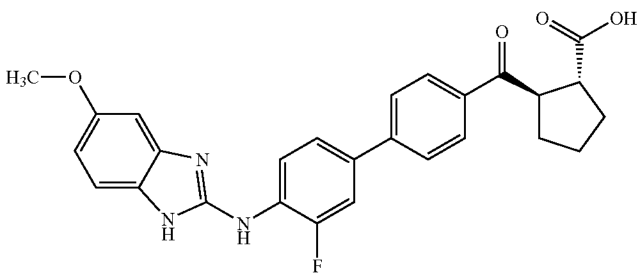 | (1R, 2R)-2-{{3'-fluoro-4'-[(5-methoxy-1H-benzimidazol-2-yl)amino]-1,1'-biphenyl-4-yl}carbonyl}cyclopentanecarboxylic acid | 474.3 | 2.29 | 1 | B | R, R-trans (from chiral intermediate) | 74 | |
| 9 | 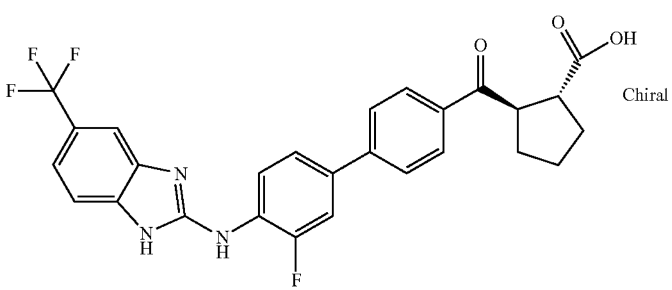 | (1R, 2R)-2-[(3'-fluoro-4'-{[5-(trifluoromethyl)-1H-benzimidazol-2-yl]amino}-1,1'-biphenyl-4-yl)carbonyl]cyclopentanecarboxylic acid | 512.3 | 2.69 | 1 | A | R, R-trans (from chiral intermediate) | 78 | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 10 | 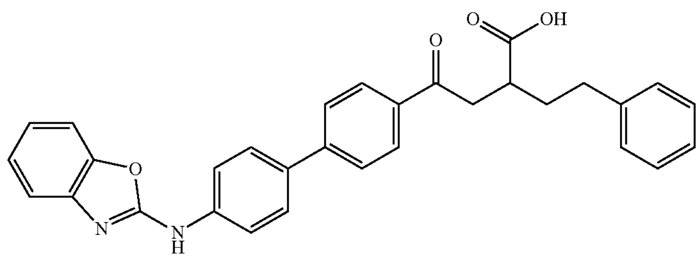 | 4-[4'-(1,3-benzoxazol-2-ylamino)-1,1'-biphenyl-4-yl]-4-oxo-2-(2-phenylethyl)butanoic acid | 491.2 | 3.68 | 1 | B | racemic mixture | | 11 |
| 11 | 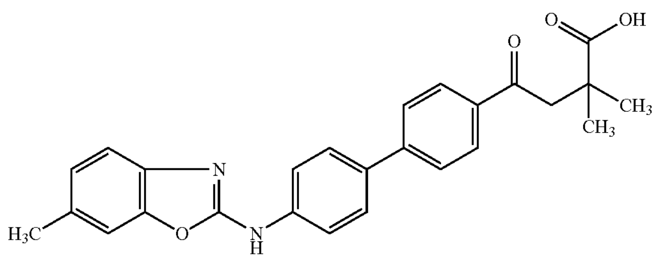 | 2,2-dimethyl-4-{4'-[(6-methyl-1,3-benzoxazol-2-yl)amino]-1,1'-biphenyl-4-yl}-4-oxobutanoic acid | 429.2 | 3.51 | 2 | B | not chiral | | 12 |
| 12 | 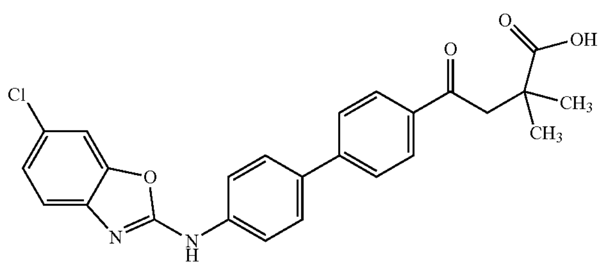 | 4-{4'-[(6-chloro-1,3-benzoxazol-2-yl)amino]-1,1'-biphenyl-4-yl}-2,2-dimethyl-4-oxobutanoic acid | 449.1 | 3.99 | 2 | B | not chiral | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 13 | 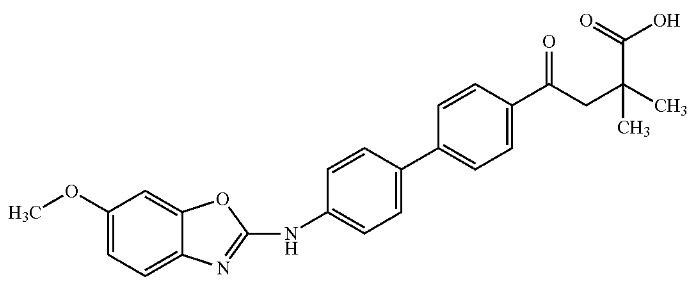 | 4-{4'-[(6-methoxy-1,3-benzoxazol-2-yl)amino]-1,1'-biphenyl-4-yl}-2,2-dimethyl-4-oxobutanoic acid | 445.2 | 3.47 | 2 | B | not chiral | | |
| 14 | 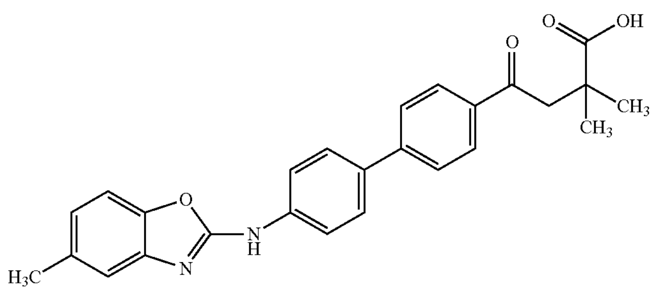 | 2,2-dimethyl-4-{4'-[(5-methyl-1,3-benzoxazol-2-yl)amino]-1,1'-biphenyl-4-yl}-4-oxobutanoic acid | 429.2 | 3.77 | 2 | B | not chiral | | |
| 15 | 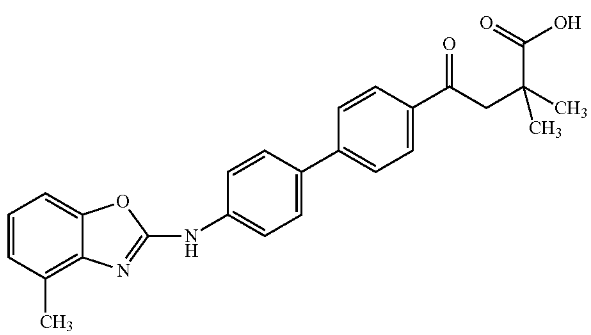 | 2,2-dimethyl-4-{4'-[(4-methyl-1,3-benzoxazol-2-yl)amino]-1,1'-biphenyl-4-yl}-4-oxobutanoic acid | 433.2 | 3.80 | 2 | B | not chiral | | 13 |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 16 | 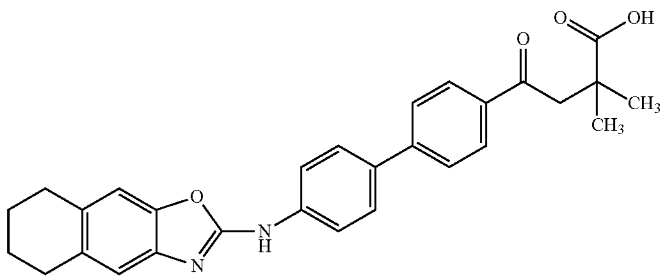 | 2,2-dimethyl-4-oxo-4-[4'-(5,6,7,8-tetrahydronaphtho[2,3-d][1,3]oxazol-2-ylamino)-1,1'-biphenyl-4-yl]butanoic acid | 469.2 | 3.99 | 2 | B | not chiral | | |
| 17 | 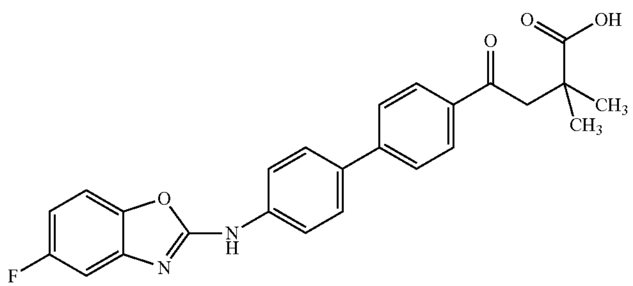 | 4-{4'-[(5-fluoro-1,3-benzoxazol-2-yl)amino]-1,1'-biphenyl-4-yl}-2,2-dimethyl-4-oxobutanoic acid | 433.2 | 3.80 | 2 | B | not chiral | | |
| 18 | 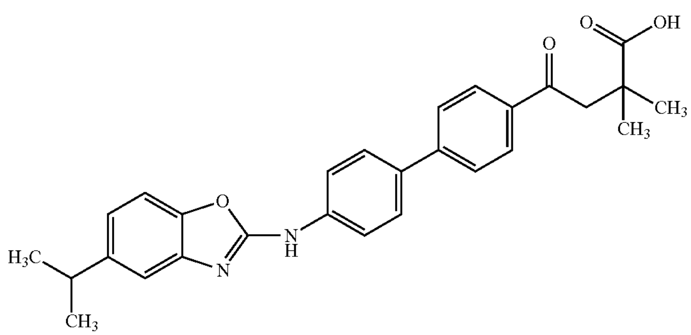 | 4-{4'-[(5-isopropyl-1,3-benzoxazol-2-yl)amino]-1,1'-biphenyl-4-yl}-2,2-dimethyl-4-oxobutanoic acid | 457.2 | 3.88 | 2 | B | not chiral | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 19 | 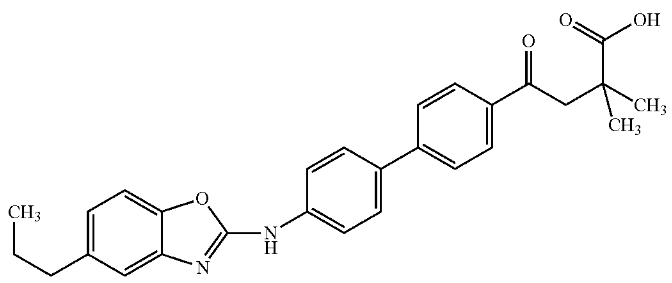 | 2,2-dimethyl-4-oxo-4-{4'-[(5-propyl-1,3-benzoxazol-2-yl)amino]-1,1'-biphenyl-4-yl}butanoic acid | 457.2 | 3.95 | 2 | B | not chiral | | |
| 20 | 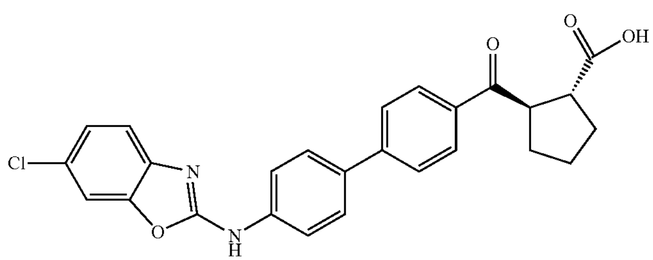 | 2-({4'-[(6-chloro-1,3-benzoxazol-2-yl)amino]-1,1'-biphenyl-4-yl}carbonyl)cyclopentane-carboxylic acid | 461.1 | 3.84 | 2 | B | trans racemic mixture | | |
| 21 | 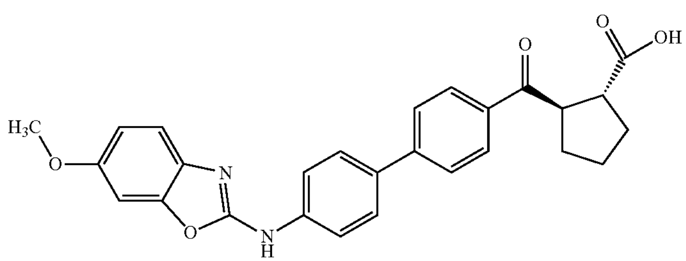 | 2-({4'-[(6-methoxy-1,3-benzoxazol-2-yl)amino]-1,1'-biphenyl-4-yl}carbonyl)cyclopentane-carboxylic acid | 457.2 | 3.55 | 2 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 22 | 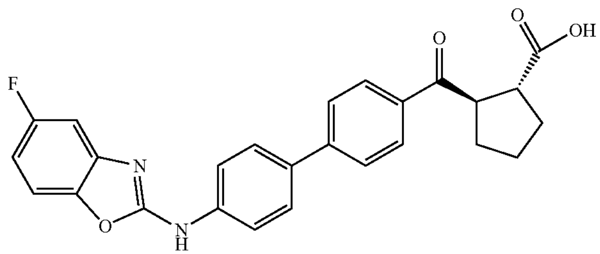 | 2-({4'-[(5-fluoro-1,3-benzoxazol-2-yl)amino]-1,1'-biphenyl-4-yl}carbonyl)cyclopentanecarboxylic acid | 445.2 | 3.66 | 2 | B | trans racemic mixture | | 14 |
| 23 | 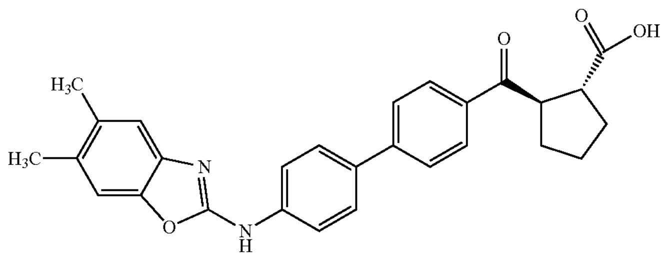 | 2-({4'-[(5,6-dimethyl-1,3-benzoxazol-2-yl)amino]-1,1'-biphenyl-4-yl}carbonyl)cyclopentanecarboxylic acid | 455.4 | 3.58 | 1 | B | trans racemic mixture | | |
| 24 | 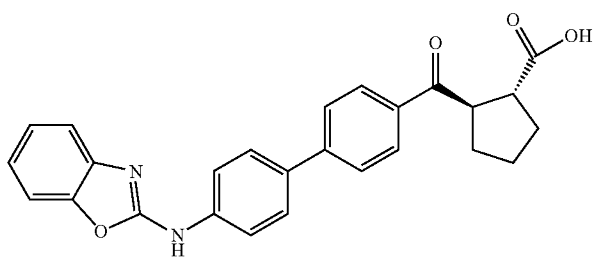 | 2-{[4'-(1,3-benzoxazol-2-ylamino)-1,1'-biphenyl-4-yl]carbonyl}cyclopentanecarboxylic acid | 427.3 | 3.31 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 25 | 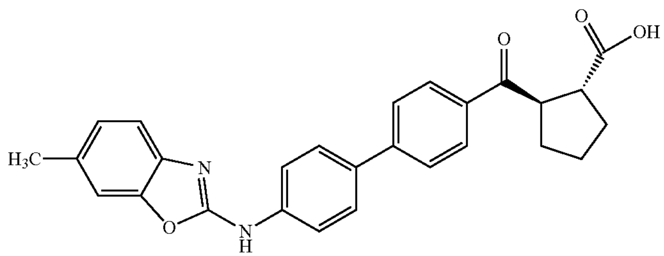 | 2-({4'-[(6-methyl-1,3-benzoxazol-2-yl)amino]-1,1'-biphenyl-4-yl}carbonyl)cyclopentanecarboxylic acid | 441.2 | 3.88 | 2 | B | trans racemic mixture | | |
| 26 | 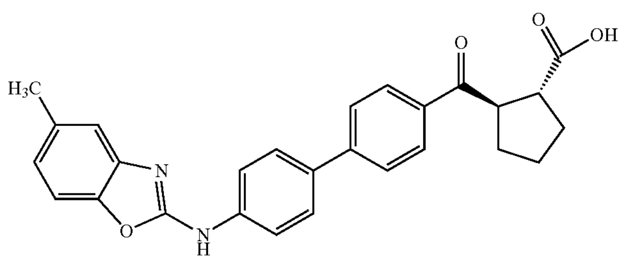 | 2-({4'-[(5-methyl-1,3-benzoxazol-2-yl)amino]-1,1'-biphenyl-4-yl}carbonyl)cyclopentanecarboxylic acid | 441.2 | 3.84 | 2 | B | trans racemic mixture | | |
| 27 | 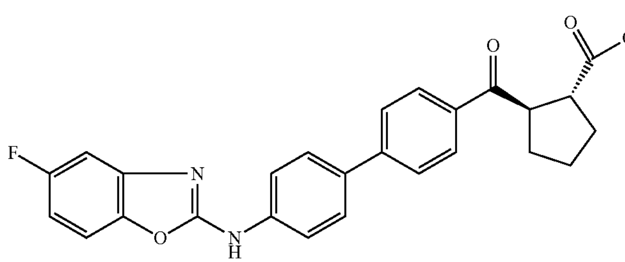 | (1R, 2R)-2-({4'-[(5-fluoro-1,3-benzoxazol-2-yl)amino]-1,1'-biphenyl-4-yl}carbonyl)cyclopentanecarboxylic acid | 445.3 | 3.41 | 1 | B | R, R-trans (from chiral intermediate) | 94 | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 28 | 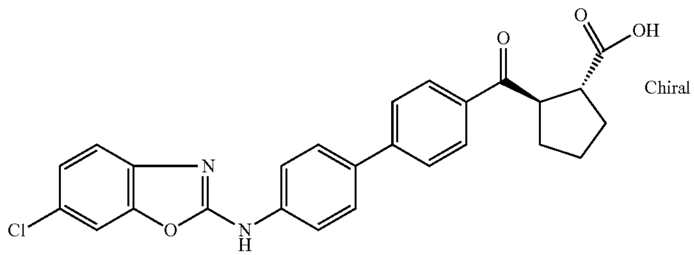 | (1R, 2R)-2-({4'-[(6-chloro-1,3-benzoxazol-2-yl)amino]-1,1'-biphenyl-4-yl}carbonyl)cyclopentane-carboxylic acid | 461.4 | 3.67 | 1 | B | R, R-trans (from chiral intermediate) | 97 | |
| 29 | 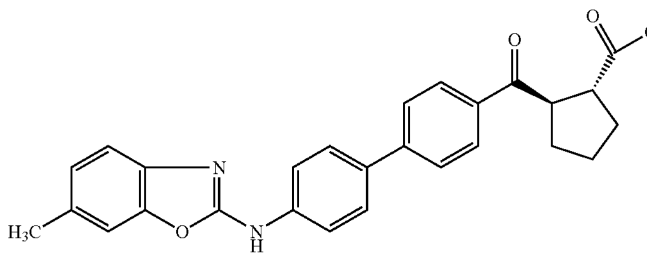 | (1R, 2R)-2-({4'-[(6-methyl-1,3-benzoxazol-2-yl)amino]-1,1'-biphenyl-4-yl}carbonyl)cyclopentane-carboxylic acid | 441.3 | 3.47 | 1 | B | R, R-trans (from chiral intermediate) | 80 | |
| 30 | 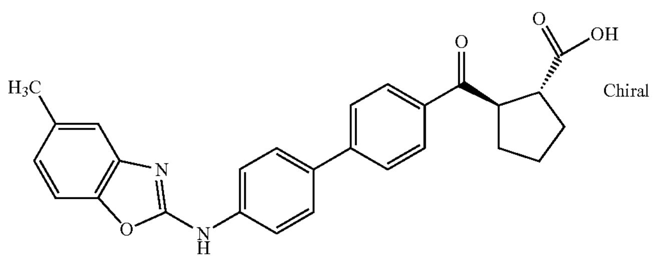 | (1R, 2R)-2-({4'-[(5-methyl-1,3-benzoxazol-2-yl)amino]-1,1'-biphenyl-4-yl}carbonyl)cyclopentane-carboxylic acid | 441.3 | 3.48 | 1 | A | R, R-trans (from chiral prep-HPLC) | 96 | 27 |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 31 | 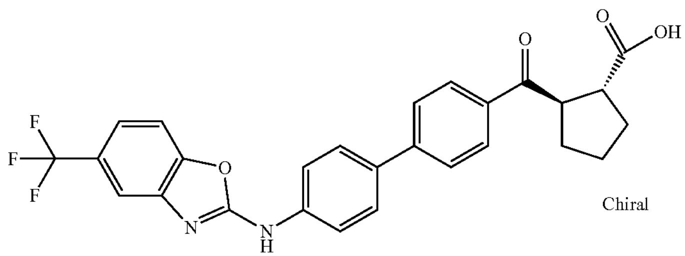 | (1R, 2R)-2-[(4'-{[5-(trifluoromethyl)-1,3-benzoxazol-2-yl]amino}-1-1'-biphenyl-4-yl]carbonyl]cyclopentane-carboxylic acid | 495.3 | 4.15 | 1 | A | R, R-trans (from chiral intermediate) | 98 | |
| 32 | 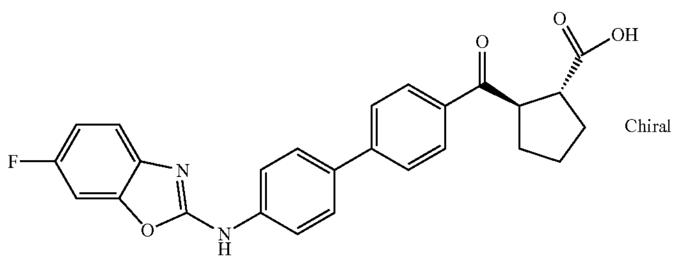 | (1R, 2R)-2-({4'-[(6-fluoro-1,3-benzoxazol-2-yl)amino]-1,1'-biphenyl-4-yl}carbonyl)cyclopentane-carboxylic acid | 445.2 | 3.39 | 1 | B | R, R-trans (from chiral prep-HPLC) | >99 | |
| 33 | 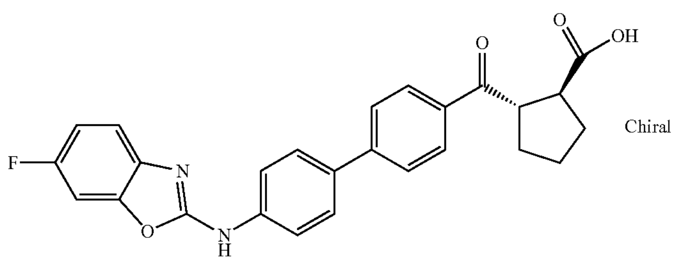 | (1S, 2S)-2-({4'-[(6-fluoro-1,3-benzoxazol-2-yl)amino]-1,1'-biphenyl-4-yl}carbonyl)cyclopentane-carboxylic acid | 445.2 | 3.39 | 1 | B | S, S-trans (from chiral prep-HPLC) | >99 | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 34 | 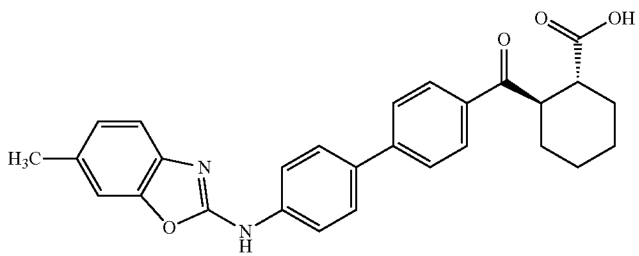 | 2-({4'-[(6-methyl-1,3-benzoxazol-2-yl)amino]-1,1'-biphenyl-4-yl}carbonyl)cyclohexanecarboxylic acid | 455.3 | 3.57 | 1 | A | trans-racemic mixture | | |
| 35 | 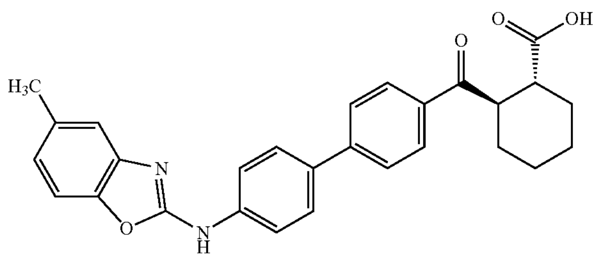 | 2-({4'-[(5-methyl-1,3-benzoxazol-2-yl)amino]-1,1'-biphenyl-4-yl}carbonyl)cyclohexanecarboxylic acid | 455.3 | 3.57 | 1 | A | trans-racemic mixture | | 31 |
| 36 | 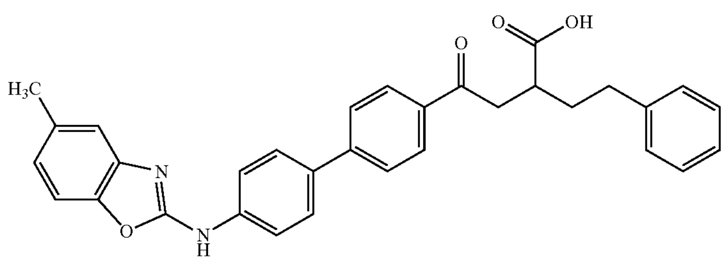 | 4-{4'-[(5-methyl-1,3-benzoxazol-2-yl)amino]-1,1'-biphenyl-4-yl}-4-oxo-2-(2-phenylethyl)butanoic acid | 505.3 | 3.74 | 1 | A | racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 37 | 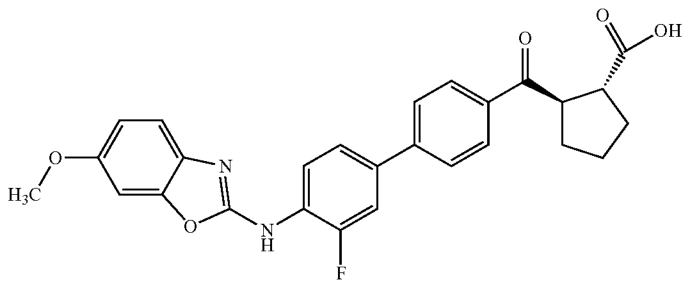 | 2-({3'-fluoro-4'-[(6-methoxy 1,3-benzoxazol-2-yl)amino]-1,1'-biphenyl-4-yl}carbonyl)cyclopentane-carboxylic acid | 475.2 | 3.29 | 2 | B | trans racemic mixture | | |
| 38 | 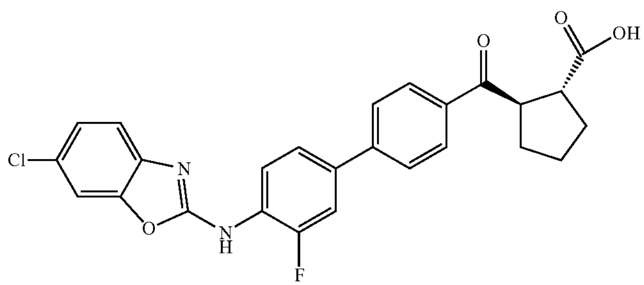 | 2-({4'-[(6-chloro-1,3-benzoxazol-2-yl)amino]-3'-fluoro-1,1'-biphenyl-4-yl}carbonyl)cyclopentane-carboxylic acid | 479.1 | 3.77 | 2 | B | trans racemic mixture | | |
| 39 | 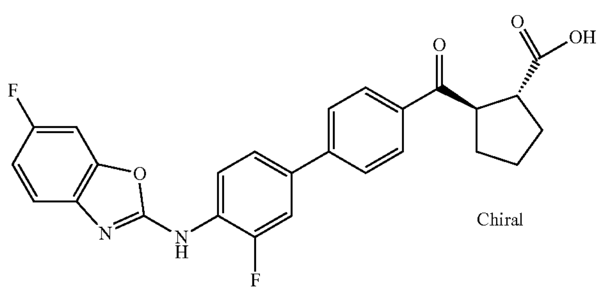 | (1R, 2R)-2-({3'-fluoro-4'-[(6-fluoro-1,3-benzoxazol-2-yl)amino]-1,1'-biphenyl-4-yl}carbonyl)cyclopentane-carboxylic acid | 463.3 | 3.44 | 1 | B | R, R-trans (from chiral prep-HPLC) | 80 | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 40 | 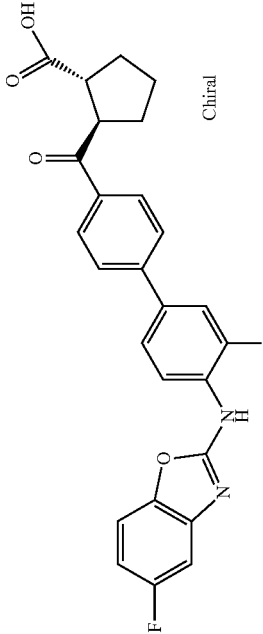 | (1R, 2R)-2-({3'-fluoro-4'-[(5-fluoro-1,3-benzoxazol-2-yl)amino]-1,1'-biphenyl-4-yl}carbonyl)cyclopentane-carboxylic acid | 463.3 | 3.42 | 1 | B | R, R-trans (from chiral prep-HPLC) | 82 | |
| 41 | 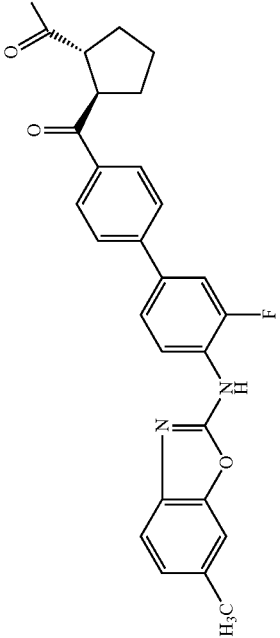 | (1R, 2R)-2-({3'-fluoro-4'-[(6-methyl-1,3-benzoxazol-2-yl)amino]-1,1'-biphenyl-4-yl}carbonyl)cyclopentane-carboxylic acid | 459.3 | 3.57 | 1 | B | R, R-trans (from chiral intermediate) | 80 | 15 |
| 42 | 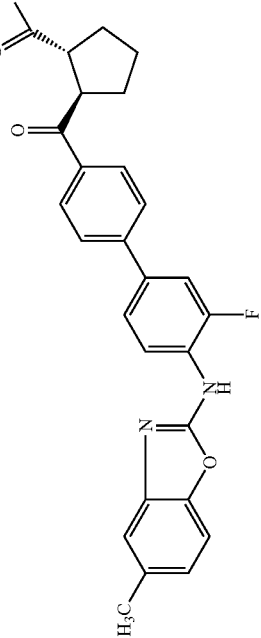 | (1R, 2R)-2-({3'-fluoro-4'-[(5-methyl-1,3-benzoxazol-2-yl)amino]-1,1'-biphenyl-4-yl}carbonyl)cyclopentane-carboxylic acid | 459.3 | 3.54 | 1 | A | R, R-trans (from chiral intermediate) | 94 | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 43 | 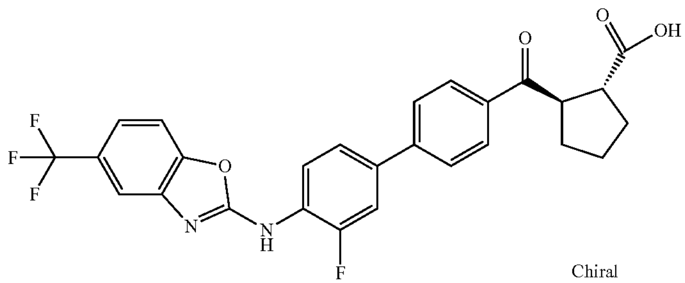 | (1R, 2R)-2-[(3'-fluoro-4'-{[5-(trifluoromethyl)-1,3-benzoxazol-2-yl]amino}-1,1'-biphenyl-4-yl)carbonyl]cyclopentanecarboxylic acid | 513.3 | 4.53 | 1 | A | R, R-trans (from chiral intermediate) | 96 | 1 |
| 44 | 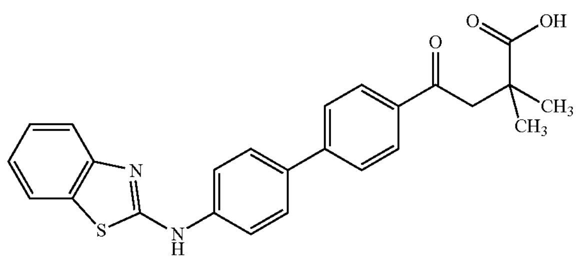 | 4-[4'-(1,3-benzothiazol-2-ylamino)-1,1'-biphenyl-4-yl]-2,2-dimethyl-4-oxobutanoic acid | 431.2 | 3.40 | 1 | B | not chiral | | |
| 45 | 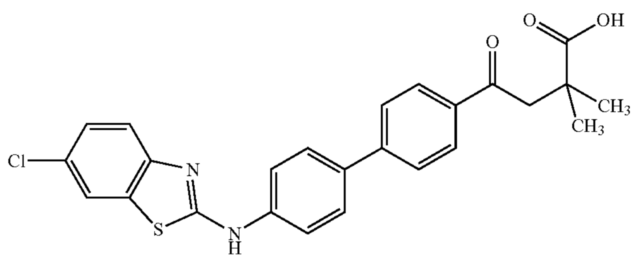 | 4-{4'-[(6-chloro-1,3-benzothiazol-2-yl)amino]-1,1'-biphenyl-4-yl}-2,2-dimethyl-4-oxobutanoic acid | 465.2 | 3.76 | 1 | B | not chiral | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 46 | 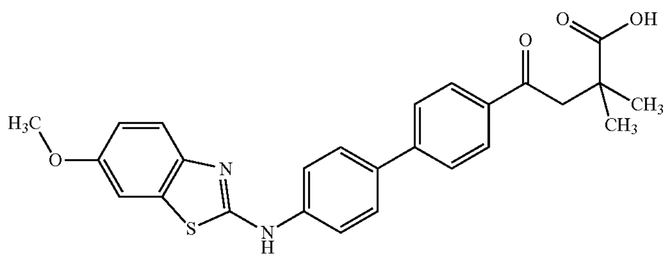 | 4-[4'-[(6-methoxy-1,3-benzothiazol-2-yl)amino]-1,1'-biphenyl-4-yl]-2,2-dimethyl-4-oxobutanoic acid | 461.2 | 3.40 | 1 | B | not chiral | | |
| 47 | 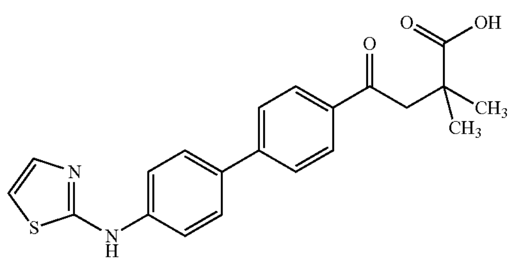 | 2,2-dimethyl-4-oxo-4-[4'-(1,3-thiazol-2-ylamino)-1,1'-biphenyl-4-yl]butanoic acid | 381.4 | 2.53 | 1 | B | not chiral | | 3 |
| 48 | 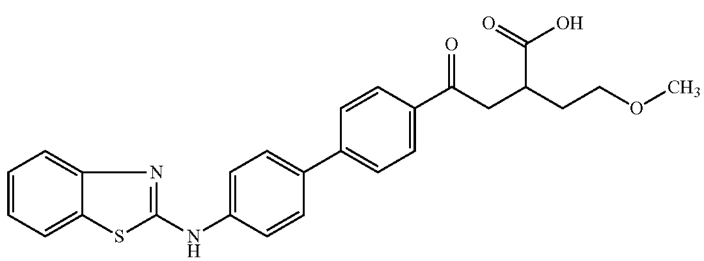 | 4-[4'-(1,3-benzothiazol-2-ylamino)-1,1'-biphenyl-4-yl]-2-(2-methoxyethyl)-4-oxobutanoic acid | 461.2 | 3.29 | 2 | B | racemic mixture | | 6 |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 49 | 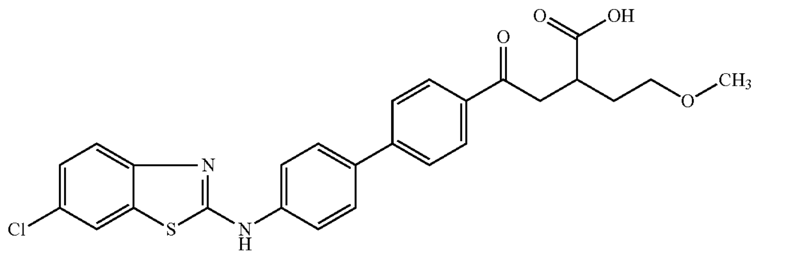 | 4-{4'-[(6-chloro-1,3-benzothiazol-2-yl)amino]-1,1'-biphenyl-4-yl}-2-(2-methoxyethyl)-4-oxobutanoic acid | 495.1 | 3.66 | 2 | B | racemic mixture | | |
| 50 | 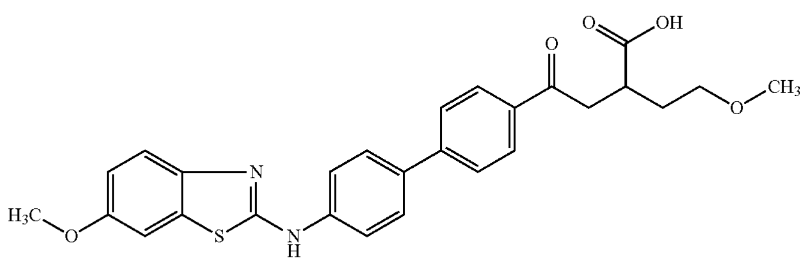 | 4-{4'-[(6-methoxy-1,3-benzothiazol-2-yl)amino]-1,1'-biphenyl-4-yl}-2-(2-methoxyethyl)-4-oxobutanoic acid | 491.2 | 3.25 | 2 | B | racemic mixture | | |
| 51 | 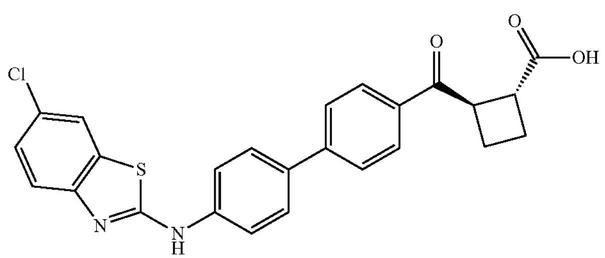 | 2-({4'-[(6-chloro-1,3-benzothiazol-2-yl)amino]-1,1'-biphenyl-4-yl}carbonyl)cyclobutanecarboxylic acid | 463.1 | 3.69 | 1 | B | trans racemic mixture | | 19 |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 52 | 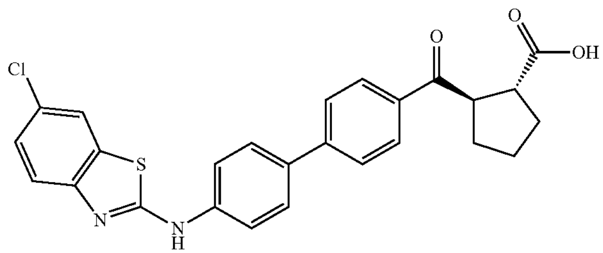 | 2-({4'-[(6-chloro-1,3-benzothiazol-2-yl)amino]-1,1'-biphenyl-4-yl}carbonyl)cyclopentanecarboxylic acid | 477.4 | 3.81 | 1 | B | trans racemic mixture | | |
| 53 | 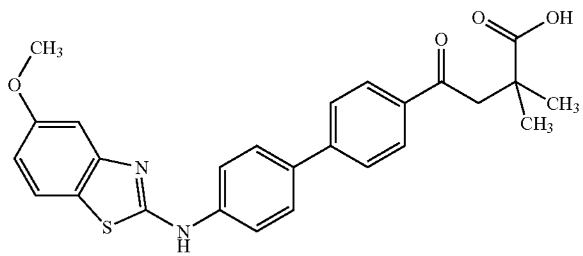 | 4-{4'-[(5-methoxy-1,3-benzothiazol-2-yl)amino]-1,1'-biphenyl-4-yl}-2,2-dimethyl-4-oxobutanoic acid | 461.4 | 3.33 | 1 | B | not chiral | | |
| 54 | 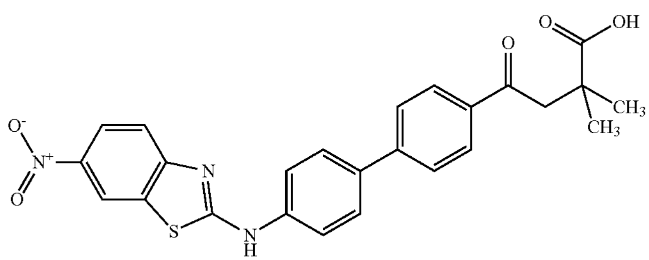 | 2,2-dimethyl-4-{4'-[(6-nitro-1,3-benzothiazol-2-yl)amino]-1,1'-biphenyl-4-yl}-4-oxobutanoic acid | 476.2 | 3.49 | 1 | B | not chiral | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 55 | 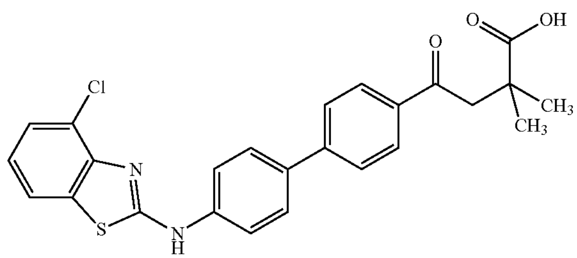 | 4-{4'-[(4-chloro-1,3-benzothiazol-2-yl)amino]-1,1'-biphenyl-4-yl}-2,2-dimethyl-4-oxobutanoic acid | 465.4 | 3.62 | 1 | B | not chiral | | |
| 56 | 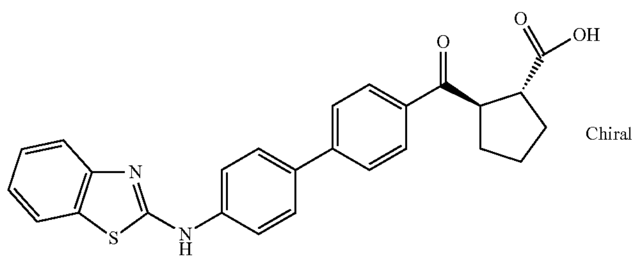 | (1R, 2R)-2-{[4'-(1,3-benzothiazol-2-ylamino)-1,1'-biphenyl-4-yl]carbonyl}cyclopentane-carboxylic acid | 443.3 | 3.43 | 1 | B | R, R-trans (from chiral intermediate) | 97 | |
| 57 | 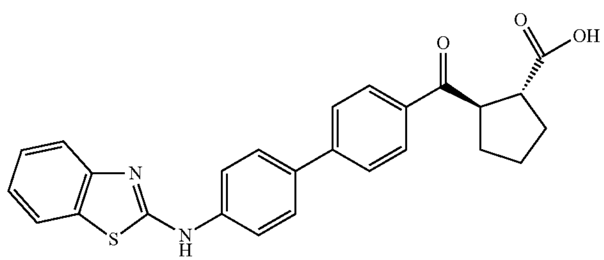 | 2-{[4'-(1,3-benzothiazol-2-ylamino)-1,1'-biphenyl-4-yl]carbonyl}cyclopentane-carboxylic acid | 443.4 | 3.48 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 58 | 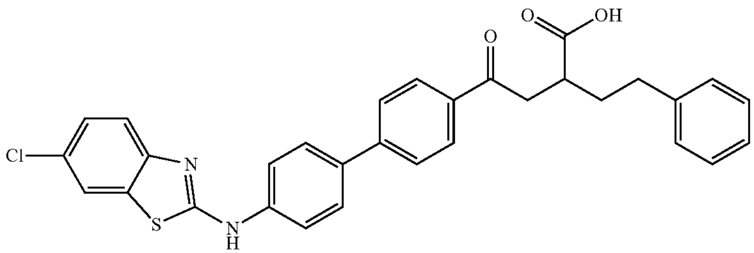 | 4-{4'-[(6-chloro-1,3-benzothiazol-2-yl)amino]-1,1'-biphenyl-4-yl}-4-oxo-2-(2-phenylethyl)butanoic acid | 541.3 | 4.07 | 1 | B | racemic mixture | | 4 |
| 59 | 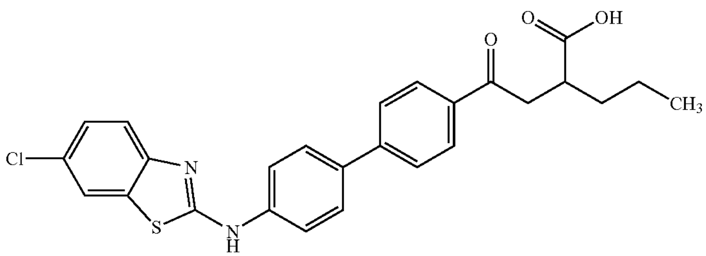 | 2-(2-{4'-[(6-chloro-1,3-benzothiazol-2-yl)amino]-1,1'-biphenyl-4-yl}-2-oxoethyl)pentanoic acid | 479.3 | 3.88 | 1 | B | racemic mixture | | 5 |
| 60 | 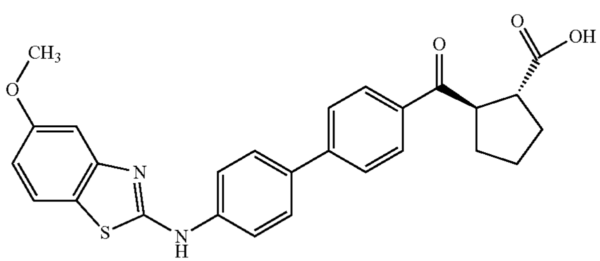 | 2-({4'-[(5-methoxy-1,3-benzothiazol-2-yl)amino]-1,1'-biphenyl-4-yl}carbonyl)cyclopentanecarboxylic acid | 473.3 | 3.42 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 61 | 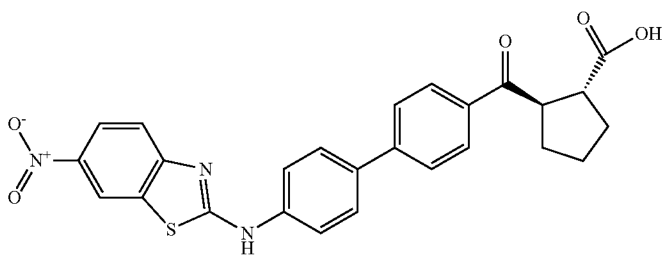 | 2-({4'-[(6-nitro-1,3-benzothiazol-2-yl)amino]-1,1'-biphenyl-4-yl}carbonyl)cyclopentane-carboxylic acid | 488.2 | 3.59 | 1 | B | trans racemic mixture | | |
| 62 | 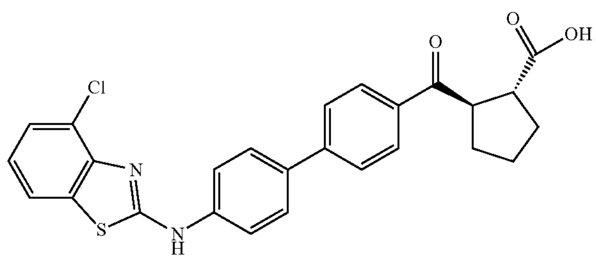 | 2-({4'-[(4-chloro-1,3-benzothiazol-2-yl)amino]-1,1'-biphenyl-4-yl}carbonyl)cyclopentane-carboxylic acid | 477.3 | 3.72 | 1 | B | trans racemic mixture | | |
| 63 | 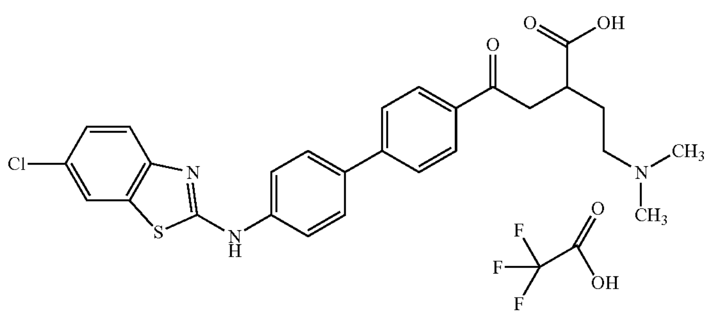 | 4-{4'-[(6-chloro-1,3-benzothiazol-2-yl)amino]-1,1'-biphenyl-4-yl}-2-[2-(dimethylamino)ethyl]-4-oxobutanoic acid (trifluoroacetate salt) | 508.1 | 2.66 | 1 | B | racemic mixture | | 7 |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 64 | 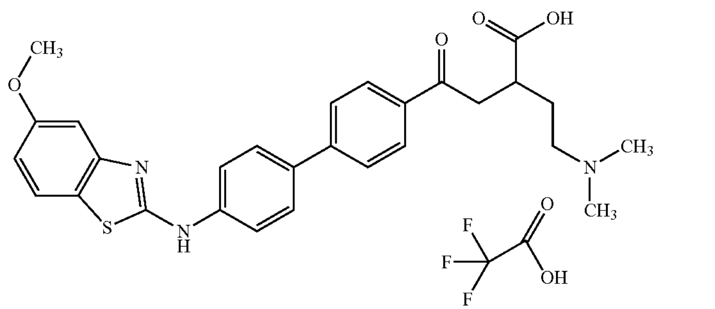 | 2-[2-(dimethylamino)ethyl]-4-{4'-[(5-methoxy-1,3-benzothiazol-2-yl)amino]-1,1'-biphenyl-4-yl}-4-oxobutanoic acid (trifluoroacetate salt) | 504.2 | 2.42 | 1 | B | racemic mixture | | |
| 65 | 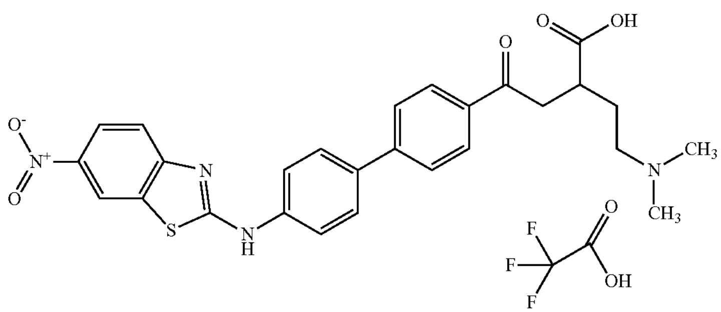 | 2-[2-(dimethylamino)ethyl]-4-{4'-[(6-nitro-1,3-benzothiazol-2-yl)amino]-1,1'-biphenyl-4-yl}-4-oxobutanoic acid (trifluoroacetate salt) | 519.2 | 2.52 | 1 | B | racemic mixture | | |
| 66 | 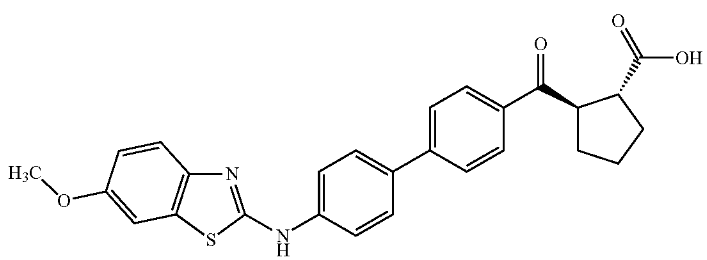 | 2-({4'-[(6-methoxy-1,3-benzothiazol-2-yl)amino]-1,1'-biphenyl-4-yl}carbonyl)cyclopentanecarboxylic acid | 473.3 | 3.41 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 67 | 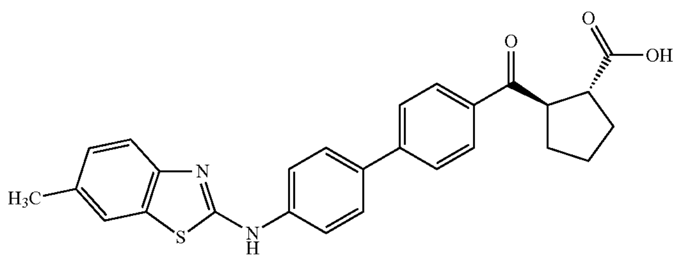 | 2-({4'-[(6-methyl-1,3-benzothiazol-2-yl)amino]-1,1'-biphenyl-4-yl}carbonyl)cyclopentane-carboxylic acid | 457.3 | 3.57 | 1 | A | trans racemic mixture | | 20 |
| 68 | 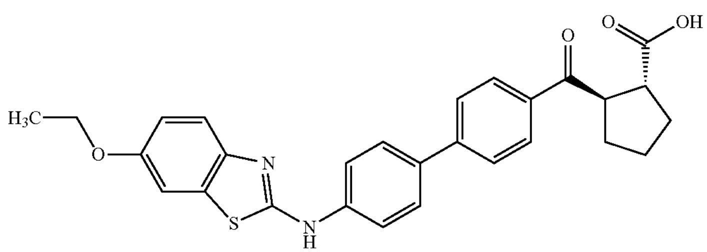 | 2-({4'-[(6-ethoxy-1,3-benzothiazol-2-yl)amino]-1,1'-biphenyl-4-yl}carbonyl)cyclopentane-carboxylic acid | 487.4 | 3.64 | 1 | B | trans racemic mixture | | |
| 69 | 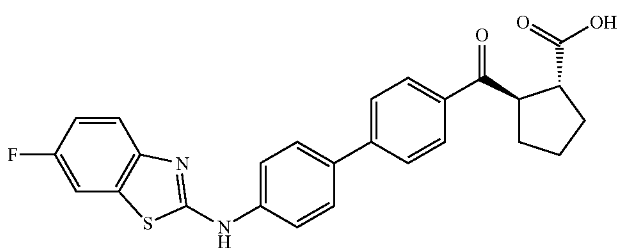 | 2-({4'-[(6-fluoro-1,3-benzothiazol-2-yl)amino]-1,1'-biphenyl-4-yl}carbonyl)cyclopentane-carboxylic acid | 461.4 | 3.63 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 70 | 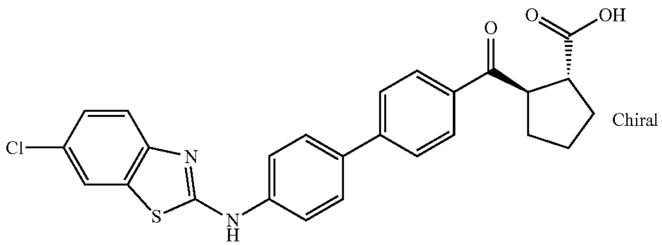 | (1R, 2R)-2-({4'-[(6-chloro-1,3-benzothiazol-2-yl)amino]-1,1'-biphenyl-4-yl}carbonyl)cyclopentane-carboxylic acid | 477.4 | 3.85 | 1 | B | R, R-trans (from chiral prep-HPLC) | 99 | |
| 71 | 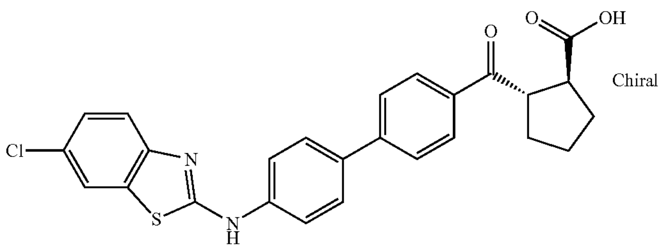 | (1S, 2S)-2-({4'-[(6-chloro-1,3-benzothiazol-2-yl)amino]-1,1'-biphenyl-4-yl}carbonyl)cyclopentane-carboxylic acid | 477.4 | 3.85 | 1 | B | S, S-trans (from chiral prep-HPLC) | 92 | |
| 72 | 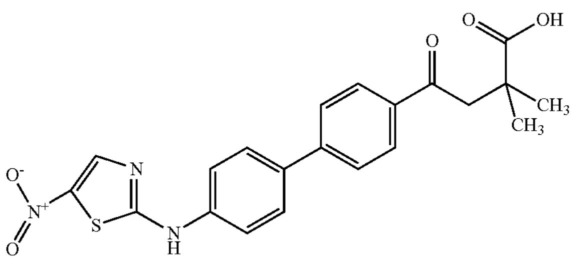 | 2,2-dimethyl-4-{4'-[(5-nitro-1,3-thiazol-2-yl)amino]-1,1'-biphenyl-4-yl}-4-oxobutanoic acid | 426.2 | 3.14 | 1 | B | not chiral | | 9 |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 73 | 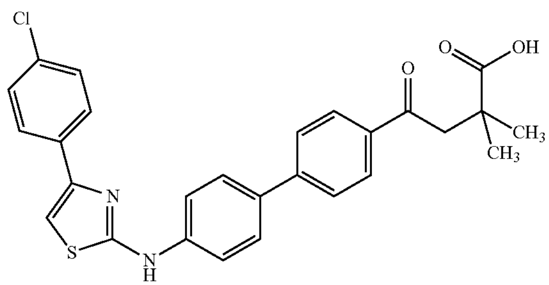 | 4-(4'-{[4-(4-chlorophenyl)-1,3-thiazol-2-yl]amino}-1,1'-biphenyl-4-yl)-2,2-dimethyl-4-oxobutanoic acid | 491.2 | 3.83 | 1 | B | not chiral | | 10 |
| 74 | 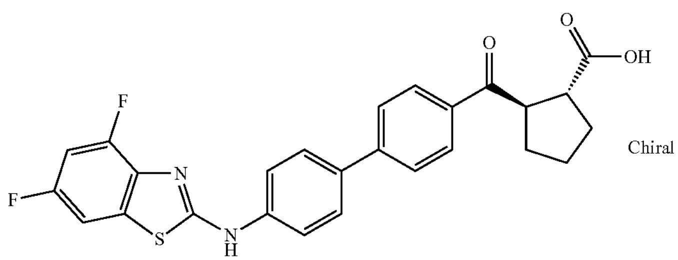 | (1R, 2R)-2-({4'-[(4,6-difluoro-1,3-benzothiazol-2-yl)amino]-1,1'-biphenyl-4-yl}carbonyl)cyclopentanecarboxylic acid | 479.2 | 3.64 | 1 | B | R, R-trans (from chiral prep-HPLC) | 99 | 23 |
| 75 | 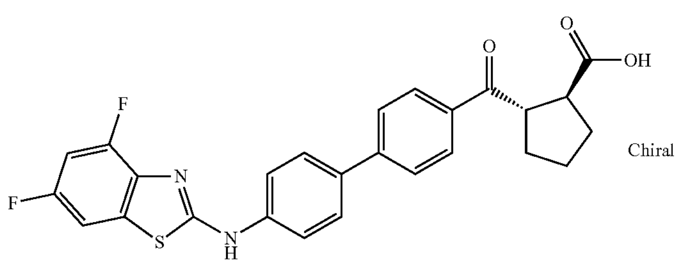 | (1S, 2S)-2-({4'-[(4,6-difluoro-1,3-benzothiazol-2-yl)amino]-1,1'-biphenyl-4-yl}carbonyl)cyclopentanecarboxylic acid | 479.2 | 3.65 | 1 | B | S, S-trans (from chiral prep-HPLC) | 74 | 24 |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 76 | 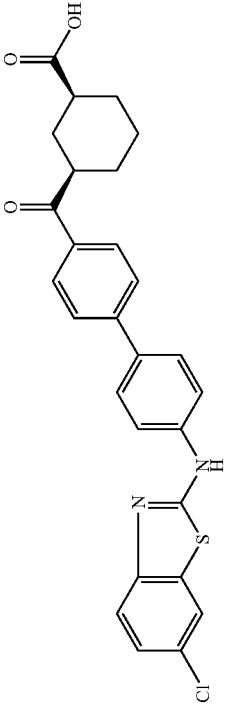 | 3-({4'-[(6-chloro-1,3-benzothiazol-2-yl)amino]-1,1'-biphenyl-4-yl}carbonyl)cyclohexanecarboxylic acid | 491.1 | 3.99 | 2 | B | cis racemic mixture | | 32 |
| 77 | 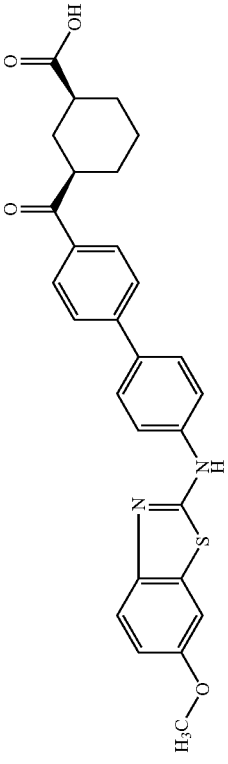 | 3-({4'-[(6-methoxy-1,3-benzothiazol-2-yl)amino]-1,1'-biphenyl-4-yl}carbonyl)cyclohexanecarboxylic acid | 487.2 | 3.11 | 2 | B | cis racemic mixture | | |
| 78 | 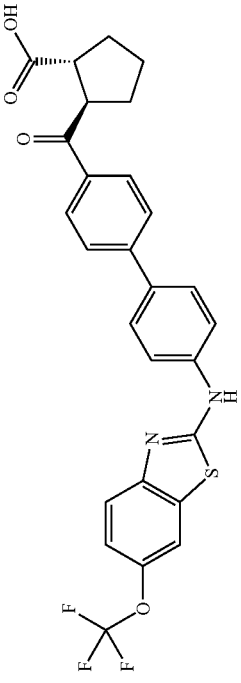 | 2-[(4'-{(6-(trifluoromethoxy)-1,3-benzothiazol-2-yl]amino}-1,1'-biphenyl-4-yl)carbonyl]cyclopentanecarboxylic acid | 527.3 | 3.87 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 79 | 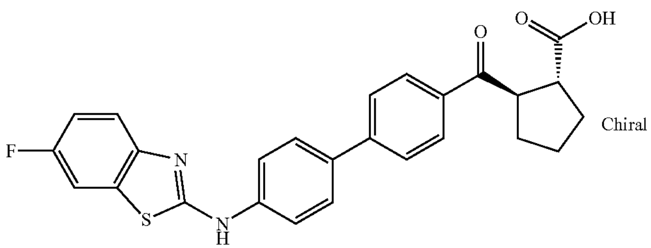 | (1R, 2R)-2-({4'-[(6-fluoro-1,3-benzothiazol-2-yl)amino]-1,1'-biphenyl-4-yl}carbonyl)cyclopentane-carboxylic acid | 461.1 | 3.63 | 1 | B | R, R-trans (from chiral prep-HPLC) | 99 | |
| 80 | 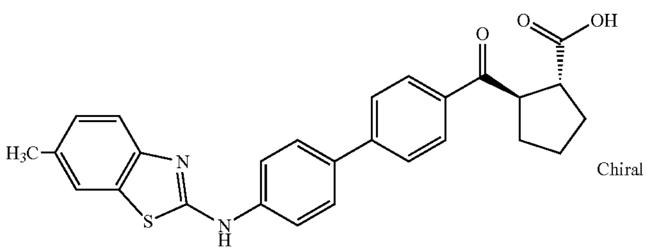 | (1R, 2R)-2-({4'-[(6-methyl-1,3-benzothiazol-2-yl)amino]-1,1'-biphenyl-4-yl}carbonyl)cyclopentane-carboxylic acid | 457.4 | 3.57 | 1 | B | R, R-trans (from chiral prep-HPLC) | 99 | |
| 81 | 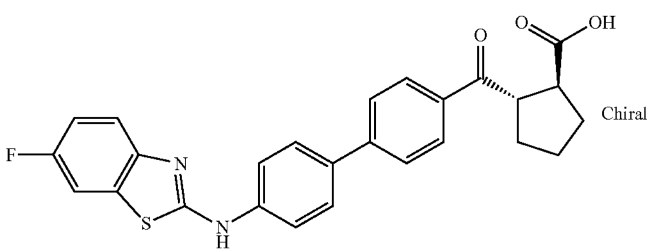 | (1S, 2S)-2-({4'-[(6-fluoro-1,3-benzothiazol-2-yl)amino]-1,1'-biphenyl-4-yl}carbonyl)cyclopentane-carboxylic acid | 461.3 | 3.55 | 1 | B | S, S-trans (from chiral prep-HPLC) | 99 | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 82 | 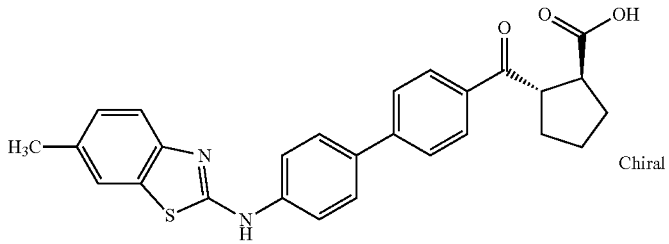 | (1S, 2S)-2-({4'-[(6-methyl-1,3-benzothiazol-2-yl)amino]-1,1'-biphenyl-4-yl}carbonyl)cyclopentanecarboxylic acid | 457.4 | 3.57 | 1 | B | S, S-trans (from chiral prep-HPLC) | 99 | |
| 83 | 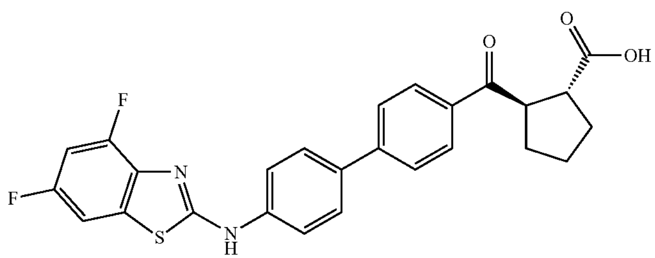 | 2-({4'-[(4,6-difluoro-1,3-benzothiazol-2-yl)amino]-1,1'-biphenyl-4-yl}carbonyl)cyclopentanecarboxylic acid | 479.3 | 4.12 | 1 | B | trans racemic mixture | | 22 |
| 84 | 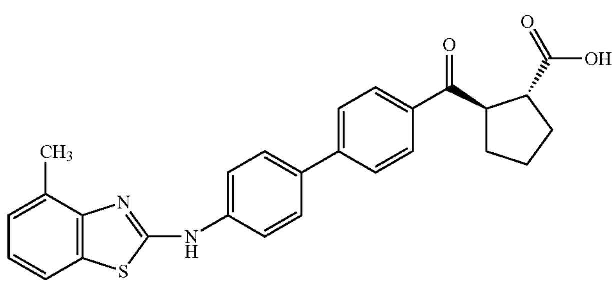 | 2-({4'-[(4-methyl-1,3-benzothiazol-2-yl)amino]-1,1'-biphenyl-4-yl}carbonyl)cyclopentanecarboxylic acid | 457.3 | 3.71 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 85 | 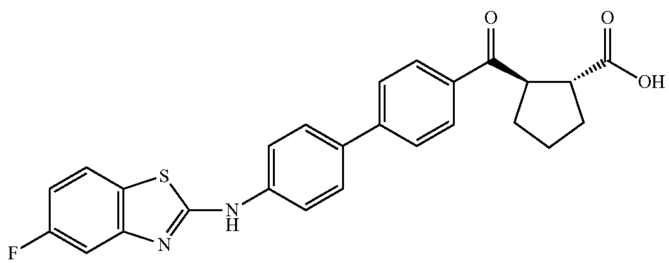 | 2-({4'-[(5-fluoro-1,3-benzothiazol-2-yl)amino]-1,1'-biphenyl-4-yl}carbonyl)cyclopentane-carboxylic acid | 461.3 | 3.56 | 1 | B | trans racemic mixture | | 16 |
| 86 | 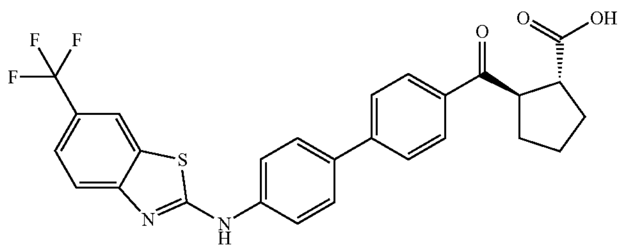 | 2-[(4'-{[6-(trifluoromethyl)-1,3-benzothiazol-2-yl]amino}-1,1'-biphenyl-4-yl)carbonyl]cyclopentane-carboxylic acid | 511.3 | 4.27 | 1 | B | trans racemic mixture | | 17 |
| 87 | 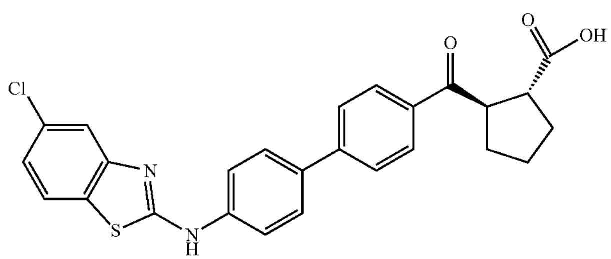 | 2-({4'-[(5-chloro-1,3-benzothiazol-2-yl)amino]-1,1'-biphenyl-4-yl}carbonyl)cyclopentane-carboxylic acid | 477.2 | 3.78 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 88 | 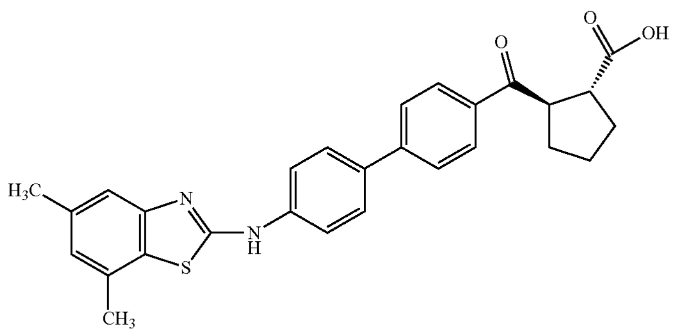 | 2-({4'-[(5,7-dimethyl-1,3-benzothiazol-2-yl)amino]-1,1'-biphenyl-4-yl}carbonyl)cyclopentanecarboxylic acid | 471.3 | 3.70 | 1 | B | trans racemic mixture | | |
| 89 | 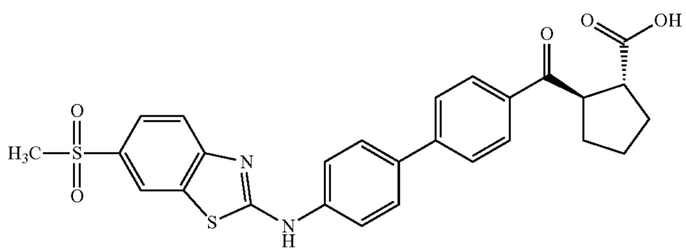 | 2-[(4'-{[6-(methylsulfonyl)-1,3-benzothiazol-2-yl]amino}-1,1'-biphenyl-4-yl)carbonyl]cyclopentanecarboxylic acid | 521.2 | 3.60 | 1 | B | trans racemic mixture | | |
| 90 | 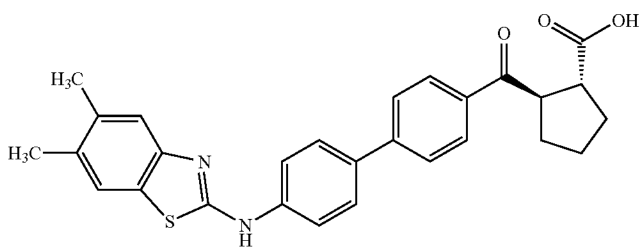 | 2-({4'-[(5,6-dimethyl-1,3-benzothiazol-2-yl)amino]-1,1'-biphenyl-4-yl}carbonyl)cyclopentanecarboxylic acid | 471.3 | 3.65 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 91 | 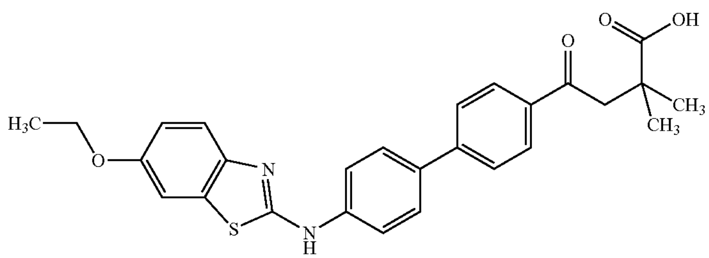 | 4-{4'-[(6-ethoxy-1,3-benzothiazol-2-yl)amino]-1,1'-biphenyl-4-yl}-2,2-dimethyl-4-oxobuttanoic acid | 475.2 | 3.47 | 1 | B | nor chiral | | |
| 92 | 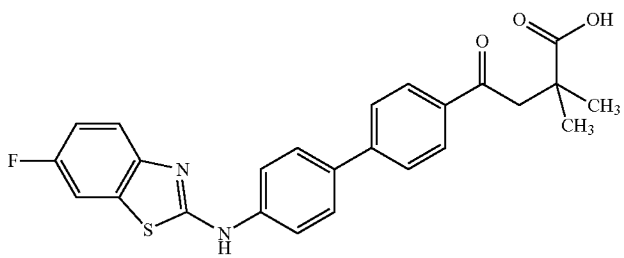 | 4-{4'-[(6-fluoro-1,3-benzothiazol-2-yl)amino]-1,1'-biphenyl-4-yl}-2,2-dimethyl-4-oxobuttanoic acid | 449.2 | 3.46 | 1 | B | not chiral | | |
| 93 | 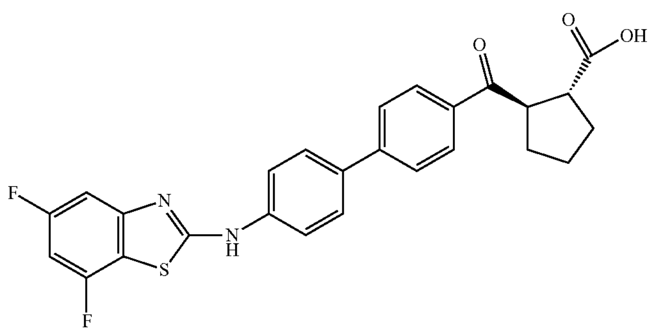 | 2-({4'-[(5,7-difluoro-1,3-benzothiazol-2-yl)amino]-1,1'-biphenyl-4-yl}carbonyl)cyclopentane-carboxylic acid | 479.2 | 3.75 | 1 | B | trans racemic mixture | | 28 |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 94 | 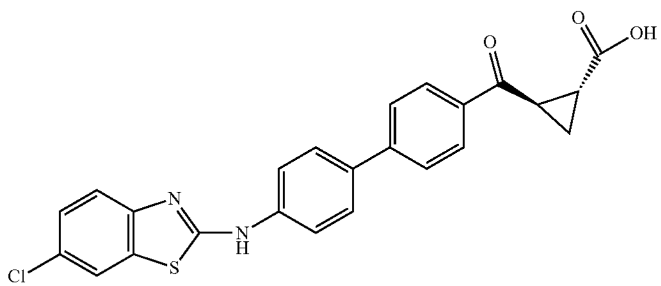 | 2-({4'-[(6-chloro-1,3-benzothiazol-2-yl)amino]-1,1'-biphenyl-4-yl}carbonyl)cyclopropane-carboxylic acid | 449.2 | 3.70 | 1 | B | trans racemic mixture | | |
| 95 | 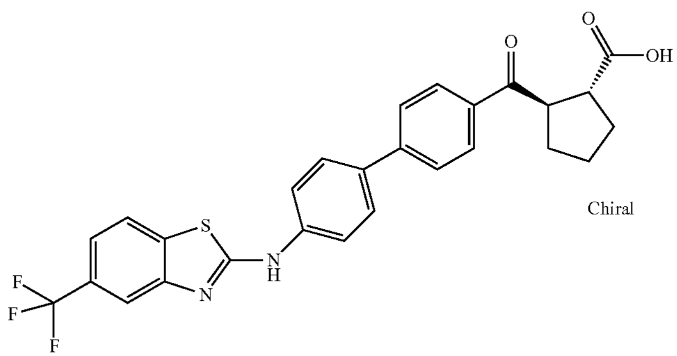 | (1R, 2R)-2-[(4'-{[5-(trifluoromethyl)-1,3-benzothiazol-2-yl]amino}-1,1'-biphenyl-4-yl)carbonyl]cyclopentane-carboxylic acid | 511.1 | 3.82 | 1 | A | R, R-trans (from chiral intermediate) | 90 | |
| 96 | 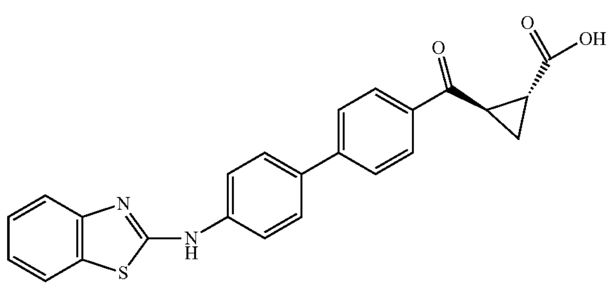 | 2-[[4'-(1,3-benzothiazol-2-ylamino)-1,1'-biphenyl-4-yl]carbonyl]cyclopropane-carboxylic acid | 415.2 | 3.21 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 97 | 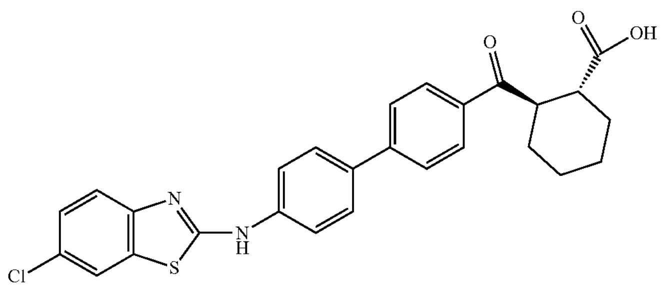 | 2-({4'-[(6-chloro-1,3-benzothiazol-2-yl)amino]-1,1'-biphenyl-4-yl}carbonyl)cyclohexanecarboxylic acid | 491.2 | 3.90 | 1 | B | trans racemic mixture | | |
| 98 | 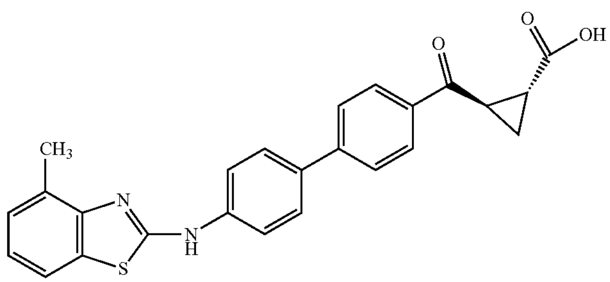 | 2-({4'-[(4-methyl-1,3-benzothiazol-2-yl)amino]-1,1'-biphenyl-4-yl}carbonyl)cyclopropanecarboxylic acid | 429.2 | 3.49 | 1 | B | trans racemic mixture | | |
| 99 | 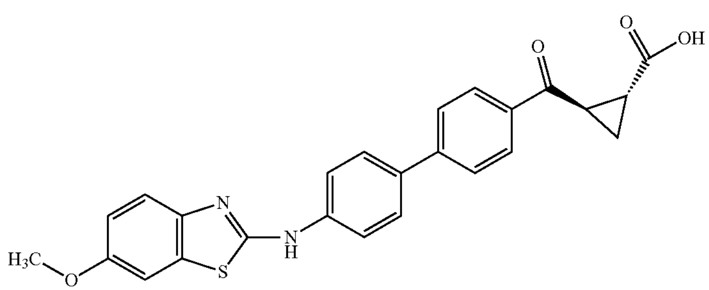 | 2-({4'-[(6-methoxy-1,3-benzothiazol-2-yl)amino]-1,1'-biphenyl-4-yl}carbonyl)cyclopropanecarboxylic acid | 445.2 | 3.17 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 100 | 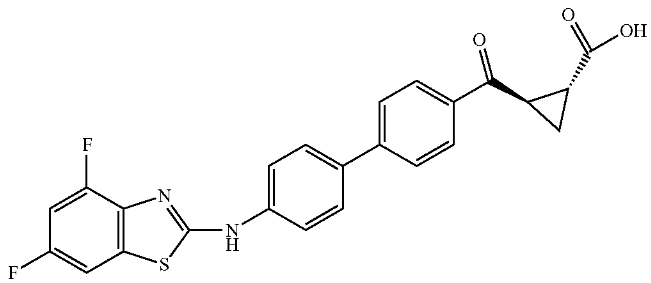 | 2-({4'-[(5,7-difluoro-1,3-benzothiazol-2-yl)amino]-1,1'-biphenyl-4-yl}carbonyl)cyclopropanecarboxylic acid | 451.1 | 3.53 | 1 | B | trans racemic mixture | | |
| 101 | 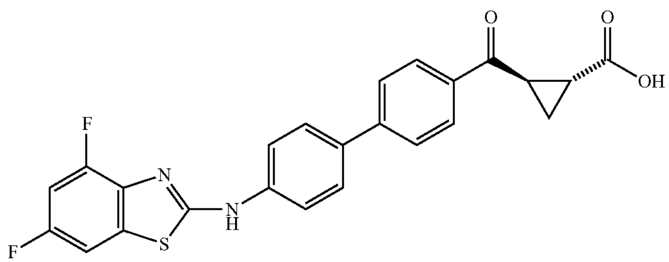 | 2-({4'-[(4,6-difluoro-1,3-benzothiazol-2-yl)amino]-1,1'-biphenyl-4-yl}carbonyl)cyclopropanecarboxylic acid | 451.1 | 3.41 | 1 | B | trans racemic mixture | | |
| 102 | 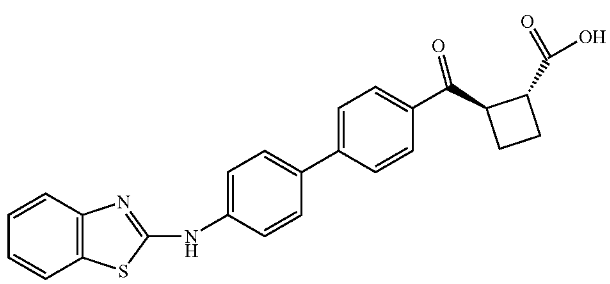 | 2-{[4'-(1,3-benzothiazol-2-ylamino)-1,1'-biphenyl-4-yl]carbonyl}cyclobutanecarboxylic acid | 429.2 | 3.27 | 1 | B | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 103 | 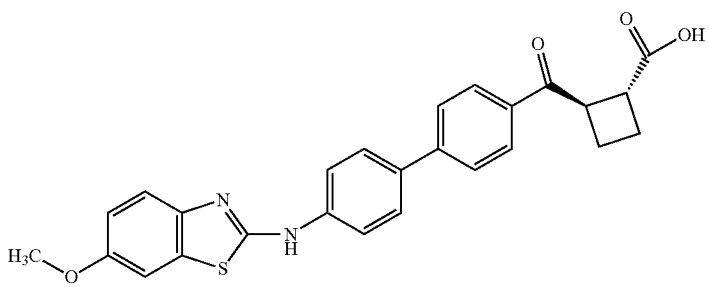 | 2-({4'-[(6-methoxy-1,3-benzothiazol-2-yl)amino]-1,1'-biphenyl-4-yl}carbonyl)cyclobutanecarboxylic acid | 459.2 | 3.42 | 1 | B | trans racemic mixture | | |
| 104 | 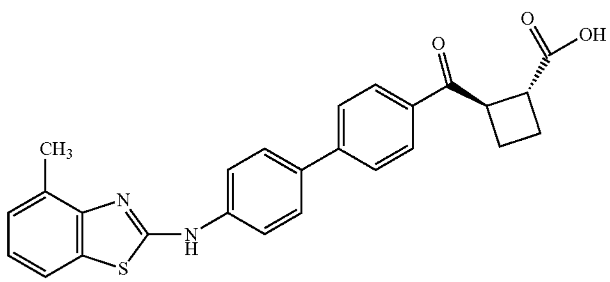 | 2-({4'-[(4-methyl-1,3-benzothiazol-2-yl)amino]-1,1'-biphenyl-4-yl}carbonyl)cyclobutanecarboxylic acid | 443.2 | 3.73 | 1 | B | trans racemic mixture | | |
| 105 | 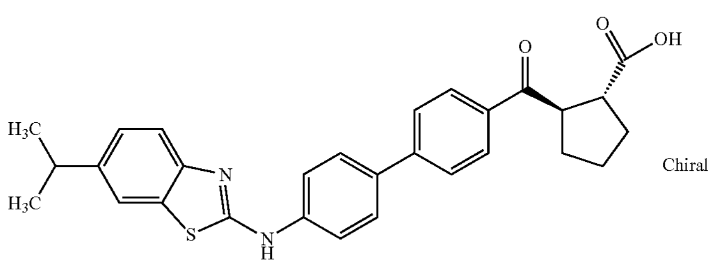 | (1R, 2R)-2-({4'-[(6-isopropyl-1,3-benzothiazol-2-yl)amino]-1,1'-biphenyl-4-yl}carbonyl)cyclopentanecarboxylic acid | 485.3 | 4.31 | 1 | A | R, R-trans (from chiral intermediate) | 90 | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 106 | 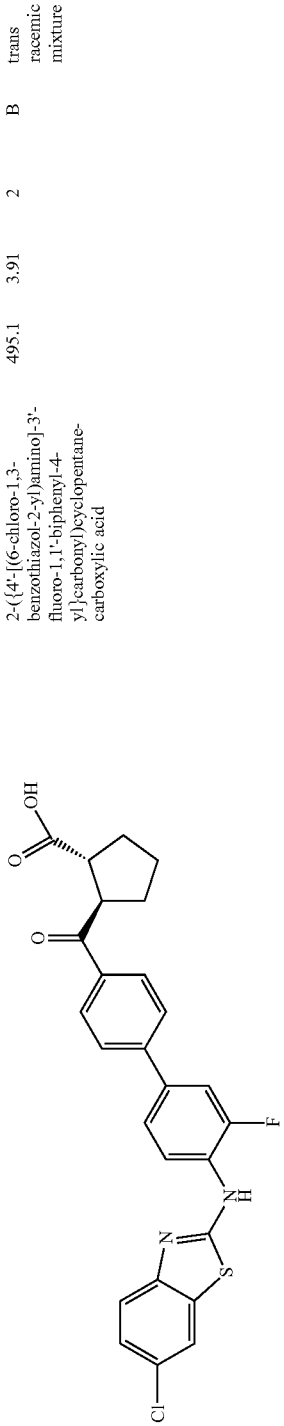 | 2-({4'-[(6-chloro-1,3-benzothiazol-2-yl)amino]-3'-fluoro-1,1'-biphenyl-4-yl}carbonyl)cyclopentanecarboxylic acid | 495.1 | 3.91 | 2 | B | trans racemic mixture | | |
| 107 | 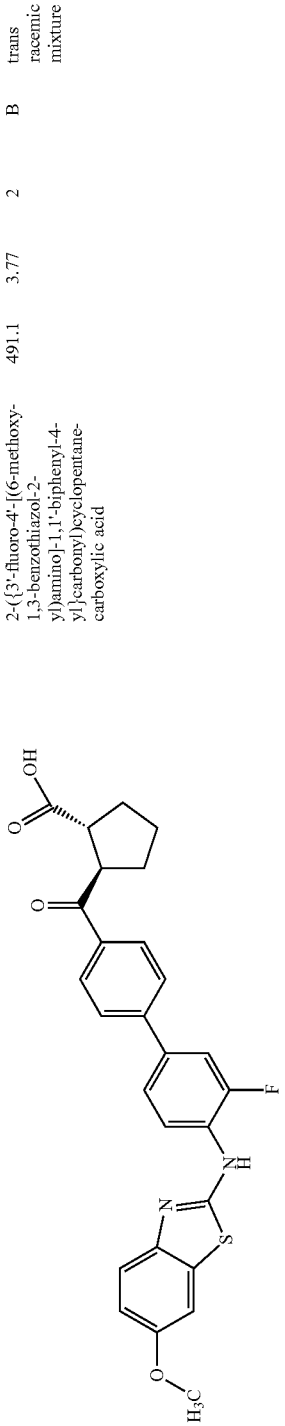 | 2-({3'-fluoro-4'-[(6-methoxy-1,3-benzothiazol-2-yl)amino]-1,1'-biphenyl-4-yl}carbonyl)cyclopentanecarboxylic acid | 491.1 | 3.77 | 2 | B | trans racemic mixture | | |
| 108 | 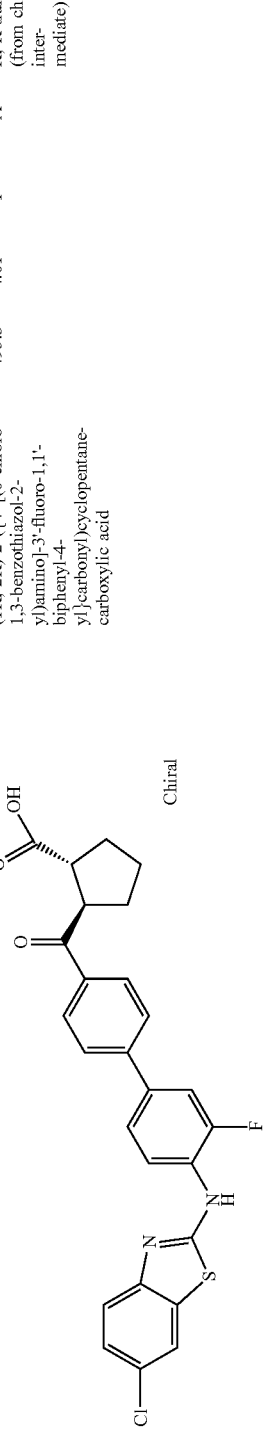 | (1R, 2R)-2-({4'-[(6-chloro-1,3-benzothiazol-2-yl)amino]-3'-fluoro-1,1'-biphenyl-4-yl}carbonyl)cyclopentanecarboxylic acid | 495.3 | 4.01 | 1 | A | R, R-trans (from chiral intermediate) | >99 | 18 |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 109 | 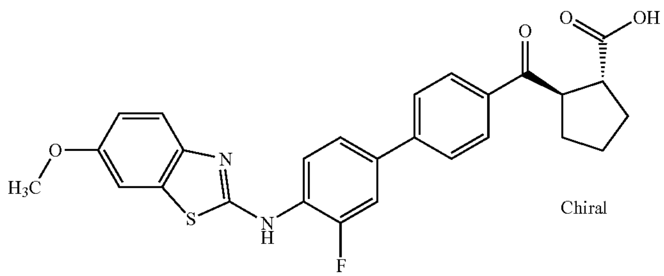 | (1R, 2R)-2-({3'-fluoro-4'-[(6-methoxy-1,3-benzothiazol-2-yl)amino]-1,1'-biphenyl-4-yl}carbonyl)cyclopentane-carboxylic acid | 491.3 | 3.56 | 1 | B | R, R-trans (from chiral intermediate) | 89 | 8 |
| 110 | 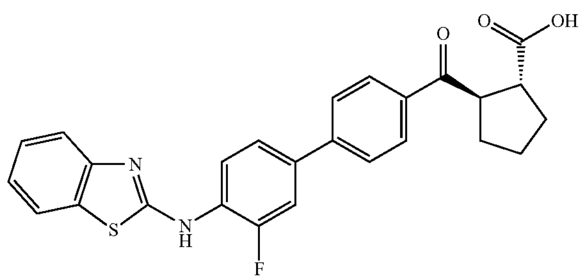 | 2-{[4'-(1,3-benzothiazol-2-yl amino)-3'-fluoro-1,1'-biphenyl-4-yl]carbonyl}cyclopentane-carboxylic acid | 461.4 | 3.60 | 1 | B | trans racemic mixture | | |
| 111 | 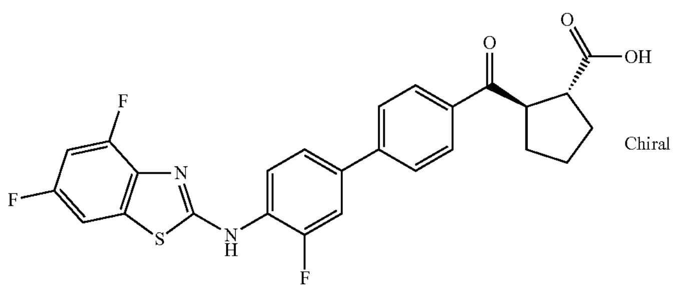 | (1R, 2R)-2-{[4'-[(4,6-difluoro-1,3-benzothiazol-2-yl)amino]-3'-fluoro-1,1'-biphenyl-4-yl]carbonyl}cyclopentane-carboxylic acid | 497.2 | 3.71 | 1 | B | R, R-trans (from chiral prep-HPLC) | >99 | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 112 | 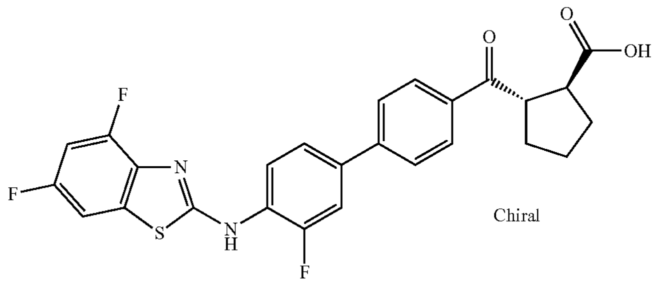 | (1S, 2S)-2-({4'-[(4,6-difluoro-1,3-benzothiazol-2-yl)amino]-3'-fluoro-1,1'-biphenyl-4-yl}carbonyl)cyclopentane-carboxylic acid | 497.2 | 3.71 | 1 | B | S, S-trans (from chiral prep-HPLC) | 95 | |
| 113 | 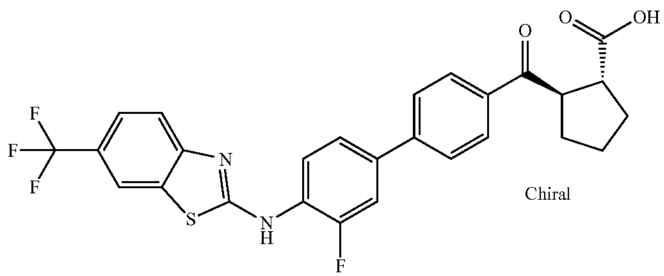 | (1R, 2R)-2-[(3'-fluoro-4'-{[6-(trifluoromethyl)-1,3-benzothiazol-2-yl]amino}-1,1'-biphenyl-4-yl)carbonyl]cyclopentane-carboxylic acid | 529.3 | 4.33 | 1 | B | R, R-trans (from chiral intermediate) | 97 | |
| 114 | 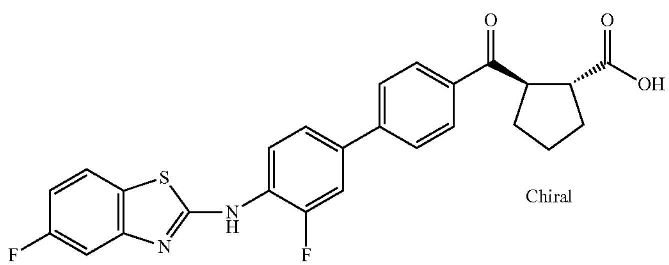 | (1R, 2R)-2-({3'-fluoro-4'-[(5-fluoro-1,3-benzothiazol-2-yl)amino]-1,1'-biphenyl-4-yl}carbonyl)cyclopentane-carboxylic acid | 479.3 | 4.10 | 1 | B | R, R-trans (from chiral intermediate) | 90 | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 115 | 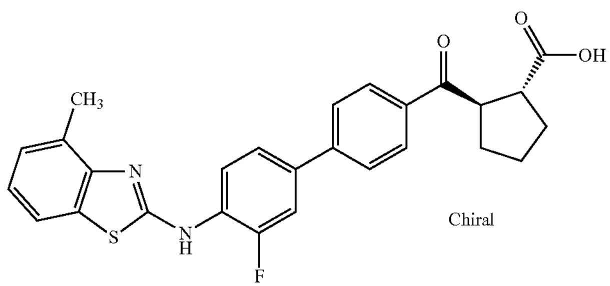 | (1R, 2R)-2-({3'-fluoro-4'-[(4-methyl-1,3-benzothiazol-2-yl)amino]-1,1'-biphenyl-4-yl}carbonyl)cyclopentane-carboxylic acid | 475.3 | 3.97 | 1 | A | R, R-trans (from chiral intermediate) | 83 | 21 |
| 116 | 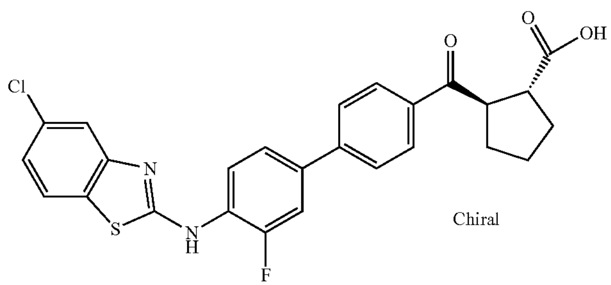 | (1R, 2R)-2-({4'-(5-chloro-1,3-benzothiazol-2-yl)amino]-3'-fluoro-1,1'-biphenyl-4-yl}carbonyl)cyclopentane-carboxylic acid | 495.2 | 3.85 | 1 | B | R, R-trans (from chiral intermediate) | 96 | |
| 117 | 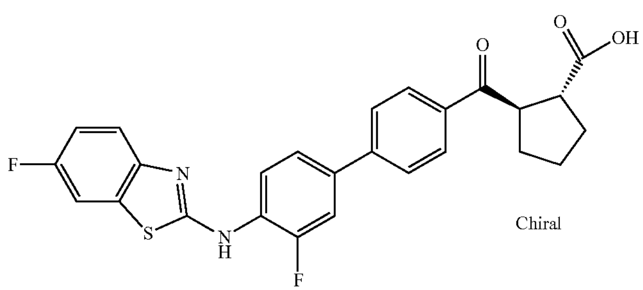 | (1R, 2R)-2-({3'-fluoro-4'-[(6-fluoro-1,3-benzothiazol-2-yl)amino]-1,1'-biphenyl-4-yl}carbonyl)cyclopentane-carboxylic acid | 479.3 | 3.64 | 1 | A | R, R-trans (from chiral intermediate) | 96 | 26 |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 118 | 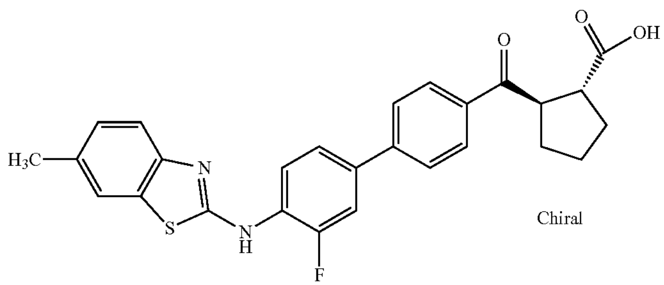 | (1R, 2R)-2-({3'-fluoro-4'-[(6-methyl-1,3-benzothiazol-2-yl)amino]-1,1'-biphenyl-4-yl}carbonyl)cyclopentanecarboxylic acid | 475.3 | 3.71 | 1 | B | R, R-trans (from chiral prep-HPLC) | 90 | |
| 119 | 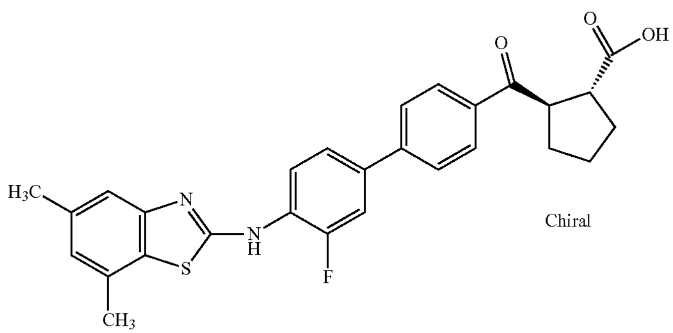 | (1R, 2R)-2-({4'-[(5,7-dimethyl-1,3-benzothiazol-2-yl)amino]-3'-fluoro-1,1'-biphenyl-4-yl}carbonyl)cyclopentanecarboxylic acid | 489.3 | 3.85 | 1 | A | R, R-trans (from chiral intermediate) | 66 | |
| 120 | 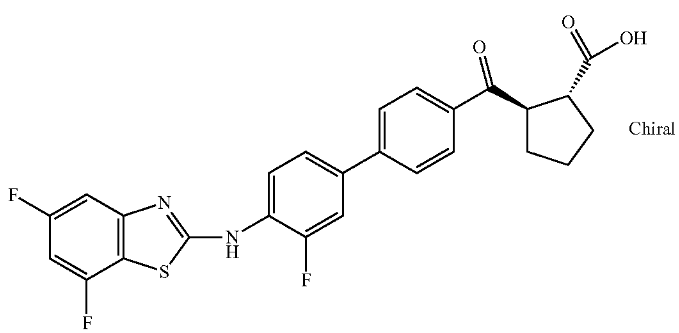 | (1R, 2R)-2-({4'-[(5,7-difluoro-1,3-benzothiazol-2-yl)amino]-3'-fluoro-1,1'-biphenyl-4-yl}carbonyl)cyclopentanecarboxylic acid | 497.2 | 3.84 | 1 | A | R, R-trans (from chiral intermediate) | 80 | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 121 | 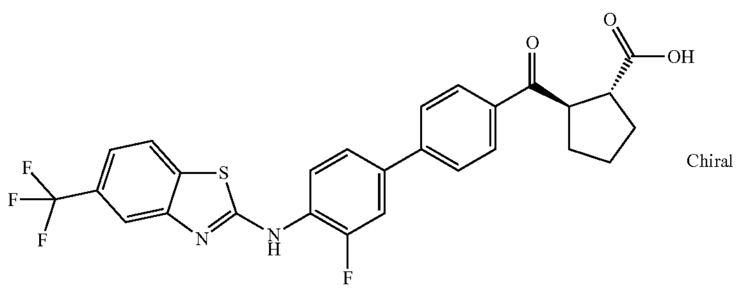 | (1R, 2R)-2-[(3'-fluoro-4'-{[5-(trifluoromethyl)-1,3-benzothiazol-2-yl]amino}-1,1'-biphenyl-4-yl)carbonyl]cyclopentane-carboxylic acid | 529.1 | 3.90 | 1 | A | R, R-trans (from chiral intermediate) | 90 | |
| 122 | 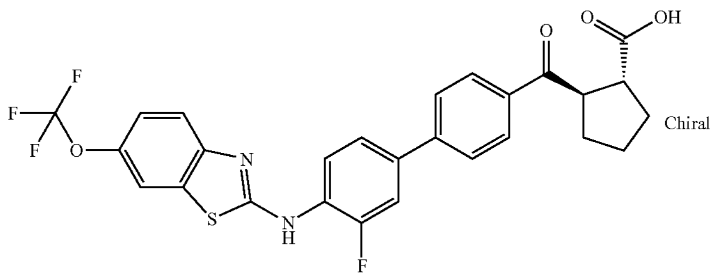 | (1R, 2R)-2-[(3'-fluoro-4'-{[6-(trifluoromethoxy)-1,3-benzothiazol-2-yl]amino}-1,1'-biphenyl-4-yl)carbonyl]cyclopentane-carboxylic acid | 545.3 | 3.93 | 1 | A | R, R-trans (from chiral intermediate) | 95 | 25 |
| 123 | 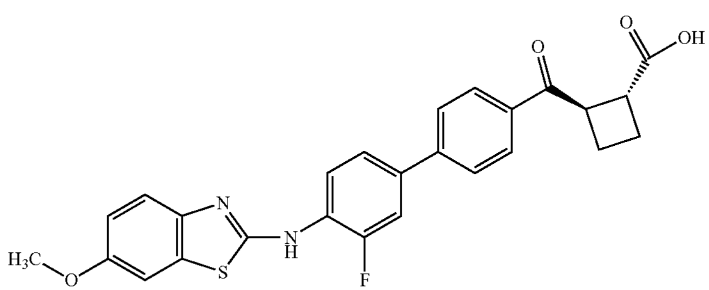 | 2-({3'-fluoro-4'-[(6-methoxy-1,3-benzothiazol-2-yl)amino]-1,1'-biphenyl-4-yl}carbonyl)cyclobutane-carboxylic acid | 477.2 | 3.54 | 1 | A | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 124 | 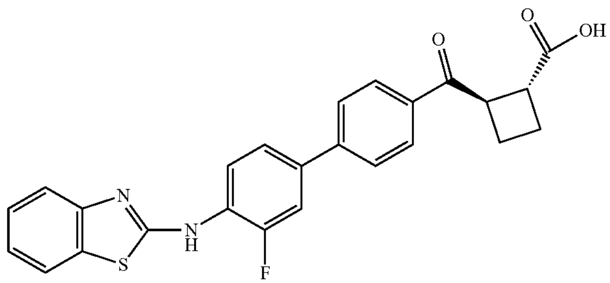 | 2-[[4'-(1,3-benzothiazol-2-ylamino)-3'-fluoro-1,1'-biphenyl-4-yl]carbonyl]cyclobutanecarboxylic acid | 447.1 | 3.56 | 1 | A | trans racemic mixture | | |
| 125 | 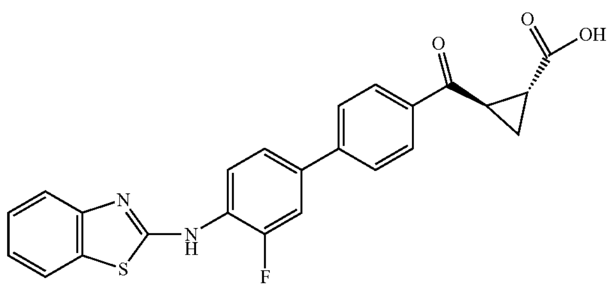 | 2-[[4'-(1,3-benzothiazol-2-ylamino)-3'-fluoro-1,1'-biphenyl-4-yl]carbonyl]cyclopropanecarboxylic acid | 433.2 | 3.31 | 1 | A | trans racemic mixture | | |
| 126 | 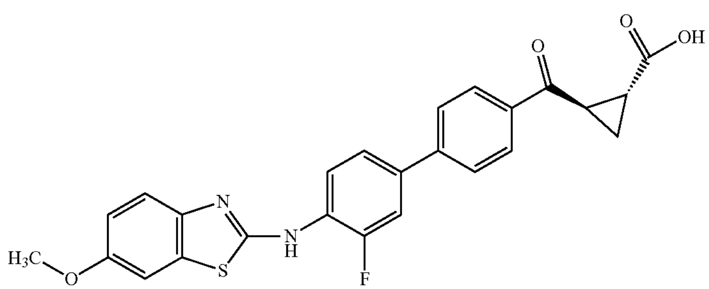 | 2-({3'-fluoro-4'-[(6-methoxy-1,3-benzothiazol-2-yl)amino]-1,1'-biphenyl-4-yl}carbonyl)cyclopropanecarboxylic acid | 463.2 | 3.47 | 1 | A | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 127 | 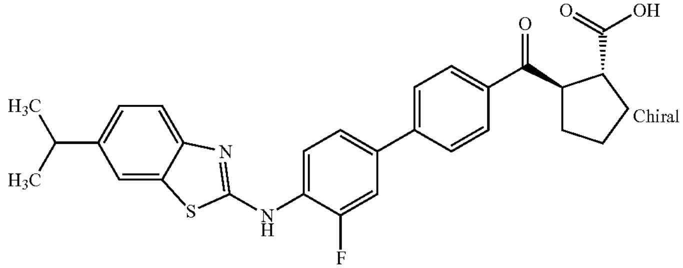 | (1R, 2R)-2-({3'-fluoro-4'-[(6-isopropyl-1,3-benzothiazol-2-yl)amino]-1,1'-biphenyl-4-yl}carbonyl)cyclopentanecarboxylic acid | 503.3 | 4.46 | 1 | A | R, R-trans (from chiral intermediate) | 90 | |
| 128 | 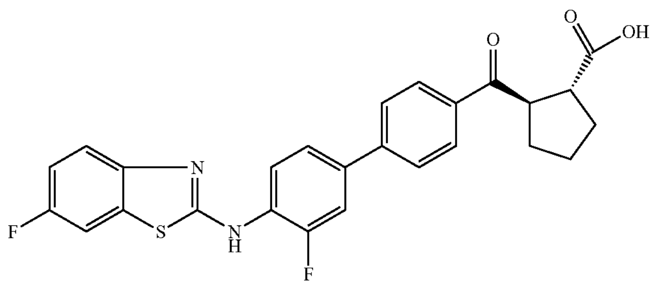 | 2-({3'-fluoro-4'-[(6-fluoro-1,3-benzothiazol-2-yl)amino]-1,1'-biphenyl-4-yl}carbonyl)cyclopentanecarboxylic acid | 479.3 | 3.65 | 1 | B | trans racemic mixture | | |
| 129 | 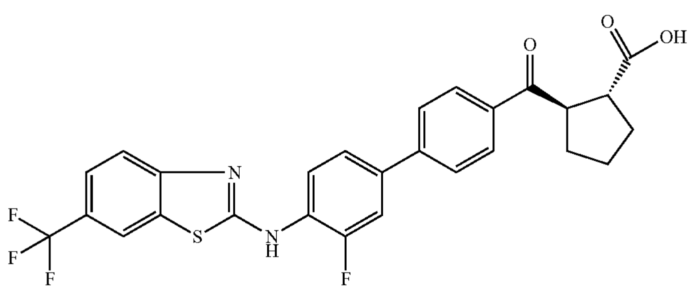 | 2-[(3'-fluoro-4'-[(6-(trifluoromethyl)-1,3-benzothiazol-2-yl]amino}-1,1'-biphenyl-4-yl]carbonyl)cyclopentanecarboxylic acid | 529.3 | 3.89 | 1 | A | trans racemic mixture | | |

TABLE 1-continued

| Entry No. | Structure | IUPAC name | LC-MS m/z (MH+) | LC-MS ret. time min | LC-MS method | synthetic route | chirality & route | % ee | Example No. described in text |
|---|---|---|---|---|---|---|---|---|---|
| 130 | 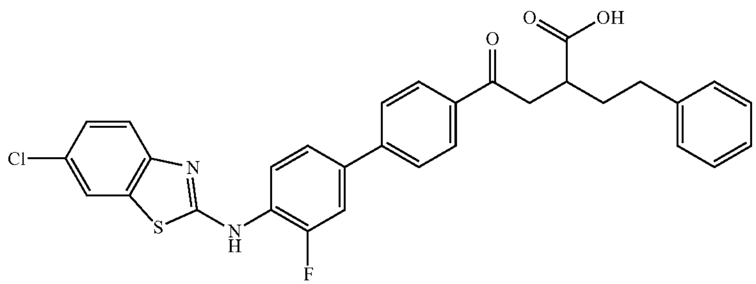 | 4-{4'-[(6-chloro-1,3-benzothiazol-2-yl)amino]-3'-fluoro-1,1'-biphenyl-4-yl}-4-oxo-2-(2-phenylethyl)butanoic acid | 559.2 | 4.13 | 1 | A | racemic mixture | | |
| 131 | 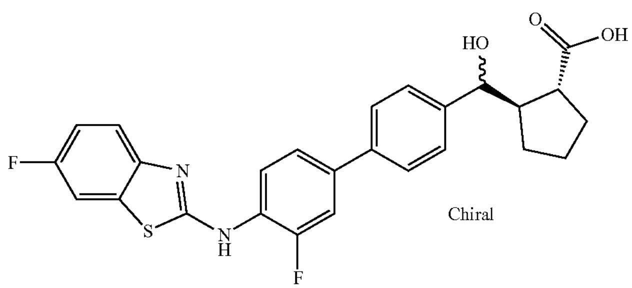 | (1R, 2R)-2-[{3'-fluoro-4'-[(6-fluoro-1,3-benzothiazol-2-yl)amino]-biphenyl-4-yl}(hydroxy)methyl]-cyclopentane-carboxylic acid | 481.3 | two isomers: 3.33 & 3.46 | 1 | N/A | R, R-trans cyclo-pentyl (from chiral inter-mediate) | | 34 |

By using the methods described above and by selecting the appropriate starting materials, other compounds of the invention can be made and are illustrated in Table 2 below.

TABLE 2

| Entry No. | Structure |
|---|---|
| 132 | 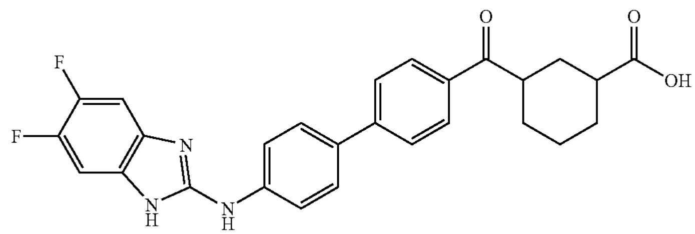 |
| 133 | 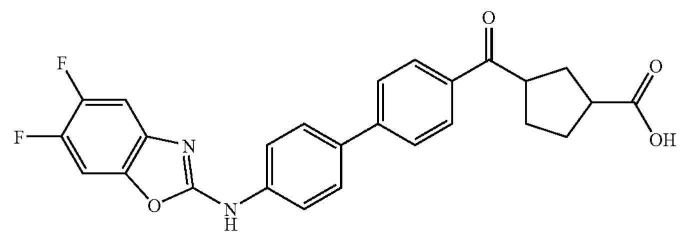 |
| 134 | 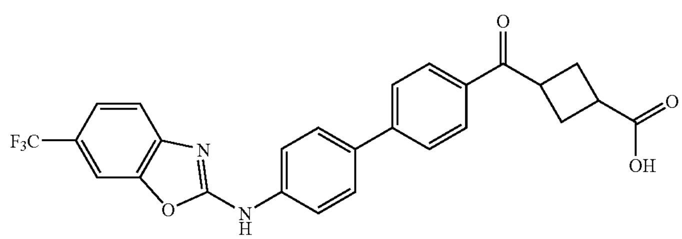 |
| 135 | 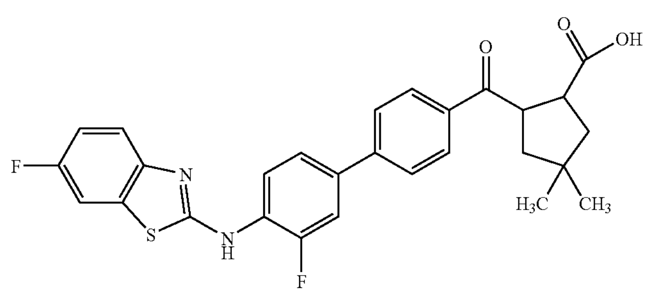 |
| 136 | 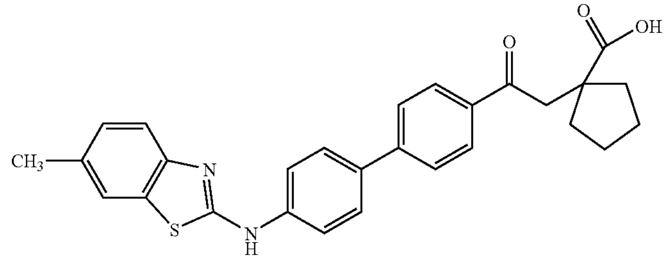 |

TABLE 2-continued
| Entry No. | Structure |
|---|---|
| 137 | |
| 138 | 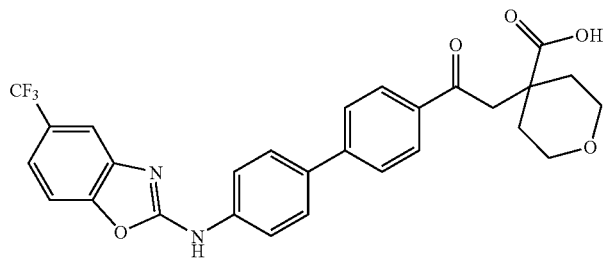 |
| 139 | 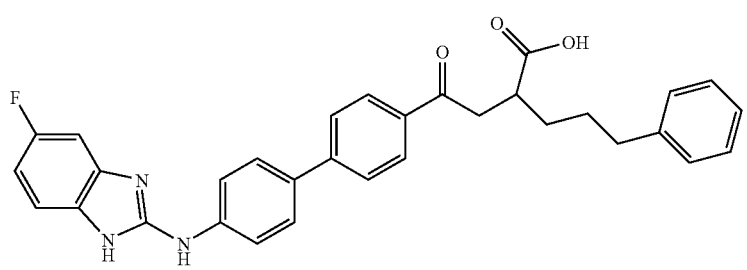 |
| 140 | 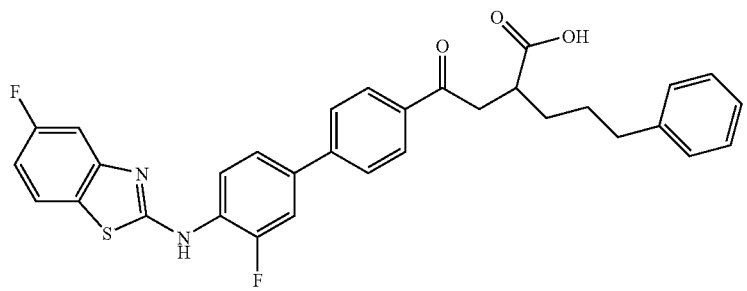 |
| 141 | 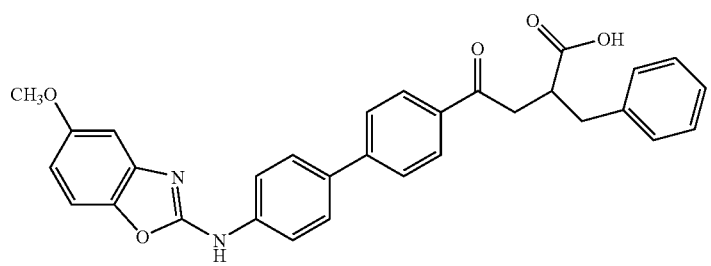 |
| 142 | 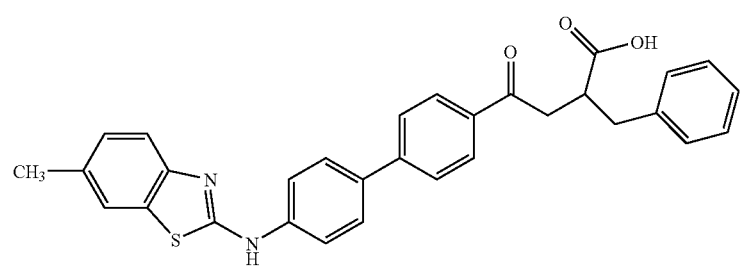 |

TABLE 2-continued
| Entry No. | Structure |
|---|---|
| 143 | 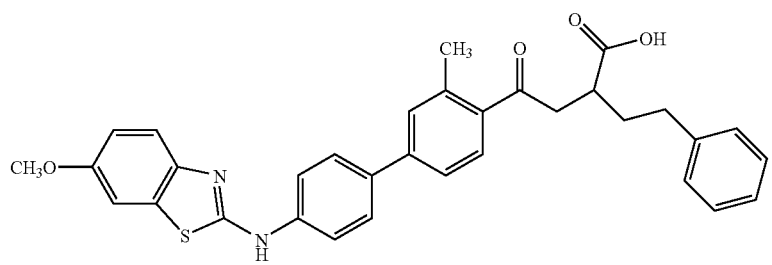 |
| 144 | 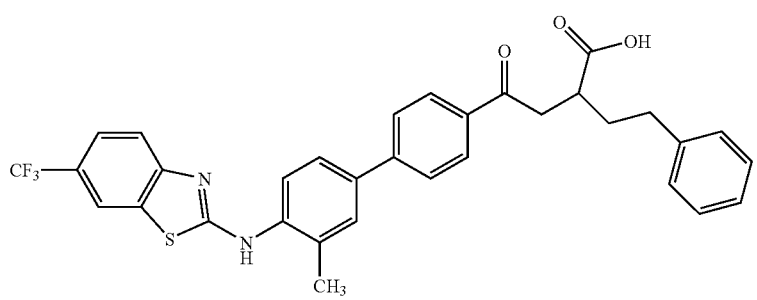 |
| 145 | 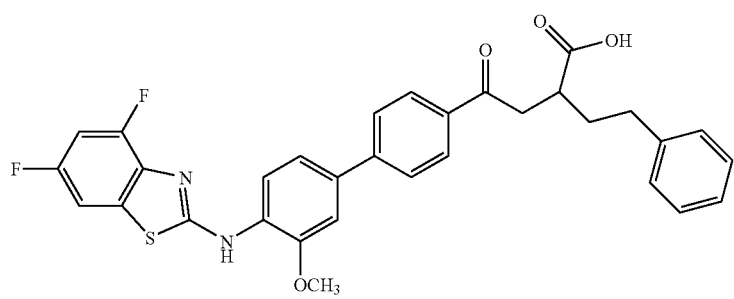 |
| 146 | 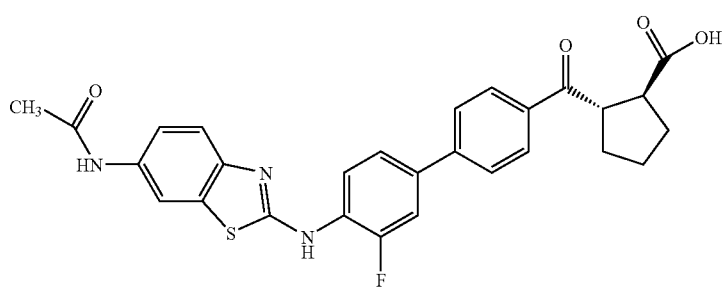 |
| 147 | 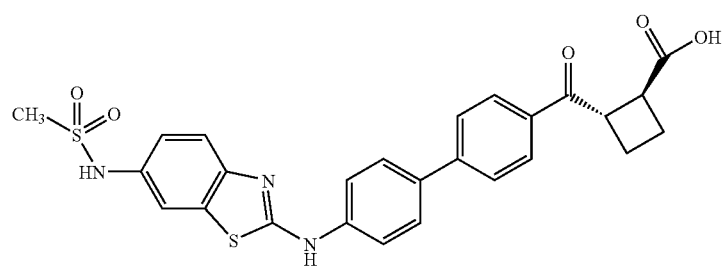 |

TABLE 2-continued

| Entry No. | Structure |
|---|---|
| 148 | 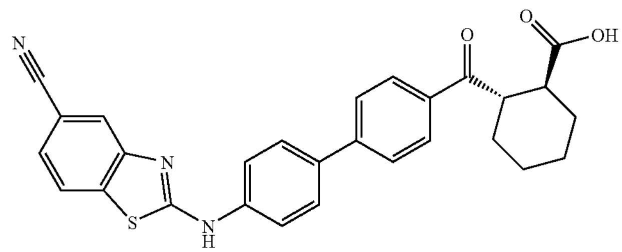 |
| 149 | 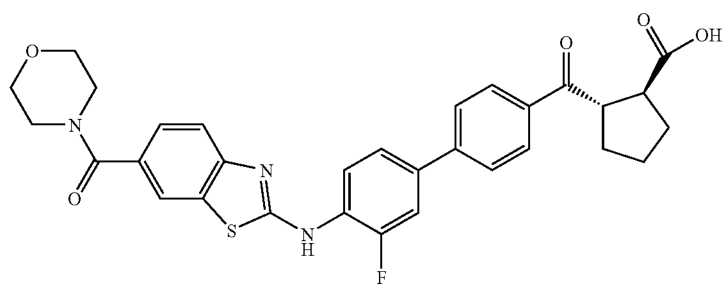 |
| 150 | 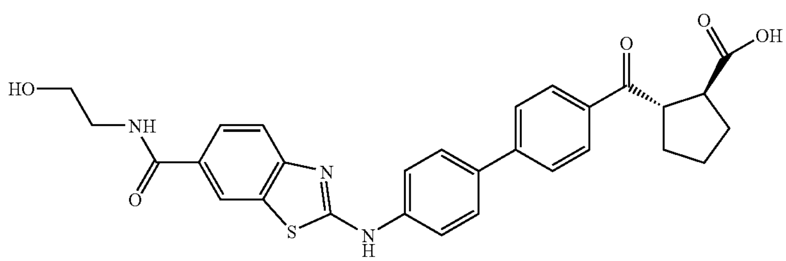 |
| 151 | 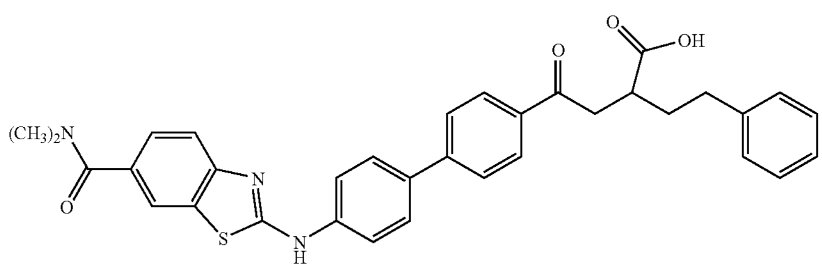 |
| 152 | 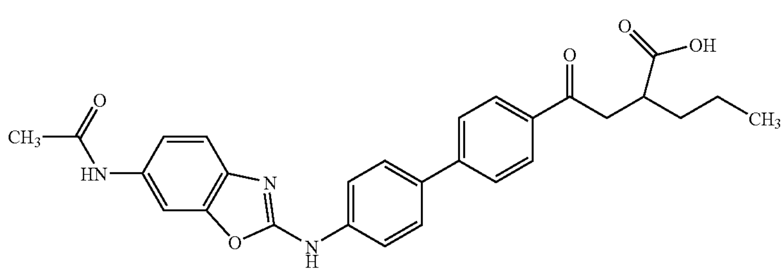 |

TABLE 2-continued
| Entry No. | Structure |
|---|---|
| 153 | 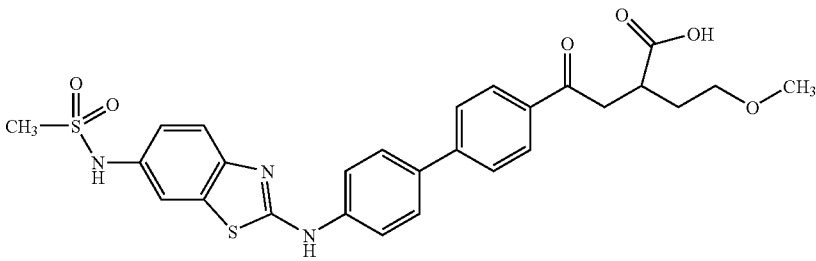 |
| 154 | 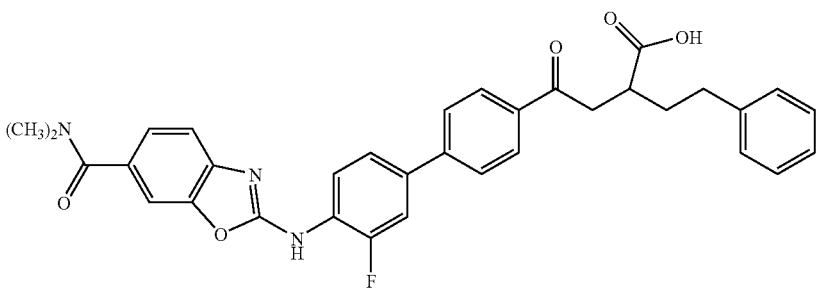 |
| 155 | 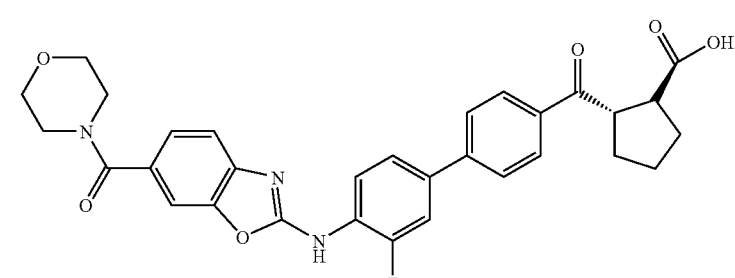 |
| 156 | 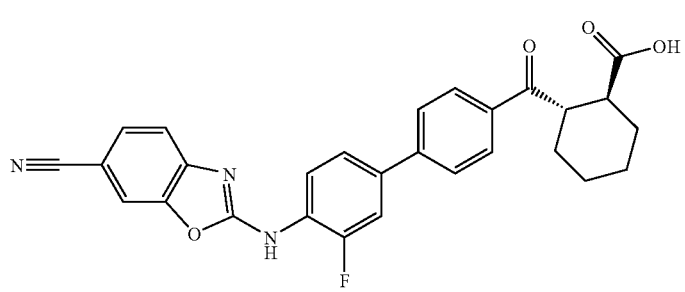 |
| 157 | 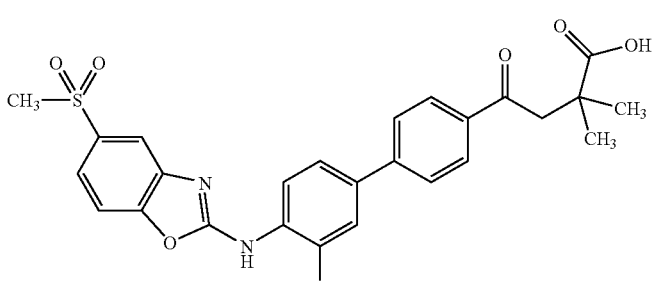 |

TABLE 2-continued

| Entry No. | Structure |
|---|---|
| 158 | (4-methoxyphenyl)-thiazol-2-yl-NH-(3-fluoro-4-biphenyl)-C(O)-cyclopropane-carboxylic acid |
| 159 | (4-methylphenyl)-thiazol-2-yl-NH-(4-biphenyl)-C(O)CH₂-CH(COOH)-CH₂CH₂-OCH₃ |
| 160 | (4-isopropylphenyl)-thiazol-2-yl-NH-(3-fluoro-4-biphenyl)-C(O)CH₂-CH(COOH)-CH₂CH₂-OCH₃ |
| 161 | (4-hydroxymethyl)-thiazol-2-yl-NH-(3-fluoro-4-biphenyl)-C(O)-cyclopentane-carboxylic acid |
| 162 | (4,5-dimethyl)-thiazol-2-yl-NH-(3-fluoro-4-biphenyl)-C(O)CH₂-C(CH₃)₂-COOH |

TABLE 2-continued

| Entry No. | Structure |
|---|---|
| 163 | 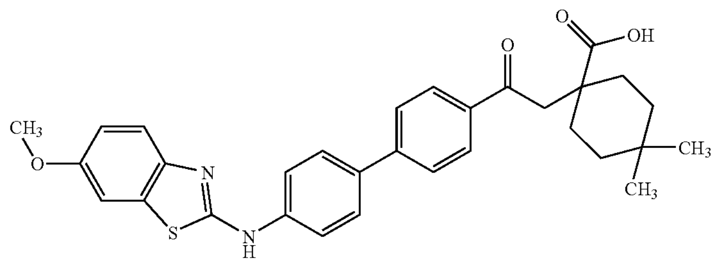 |
| 164 | 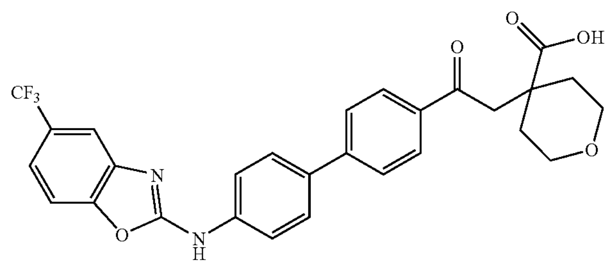 |
| 165 | 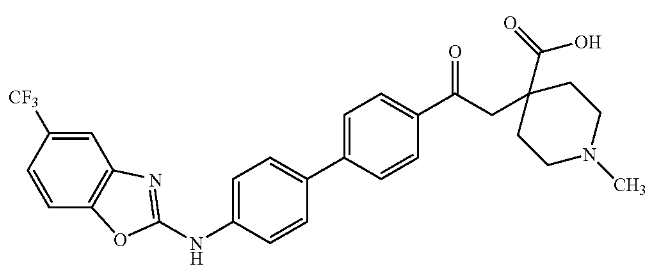 |
| 166 | 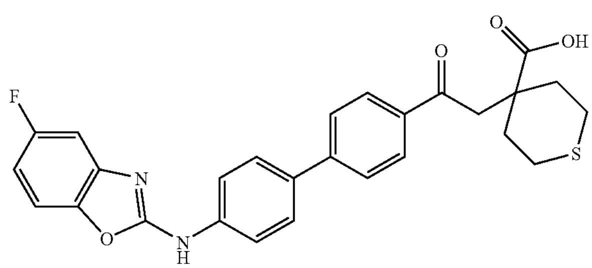 |
| 167 | 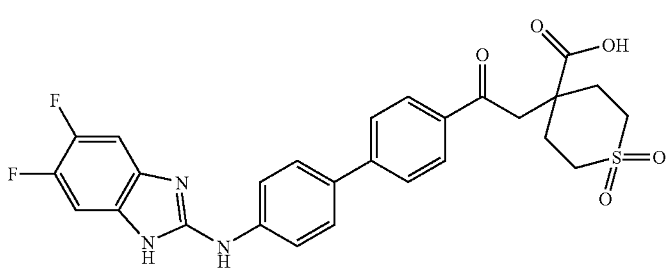 |

TABLE 2-continued
| Entry No. | Structure |
|---|---|
| 168 | 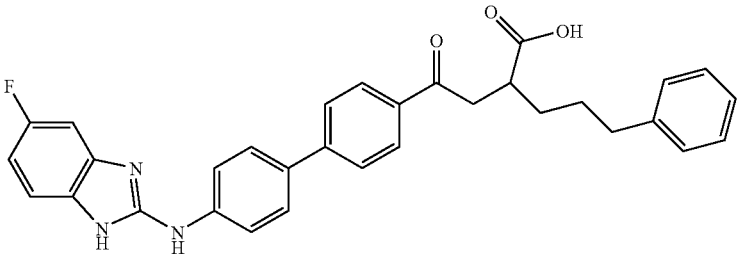 |
| 169 | 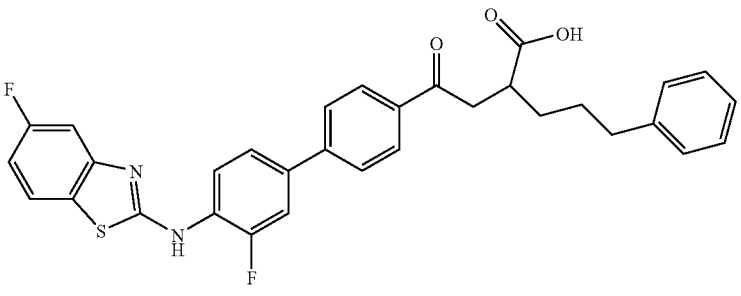 |
| 170 | 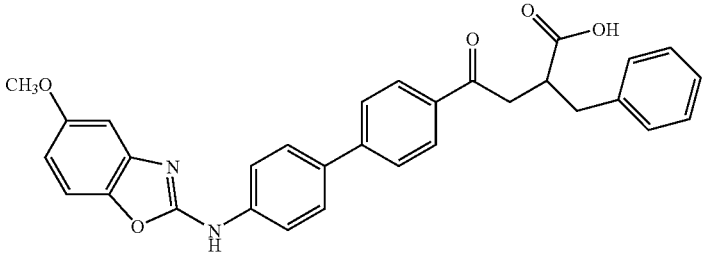 |
| 171 | 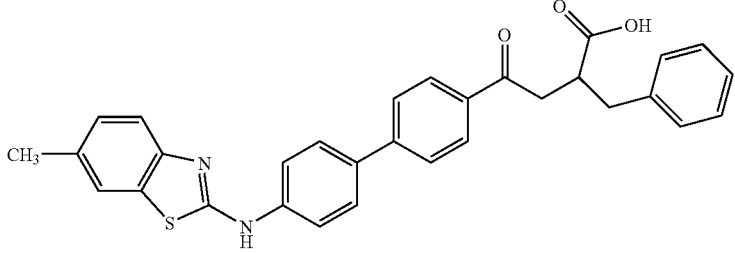 |
| 172 | 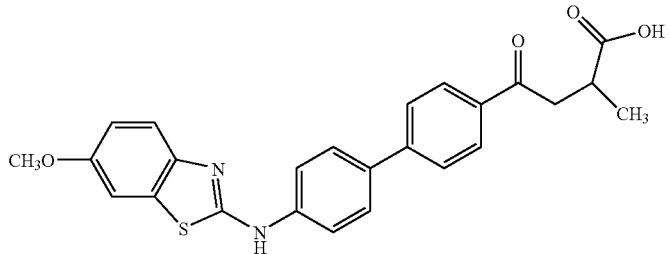 |

TABLE 2-continued

| Entry No. | Structure |
|---|---|
| 173 | 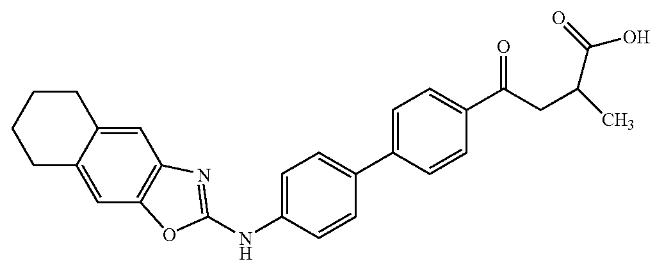 |
| 174 | 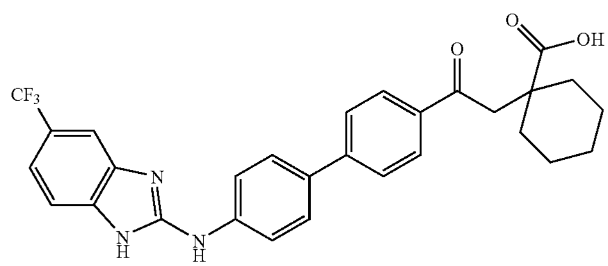 |
| 175 | 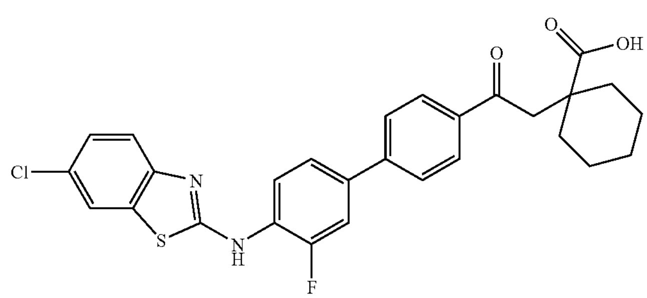 |
| 176 | 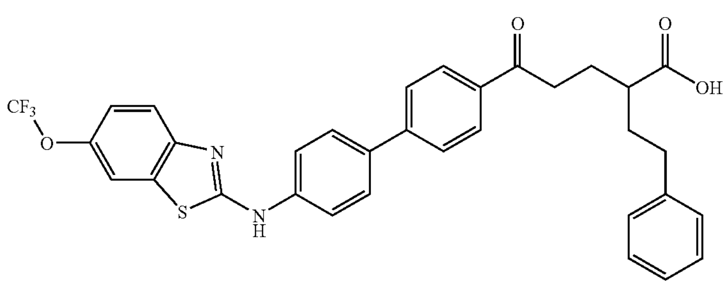 |
| 177 | 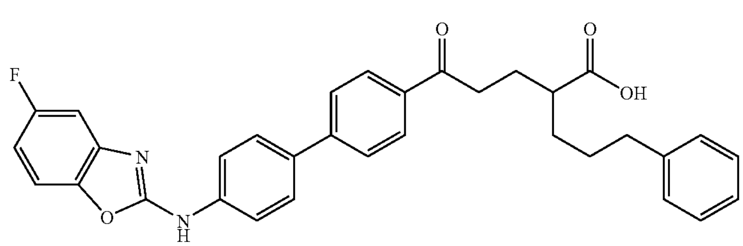 |

TABLE 2-continued
| Entry No. | Structure |
|---|---|
| 178 | 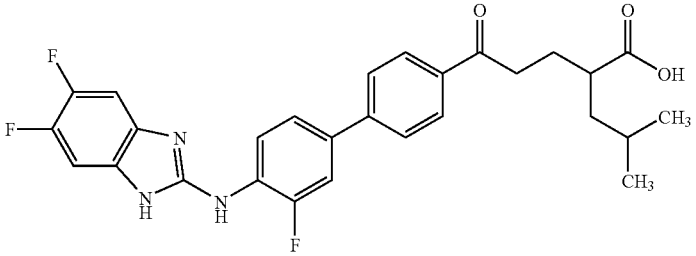 |
| 179 | 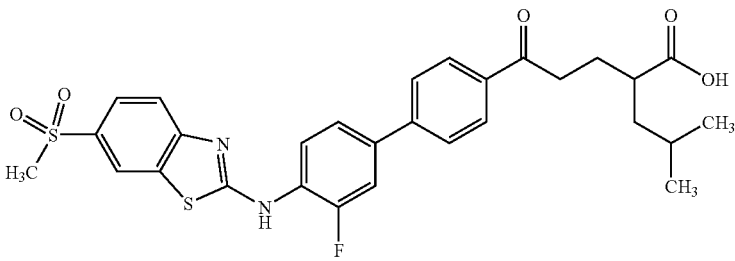 |
| 180 | 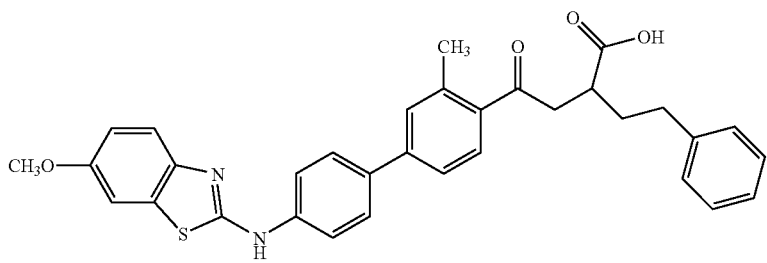 |
| 181 | 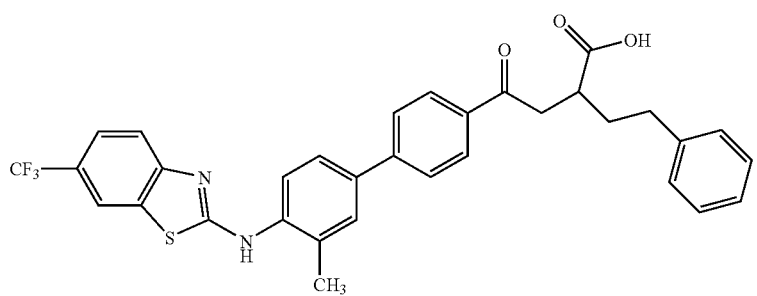 |
| 182 | 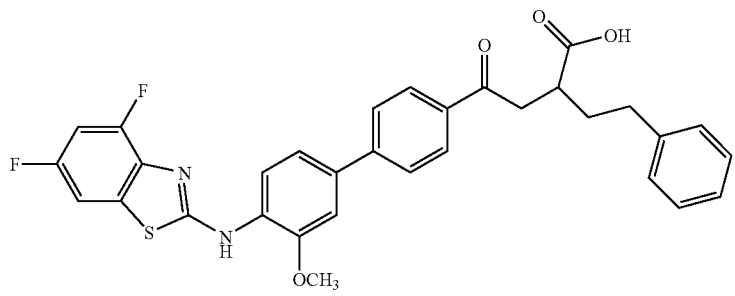 |

TABLE 2-continued

| Entry No. | Structure |
|---|---|
| 183 | (acetamido-benzothiazol-2-ylamino)(3-fluoro)phenyl-biphenyl-carbonyl cyclopentanecarboxylic acid |
| 184 | (methylsulfonamido-benzothiazol-2-ylamino)phenyl-biphenyl-carbonyl cyclobutanecarboxylic acid |
| 185 | (cyano-benzothiazol-2-ylamino)phenyl-biphenyl-carbonyl cyclohexanecarboxylic acid |
| 186 | (morpholinocarbonyl-benzothiazol-2-ylamino)(3-fluoro)phenyl-biphenyl-carbonyl cyclopentanecarboxylic acid |
| 187 | (2-hydroxyethylaminocarbonyl-benzothiazol-2-ylamino)phenyl-biphenyl-carbonyl cyclopentanecarboxylic acid |

TABLE 2-continued

| Entry No. | Structure |
|---|---|
| 188 | 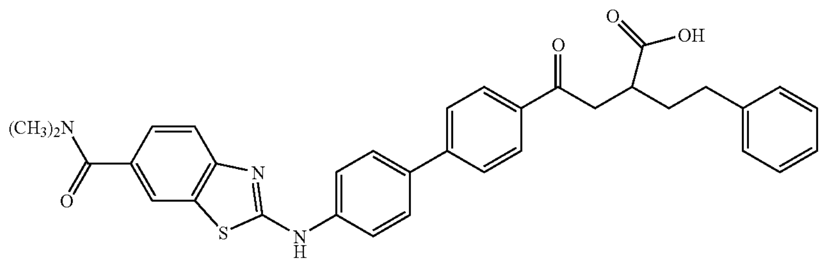 |
| 189 | 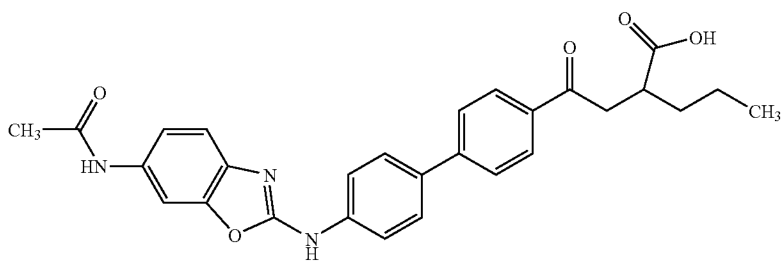 |
| 190 | 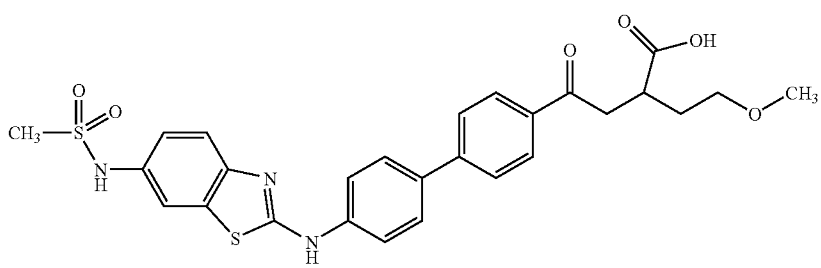 |
| 191 | 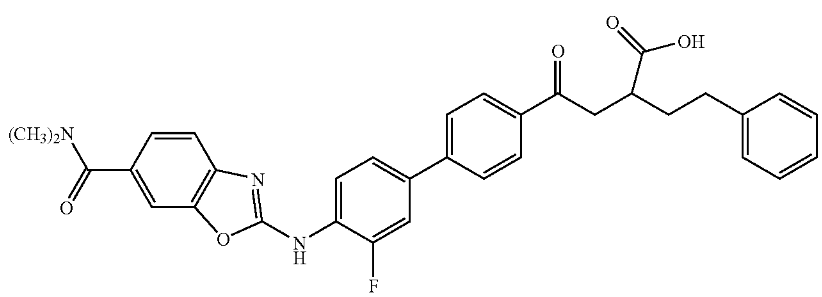 |
| 192 | 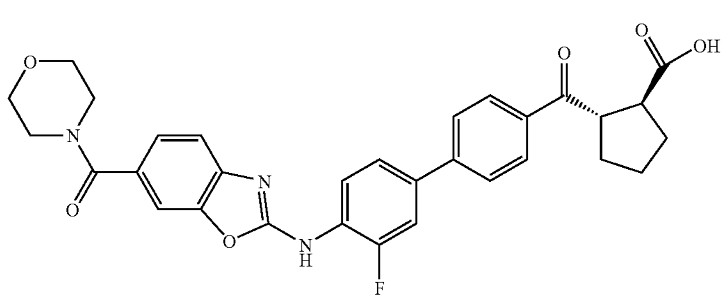 |

TABLE 2-continued

| Entry No. | Structure |
|---|---|
| 193 | 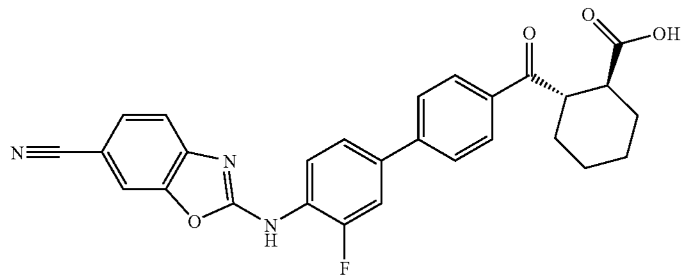 |
| 194 | 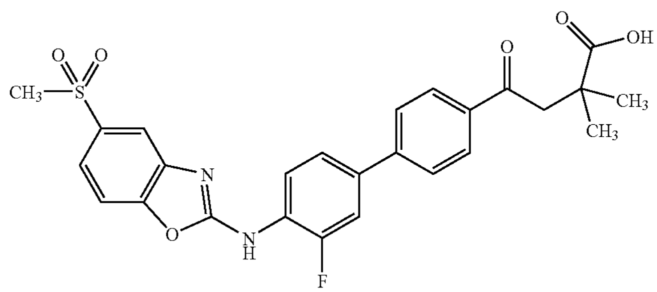 |
| 195 | 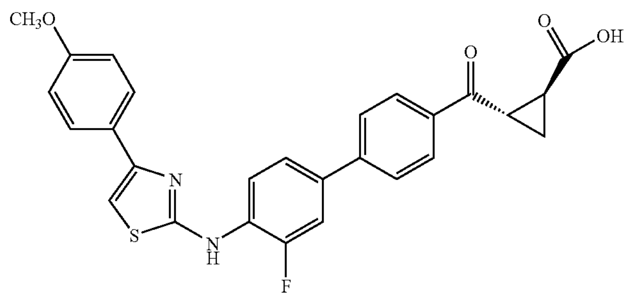 |
| 196 | 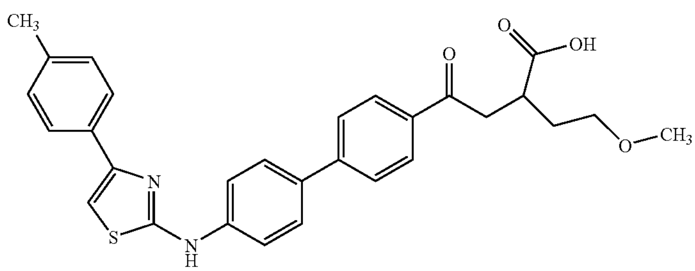 |
| 197 | 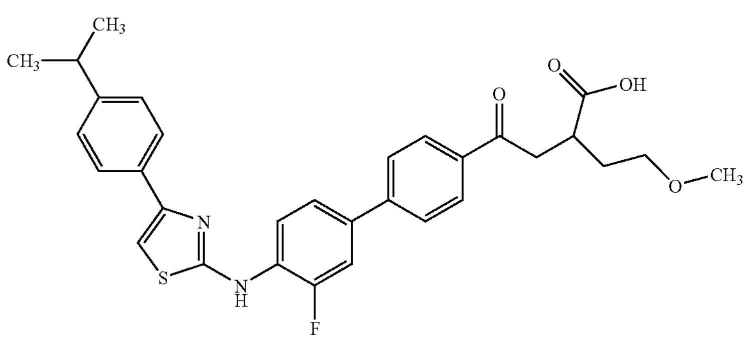 |

TABLE 2-continued

| Entry No. | Structure |
|---|---|
| 198 | 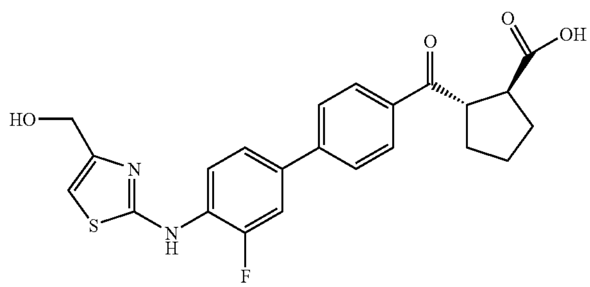 |
| 199 | 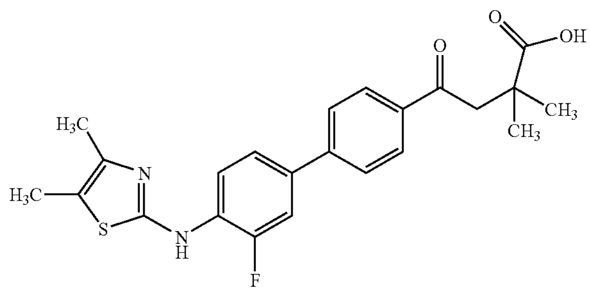 |
| 200 | 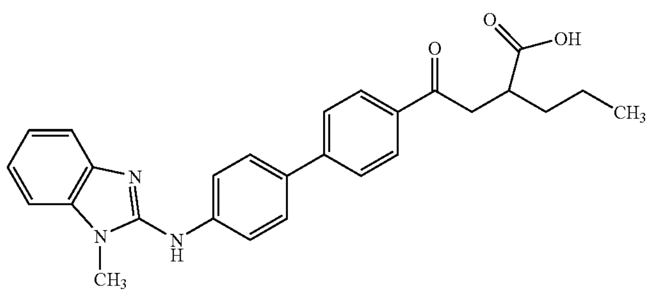 |
| 201 | 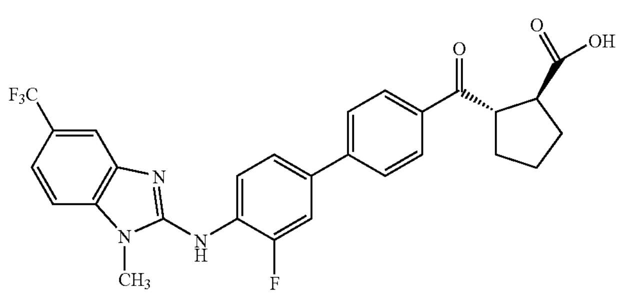 |
| 202 | 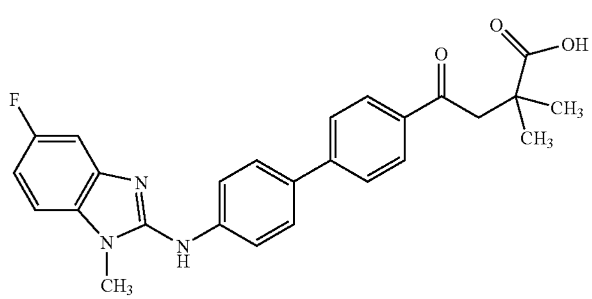 |

TABLE 2-continued

| Entry No. | Structure |
|---|---|
| 203 | 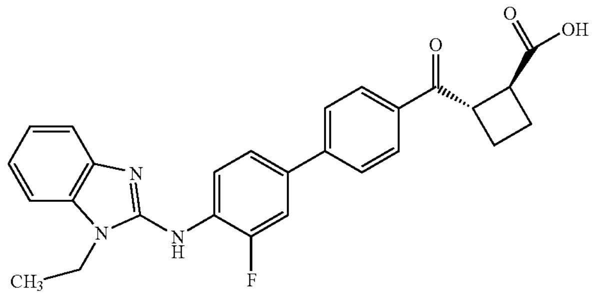 |
| 204 | 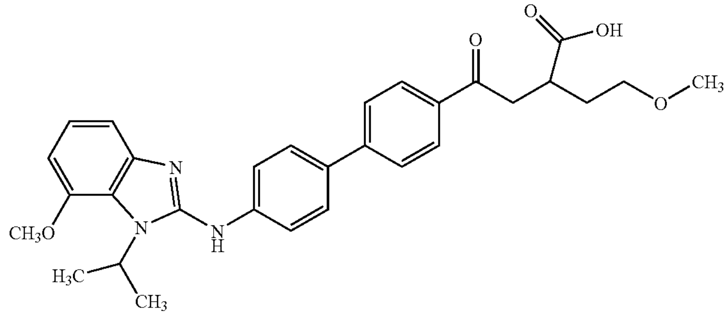 |
| 205 | 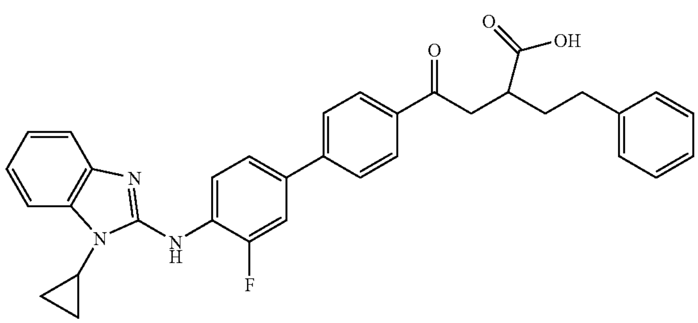 |
| 206 | 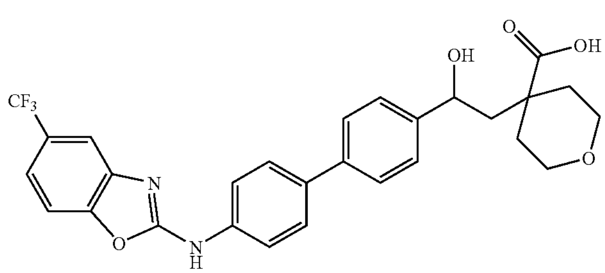 |
| 207 | 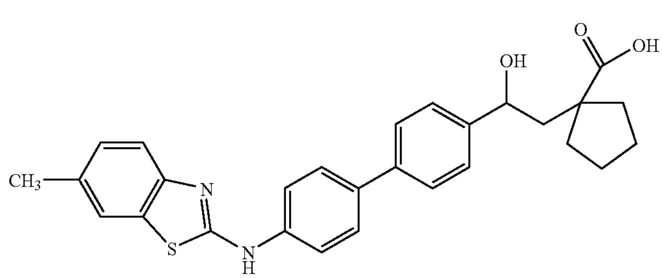 |

US 7,091,228 B2
213 214
TABLE 2-continued
| Entry No. | Structure |
|---|---|
| 208 | 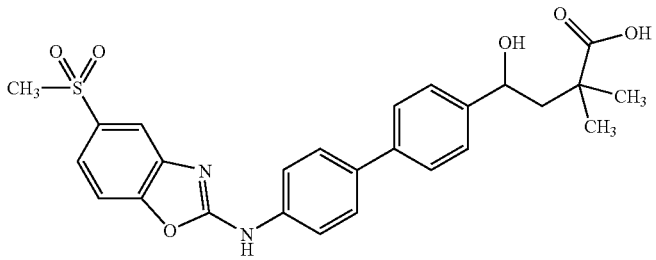 |
| 209 | 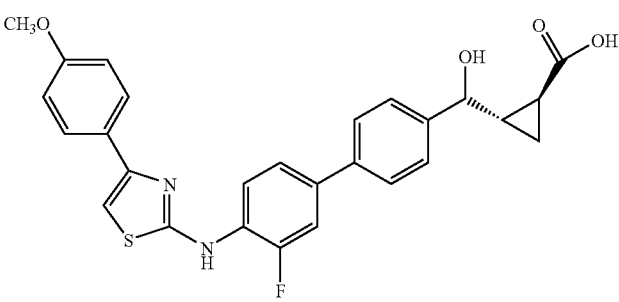 |
| 210 | 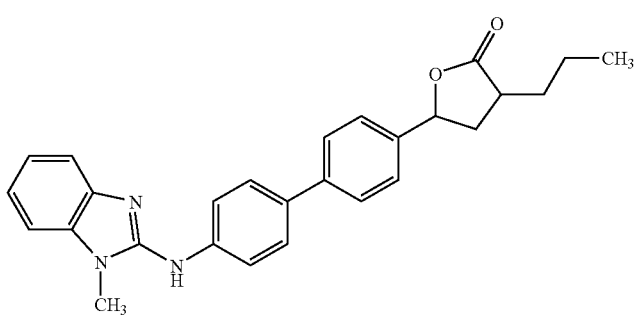 |
| 211 | 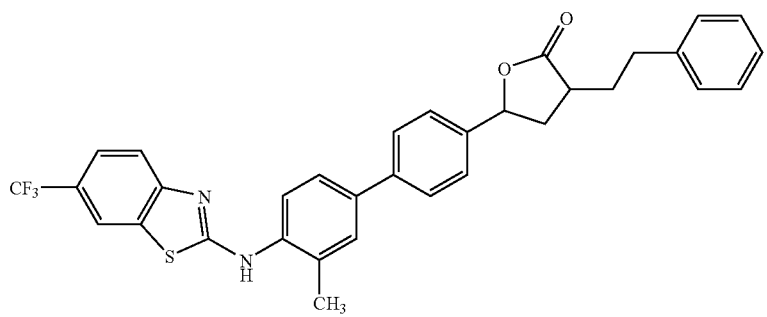 |
| 212 | 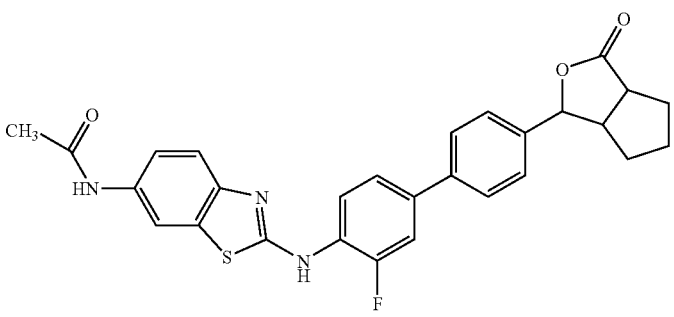 |

TABLE 2-continued

| Entry No. | Structure |
|---|---|
| 213 | 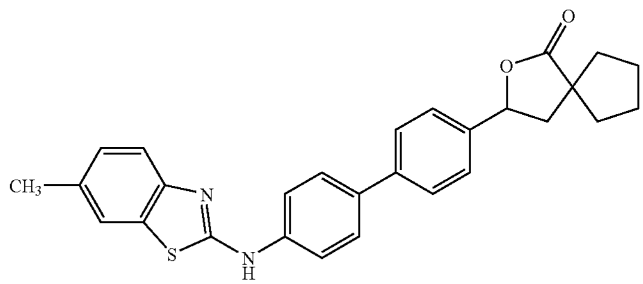 |
| 214 | 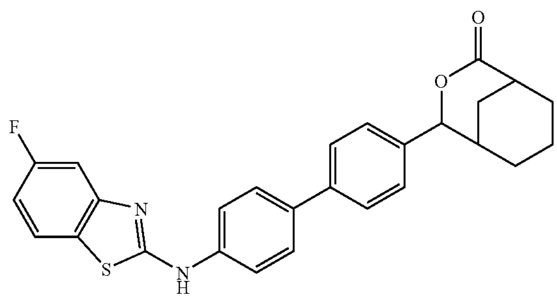 |
| 215 | 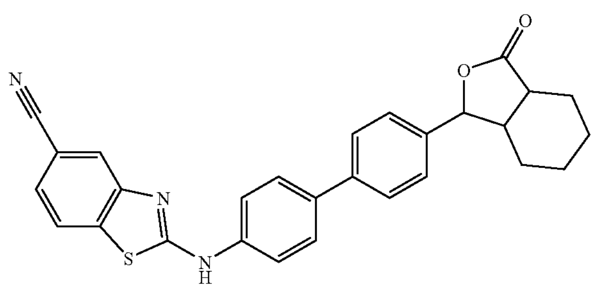 |

Methods of Use

As used herein, various terms are defined below.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

The term "subject" as used herein includes mammals (e.g., humans and animals).

The term "treatment" includes any process, action, application, therapy, or the like, wherein a subject, including a human being, is provided medical aid with the object of improving the subject's condition, directly or indirectly, or slowing the progression of a condition or disorder in the subject.

The term "combination therapy" or "co-therapy" means the administration of two or more therapeutic agents to treat an obese condition and/or disorder. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner.

The phrase "therapeutically effective" means the amount of each agent administered that will achieve the goal of improvement in an obese condition or disorder severity, while avoiding or minimizing adverse side effects associated with the given therapeutic treatment.

The term "pharmaceutically acceptable" means that the subject item is appropriate for use in a pharmaceutical product.

The compounds of Formula (I),Formula (Ia), and Formula (Ib) of this invention are expected to be valuable as therapeutic agents. Accordingly, an embodiment of this invention includes a method of treating the various conditions in a patient (including mammals) which comprises administering to said patient a composition containing an amount of the compound of Formula (I), Formula (Ia), or Formula (Ib) that is effective in treating the target condition.

An object of this invention is to provide methods for treating obesity and inducing weight loss in an individual by administration of a compound of the invention. The method of the invention comprises administering to an individual a therapeutically effective amount of at least one compound of the invention, or a prodrug thereof, which is sufficient to induce weight loss. The invention further comprises a method of preventing weight gain in an individual by administering an amount of at least one compound of the invention, or a prodrug thereof, which is sufficient to prevent weight gain.

The present invention also relates to the use of the compounds of this invention for the treatment of obesity-related diseases including associated dyslipidemia and other obesity- and overweight-related complications such as, for example, cholesterol gallstones, gallbladder disease, gout, cancer (e.g., colon, rectum, prostate, breast, ovary, endometrium, cervix, gallbladder, and bile duct), menstrual abnormalities, infertility, polycystic ovaries, osteoarthritis, and sleep apnea, as well as for a number of other pharmaceutical uses associated therewith, such as the regulation of appetite and food intake, dyslipidemia, hypertriglyceridemia, Syndrome X, type 2 diabetes (non-insulin-dependent diabetes), atherosclerotic diseases such as heart failure, hyperlipidemia, hypercholesteremia, low HDL levels, hypertension, cardiovascular disease (including atherosclerosis, coronary heart disease, coronary artery disease, and hypertension), cerebrovascular disease such as stroke, and peripheral vessel disease. The compounds of this invention may also be useful for treating physiological disorders related to, for example, regulation of insulin sensitivity, inflammatory response, plasma triglycerides, HDL, LDL and cholesterol levels and the like.

Compounds of Formula (I), Formula (Ia), or Formula (Ib) may be administered alone or in combination with one or more additional therapeutic agents. Combination therapy includes administration of a single pharmaceutical dosage formulation which contains a compound of Formula (I), Formula (Ia), or Formula (Ib) and one or more additional therapeutic agents, as well as administration of the compound of Formula (I), Formula (Ia), or Formula (Ib) and each additional therapeutic agents in its own separate pharmaceutical dosage formulation. For example, a compound of Formula (I), Formula (Ia), or Formula (Ib) and a therapeutic agent may be administered to the patient together in a single oral dosage composition such as a tablet or capsule, or each agent may be administered in separate oral dosage formulations.

Where separate dosage formulations are used, the compound of Formula (I), Formula (Ia), or Formula (Ib) and one or more additional therapeutic agents may be administered at essentially the same time (e.g., concurrently) or at separately staggered times (e.g., sequentially).

For example, the compounds of Formula (I), Formula (Ia), or Formula (Ib) may be used in combination with other therapies and drugs useful for the treatment of obesity. For example, anti-obesity drugs include β-3 agonists such as CL-316,243; CB-1 antagonists; neuropeptide Y5 inhibitors; appetite suppressants, such as, for example, sibutramine (Meridia); and lipase inhibitors, such as, for example, orlistat (Xenical). The compounds of the present invention may also be administered in combination with a drug compound that modulates digestion and/or metabolism such as drugs that modulate thermogenesis, lipolysis, gut motility, fat absorption, and satiety.

In addition, the compounds of Formula (I), Formula (Ia), or Formula (Ib) may be administered in combination with one or more of the following agents for the treatment of diabetes or diabetes-related disorders including PPAR ligands (agonists, antagonists), insulin secretagogues, for example, sulfonylurea drugs and non-sulfonylurea secretagogues, α-glucosidase inhibitors, insulin sensitizers, hepatic glucose output lowering compounds, and insulin and insulin derivatives. Such therapies may be administered prior to, concurrently with, or following administration of the compounds of the invention. Insulin and insulin derivatives include both long and short acting forms and formulations of insulin. PPAR ligands may include agonists and/or antagonists of any of the PPAR receptors or combinations thereof. For example, PPAR ligands may include ligands of PPAR-α, PPAR-γ, PPAR-δ or any combination of two or three of the receptors of PPAR. PPAR ligands include, for example, rosiglitazone, troglitazone, and pioglitazone. Sulfonylurea drugs include, for example, glyburide, glimepiride, chlorpropamide, tolbutamide, and glipizide. α-glucosidase inhibitors that may be useful in treating diabetes when administered with a compound of the invention include acarbose, miglitol, and voglibose. Insulin sensitizers that may be useful in treating diabetes include PPAR-γ agonists such as the glitazones (e.g., troglitazone, pioglitazone, englitazone, MCC-555, rosiglitazone, and the like) and other thiazolidinedione and non-thiazolidinedione compounds; biguanides such as metformin and phenformin; protein tyrosine phosphatase-1B (PTP-1B) inhibitors; dipeptidyl peptidase IV (DPP-IV) inhibitors, and 11 beta-HSD inhibitors. Hepatic glucose output lowering compounds that may be useful in treating diabetes when administered with a compound of the invention include glucagon antagonists and metformin, such as Glucophage and Glucophage XR. Insulin secretagogues that may be useful in treating diabetes when administered with a compound of the invention include sulfonylurea and non-sulfonylurea drugs: GLP-1, GIP, PACAP, secretin, and derivatives thereof; nateglinide, meglitinide, repaglinide, glibenclamide, glimepiride, chlorpropamide, glipizide. GLP-1 includes derivatives of GLP-1 with longer half-lives than native GLP-1, such as, for example, fatty-acid derivatized GLP-1 and exendin.

Compounds of the invention may also be used in methods of the invention in combination with drugs commonly used to treat lipid disorders in patients. Such drugs include, but are not limited to, HMG-CoA reductase inhibitors, nicotinic acid, fatty acid lowering compounds (e.g., acipimox); lipid lowering drugs (e.g., stanol esters, sterol glycosides such as tiqueside, and azetidinones such as ezetimibe), ACAT inhibitors (such as avasimibe), bile acid sequestrants, bile acid reuptake inhibitors, microsomal triglyceride transport inhibitors, and fibric acid derivatives. HMG-CoA reductase inhibitors include, for example, lovastatin, simvastatin, pravastatin, fluvastatin, atorvastatin, rivastatin, itavastatin, cerivastatin, and ZD-4522. Fibric acid derivatives include, for example, clofibrate, fenofibrate, bezafibrate, ciprofibrate, beclofibrate, etofibrate, and gemfibrozil. Sequestrants include, for example, cholestyramine, colestipol, and dialkylaminoalkyl derivatives of a cross-linked dextran.

Compounds of the invention may also be used in combination with anti-hypertensive drugs, such as, for example, β-blockers and ACE inhibitors. Examples of additional anti-hypertensive agents for use in combination with the compounds of the present invention include calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, neutral endopeptidase (NEP)

inhibitors, vasopepsidase inhibitors (dual NEP-ACE inhibitors) (e.g., omapatrilat and gemopatrilat), and nitrates.

The compounds of Formula (I), Formula (Ia), and Formula (Ib) may also be utilized, in free base form or in compositions, as well as in research and diagnostics or as analytical reference standards, and the like, which are well known in the art. Therefore, the present invention includes compositions which are comprised of an inert carrier and an effective amount of a compound of Formula (I), Formula (Ia), or Formula (Ib), or a salt, or ester thereof. An inert carrier is any material which does not interact with the compound to be carried and which lends support, means of conveyance, bulk, traceable material, and the like to the compound to be carried. An effective amount of the compound is that amount which produces a result or exerts an influence on the particular procedure being performed.

It is anticipated that prodrug forms of the compounds of this invention will prove useful in certain circumstances, and such compounds are also intended to fall within the scope of the invention. Prodrug forms may have advantages over the parent compounds exemplified herein, in that they are better absorbed, better distributed, more readily penetrate the central nervous system, are more slowly metabolized or cleared, etc. Prodrug forms may also have formulation advantages in terms of crystallinity or water solubility. For example, compounds of the invention having one or more hydroxyl groups may be converted to esters or carbonates bearing one or more carboxyl, hydroxyl or amino groups, which are hydrolyzed at physiological pH values or are cleaved by endogenous esterases or lipases in vivo (see, e.g., U.S. Pat. Nos. 4,942,184; 4,960,790; 5,817,840; and 5,824,701, all of which are incorporated herein by reference in their entirety, and references therein).

Pharmaceutical Compositions

Based on the above tests, or other well known assays used to determine the efficacy for treatment of conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range from about 0.001 mg/kg to about 200 mg/kg, and preferably from about 0.01 mg/kg to about 200 mg/kg body weight per day. A unit dosage may contain from about 0.05 mg to about 1500 mg of active ingredient, and may be administered one or more times per day. The daily dosage for administration by injection, including intravenous, intramuscular, subcutaneous, and parenteral injections, and use of infusion techniques may be from about 0.01 to about 200 mg/kg. The daily rectal dosage regimen may be from 0.01 to 200 mg/kg of total body weight. The transdermal concentration may be that required to maintain a daily dose of from 0.01 to 200 mg/kg.

Of course, the specific initial and continuing dosage regimen for each patient will vary according to the nature and severity of the condition as determined by the attending diagnostician, the activity of the specific compound employed, the age of the patient, the diet of the patient, time of administration, route of administration, rate of excretion of the drug, drug combinations, and the like. The desired mode of treatment and number of doses of a compound of the present invention or a pharmaceutically acceptable salt thereof may be ascertained by those skilled in the art using conventional treatment tests.

The compounds of this invention may be utilized to achieve the desired pharmacological effect by administration to a subject in need thereof in an appropriately formulated pharmaceutical composition. A subject, for example, may be a mammal, including a human, in need of treatment for a particular condition or disease. Therefore, the present invention includes pharmaceutical compositions which are comprised of a pharmaceutically acceptable carrier and a pharmaceutically effective amount of a compound identified by the methods described herein, or a pharmaceutically acceptable salt or ester thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of a compound is that amount which produces a result or exerts an influence on the particular condition being treated. The compounds identified by the methods described herein may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol, ethers such as poly(ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

Commonly used pharmaceutical ingredients which may be used as appropriate to formulate the composition for its intended route of administration include: acidifying agents, for example, but are not limited to, acetic acid, citric acid, fumaric acid, hydrochloric acid, nitric acid; and alkalinizing agents such as, but are not limited to, ammonia solution, ammonium carbonate, diethanolamine, monoethanolamine, potassium hydroxide, sodium borate, sodium carbonate, sodium hydroxide, triethanolamine, trolamine.

Other pharmaceutical ingredients include, for example, but are not limited to, adsorbents (e.g., powdered cellulose and activated charcoal); aerosol propellants (e.g., carbon dioxide, $CCl_2F_2$, $F_2ClC-CClF_2$ and $CClF_3$); air displacement agents (e.g., nitrogen and argon); antifungal preservatives (e.g., benzoic acid, butylparaben, ethylparaben, methylparaben, propylparaben, sodium benzoate); antimicrobial preservatives (e.g., benzalkonium chloride, benzethonium chloride, benzyl alcohol, cetylpyridinium chloride, chlorobutanol, phenol, phenylethyl alcohol, phenylmercuric nitrate and thimerosal); antioxidants (e.g., ascorbic acid, ascorbyl palmitate, butylated hydroxyani sole, butylated hydroxytoluene, hypophosphorus acid, monothioglycerol, propyl gallate, sodium ascorbate, sodium bisulfite, sodium formaldehyde sulfoxylate, sodium metabisulfite); binding materials (e.g., block polymers, natural and synthetic rubber, polyacrylates, polyurethanes, silicones and styrene-butadiene copolymers); buffering agents (e.g., potassium metaphosphate, potassium phosphate monobasic, sodium acetate, sodium citrate anhydrous and sodium citrate dihydrate); carrying agents (e.g., acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (e.g., edetate disodium and edetic acid); colorants (e.g., FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (e.g., bentonite); emulsifying agents (but are not limited to, acacia, cetomacrogol, cetyl alcohol, glyceryl monostearate, lecithin, sorbitan monooleate, polyethylene 50 stearate); encapsulating agents (e.g., gelatin and cellulose acetate phthalate); flavorants (e.g., anise oil, cinnamon oil, cocoa, menthol, orange oil, peppermint oil and vanillin); humectants (e.g., glycerin, propylene glycol and sorbitol); levigating agents (e.g., mineral oil and glycerin); oils (e.g., arachis oil, mineral oil, olive oil, peanut oil, sesame oil and vegetable oil); ointment bases (e.g., lanolin, hydrophilic ointment, polyethylene glycol ointment, petrolatum, hydrophilic petrolatum, white ointment, yellow ointment, and rose water ointment); penetration enhancers (transdermal delivery) (e.g., monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (e.g., diethyl phthalate and glycerin); solvents (e.g., alcohol, corn oil, cottonseed oil, glycerin, isopropyl alcohol, mineral oil, oleic acid, peanut oil, purified water, water for injection, sterile water for injection and sterile water for irrigation); stiffening agents (e.g., cetyl alcohol, cetyl esters wax, microcrystalline wax, paraffin, stearyl alcohol, white wax and yellow wax); suppository bases (e.g., cocoa butter and polyethylene glycols (mixtures)); surfactants (e.g., benzalkonium chloride, nonoxynol 10, oxtoxynol 9, polysorbate 80, sodium lauryl sulfate and sorbitan monopalmitate); suspending agents (e.g., agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening e.g., aspartame, dextrose, glycerin, mannitol, propylene glycol, saccharin sodium, sorbitol and sucrose); tablet anti-adherents (e.g., magnesium stearate and talc); tablet binders (e.g., acacia, alginic acid, carboxymethylcellulose sodium, compressible sugar, ethylcellulose, gelatin, liquid glucose, methylcellulose, povidone and pregelatinized starch); tablet and capsule diluents (e.g., dibasic calcium phosphate, kaolin, lactose, mannitol, microcrystalline cellulose, powdered cellulose, precipitated calcium carbonate, sodium carbonate, sodium phosphate, sorbitol and starch); tablet coating agents (e.g., liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (e.g., dibasic calcium phosphate); tablet disintegrants (e.g., alginic acid, carboxymethylcellulose calcium, microcrystalline cellulose, polacrillin potassium, sodium alginate, sodium starch glycollate and starch); tablet glidants (e.g., colloidal silica, corn starch and talc); tablet lubricants (e.g., calcium stearate, magnesium stearate, mineral oil, stearic acid and zinc stearate); tablet/capsule opaquants (e.g., titanium dioxide); tablet polishing agents (e.g., camuba wax and white wax); thickening agents (e.g., beeswax, cetyl alcohol and paraffin); tonicity agents (e.g., dextrose and sodium chloride);viscosity increasing agents (e.g., alginic acid, bentonite, carbomers, carboxymethylcellulose sodium, methylcellulose, povidone, sodium alginate and tragacanth); and wetting agents (e.g., heptadecaethylene oxycetanol, lecithins, polyethylene sorbitol monooleate, polyoxyethylene sorbitol monooleate, and polyoxyethylene stearate).

The compounds identified by the methods described herein may be administered as the sole pharmaceutical agent or in combination with one or more other pharmaceutical agents where the combination causes no unacceptable adverse effects. For example, the compounds of this invention can be combined with known anti-obesity, or with known antidiabetic or other indication agents, and the like, as well as with admixtures and combinations thereof.

The compounds identified by the methods described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Formulations suitable for subcutaneous, intravenous, intramuscular, and the like; suitable pharmaceutical carriers;

and techniques for formulation and administration may be prepared by any of the methods well known in the art (see, e.g., Remington's Pharmaceutical Sciences, Mack Publishing Co., Easton, Pa., 20$^{th}$ edition, 2000).

Biological Activity of the Compounds

In order that this invention may be better understood, the following examples are set forth. These examples are for the purpose of illustration only, and are not to be construed as limiting the scope of the invention in any manner. All publications mentioned herein are incorporated by reference in their entirety.

Demonstration of the activity of the compounds of the present invention may be accomplished through in vitro, ex vivo, and in vivo assays that are well known in the art. For example, to demonstrate the efficacy of a pharmaceutical agent for the treatment of obesity and related disorders, the following assays may be used.

Evaluation of Compound Effect on the Inhibition of DGAT-1 Enzyme Activity

The human DGAT-1 gene (see, e.g., U.S. Pat. No. 6,100,077) was isolated from a human cDNA library by PCR. Recombinant AcNPV baculovirus was constructed in which the gene for occlusion body forming protein polyhedrin was replaced with the DGAT-1 gene. The DGAT-1 gene sequence was inserted into the AcNPV genome 3' to the polyhedrin promoter sequence placing DGAT-1 under the transcriptional control of the polyhedrin promoter. *Spodoptera frugiperda*-derived Sf9 insect cells were infected with DGAT-1-containing recombinant baculovirus at the multiplicity of infection of 5 and harvested 48 h post-infection. DGAT-1-expressing insect cells were homogenized in 10 mM Tris, 250 mM sucrose, pH 7.5 at the concentration of 100 mg of wet cell biomass per mL. The homogenate was centrifuged at 25,000 g for 30 minutes. The 25,000 g pellet was discarded and the supernatant was centrifuged at 100,000 g for 1 h. The 100,000 g supernatant was discarded and the 100,000 g DGAT-1-containing membrane pellet was re-suspended in 10 mM Tris, 50% (v/v) glycerol pH 7.5.

DGAT-1 enzyme activity was determined by a phase partitioning protocol. Specifically, DGAT-1 containing membranes were incubated in 20 μM didecanoyl glycerol, 5 μM $^{14}$C-decanoyl-CoA, 2 mM MgCl$_2$, 0.04% BSA, 20 mM HEPES, pH 7.5 buffer in the presence of varying concentrations of inhibitors. Assays were performed in 100 μl volumes in 96-well microtiter plates 0.5 μg total membrane protein per well. The assay was initiated by substrate and mixed gently for 1 h at ambient temperature. Activity was quenched by the addition of 25 μl of 0.1% phosphoric acid solution. Selective extraction of the hydrophobic tridecanoylglycerol product was accomplished by the addition of 150 μl phase partitioning scintillation fluid Microscint® (Packard, Inc.) and vigorous mixing for 30 minutes. Quantification of the product was accomplished by a MicroBeta® scintillation counter (Wallac, Inc.) after settling for approximately 16 h at ambient temperatures.

Evaluation of Compound Effect on the Inhibition of Cellular Triplyceride Deposition The cell-based assay for DGAT-1 was conducted with human colorectal adenocarcinoma cells HT-29 (HTB-38, ATCC). HT-29 cells were grown in 75 cm$^2$ plate until ~90% confluent in DMEM media with 10% FBS, PSF, glutamine, and 10 mM acetate. Cells were then re-plated in 24-well plates to give 1:1.2 dilution and grown approximately 16 h. Triacylglyceride formation was stimulated by the addition of lauric acid to 0.01% final concentration in the presence of varying concentrations of inhibitors. After 6 h, cells were released from the plate by trypsin, collected by centrifugation, re-suspended in water, transferred to glass HPLC, frozen at −70° C., and lyophilized. Freeze dried cell pellets were re-suspended in 150 μl HPLC grade tetrahydrofuran and sealed in the vials. Vials were sonicated for 30 minutes with heating in a sonicating water bath (Fisher, Inc.). Cellular triacylglycerides were quantified by HPLC (HP1100, Agilent, Inc.) utilizing evaporative light-scattering detection (PL-ELS 1000, Polymer Labs, Inc.). Chromatographic separation was accomplished by 30 to 100% B buffer in 4 minutes followed by 3 minutes at 100% B buffer using a PLRP S 100 column (5 micron, 150×4.6 mm, Polymer Labs, Inc.) at 50° C. (A: 50% acetonitrile, 2.5% methanol, B: 100% tetrahydrofuran). Sample injections were 20 μl and the detector was set at 0.4 SLM, 40° C. nebulizer and 80° C. evaporator. Non-polar fatty acids and glycerol lipids were identified and quantified by using commercially available standards.

Evaluation of Compound Efficacy on the Reduction of Body Weight in Diet-Induced Obese Mice The purpose of this protocol is to determine the effect of chronic administration of a compound on the body weight of mice made obese by exposure to a 45% kcal/g high fat diet for more than 10 weeks. The body weight of mice selected for these studies was higher than three standard deviations from the weight of a control group of mice fed standard low fat (5–6% fat) mouse chow. Diet-induced obese (DIO) animals have been used frequently in the determination of compound efficacy in the reduction of body weight (see, e.g., Brown, et al., Brit. J. Pharmacol. 132:1898–1904, 2001; Guerre-Millo, et al., J. Biol. Chem. 275(22): 16638–42, 2000; Han, et al., Intl. J. Obesity and Related Metabolic Disorders 23(2):174–79, 1999; Surwit, et al., Endocrinol. 141(10):3630–37, 2000).

This animal model has been successfully used in the identification and characterization of the efficacy profile of compounds that are or have been used in the management of body weight in obese humans (see, e.g., Brown, et al., 2001; Guerre-Millo, et al., 2000; Han, et al., 1999).

A typical study included 60–80 male C57b1/J6 mice (n=10/treatment group) with an average body weight of approximately 45 g. Mice were kept in standard animal rooms under controlled temperature and humidity and a 12 hour/12 hour light/dark cycle. Water and food were continuously available. Mice were individually housed. Animals were sham dosed with study vehicle for at least four days before the recording of two-day baseline measurements of body weight and 24-hour food and water consumption. Mice were assigned to one of 6–8 treatment groups based upon their body weight on baseline. The groups were set up so that the mean and standard error of the mean of body weight were similar.

Animals were orally gavaged (5 mL/kg) daily before the dark phase of the light/dark cycle for a pre-determined number of days (typically 8–14 days) with their assigned dose/compound. Body weight, and food and water consumption were measured. Data was analyzed using appropriate statistics following the research design. On the final day, animals were euthanized using CO$_2$ inhalation.

Compounds were typically dosed at 5 or 10 mg/kg p.o. q.d. as a suspension formulation in 50:50 PEG/water, or p.o. b.i.d. as a suspension formulation in 0.5% methylcellulose, and compounds were considered to be active if a statistically significant reduction in body weight was observed for the treated animals after a treatment period of at least seven days, relative to vehicle-treated control animals.

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

What is claimed:

1. A compound of Formula (I)

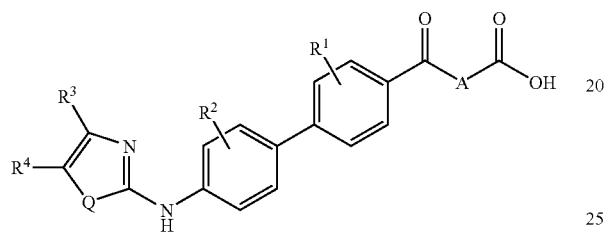

(I)

wherein

Q is S;

A is a linker selected from

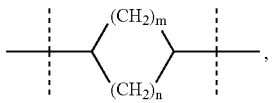

wherein m is 0 and n is 1, 2, 3, or 4, or
m is 1 and n is 1, 2, or 3, and
wherein said linker is optionally substituted by one or two $R^8$ groups;

$R^1$ and $R^2$ are independently selected from hydrogen, halo, $(C_1-C_6)$alkyl, and $(C_1-C_6)$alkoxy;

$R^3$ is selected from
  hydrogen,
  $(C_1-C_6)$alkyl optionally substituted by hydroxy, and
  phenyl optionally substituted with $(C_1-C_6)$alkyl, $(C_1-C_6)$alkoxy, or halo;

$R^4$ is selected from hydrogen, nitro, and $(C_1-C_6)$alkyl; or $R^3$ and $R^4$ may, when taken together with the carbon atoms to which they are attached, form a benzene ring optionally substituted with up to two substituents selected from
  halo, $(C_1-C_6)$alkyl, $(C_1-C_6)$alkoxy, nitro, cyano, $(C_1-C_6)$haloalkyl, $(C_1-C_6)$haloalkoxy, aminocarbonyl, $(C_1-C_6)$alkylaminocarbonyl, bis[$(C_1-C_6)$alkyl]aminocarbonyl, aminosulfonyl, $(C_1-C_6)$alkylaminosulfonyl, bis[$(C_1-C_6)$alkyl]aminosulfonyl, $(C_1-C_6)$alkylcarbonylamino, $(C_1-C_6)$alkylsulfonylamino, and hydroxy-$(C_2-C_6)$alkylaminocarbonyl, and
  when two of said benzene ring substituents are $(C_1-C_6)$alkyl and are attached to adjacent carbon atoms of the benzene ring, they may be joined together to form a 5–7-membered carbocyclic ring;

$R^8$ is $(C_1-C_6)$alkyl;

or the pharmaceutically acceptable salts and esters thereof.

2. The compound of claim 1, wherein

Q is S;

A is

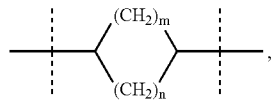

wherein m is 0 and n is 1, 2, 3, or 4, or
m is 1 and n is 1, 2, or 3, and
wherein said linker is optionally substituted by one or two $R^8$ groups;

$R^3$ and $R^4$ may, when taken together with the carbon atoms to which they are attached, form a benzene ring optionally substituted with up to two substituents selected from
  halo, $(C_1-C_6)$alkyl, $(C_1-C_6)$alkoxy, nitro, cyano, $(C_1-C_6)$haloalkyl, $(C_1-C_6)$haloalkoxy, aminocarbonyl, $(C_1-C_6)$alkylaminocarbonyl, bis[$(C_1-C_6)$alkyl]aminocarbonyl, aminosulfonyl, $(C_1-C_6)$alkylaminosulfonyl, bis[$(C_1-C_6)$alkyl]aminosulfonyl, $(C_1-C_6)$alkylcarbonylamino, $(C_1-C_6)$alkylsulfonylamino, hydroxy-$(C_2-C_6)$alkylaminocarbonyl, and $R^1$, $R^2$, $R^5$, and $R^8$ are as defined in claim 1.

3. The compound of claim 1, wherein

Q is S;

A is

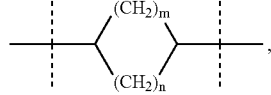

wherein m is 1 and n is 1, 2, or 3, and
wherein said linker is optionally substituted by one or two $R^8$ groups;

$R^3$ and $R^4$ may, when taken together with the carbon atoms to which they are attached, form a benzene ring optionally substituted with up to two substituents selected from
  halo, $(C_1-C_6)$alkyl, $(C_1-C_6)$alkoxy, nitro, cyano, $(C_1-C_6)$haloalkyl, $(C_1-C_6)$haloalkoxy, aminocarbonyl, $(C_1-C_6)$alkylaminocarbonyl, bis[$(C_1-C_6)$alkyl]aminocarbonyl, aminosulfonyl, $(C_1-C_6)$alkylaminosulfonyl, bis[$(C_1-C_6)$alkyl]aminosulfonyl, $(C_1-C_6)$alkylcarbonylamino, $(C_1-C_6)$alkylsulfonylamino, and hydroxy-$(C_2-C_6)$alkylaminocarbonyl, $R^1$, $R^2$, and $R^8$ are as defined in claim 1.

4. The compound of claim 1, wherein

Q is S;

A is

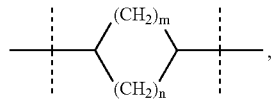

wherein m is 0 and n is 1, 2, 3, or 4, and
wherein said linker is optionally substituted by one or two $R^8$ groups;

R³ and R⁴ may, when taken together with the carbon atoms to which they are attached, form a benzene ring optionally substituted with up to two substituents selected from halo, (C₁–C₆)alkyl, (C₁–C₆)alkoxy, nitro, cyano, (C₁–C₆)haloalkyl, (C₁–C₆)haloalkoxy, aminocarbonyl, (C₁–C₆)alkylaminocarbonyl, bis[(C₁–C₆)alkyl]aminocarbonyl, aminosulfonyl, (C₁–C₆)alkylaminosulfonyl, bis[(C₁–C₆)alkyl]aminosulfonyl, (C₁–C₆)alkylcarbonylamino, (C₁–C₆)alkylsulfonylamino, hydroxy-(C₂–C₆)alkylaminocarbonyl, R¹, R², and R⁸ are as defined in claim 1.

5. The compound of claim 1 selected from the group consisting of:

trans-2-({4'-[(6-chloro-1,3-benzothiazol-2-yl)amino]-1,1'-biphenyl-4-yl}carbonyl) cyclopentane-carboxylic acid;

trans-2-({4'-[(6-chloro-1,3-benzothiazol-2-yl)amino]-1,1'-biphenyl-4-yl}carbonyl) cyclopentane-carboxylic acid;

trans-(1R,2R)-2-{[4'-(1,3-benzothiazol-2-ylamino)-1,1'-biphenyl-4-yl]carbonyl}cyclopentane-carboxylic acid;

trans-2-{[4'-(1,3-benzothiazol-2-ylamino)-1,1'-biphenyl-4-yl]carbonyl}cyclopentane-carboxylic acid;

trans-2-({4'-[(5-methoxy-1,3-benzothiazol-2-yl)amino]-1,1'-biphenyl-4-yl}carbonyl)cyclopentane-carboxylic acid;

trans-2-({4'-[(6-nitro-1,3-benzothiazol-2-yl)amino]-1,1'-biphenyl-4-yl}carbonyl)cyclopentane-carboxylic acid;

trans-2-({4'-[(4-chloro-1,3-benzothiazol-2-yl)amino]-1,1'-biphenyl-4-yl}carbonyl) cyclopentane-carboxylic acid;

trans-2-({4'-[(6-methoxy-1,3-benzothiazol-2-yl)amino]-1,1'-biphenyl-4-yl}carbonyl)cyclopentane-carboxylic acid;

trans-2-({4'-[(6-methyl-1,3-benzothiazol-2-yl)amino]-1,1'-biphenyl-4-yl}carbonyl)cyclopentane-carboxylic acid;

trans-2-({4'-[(6-ethoxy-1,3-benzothiazol-2-yl)amino]-1,1'-biphenyl-4-yl}carbonyl)cyclopentane-carboxylic acid;

trans-2-({4'-[(6-fluoro-1,3-benzothiazol-2-yl)amino]-1,1'-biphenyl-4-yl}carbonyl)cyclopentane-carboxylic acid;

trans-(1R,2R)-2-({4'-[(6-chloro-1,3-benzothiazol-2-yl)amino]-1,1'-biphenyl-4-yl}carbonyl)-cyclopentane-carboxylic acid;

trans-(1S,2S)-2-({4'-[(6-chloro-1,3-benzothiazol-2-yl)amino]-1,1'-biphenyl-4-yl}carbonyl)-cyclopentane-carboxylic acid;

2,2-dimethyl-4-{4'-[(5-nitro-1,3-thiazol-2-yl)amino]-1,1'-biphenyl-4-yl}-4-oxobutanoic acid;

trans-(1R,2R)-2-({4'-[(4,6-difluoro-1,3-benzothiazol-2-yl)amino]-1,1'-biphenyl-4-yl}carbonyl)cyclopentane-carboxylic acid;

trans-(1S,2S)-2-({4'-[(4,6-difluoro-1,3-benzothiazol-2-yl)amino]-1,1'-biphenyl-4-yl}carbonyl)cyclopentane-carboxylic acid;

cis-3-({4'-[(6-chloro-1,3-benzothiazol-2-yl)amino]-1,1'-biphenyl-4-yl}carbonyl)cyclohexane-carboxylic acid;

cis-3-({4'-[(6-methoxy-1,3-benzothiazol-2-yl)amino]-1,1'-biphenyl-4-yl}carbonyl)cyclohexane-carboxylic acid;

trans-2-[(4'-{[6-(trifluoromethoxy)-1,3-benzothiazol-2-yl]amino}-1,1'-biphenyl-4-yl)carbonyl]cyclopentane-carboxylic acid;

trans-(1R,2R)-2-({4'-[(6-fluoro-1,3-benzothiazol-2-yl)amino]-1,1'-biphenyl-4-yl}carbonyl)-cyclopentane-carboxylic acid;

trans-(1R,2R)-2-({4'-[(6-methyl-1,3-benzothiazol-2-yl)amino]-1,1'-biphenyl-4-yl}carbonyl)-cyclopentane-carboxylic acid;

trans-(1S,2S)-2-({4'-[(6-fluoro-1,3-benzothiazol-2-yl)amino]-1,1'-biphenyl-4-yl}carbonyl)-cyclopentane-carboxylic acid;

trans-(1S,2S)-2-({4'-[(6-methyl-1,3-benzothiazol-2-yl)amino]-1,1'-biphenyl-4-yl}carbonyl)-cyclopentane-carboxylic acid;

trans-2-({4'-[(4,6-difluoro-1,3-benzothiazol-2-yl)amino]-1,1'-biphenyl-4-yl}carbonyl)cyclopentane-carboxylic acid;

trans-2-({4'-[(4-methyl-1,3-benzothiazol-2-yl)amino]-1,1'-biphenyl-4-yl}carbonyl)cyclopentane-carboxylic acid;

trans-2-({4'-[(5-fluoro-1,3-benzothiazol-2-yl)amino]-1,1'-biphenyl-4-yl}carbonyl)cyclopentane-carboxylic acid;

trans-2-[(4'-{[6-(trifluoromethyl)-1,3-benzothiazol-2-yl]amino}-1,1'-biphenyl-4-yl)carbonyl]-cyclopentane-carboxylic acid;

trans-2-({4'-[(5-chloro-1,3-benzothiazol-2-yl)amino]-1,1'-biphenyl-4-yl}carbonyl)cyclopentane-carboxylic acid;

trans-2-({4'-[(5,7-dimethyl-1,3-benzothiazol-2-yl)amino]-1,1'-biphenyl-4-yl}carbonyl)cyclopentane-carboxylic acid;

trans-2-[(4'-{[6-(methylsulfonyl)-1,3-benzothiazol-2-yl]amino}-1,1'-biphenyl-4-yl)carbonyl]-cyclopentane-carboxylic acid;

trans-2-({4'-[(5,6-dimethyl-1,3-benzothiazol-2-yl)amino]-1,1'-biphenyl-4-yl}carbonyl)cyclopentane-carboxylic acid;

trans-2-({4'-[(5,7-difluoro-1,3-benzothiazol-2-yl)amino]-1,1'-biphenyl-4-yl}carbonyl)cyclopentane-carboxylic acid;

trans-2-({4'-[(6-chloro-1,3-benzothiazol-2-yl)amino]-1,1'-biphenyl-4-yl}carbonyl)cyclopentane-carboxylic acid;

trans-(1R,2R)-2-[(4'-{[5-(trifluoromethyl)-1,3-benzothiazol-2-yl]amino}-1,1'-biphenyl-4-yl)-carbonyl]cyclopentane-carboxylic acid;

trans-2-{[4'-(1,3-benzothiazol-2-ylamino)-1,1'-biphenyl-4-yl]carbonyl}cyclopropane-carboxylic acid;

trans-2-({4'-[(6-chloro-1,3-benzothiazol-2-yl)amino]-1,1'-biphenyl-4-yl}carbonyl)cyclohexane-carboxylic acid;

trans-2-({4'-[(4-methyl-1,3-benzothiazol-2-yl)amino]-1,1'-biphenyl-4-yl}carbonyl)cyclopropane-carboxylic acid;

trans-2-({4'-[(6-methoxy-1,3-benzothiazol-2-yl)amino]-1,1'-biphenyl-4-yl}carbonyl)cyclopropane-carboxylic acid;

trans-2-({4'-[(5,7-difluoro-1,3-benzothiazol-2-yl)amino]-1,1'-biphenyl-4-yl}carbonyl)cyclopropane-carboxylic acid;

trans-2-({4'-[(4,6-difluoro-1,3-benzothiazol-2-yl)amino]-1,1'-biphenyl-4-yl}carbonyl)cyclopropane-carboxylic acid;

trans-2-{[4'-(1,3-benzothiazol-2-ylamino)-1,1'-biphenyl-4-yl]carbonyl}cyclobutane-carboxylic acid;

trans-2-({4'-[(6-methoxy-1,3-benzothiazol-2-yl)amino]-1,1'-biphenyl-4-yl}carbonyl)cyclobutane-carboxylic acid;

trans-2-({4'-[(4-methyl-1,3-benzothiazol-2-yl)amino]-1,1'-biphenyl-4-yl}carbonyl)cyclobutane-carboxylic acid;
trans-(1R,2R)-2-({4'-[(6-isopropyl-1,3-benzothiazol-2-yl)amino]-1,1'-biphenyl-4-yl}carbonyl)cyclopentane-carboxylic acid;
trans-2-({4'-[(6-chloro-1,3-benzothiazol-2-yl)amino]-3'-fluoro-1,1'-biphenyl-4-yl}carbonyl)-cyclopentane-carboxylic acid;
trans-2-({3'-fluoro-4'-[(6-methoxy-1,3-benzothiazol-2-yl)amino]-1,1'-biphenyl-4-yl}carbonyl)-cyclopentane-carboxylic acid;
trans-(1R,2R)-2-({4'-[(6-chloro-1,3-benzothiazol-2-yl)amino]-3'-fluoro-1,1'-biphenyl-4-yl}carbonyl)-cyclopentane-carboxylic acid
trans-(1R,2R)-2-({3'-fluoro-4'-[(6-methoxy-1,3-benzothiazol-2-yl)amino]-1,1'-biphenyl-4-yl}carbonyl)-cyclopentane-carboxylic acid
trans-2-{[4'-(1,3-benzothiazol-2-ylamino)-3'-fluoro-1,1'-biphenyl-4-yl]carbonyl}cyclopentane-carboxylic acid;
trans-(1R,2R)-2-({4'-[(4,6-difluoro-1,3-benzothiazol-2-yl)amino]-3'-fluoro-1,1'-biphenyl-4-yl}carbonyl)-cyclopentane-carboxylic acid;
trans-(1S,2S)-2-({4'-[(4,6-difluoro-1,3-benzothiazol-2-yl)amino]-3'-fluoro-1,1'-biphenyl-4-yl}carbonyl)-cyclopentane-carboxylic acid;
trans-(1R,2R)-2-[(3'-fluoro-4'-{[6-(trifluoromethyl)-1,3-benzothiazol-2-yl]amino}-1,1'-biphenyl-4-yl)carbonyl]cyclopentane-carboxylic acid;
trans-(1R,2R)-2-({3'-fluoro-4'-[(5-fluoro-1,3-benzothiazol-2-yl)amino]-1,1'-biphenyl-4-yl}carbonyl)-cyclopentane-carboxylic acid;
trans-(1R,2R)-2-({3'-fluoro-4'-[(4-methyl-1,3-benzothiazol-2-yl)amino]-1,1'-biphenyl-4-yl}-carbonyl)cyclopentane-carboxylic acid;
trans-(1R,2R)-2-({4'-[(5-chloro-1,3-benzothiazol-2-yl)amino]-3'-fluoro-1,1'-biphenyl-4-yl}carbonyl)cyclopentane-carboxylic acid;
trans-(1R,2R)-2-({3'-fluoro-4'-[(6-fluoro-1,3-benzothiazol-2-yl)amino]-1,1'-biphenyl-4-yl}carbonyl)cyclopentane-carboxylic acid;
trans-(1R,2R)-2-({3'-fluoro-4'-[(6-methyl-1,3-benzothiazol-2-yl)amino]-1,1'-biphenyl-4-yl}-carbonyl)cyclopentane-carboxylic acid;
trans-(1R,2R)-2-({4'-[(5,7-dimethyl-1,3-benzothiazol-2-yl)amino]-3'-fluoro-1,1'-biphenyl-4-yl}carbonyl)cyclopentane-carboxylic acid;
trans-(1R,2R)-2-({4'-[(5,7-difluoro-1,3-benzothiazol-2-yl)amino]-3'-fluoro-1,1'-biphenyl-4-yl}carbonyl)cyclopentane-carboxylic acid
trans-(1R,2R)-2-[(3'-fluoro-4'-{[5-(trifluoromethyl)-1,3-benzothiazol-2-yl]amino)}-1,1'-biphenyl-4-yl)carbonyl]cyclopentane-carboxylic acid;
trans-(1R,2R)-2-[(3'-fluoro-4'-{[6-(trifluoromethoxy)-1,3-benzothiazol-2-yl]amino}-1,1'-biphenyl-4-yl)carbonyl]cyclopentane-carboxylic acid;
trans-2-({3'-fluoro-4'-[(6-methoxy-1,3-benzothiazol-2-yl)amino]-1,1'-biphenyl-4-yl}carbonyl)cyclobutane-carboxylic acid;
trans-2-{[4'-(1,3-benzothiazol-2-ylamino)-3'-fluoro-1,1'-biphenyl-4-yl]carbonyl}cyclobutane-carboxylic acid;
trans-2-{[4'-(1,3-benzothiazol-2-ylamino)-3'-fluoro-1,1'-biphenyl-4-yl]carbonyl}cyclopropane-carboxylic acid;
trans-2-({3'-fluoro-4'-[(6-methoxy-1,3-benzothiazol-2-yl)amino]-1,1'-biphenyl-4-yl}carbonyl)cyclopropane-carboxylic acid
trans-(1R,2R)-2-({3'-fluoro-4'-[(6-isopropyl-1,3-benzothiazol-2-yl)amino]-1,1'-biphenyl-4-yl}carbonyl)cyclopentane-carboxylic acid;
trans-2-({3'-fluoro-4'-[(6-fluoro-1,3-benzothiazol-2-yl)amnino]-1,1'-biphenyl-4-yl}carbonyl)-cyclopentane-carboxylic acid;
trans-2-[(3'-fluoro-4'-{[6-(trifluoromethyl)-1,3-benzothiazol-2-yl]amino}-1,1'-biphenyl-4-yl)-carbonyl]cyclopentane-carboxylic acid;
(1R,2R)-2-[{3'-fluoro-4'-[(6-fluoro-1,3-benzothiazol-2-yl)amino]biphenyl-4-yl}(hydroxy)-methyl]cyclopentanecarboxylic acid.

6. A therapeutic composition comprising a therapeutically effective amount of a compound of claim 1, or a pharmaceutically acceptable salt or ester, in combination with a pharmaceutically acceptable carrier.

7. A therapeutic composition comprising a therapeutically effective amount of a compound of claim 1, or a pharmaceutically acceptable salt or ester thereof, in combination with a pharmaceutically acceptable carrier and one or more pharmaceutical agents.

8. The therapeutic composition of claim 7, wherein said pharmaceutical agent is an anti-obesity agent selected from the group consisting of β-3 agonists, CB-1 antagonists, neuropeptide Y5 inhibitors, appetite suppressants, and lipase inhibitors.

9. The therapeutic composition of claim 7, wherein said pharmaceutical agent is an agent for the treatment of diabetes selected from the group consisting of insulin, insulin derivatives, PPAR ligands, sulfonylurea drugs, α-glucosidase inhibitors, biguanides, PTP-1B inhibitors, DPP-IV inhibitors, 11-beta-HSD inhibitors, GLP-1 and GLP-1 derivatives, GIP and GIP derivatives, PACAP and PACAP derivatives, and secretin and secretin derivatives.

10. The therapeutic composition of claim 7, wherein said pharmaceutical agent is an agent for the treatment of lipid disorders selected from the group consisting of HMG-CoA inhibitors, nicotinic acid, fatty acid lowering compounds, lipid lowering drugs, ACAT inhibitors, bile sequestrants, bile acid reuptake inhibitors, microsomal triglyceride transport inhibitors, and fibric acid derivatives.

11. The therapeutic composition of claim 7, wherein said pharmaceutical agent is an anti-hypertensive agent selected from the group consisting of β-blockers, calcium channel blockers, diuretics, renin inhibitors, ACE inhibitors, AT-1 receptor antagonists, ET receptor antagonists, and nitrates.

12. A pharmaceutical composition comprising a therapeutically effective amount of a compound of claim 5, or, or a pharmaceutically acceptable salt or ester, in combination with a pharmaceutically acceptable carrier.

13. A pharmaceutical composition comprising a therapeutically effective amount of a compound of claim 5, or, or a pharmaceutically acceptable salt or ester thereof, in combination with a pharmaceutically acceptable carrier and one or more pharmaceutical agents.

14. A method of treating obesity comprising the step of administering to a subject in need thereof a therapeutically effective amount of a compound of claim 1 or a composition of claim 6.

15. A method of inducing weight loss comprising the step of administering to a subject in need thereof a therapeutically effective amount of a compound of claim 1 or a composition of claim 6.

16. A method of treating obesity comprising the step of administering to a subject in need thereof a therapeutically effective amount of a compound of claim 1 in combination with one or more therapeutic agents.

17. The method of claim 16, wherein the compound of claim 1 and one or more therapeutic agents are administered as a single pharmaceutical dosage formulation.

18. A method of treating obesity comprising the step of administering to a subject in need thereof a therapeutically effective amount of a composition of claim 7, 8, 9, 10, or 11.

19. A process for the preparation of a compound of Formula (VIII) comprising the steps of:
reacting a compound of Formula (II)

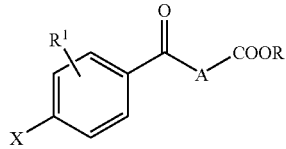

(II)

wherein
R is hydrogen or $(C_1-C_6)$alkyl;
X is Cl, Br, or I; and
$R^1$ and A are as defined in claim 1;
with a boronic ester reagent to give a compound of Formula (X)

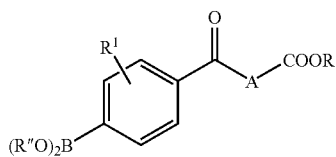

(X)

wherein
R is hydrogen or $(C_1-C_6)$alkyl; and
$R^1$ and A are as defined in claim 1;

and coupling the compound of Formula (X) with a compound of Formula (IX)

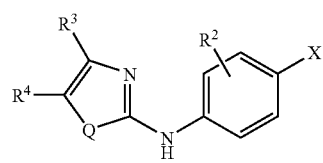

(IX)

wherein
$R^2$, $R^3$, $R^4$, and Q are as defined in claim 1;
in the presence of a palladium catalyst, and optionally in the presence of a base, to give the compound of Formula (VIII)

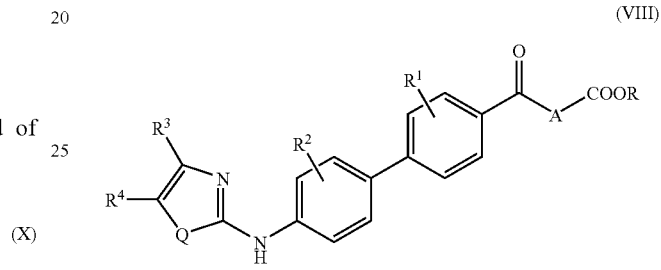

(VIII)

wherein
R is hydrogen or $(C_1-C_6)$alkyl,
$R^1$, $R^2$, $R^3$, $R^4$, A, and Q are as defined in claim 1.

20. The process of claim 19, wherein the boronic ester reagent is pinnacol borane and the base is potassium carbonate.

* * * * *

UNITED STATES PATENT AND TRADEMARK OFFICE
CERTIFICATE OF CORRECTION

PATENT NO.         : 7,091,228 B2
APPLICATION NO. : 10/839833
DATED                 : August 15, 2006
INVENTOR(S)       : Roger Smith et al.

Page 1 of 1

It is certified that error appears in the above-identified patent and that said Letters Patent is hereby corrected as shown below:

Please amend column 232, Claim 5, beginning on line 6 as follows:

** carboxylic acid; and trans-2-[(3'-fluoro-4'-{[6-(trifluoromethyl)-1,3-benzothiazol-2-yl]amino}-1,1'-biphenyl-4-yl)-carbonyl]cyclopentane-carboxylic acid;

~~(1R,2R)-2-[{3'-fluoro-4'-[(6-fluoro-1,3-benzothiazol-2-yl)amino]biphenyl-4-yl}(hydroxy)-methyl]cyclopentanecarboxylic acid.~~ **

Signed and Sealed this

Eighth Day of December, 2009

David J. Kappos
*Director of the United States Patent and Trademark Office*